US006582919B2

(12) United States Patent
Danenberg

(10) Patent No.: US 6,582,919 B2
(45) Date of Patent: Jun. 24, 2003

(54) METHOD OF DETERMINING EPIDERMAL GROWTH FACTOR RECEPTOR AND HER2-NEU GENE EXPRESSION AND CORRELATION OF LEVELS THEREOF WITH SURVIVAL RATES

(75) Inventor: Kathleen D. Danenberg, Altadena, CA (US)

(73) Assignee: Response Genetics, Inc., Los Angeles, CA (US)

( * ) Notice: Subject to any disclaimer, the term of this patent is extended or adjusted under 35 U.S.C. 154(b) by 0 days.

(21) Appl. No.: 09/877,177

(22) Filed: Jun. 11, 2001

(65) Prior Publication Data

US 2002/0192652 A1 Dec. 19, 2002

(51) Int. Cl.[7] ............................ C12Q 1/68; G01N 1/30; C12P 19/34; C07H 21/04

(52) U.S. Cl. ........................ 435/6; 435/40.52; 435/91.1; 435/91.2; 536/23.1; 536/23.5; 536/24.33

(58) Field of Search ........................ 435/6, 40.52, 91.1, 435/91.2; 536/23.1, 23.5, 24.33

(56) References Cited

U.S. PATENT DOCUMENTS

| | | | |
|---|---|---|---|
| 5,639,613 A | 6/1997 | Shay et al. | 435/6 |
| 5,693,474 A | 12/1997 | Shay et al. | 435/6 |
| 5,789,427 A | 8/1998 | Chen et al. | 514/352 |
| 5,804,396 A | 9/1998 | Plowman | 435/7.23 |
| 6,057,156 A | 5/2000 | Akhtar et al. | 435/366 |
| 6,180,349 B1 | 1/2001 | Ginzinger et al. | 435/6 |
| 6,183,995 B1 | 2/2001 | Burmer et al. | 435/91.1 |
| 6,204,375 B1 | 3/2001 | Lader | 536/25.4 |
| 6,207,408 B1 | 3/2001 | Essenfeld et al. | 435/40.5 |
| 6,248,535 B1 | 6/2001 | Danenberg et al. | 435/6 |

OTHER PUBLICATIONS

Ke et al. (Head and Neck (1998) 20(4): 320–7).*

Menard et al. (Journal of Cellular Physiology (Feb. 2000) 182(2) 150–62).*

Cox et al. (International Journal of Cancer (2001) 92(4): 480–3).*

Sylvie Menard, Role of HER2 Gene Overexpression . . . , 2000, pp. 150–162.*

G. Cox, Herceptest: HER2 Expression . . . , 2001, pp. 480–483.*

Li Dao Ke, Differential Expression . . . , Mar. 1997, pp. 320–327.*

Ichikawa, et al, "Expression of Dihydropyrimidine Dehydrogenase (DPD) and Thymidylate Synthase (TS) mRNA in Primary Tumor Predicts the Anti–Tumor Effect in 5–Fluorouracil (FU Based Chemotherapy for Gastrointestinal (GI Cancer", American Association for Cancer Research, Proceedings of the American Association for Cancer Research, 92$^{nd}$ Annual Meeting, vol. 42, Mar. 2001. Abstract No. 3326.

Miyauchi, et al., "Further study of hepatitis C virus RNA detection in formalin –fixed, paraffin –embedded liver tissues by ligation –dependent polymerase chain reaction" Pathology International 1998:48: 428–432.

G. Stanta, et al., *RNA Quantitative Analysis from Fixed and Paraffin–Embedded Tissues*, Methods in Molecular Biology (1998) vol. 86, pp. 113–119.

G. Stanta, et al., *RNA Extraction from Formalin–Fixed and Paraffin–Embedded Tissues*, Methods in Molecular Biology (1998) vol. 86, pp. 23–26.

* cited by examiner

*Primary Examiner*—Kenneth R. Horlick
*Assistant Examiner*—Alexander H. Spiegler
(74) *Attorney, Agent, or Firm*—Kenyon & Kenyon

(57) ABSTRACT

The present invention relates to prognostic methods which are useful in medicine, particularly cancer chemotherapy. The object of the invention to provide a method for assessing HER2-neu and/or EGFR expression levels in fixed or fixed and paraffin embedded tissues and prognosticate the probable sensitivity of a patient's tumor to treatment with receptor tyrosine kinase targeted chemotherapy by examination of the amount of HER2-neu and/or EGFR mRNA in a patient's tumor cells and comparing it to a predetermined threshold expression level for those genes. More specifically, the invention provides to oligonucleotide primer pairs EGFR and HER2-neu and methods comprising their use for detecting levels of EGFR and HER2-neu mRNA, respectively.

28 Claims, 9 Drawing Sheets

RELATIONSHIPS WITH HER2 neu AND EGFR mRNA EXPRESSION

| VARIABLE | EGFR | | | HER2 neu | | |
|---|---|---|---|---|---|---|
| | LOW | HIGH | *P* | LOW | HIGH | *P* |
| SEX | | | | | | |
| MALE | 40 | 25 | | 45 | 20 | |
| FEMALE | 15 | 3 | 0.84 | 20 | 9 | 0.13 |
| SMOKING | | | | | | |
| SMOKER | 48 | 25 | | 46 | 27 | |
| NON-SMOKER | 7 | 3 | 0.79 | 8 | 2 | 0.29 |
| pT CATEGORY | | | | | | |
| pT1 | 11 | 5 | | 12 | 4 | |
| pT2 | 35 | 19 | | 33 | 21 | |
| pT3 | 9 | 4 | 0.93 | 9 | 4 | 0.56 |
| pN CATEGORY | | | | | | |
| pN0 | 31 | 15 | | 32 | 14 | |
| pN1 | 15 | 7 | | 15 | 7 | |
| pN2 | 9 | 6 | 0.85 | 7 | 8 | 0.25 |
| UICC STAGE | | | | | | |
| I | 26 | 15 | | 28 | 13 | |
| II | 13 | 3 | | 12 | 4 | |
| IIIa | 16 | 10 | 0.37 | 14 | 12 | 0.31 |
| HISTOLOGY | | | | | | |
| SQUAMOUS CELL CARCINOMA | 26 | 13 | | 28 | 11 | |
| ADENOCARCINOMA | 20 | 12 | | 16 | 16 | |
| LARGE CELL CARCINOMA | 9 | 3 | 0.74 | 10 | 2 | 0.57 |
| GRADING | | | | | | |
| WELL DIFFERENTIATED | 1 | 0 | | 1 | 0 | |
| MODERATELY DIFFERENTIATED | 13 | 5 | | 13 | 5 | |
| POORLY DIFFERENTIATED | 41 | 23 | 0.63 | 40 | 24 | 0.57 |

FIG.4

SURVIVAL IN NSCLC BASED ON CLINICAL AND MOLECULAR PARAMETERS

| PARAMETER | | N | 5-YEAR SURVIVAL (%) ± SD | MEDIAN SURVIVAL (MONTHS) | CI 95% | P VALUE |
|---|---|---|---|---|---|---|
| UICC STAGE | I | 41 | 68.2 ± 0.07 | N.R. | – | <0.0001 |
| | II | 16 | 43.8 ± 0.12 | 33.97 ± 5.70 | 22.80; 45.14 | |
| | IIIa | 26 | 11.5 ± 0.06 | 19.00 ± 5.14 | 8.92; 29.08 | |
| pT | $pT_1$ | 16 | 68.8 ± 0.12 | N.R. | – | 0.0157 |
| | $pT_2$ | 34 | 44.4 ± 0.07 | 46.77 ± 18.51 | 10.49; 83.05 | |
| | $pT_3$ | 26 | 23.1 ± 0.12 | 26.67 ± 6.09 | 14.73; 38.61 | |
| pN | $pN_0$ | 44 | 67.3 ± 0.07 | N.R. | – | <0.0001 |
| | $pN_1$ | 22 | 31.8 ± 0.10 | 33.71 ± 6.86 | 20.22; 47.12 | |
| | $pN_2$ | 15 | 0 | 16.70 ± 4.01 | 8.84; 24.56 | |
| HER2-neu | LOW | 54 | 57.4 ± 0.07 | N.R. | – | 0.0044 |
| | HIGH | 29 | 24.1 ± 0.08 | 31.10 ± 4.66 | 21.96; 40.24 | |
| EGFR | LOW | 55 | 50.8 ± 0.07 | N.R. | – | N.S. |
| | HIGH | 28 | 35.7 ± 0.09 | 32.37 ± 12.22 | 8.43; 56.31 | |
| DOUBLE MARKER | DOUBLE LOW | 40 | 59.9 ± 0.08 | N.R. | – | 0.0037 |
| | EGFR HIGH | 14 | 50.0 ± 0.13 | 45.47 | – | |
| | HER-2 HIGH | 15 | 26.7 ± 0.11 | 31.10 ± 8.33 | 14.77; 47.73 | |
| | DOUBLE HIGH | 14 | 21.4 ± 0.11 | 22.03 ± 10.07 | 2.30; 41.76 | |

ABBREVIATIONS: N.R. (NOT REACHED); – (CANNOT BE CALCULATED); CI 95% (95% CONFIDENCE INTERVAL); N.S. (NOT SIGNIFICANT); N (NUMBER OF PATIENTS).

FIG.5

COX-PROPORTIONAL HAZARD REGRESSION MODELS

| MODEL | PARAMETER | HAZARDS RATIO | CI 95% | *P* VALUE |
|---|---|---|---|---|
| A | STAGE | | | 0.0001 |
| | I/IIIa | 0.219 | 0.11–0.44 | 0.0001 |
| | II/IIIa | 0.524 | 0.23–1.17 | 0.177 |
| | HER2–neu | 1.894 | 1.02–3.51 | 0.043 |
| B | pT | | | 0.127 |
| | $pT_1/pT_3$ | 0.311 | 0.10–0.97 | 0.044 |
| | $pT_2/pT_3$ | 0.692 | 0.32–1.50 | 0.354 |
| | pN | | | 0.0001 |
| | $pN_0/pN_2$ | 0.143 | 0.07–0.31 | 0.0001 |
| | $pN_1/pN_2$ | 0.333 | 0.14–0.75 | 0.008 |
| | HER2–neu | 1.890 | 1.03–3.48 | 0.041 |
| C | STAGE | | | 0.0001 |
| | I/IIIa | 0.554 | 0.11–0.44 | 0.0001 |
| | II/IIIa | 0.554 | 0.24–1.26 | 0.159 |
| | DOUBLE MARKER | 1.331 | 1.03–1.73 | 0.03 |
| D | pT | | | 0.168 |
| | $pT_1/pT_3$ | 0.335 | 0.11–1.05 | 0.061 |
| | $pT_2/pT_3$ | 0.704 | 0.32–1.55 | 0.384 |
| | pN | | | 0.0001 |
| | $pN_0/pN_2$ | 0.143 | 0.07–0.31 | 0.0001 |
| | $pN_1/pN_2$ | 0.143 | 0.14–0.74 | 0.007 |
| | DOUBLE MARKER | 1.280 | 1.00–1.63 | 0.046 |

ABBREVIATIONS: CI 95% (CONFIDENCE INTERVAL FOR HAZARDS RATIO); PARAMETER SECTION: e.g. STAGE I/IIIa MEANS STAGE I COMPARED TO STAGE IIIa.

FIG.6

| | | From "Test" Reactions | | | | From "Calibration" Reactions | | | | Uncorrected Gene Expression (UGE) | Known *EGFR* Values | Derivation of $K_{EGFR}$ (Avg. K) | | Relative *EGFR* exp. |
|---|---|---|---|---|---|---|---|---|---|---|---|---|---|---|
| | Sample | $C_T$ *EGFR* | $C_T$ β-ACTIN | $\Delta C_T$ | $2^{-\Delta C_T}$ | $C_T$ *EGFR* | $C_T$ β-ACTIN | $\Delta C_T$ | $2^{-\Delta C_T}$ | $2^{-\Delta C_T}/2^{-\Delta C_T}$ | | K | $K_{EGF-R}$ | |
| Experimental | Unknown 1 | 32.7 | 26.8 | 5.9 | 0.0167 | – | – | – | – | 0.525 | – | | $26.95 \times 10^{-3}$ | $14.4 \times 10^{-3}$ |
| | Unknown 2 | 32.88 | 26.43 | 6.45 | 0.0114 | – | – | – | – | 0.358 | – | | $26.95 \times 10^{-3}$ | $9.66 \times 10^{-3}$ |
| | Calib. RNA | – | – | – | – | 27.01 | 22.04 | 4.97 | 0.0319 | 0.0319/0.0319= 1 | | | | |
| From Published Data | 60N | 31.61 | 23.86 | 7.75 | 0.00464 | – | – | – | – | 0.2117 | $5.70 \times 10^{-3}$ | $26.95 \times 10^{-3}$ | $26.95 \times 10^{-3}$ | – |
| | 60T | 29.08 | 20.65 | 8.43 | 0.0029 | – | – | – | – | 0.1321 | $3.56 \times 10^{-3}$ | $26.95 \times 10^{-3}$ | $26.95 \times 10^{-3}$ | – |
| | SF12A | 28.71 | 20.76 | 7.95 | 0.0040 | – | – | – | – | 0.184 | $4.97 \times 10^{-3}$ | $26.95 \times 10^{-3}$ | $26.95 \times 10^{-3}$ | – |
| | SF12B | 24.69 | 19.87 | 4.82 | 0.0354 | – | – | – | – | 1.613 | $43.5 \times 10^{-3}$ | $26.95 \times 10^{-3}$ | $26.95 \times 10^{-3}$ | – |
| | CTR11 | 24.03 | 16.3 | 7.73 | 0.0047 | – | – | – | – | 0.215 | $5.78 \times 10^{-3}$ | $26.95 \times 10^{-3}$ | $26.95 \times 10^{-3}$ | – |
| | ADCOL | 26.04 | 17.06 | 8.98 | 0.00198 | – | – | – | – | 0.090 | $2.43 \times 10^{-3}$ | $26.95 \times 10^{-3}$ | $26.95 \times 10^{-3}$ | – |
| | Calib. RNA | – | – | – | – | 25.96 | 18.57 | 7.39 | 0.00596 | 0.00596/ 0.00596 = 1 | – | – | – | – |

FIG.7 CHART ILLUSTRATING HOW TO CALCULATE *EGFR* EXPRESSION RELATIVE TO AN INTERNAL CONTROL GENE

| | | From "Test" Reactions | | | | From "Calibration" Reactions | | | | Uncorrected Gene Expression (UGE) | Known *HER-2/neu* Values | Derivation of $K_{EGFR}$ (Avg. K) | | Relative *HER-2/neu* exp. |
|---|---|---|---|---|---|---|---|---|---|---|---|---|---|---|
| | Sample | $C_T$ *HER-2/neu* | $C_T$ β-ACTIN | $\Delta C_T$ | $2^{-\Delta C_T}$ | $C_T$ *HER2-neu* | $C_T$ β-ACTIN | $\Delta C_T$ | $2^{-\Delta C_T}$ | $2^{-\Delta C_T}/2^{-\Delta C_T}$ | | K | $K_{HER-2/neu}$ | |
| Experimental | Unknown 1 | 21.5 | 16.3 | 5.2 | 0.0272 | – | – | – | – | 1.43 | – | | 13.3 x $10^{-3}$ | 19.1 x $10^{-3}$ |
| | Unknown 2 | 23.22 | 17.06 | 6.16 | 0.0139 | – | – | – | – | 0.74 | – | | 13.3 x $10^{-3}$ | 9.8 x $10^{-3}$ |
| | Calib. RNA | – | – | – | – | 24.29 | 18.57 | 5.72 | 0.0189 | 0.0189/0.0189= 1 | | | | |
| From Published Data | 60N | 30.28 | 23.86 | 6.42 | 0.012 | – | – | – | – | 0.702 | 9.34 x $10^{-3}$ | 13.3 x $10^{-3}$ | 13.3 x $10^{-3}$ | – |
| | 60T | 27.87 | 20.65 | 7.22 | 0.0067 | – | – | – | – | 0.403 | 5.36 x $10^{-3}$ | 13.3x $10^{-3}$ | 13.3 x $10^{-3}$ | – |
| | SF12A | 25.01 | 20.76 | 4.25 | 0.0525 | – | – | – | – | 3.16 | 42.03 x$10^{-3}$ | 13.3 x $10^{-3}$ | 13.3 x $10^{-3}$ | – |
| | SF12B | 26.07 | 19.87 | 6.2 | 0.0136 | – | – | – | – | 0.817 | 10.88 x$10^{-3}$ | 13.3 x $10^{-3}$ | 13.3 x $10^{-3}$ | – |
| | CTR11 | 21.5 | 16.3 | 5.2 | 0.0272 | – | – | – | – | 1.635 | 21.76 x$10^{-3}$ | 13.3 x $10^{-3}$ | 13.3 x $10^{-3}$ | – |
| | ADCOL | 23.22 | 17.06 | 6.16 | 0.014 | – | – | – | – | 0.841 | 11.18 x$10^{-3}$ | 13.3 x $10^{-3}$ | 13.3 x $10^{-3}$ | – |
| | Calib. RNA | – | – | – | – | 25.0 | 19.09 | 5.91 | 0.0166 | 0.0166/ 0.0166 = 1 | – | – | – | – |

FIG.8

CHART ILLUSTRATING HOW TO CALCULATE *HER2-neu* EXPRESSION RELATIVE TO AN INTERNAL CONTROL GENE

METHOD OF DETERMINING EPIDERMAL GROWTH FACTOR RECEPTOR AND HER2-NEU GENE EXPRESSION AND CORRELATION OF LEVELS THEREOF WITH SURVIVAL RATES

FIELD OF THE INVENTION

The present invention relates to prognostic methods which are useful in medicine, particularly cancer chemotherapy. More particularly, the invention relates to assessment of surviviability of a patient whose tumor cell gene expression is analyzed. Additionally, the sensitivity of tumor cells to receptor tyrosine kinase targeted chemotherapeutic regimen is assayed by examining the mRNA expression of the EGFR and Her2-neu genes in humans.

BACKGROUND OF THE INVENTION

Lung cancer is the leading cause of cancer-related deaths among both males and females in western countries. In the United States, approximately 171,000 new cases of lung cancer are diagnosed and 160,000 individuals die from this disease each year. Despite improvements in the detection and treatment of lung cancer in the past two decades, the overall 5-year survival remains less than 15%. Ginsberg, et al., In: DeVita, et al., *Cancer: Principles in Practice of Oncology*, Ed. 5, pp. 858–910. Philadelphia Lipincott-Raven Publishers, 1997. To further improve the survival rate in patients with Non-Small Cell Lung Carcinoma (NSCLC), their prognostic classification based on molecular alterations is crucial. Such classification will provide more accurate and useful diagnostic tools and, eventually, more effective therapeutic options.

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes. These generally are referred to as anti-metabolite drugs. Other classes of chemotherapeutic drugs inflict damage on cellular DNA. Drugs of these classes generally are referred to as genotoxic. Additionally, a class of chemotherapeutic agents specifically inhibit mitogenic signaling through receptor tyrosine kinases (RTKs), in cells where RTKs are over active. (Drugs of the Future, 1992, 17, 119).

Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies. Therefore, it is of importance to assess the expression status of genetic determinants targeted by specific chemotherapeutic agents. For example, if a tumor expresses high levels of DNA repair genes, it is likely that the tumor will not respond well to low doses of DNA-damaging genotoxic agents. Thus, the expression status of genetic determinants of a tumor will help the clinician develop an appropriate chemotherapeutic regimen specific to the genetic repertoire of the tumor.

Receptor tyrosine kinases (RTKs) are important in the transduction of mitogenic signals. RTKs are large membrane spanning proteins which possess an extracellular ligand binding domain for growth factors such as epidermal growth factor (EGF) and an intracellular portion which functions as a kinase to phosphorylate tyrosine amino acid residues on cytosol proteins thereby mediating cell proliferation. Various classes of receptor tyrosine kinases are known based on families of growth factors which bind to different receptor tyrosine kinases. (Wilks, Advances in Cancer Research, 1993, 60, 43–73)

Class I kinases such as the EGF-R family of receptor tyrosine kinases include the EGF, HER2-neu, erbB, Xmrk, DER and let23 receptors. These receptors are frequently present in common human cancers such as breast cancer (Sainsbury et al., Brit. J. Cancer, 1988, 58, 458; Guerin et al., Oncogene Res., 1988, 3, 21), squamous cell cancer of the lung (Hendler et al., Cancer Cells, 1989, 7, 347), bladder cancer (Neal et al., Lancet, 1985, 366), oesophageal cancer (Mukaida et al, Cancer, 1991, 68, 142), gastrointestinal cancer such as colon, rectal or stomach cancer (Bolen et al., Oncogene Res., 1987, 1, 149), leukaemia (Konaka et al., Cell, 1984, 37, 1035) and ovarian, bronchial or pancreatic cancer (European Patent Specification No. 0400586). As further human tumor tissues are tested for the EGF family of receptor tyrosine kinases it is expected that its widespread prevalence will be established in other cancers such as thyroid and uterine cancer.

Specifically, EGFR tyrosine kinase activity is rarely detected in normal cells whereas it is more frequently detectable in malignant cells (Hunter, Cell, 1987, 50, 823). It has been more recently shown that EGFR is overexpressed in many human cancers such as brain, lung squamous cell, bladder, gastric, breast, head and neck, oesophageal, gynaecological and thyroid tumours. (W J Gullick, Brit. Med. Bull., 1991, 47, 87). Receptor tyrosine kinases are also important in other cell-proliferation diseases such as psoriasis. EGFR disorders are those characterized by EGFR expression by cells normally not expressing EGFR, or increased EGFR activation leading to unwanted cell proliferation, and/or the existence of inappropriate EGFR levels. The EGFR is known to be activated by its ligand EGF as well as transforming growth factor-alpha (TGF-$\alpha$).

The Her2-neu protein is also a member of the class I receptor tyrosine kinase (RTK) family. Yarden and Ullrich, Annu. Rev. Biochem. 57:443, 1988; Ullrich and Schlessinger, Cell 61:203, 1990. Her2-neu protein is structurally related to EGFR. Carraway, et al., Cell 78:5, 1994; Carraway, et al., J. Biol. Chem. 269:14303, 1994. These receptors share a common molecular architecture and contain two cysteine-rich regions within their cytoplasmic domains and structurally related enzymatic regions within their cytoplasmic domains.

Ligand-dependent activation of Her2-neu protein is thought to be mediated by neuactivating factor (NAF) which can directly bind to p165(Her2-neu) and stimulate enzymatic activity. Dougall et al., Oncogene 9:2109, 1994; Samata et al., Proc. Natl. Acad. Sci. USA 91:1711, 1994. Ligand-independent homodimerization of Her2-neu protein and resulting receptor activation is facilitated by over-expression of Her2-neu protein. An activated Her2-neu complex acts as a phosphokinase and phosphorylates different cytoplasmic proteins. HER2-neu disorders are characterized by inappropriate activity or over-activity of HER2- neu have increased HER2-neu expression leading to unwanted cell proliferation such as cancer.

Inhibitors of receptor tyrosine kinases EGFR and HER2-neu are employed as selective inhibitors of the growth of mammalian cancer cells (Yaish et al. Science, 1988, 242, 933). For example, erbstatin, an EGF receptor tyrosine kinase inhibitor, reduced the growth of EGFR expressing human mammary carcinoma cells injected into athymic nude mice, yet had no effect on the growth of tumors not expressing EGFR. (Toi et al., Eur. J. Cancer Clin. Oncol., 1990, 26, 722.) Various derivatives of styrene are also stated to possess tyrosine kinase inhibitory properties (European Patent Application Nos. 0211363, 0304493 and 0322738) and to be of use as anti-tumour agents. Two such styrene derivatives are Class I RTK inhibitors whose effectiveness has been demonstrated by attenuating the growth of human squamous cell carcinoma injected into nude mice (Yoneda et al., Cancer Research, 1991, 51, 4430). It is also known from European Patent Applications Nos. 0520722 and 0566226 that certain 4-anilinoquinazoline derivatives are useful as inhibitors of receptor tyrosine kinases. The very tight structure-activity relationships shown by these compounds suggests a clearly-defined binding mode, where the quinazoline ring binds in the adenine pocket and the anilino ring binds in an adjacent, unique lipophilic pocket. Three 4-anilinoquinazoline analogues (two reversible and one irreversible inhibitor) have been evaluated clinically as anticancer drugs. Denny, Farmaco January–February 2001;56(1–2) :51–6. Recently, the U.S. FDA approved the use of the monoclonal antibody trastazumab (Herceptin®) for the treatment of HER2-neu overexpressing metastatic breast cancers. Scheurle, et al., Anticancer Res 20:2091–2096, 2000.

Because effective chemotherapy against tumors often requires a combination of agents, the identification and quantification of determinants of resistance or sensitivity to each single drug has become an important tool to design individual combination chemotherapy. Studies have unsuccessfully attempted to reliably correlate the relative levels of expression of EGFR and/or HER2-neu in malignant cells from cancer patients with survivability.

The prognostic importance of EGFR and in NSCLC has heretofore remained controversial. Studies using binding assays correlated increased EGFR expression with advanced stage NSCLC and shortened overall survival, whereas studies using semi-quantitative techniques for measuring EGFR mRNA or protein expression failed to show a consistent correlation with clinical outcome. Veale et al., Br. J. Caner 68:162–165, 1993; Fujino et al., Eur. Cancer 32:2070–2074, 1996; Rusch, et al., Cancer Res 53:2379–2385, 1993; Pfeiffer, et al., Br J Cancer 74:86–91, 1996; Pastorino, et al.,. J Clin Oncol 15:2858–2865, 1997. Studies of EGFR expression in NSCLC tumors using immunohistochemical methods have shown frequencies for EGFR overexpression between 32% and 47% in NSCLC tumors. Veale et al., Br. J. Caner 55:513–516, 1987; Veale et al., Br. J. Caner 68:162–165, 1993; Fujino et al., Eur. Cancer 32:2070–2074, 1996; Rusch, et al., Cancer Res 53:2379–2385, 1993; Pastorino et al., J. Clin. Onc. 15:2858–2865, 1997; Tateishi, et al., Eur J Cancer 27:1372–75, 1991; Rachwal, et al., Br J Cancer 72:56–64,1995; Rusch, et al., Cancer Res 15:2379–85,1993; Pfeiffer, et al., Br J Cancer 78:96–9, 1998; Ohsaki, et al., Oncol Rep 7:603–7,2000. Moreover, significant differences in EGFR expression has been reported among histological subtypes, generally with higher EGFR expression in SCC compared to AC and LC. Fujino et al., Eur. Cancer 32:2070–2074, 1996; Veale et al., Br. J. Caner 55:513–516, 1987; Pastorino et al., J. Clin. Onc. 15:2858–2865, 1997; Pfeiffer, et al., Br J Cancer 78:96–9, 1998; Ohsaki et al., Oncol. Rep. &:603–7, 2000. However, these studies reported no consistent correlation of EGFR overexpression with lung cancer patient survival.

Observations of a purported correlation of EGFR overexpression with a decrease in patient survival were made in some inconclusive studies. Veale et al., 1987; Ohsaki et al., 2000. However, Veale et al., analyzed a population of only nineteen NSCLC patients. Ohsaki et al., correlated EGFR protein expression with poor prognosis in NSCLC patients with p53 overexpression (P=0.024).

As with EGFR, the prognostic importance of HER2-neu and in NSCLC has heretofore remained controversial. HER2-neu protein overexpression has been demonstrated in NSCLC, including squamous cell carcinoma, adenocarcinoma, and large cell carcinoma. Veale et al., 1987; Schneider, et al., Cancer Res 49:4968–4971, 1989; Kern et al., Cancer Res. 50:5184–5191, 1990; Weiner, et al., Cancer Res 50:421425, 1990; Scheurle, et al., Anticancer Res. 20:2091–2096, 2000. Earlier studies, using protein assays, reported an association of HER2-neu protein overexpression and inferior overall survival in pulmonary adenocarcinomas (AC). Kern, et al., Cancer Res 50:5184–5191, 1990; Kern et al., J Clin Invest 93:516–20, 1994. However, contradictory studies reported no correlation of HER2-neu protein overexpression with inferior overall survival in pulmonary adenocarcinomas (AC). Pfeiffer et al., Br. J. Cancer 74:86–91, 1996.

Another critical question is the evaluation of interrelationships between HER2-neu and EGFR co-overexpression as prognosticators of cancer. Tateishi et al., (Eur. J. Cancer 27:1372–75, 1991), measured EGFR and HER2-neu protein co-expression, in 13% of AC analysed, and found that co-overexpression of these two genes correlated with inferior 5-year survival. However, as with HER2-neu overexpression alone, association between HER2-neu and EGFR co-expression and survival in squamous cell carcinoma (SCC) and large cell carcinoma (LCC) of the lung has not been reported.

Inconsistent methodologies for the determination of EGFR and HER2-neu expression levels has been at the root of the problem in determining to what extent expression of these genes may be used to prognosticate cancer patient survivability. Heretofore investigations of HER2-neu and EGFR expression in NSCLC has resulted in enormous variations in frequencies of NSCLC tumors scored positive for both EGFR and HER2-neu expression. Overexpression of HER2-neu, defined as positive protein staining in adenocarcinomas (AC), was reported in 13–80%, in 2–45% in squamous cell carcinomas (SCC), and in 0–20% in large cell carcinomas (LC) by using paraffin embedded tissue on light microscope slides and HER2-neu antisera. Pfeiffer et at., 1996; Kern et al., 1990; Kern et al., 1994; Tateishi et al., 1991; Shi, et al., Mol Carcing 5:213–8, 1992; Bongiorno, et al., J Thorac Cardiovasc Surg 107:590–5,1994; Harpole, et al., Clin Cancer Res 1:659–64, 1995; Volm et al., Anticancer Res 12:11–20,1992. Moroever, a recent report illustrates the non-specificity of current protocols designed to assess HER2-neu expression levels. The HercepTest® for measurement of HER2-neu expression in invasive breast cancers was shown to have very high false positivity. Jacobs et al., J Clin Oncol 17:1983–1987, 1999.

If a precise, accurate, and consistent method for determining the expression levels of EGFR and HER2-neu existed, one could ascertain what expression levels correlate to patient survivability and whether or not a receptor tyrosine kinase targeted chemotherapy is appropriate. Consistent demonstration of EGFR and/or HER2-neu overexpression in NSCLC, using a standardized method, is desirable in establishing clinical trials for current and future receptor tyrosine kinase targeted chemotherapies, e.g., chemotherapeutic agents, antibody-based drugs, to treat cancers overexpressing these receptors.

The current protocols for measuring EGFR and/or HER2-neu gene expression, aside from being insufficiently accurate for tumor prognostication, suffer from a second limitation in that they require a significant amount of fresh tissue that contains non-degraded mRNA. Most patient derived pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

The use of frozen tissue by health care professionals poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintaining frozen tissue integrity during transport using specialized couriers equipped with liquid nitrogen and dry ice, comes only at a great expense.

Routine biopsies generally comprise a heterogenous mix of stromal and tumorous tissue. Unlike with fresh or frozen tissue, FPE biopsy tissue samples are readily microdissected and separated into stromal and tumor tissue and therefore, offer andvantage over the use of fresh or frozen tissue. However, isolation of RNA from fixed tissue, and especially fixed and paraffin embedded tissue, results in highly degraded RNA, which is generally not thought to be applicable to gene expression studies.

A number of techniques exist for the purification of RNA from biological samples, but none is reliable for isolation of RNA from FPE samples. For example, Chomczynski (U.S. Pat. No. 5,346,994) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded (FPE) tissue samples.

Other known techniques for isolating RNA typically utilize either guanidine salts or phenol extraction, as described for example in Sambrook, J. et al., (1989) at pp. 7.3–7.24, and in Ausubel, F. M. et al., (1994) at pp. 4.0.3–4.4.7. Again, none of the known methods provides reproducible quantitative results in the isolation of RNA from paraffin-embedded tissue samples.

Techniques for the isolation of RNA from paraffin-embedded tissues are thus particularly needed for the study of gene expression in tumor tissues, since expression levels of certain receptors or enzymes can then be used to determine the likelihood of success or appropriateness of a particular treatment.

We report here a significant association between high levels of the intratumoral EGFR mRNA and high levels of intratumoral HER2-neu mRNA with an inferior survivability. Accordingly, it is the object of the invention to provide a method of quantifying EGFR and/or HER2-neu mRNA from tumor tissue in order to provide an early prognosis for receptor tyrosine kinase targeted chemotherapies. It is also the object of the invention to provide a method for assessing EGFR and/or HER2-neu levels in tissues fixed and paraffin-embedded (FPE) and predicting the probable sensitivity of a patient's tumor to treatment with receptor tyrosine kinase targeted chemotherapy by examining the amount EGFR and/or HER2-neu mRNA in a patient's tumor cells and comparing it to a predetermined threshold expression level.

SUMMARY OF THE INVENTION

In one aspect of the invention there is provided a method for assessing levels of expression of EGFR mRNA obtained from fresh, frozen, fixed or fixed and paraffin-embedded (FPE) tumor cells.

In another aspect of the invention there is provided a method for assessing levels of expression of HER2-neu mRNA obtained from fresh, frozen, fixed or fixed and paraffin-embedded (FPE) tumor cells.

In another aspect of the invention there is provided a method of quantifying the amount of EGFR mRNA expression relative to an internal control from a fresh, frozen, fixed or fixed and paraffin-embedded (FPE) tissue sample. This method includes isolation of total mRNA from said sample and determining the quantity of EGFR mRNA relative to the quantity of an internal control gene's mRNA.

In another aspect of the invention there is provided a method of quantifying the amount of HER2-neu mRNA expression relative to an internal control from a fresh, frozen, fixed or fixed and paraffin-embedded (FPE) tissue sample. This method includes isolation of total mRNA from said sample and determining the quantity of HER2-neu mRNA relative to the quantity of an internal control gene's mRNA.

In an embodiment of this aspect of the invention, there are provided oligonucleotide primers having the sequence of EGFR-1753F (SEQ ID NO: 1) or EGFR-1823R (SEQ ID NO:2) and sequences substantially identical thereto. The invention also provides for oligonucleotide primers having a sequence that hybridizes to SEQ ID NO: 1 or SEQ ID NO:2 or their complements under stringent conditions.

In another embodiment of this aspect of the invention, there are provided oligonucleotide primers having the sequence of HER2-neu 267 IF (SEQ ID NO: 4) or HER2-neu 2699R (SEQ ID NO: 5) and sequences substantially identical thereto. The invention also provides for oligonucleotide primers having a sequence that hybridizes to SEQ ID NO: 4 or SEQ ID NO: 5 or their complements under stringent conditions.

In yet another aspect of the invention there is provided a method for determining a receptor tyrosine kinase targeted chemotherapeutic regimen for a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining a gene expression level of EGFR in both samples; dividing the level of EGFR expression in the tumor sample with the EGFR expression level in the matching non-malignant tissue sample to determine a differential expression level; comparing the differential EGFR gene expression level with a predeterimined threshold level for the EGFR gene; and determining a chemotherapeutic regimen based on results of the comparison of the differential EGFR gene expression level with the predetermined threshold level.

In yet another aspect of the invention there is provided a method for determining a receptor tyrosine kinase targeted chemotherapeutic regimen for a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining a gene expression level of HER2-neu in both samples; dividing the level of HER2-neu expression in the tumor sample with the HER2-neu expression level in the matching non-malignant tissue sample to determine a differential expression level; comparing the differential HER2-neu gene expression levels with a predeterimined threshold level for the HER2-neu gene; and determining a chemotherapeutic regimen based on results of the comparison of the differential HER2-neu gene expression level with the predetermined threshold level.

In yet another aspect of the invention there is provided a method for determining a receptor tyrosine kinase targeted chemotherapeutic regimen for a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining gene expression levels of HER2-neu and EGFR in both of the samples; dividing the level of EGFR expression in the tumor sample with the EGFR expression level in the matching non-malignant tissue sample to determine a EGFR differential expression level; dividing the level of HER2-neu expression in the tumor sample with the HER2-neu expression level in the matching non-malignant tissue sample to determine a differential HER2-neu expression level; comparing the differential HER2-neu and EGFR gene expression levels with a predeterimined threshold level for each of the HER2-neu and EGFR genes; and determining a chemotherapeutic regimen based on results of the comparison of the differential HER2-neu and EGFR gene expression levels with the predetermined threshold levels.

In yet another aspect of the invention there is provided a method for determining the survivability of a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining a gene expression level of EGFR in both samples; dividing the level of EGFR expression in the tumor sample with the EGFR expression level in the matching non-malignant tissue sample to determine a differential expression level; comparing the differential EGFR gene expression level with a predeterimined threshold level for the EGFR gene; and determining the survivability of a patient based on results of the comparison of the differential EGFR gene expression levels with the predetermined threshold level.

In yet another aspect of the invention there is provided a method for determining the survivability of a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining a gene expression level of HER2-neu in both samples; dividing the level of HER2-neu expression in the tumor sample with the EGFR expression level in the matching non-malignant tissue sample to determine a differential expression level; comparing the differential HER2-neu gene expression levels with a predeterimined threshold level for the HER2-neu gene; and determining the survivability of a patient based on results of the comparison of the differential HER2-neu gene expression levels with the predetermined threshold level.

In yet another aspect of the invention there is provided a method for determining the survivability of a patient, comprising isolating RNA from a fresh, frozen, fixed or fixed and paraffin-embedded (FPE) tumor sample; isolating RNA from a fresh, frozen, fixed or fixed and paraffin-embedded (FPE) matching non-malignant tissue sample; determining gene expression levels of HER2-neu and EGFR in both of the samples; dividing the level of EGFR expression in the tumor sample with the EGFR expression level in the matching non-malignant tissue sample to determine a EGFR differential expression level; dividing the level of HER2-neu expression in the tumor sample with the HER2-neu expression level in the matching non-malignant tissue sample to determine a HER2-neu differential expression level; comparing the differential HER2-neu and EGFR gene expression levels with a predetermined threshold level for each of the HER2-neu and EGFR genes; and determining the survivability of a patient based on results of the comparison of the EGFR and HER2-neu gene expression levels with the predetermined threshold levels.

The invention further relates to a method of normalizing the uncorrected gene expression (UGE) of EGFR and HER2-neu relative to an internal control gene in a tissue sample analyzed using TaqMan® technology to known EGFR and HER2-neu expression levels relative to an internal control from samples analyzed by pre-TaqMan® technology.

BRIEF DESCRIPTION OF THE DRAWINGS

FIG. 4. Table showing high and low EGFR and HER2-neu expression in patients and tumors.

FIG. 5. Table showing the survival of patients based on clinical and molecular parameters.

FIG. 6. Table showing Cox-proportional hazard regression models. Double marker refers to both EGFR and HER2-neu expression.

FIG. 7 is a chart illustrating how to calculate EGFR expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with known relative EGFR values determined by pre-TaqMan® technology. This is accomplished by multiplying UGE to a correction factor $K_{EGFR}$. The internal control gene in the figure is β-actin and the calibrator RNA is Human Liver Total RNA (Stratagene, Cat #735017).

FIG. 8 is a chart illustrating how to calculate HER2-neu expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with previously published HER2-neu values. This is accomplished by multiplying UGE to a correction factor $K_{HER2\text{-}neu}$. The internal control gene in the figure is β-actin and the calibrator RNA is Human Liver Total RNA (Stratagene, Cat #735017).

DETAILED DESCRIPTION OF THE INVENTION

Figure 1:
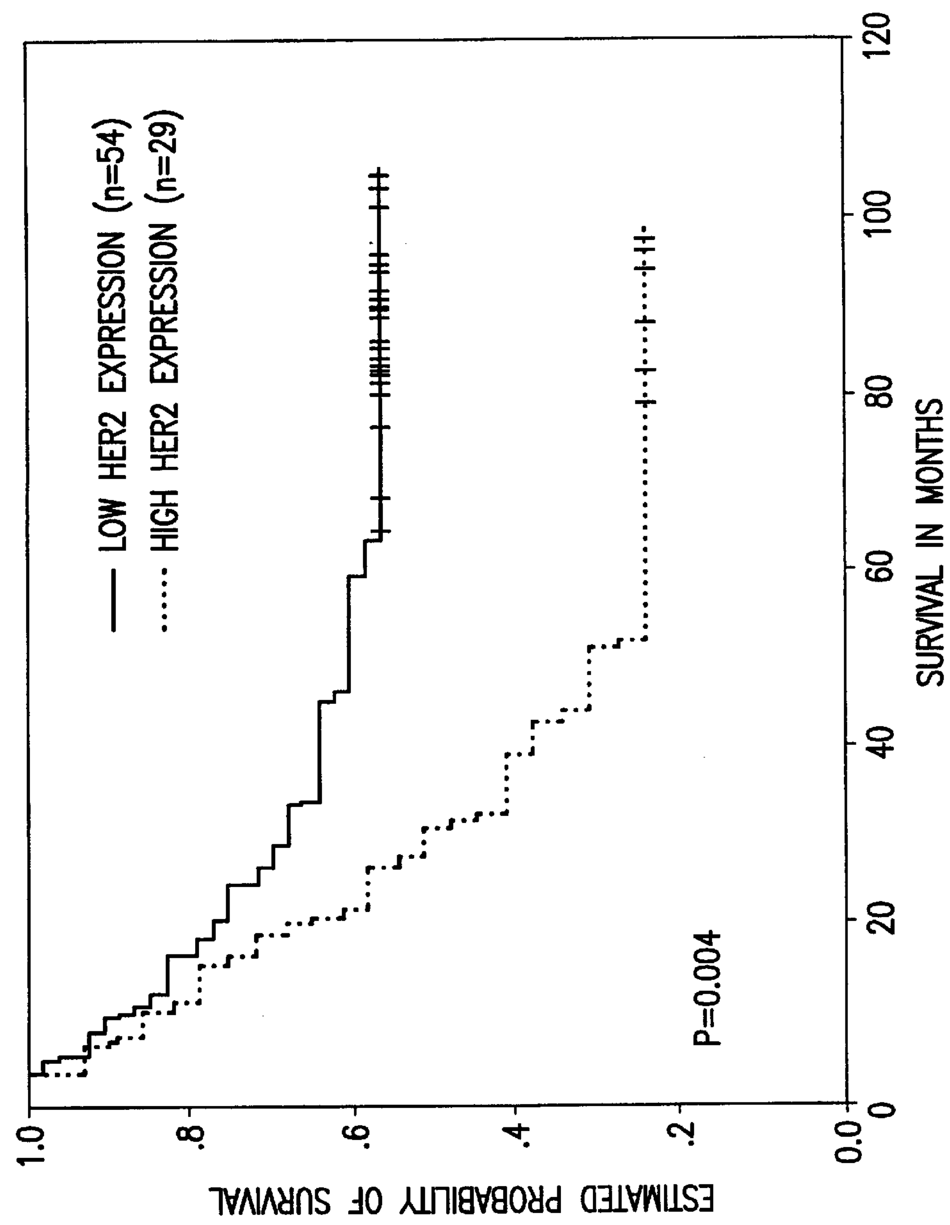
FIG. 1. Estimated probability of survival of curatively resected non-small cell lung cancer patients versus the HER2-neu mRNA expression status. The median survival was not reached in the low HER2-neu expression group compared to 31.1 months (95% C.I: 21.96–40.24) in the high HER2-neu expression group (P=0.004).

Tumors expressing high levels of HER2-neu and/or EGFR mRNA are considered likely to be sensitive to receptor tyrosine kinase targeted chemotherapy. Conversely, those tumors expressing low amounts of HER2-neu and EGFR mRNA are not likely to be sensitive to receptor tyrosine kinase targeted chemotherapy. A patient's differential HER2-neu and EGFR mRNA expression status is judged by comparing it to a predetermined threshold expression level.

The invention provides a method of quantifying the amount of HER2-neu and/or EGFR mRNA expression in fresh, frozen, fixed or fixed and paraffin-embedded (FPE) tissue relative to gene expression of an internal control. The present inventors have developed oligonucleotide primers that allow accurate assessment of HER2-neu and EGFR gene expression in fresh, frozen, fixed or fixed and embedded tissues. The oligonucleotide primers, EGFR-1753F (SEQ ID NO: 1), EGFR-1823R (SEQ ID NO: 2), or oligonucleotide primers substantially identical thereto, preferably are used together with RNA extracted from fresh, frozen, fixed or fixed and paraffin embedded (FPE) tumor samples. The invention also provides oligonucleotide primers, HER2-neu 2671F (SEQ ID NO: 4), HER2-neu 2699R (SEQ ID NO: 5), or oligonucleotide primers substantially identical thereto, preferably are used together with RNA extracted from fresh, frozen, fixed or fixed and paraffin embedded (FPE) tumor samples. This measurement of HER2-neu and/or EGFR gene expression may then be used for prognosis of receptor tyrosine kinase targeted chemotherapy This embodiment of the invention involves, a method for reliable extraction of RNA from fresh, frozen, fixed or FPE samples, determination of the content of EGFR mRNA in the sample by using a pair of oligonucleotide primers, preferably oligionucleotide primer pair EGFR-1753F (SEQ ID NO: 1) and EGFR-1823R (SEQ ID NO: 2), or oligonucleotides substantially identical thereto, for carrying out reverse transcriptase polymerase chain reaction.

Another embodiment of the invention involves a method for reliable extraction of RNA from fresh, frozen, fixed or FPE samples, and determination of the content of HER2-neu mRNA in the sample by using a pair of oligonucleotide primers oligonucleotide primers, HER2-neu 2671F (SEQ ID NO: 4), HER2-neu 2699R (SEQ ID NO: 5), or oligonucleotide primers substantially identical thereto.

"Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Selective hybridization exists when the hybridization is more selective than total lack of specificity. See, Kanehisa, Nucleic Acids Res., 12:203–213 (1984).

The methods of the present invention can be applied over a wide range of tumor types. This allows for the preparation of individual "tumor expression profiles" whereby expression levels of HER2-neu and/or EGFR are determined in individual patient samples and response to various chemotherapeutics is predicted. Preferably, the methods of the invention are applied to solid tumors, most preferably NSCLC tumors.

A "differential expression level" as defined herein refers to the difference in the level of expression of either EGFR or HER2-neu in a tumor with respect to the level of expression of either EGFR or HER2-neu in a matching non-malignant tissue sample, respectively. The differential expression level is determined by dividing the UGE of a particular gene from the tumor sample with the UGE of the same gene from a matching non-malignant tissue sample.

A "predetermined threshold level", as defined herein relating to EGFR expression, is a level of differential EGFR expression above which (i.e., high), tumors are likely to be sensitive to a receptor tyrosine kinase targeted chemotherapeutic regimen. A high differential EGFR expression level is prognostic of lower patient survivability. Tumors with expression levels below this threshold level are not likely to be affected by a receptor tyrosine kinase targeted chemotherapeutic regimen. A low differential EGFR expression level is prognostic of higher patient survivability. Whether or not differential expression is above or below a "predetermined threshold level" is determined by the method used by Mafune et al., who calculated individual differential tumor/normal (T/N) expression ratios in matching non-malignant tissues obtained from patients with squamous cell carcinoma of the esophagus. Mafune et al., Clin Cancer Res 5:4073–4078, 1999. This method of analysis leads to a precise expression value for each patient, being based on the individual background expression obtained from matching non-malignant tissue. The differential expression of EGFR is considered "high" and indicative of low survivability if the UGE of EGFR: β-actin in a tumor sample divided by the UGE of EGFR: β-actin in a matching non-malignant tissue sample, is above the predetermined threshold value of about 1.8. The differential expression of EGFR is considered "low" and indicative of high survivability if the UGE of EGFR: β-actin in a tumor sample divided by the UGE of EGFR: β-actin in a matching n+on-malignant tissue sample, is below the predetermined threshold value of about 1.8.

A "predetermined threshold level", as defined herein relating to differential HER2-neu expression, is a level of HER2-neu expression above which (i.e., high), tumors are likely to be sensitive to a receptor tyrosine kinase targeted chemotherapeutic regimen. A high differential HER2-neu expression level is prognostic of lower patient survivability. Tumors with expression levels below this threshold level are not likely to be affected by a receptor tyrosine kinase targeted chemotherapeutic regimen. A low differential HER2-neu expression level is prognostic of higher patient survivability. The differential expression of HER2-neu is considered "high" and indicative of low survivability if the UGE of HER2-neu: β-actin in a tumor sample divided by the UGE of HER2-neu: β-actin in a matching non-malignant tissue sample, is above the predetermined threshold value of about 1.8. The differential expression of HER2-neu is considered "low" and indicative of high survivability if the UGE of HER2-neu: β-actin in a tumor sample divided by the UGE of HER2-neu: β-actin in a matching non-malignant tissue sample, is below the predetermined threshold value of about 1.8.

A "threshold level" for HER2-neu was determined using the following results and method. The corrected HER2-neu mRNA expression, expressed as the ratio between HER2-neu and β-Actin PCR product, was $4.17\times10^{-3}$ (range $0.28–23.86\times10^{3}$) in normal lung and $4.35\times10^{-3}$ (range: $0.21–68.11\times10^{-3}$) in tumor tissue (P=0.019 Wilcoxon test). The maximal chi-square method by Miller and Siegmund (Miller et al., Biometrics 38:1011–1016, 1982) and Halpern (Biometrics 38:1017–1023, 1982) determined a threshold value of 1.8 to segregate patients into low and high differential HER2-neu expressors. By this criterion, 29 (34.9%) patients had a high differential HER2-neu expression and 54 (65.1%) had a low differential HER2-neu expression.

A "threshold level" for EGFR was determined using the following results and method. The median corrected EGFR mRNA expression was $8.17\times10^{-3}$ (range: $0.31–46.26\times10^{-3}$) in normal lung and $7.22\times10^{-3}$ (range: $0.27–97.49\times10^{-3}$) in tumor tissue (P=n.s.). The maximal chi-square method (Miller (1982); Halpern (1982)) determined a threshold value of 1.8 to segregate patients into low and high differential EGFR expressors. By this criterion, 28 (33.7%) patients had a high differential EGFR expression and 55 (66.3%) had a low differential EGFR expression status.

In performing the method of the present invention either differential EGFR expression levels or differential HER2-neu expression levels are assayed in a patient to prognosticate the efficacy of a receptor tyrosine kinase targeted chemotherapeutic regimen. Moreover, in the method of the present invention differential HER2-neu expression levels are assayed in a patient prognosticate the efficacy of a receptor tyrosine kinase targeted chemotherapeutic regimen. Additionally, in the method of the present invention differential EGFR expression levels are assayed in a patient to prognosticate the efficacy of a receptor tyrosine kinase targeted chemotherapeutic regimen. Alternatively, both differential EGFR expression levels and differential HER2-neu expression levels are assayed in a patient to prognosticate the efficacy of a receptor tyrosine kinase targeted chemotherapeutic regimen.

"Matching non-malignant sample" as defined herein refers to a sample of non-cancerous tissue derived from the same individual as the tumor sample to be analyzed for differential EGFR and/or differential HER2-neu expression. Preferably a matching non-malignant sample is derived from the same organ as the organ from which the tumor sample is derived. Most preferably, the matching non-malignant tumor sample is derived from the same organ tissue layer from which the tumor sample is derived. Also, it is preferable to take a matching non-malignant tissue sample at the same time a tumor sample is biopsied. In a preferred embodiment tissues from the following two locations are analyzed: lung tumor and non-malignant lung tissue taken from the greatest distance form the tumor or colon tumor and non-malignant colon tissue taken from the greatest distance form the tumor as possible under the circumstances.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh tumor samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

However, tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. See Plenat et al., Ann Pathol January 2001 ;21(1):29–47. Non-embedded, fixed tissue as well as fixed and embedded tissue may also be used in the present methods. Solid supports for embedding fixed tissue are envisioned to be removable with organic solvents for example, allowing for subsequent rehydration of preserved tissue.

RNA is extracted from paraffin-embedded (FPE) tissue cells by any of the methods as described in U.S. patent application Ser. No. 09/469,338, filed Dec. 20, 1999, now U.S. Pat. No. 6,248,535, which is hereby incorporated by reference in its entirety. As used herein, FPE tissue means tissue that has been fixed and embedded in a solid removable support, such as storable or archival tissue samples. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of lower alcohol. Suitable lower alcohols, for example include, methanol, ethanol, propanols and butanols. Deparaffinized samples may be rehydrated with successive washes with lower alcoholic solutions of decreasing concentration, for example. Alternatively, the sample is simulatneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective concentration of chaotropic agent" is chosen such that RNA is purified from a paraffin-embedded sample in an amount of greater than about 10-fold that isolated in the absence of a chaotropic agent. Chaotropic agents include, for example: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

RNA is then recovered from the chaotropic solution by, for example, phenol chloroform extraction, ion exchange chromatography or size-exclusion chromatography. RNA may then be further purified using the techniques of extraction, electrophoresis, chromatography, precipitation or other suitable techniques.

The quantification of HER2-neu or EGFR mRNA from purified total mRNA from fresh, frozen or fixed is preferably carried out using reverse-transcriptase polymerase chain reaction (RT-PCR) methods common in the art, for example. Other methods of quantifying of HER2-neu or EGFR mRNA include for example, the use of molecular beacons and other labeled probes useful in multiplex PCR. Additionally, the present invention envisages the quantification of HER2-neu and/or EGFR mRNA via use of a PCR-free systems employing, for example fluorescent labeled probes similar to those of the Invader® Assay (Third Wave Technologies, Inc.). Most preferably, quantification of HER2-neu and/or EGFR cDNA and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996;6:986–994) and Gibson et al.(Genome Res 1996;6:995–1001). The output of the ABI 7700 (TaqMan® Instrument) is expressed in Ct's or "cycle thresholds". With the TaqMan® system, a highly expressed gene having a higher number of target molecules in a sample generates a signal with fewer PCR cycles (lower Ct) than a gene of lower relative expression with fewer target molecules (higher Ct).

As used herein, a "house keeping" gene or "internal control" is any constitutively or globally expressed gene whose presence enables an assessment of HER2-neu and/or EGFR mRNA levels. Such an assessment comprises a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302–2306.

A control for variations in RNA recovery requires the use of "calibrator RNA." The "calibrator RNA" is intended to be any available source of accurately pre-quantified control RNA. Preferably, Human Liver Total RNA (Stratagene, Cat #735017) is used.

"Uncorrected Gene Expression (UGE)" as used herein refers to the numeric output of HER2-neu and/or EGFR expression relative to an internal control gene generated by the TaqMan® instrument. The equation used to determine UGE is shown in Examples 3 and 4, and illustrated with sample calculations in FIGS. 7 and 8.

These numerical values allow the determination of whether or not the differential gene expression (i.e., "UGE" or of a particular tumor sample divided by the "UGE" of a matching non-tumor sample) falls above or below the "predetermined threshold" level. The predetermined threshold level for EGFR and HER2-neu is about 1.8.

A further aspect of this invention provides a method to normalize uncorrected gene expression (UGE) values acquired from the TaqMan® instrument with "known relative gene expression" values derived from non-TaqMan® technology. Preferably, TaqMan® derived HER2-neu and/or EGFR UGE values from a tissue sample are normalized to samples with known non-TaqMan® derived relative HER2-neu and/or EGFR: β-actin expression values.

"Corrected Relative EGFR Expression" as used herein refers to normalized EGFR expression whereby UGE is multiplied with a EGFR specific correction factor ($K_{EGFR}$), resulting in a value that can be compared to a known range of EGFR expression levels relative to an internal control gene. Example 3 and FIG. 7 illustrate these calculations in detail. $K_{EGFR}$ specific for EGFR, the internal control β-actin and calibrator Human Liver Total RNA (Stratagene, Cat #735017), is $26.95\times10^{-3}$. These numerical values also allow the determination of whether or not the "Corrected Relative Expression" of a particular tumor sample divided by the "Corrected Relative Expression" of a matching non-tumor sample (i.e., differential expression) falls above or below the "predetermined threshold" level. The predetermined threshold level for HER2-neu or EGFR is about 1.8. In determining whether the differential expression of either EGFR or HER2-neu in a tumor sample is 1.8 times greater than in a matching non-tumor sample, one will readily recognize that either UGE values or Corrected Relative Expression values can be used. For example, if one divides the Corrected Relative Expression level of the tumor with that of the matching non-tumor sample, the K-factor cancels out and one is left with same ratio as if one had used UGE values.

"Known relative gene expression" values are derived from previously analyzed tissue samples and are based on the ratio of the RT-PCR signal of a target gene to a constitutively expressed internal control gene (e.g. β-Actin, GAPDH, etc.). Preferably such tissue samples are formalin fixed and paraffin-embedded (FPE) samples and RNA is extracted from them according to the protocol described in Example 1. To quantify gene expression relative to an internal control standard quantitative RT-PCR technology known in the art is used. Pre-TaqMan® technology PCR reactions are run for a fixed number of cycles (i.e., 30) and endpoint values are reported for each sample. These values are then reported as a ratio of EGFR expression to β-actin expression.

$K_{EGFR}$ may be determined for an internal control gene other than β-actin and/or a calibrator RNA different than Human Liver Total RNA (Stratagene, Cat #735017). To do so, one must calibrate both the internal control gene and the calibrator RNA to tissue samples for which EGFR expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1. Such a determination can be made using standard pre-TaqMan®, quantitative RT-PCR techniques well known in the art. Upon such a determination, such samples have "known relative gene expression" levels of EGFR useful in the determining a new $K_{EGFR}$ specific for the new internal control and/or calibrator RNA as described in Example 3.

"Corrected Relative HER2-neu Expression" as used herein refers to normalized HER2-neu expression whereby UGE is multiplied with a HER2-neu specific correction factor ($K_{HER2\text{-}neu}$), resulting in a value that can be compared to a known range of HER2-neu expression levels relative to an internal control gene. Example 4 and FIG. 8 illustrate these calculations in detail. $K_{HER2\text{-}neu}$ specific for HER2-neu, the internal control β-actin and calibrator Human Liver Total RNA (Stratagene, Cat #735017), is $13.3\times10^{-3}$.

$K_{HER2\text{-}neu}$ may be determined for an internal control gene other than β-actin and/or a calibrator RNA different than Human Liver Total RNA (Stratagene, Cat #735017). To do so, one must calibrate both the internal control gene and the calibrator RNA to tissue samples for which HER2-neu expression levels relative to that particular internal control gene have already been determined (i.e., "known relative gene expression"). Preferably such tissue samples are formalin fixed and paraffin-embedded (FPE) samples and RNA is extracted from them according to the protocol described in herein. Such a determination can be made using standard pre-TaqMan®, quantitative RT-PCR techniques well known in the art, for example. Upon such a determination, such samples have "known relative gene expression" levels of HER2-neu useful in the determining a new $K_{HER2\text{-}neu}$ specific for the new internal control and/or calibrator RNA as described in Example 4.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of NSCLC tumors.

Pre-chemotherapy treatment tumor biopsies are usually available only as fixed paraffin embedded (FPE) tissues, generally containing only a very small amount of heterogeneous tissue. Such FPE samples are readily amenable to microdissection, so that HER2-neu and/or EGFR gene expression may be determined in tumor tissue uncontaminated with non-malignant stromal tissue. Additionally, comparisons can be made between non-malignant stromal and tumor tissue within a biopsy tissue sample, since such samples often contain both types of tissues.

Generally, any oligonucleotide pairs that flank a region of EGFR gene, as shown in SEQ ID NO: 10, may be used to carry out the methods of the invention. Primers hybridizing under stringent conditions to a region of the EGFR gene for use in the present invention will amplify a product between 20–1000 base pairs, preferably 50–100 base pairs, most preferably less than 100 base pairs.

The invention provides specific oligonucleotide primer pairs and oligonucleotide primers substantially identical thereto, that allow particularly accurate assessment of EGFR expression using fresh, frozen, fixed or FPE tissues. Preferable are oligonucleotide primers, EGFR-1753F (SEQ ID NO: 1) and EGFR-1823R (SEQ ID NO: 2), (also referred to herein as the oligonucleotide primer pair EGFR) and oligonucleotide primers substantially identical thereto. The oliogonucleotide primers EGFR-1753F (SEQ ID NO: 1) and EGFR-1823R, (SEQ ID NO: 2) have been shown to be particularly effective for measuring EGFR mRNA levels using RNA extracted from fresh, frozen, fixed or FPE cells by any of the methods for mRNA isolation, for example as described Example 1.

Furthermore, any oligonucleotide pairs that flank a region of HER2-neu gene, as shown in SEQ ID NO: 11, may be used to carry out the methods of the invention. Primers hybridizing under stringent conditions to a region of the HER2-neu gene for use in the present invention will amplify a product between about 20–1000 base pairs, preferably about 50–100 base pairs, most preferably less than about 100 base pairs.

The invention provides specific oligonucleotide primers pairs and oligonucleotide primers substantially identical thereto, that allow particularly accurate assessment of HER2-neu expression in fresh, frozen, fixed or FPE tissues. Preferable are oligonucleotide primers, HER2-neu 2671F (SEQ ID NO: 4) and HER2-neu 2699R (SEQ ID NO: 5), (also referred to herein as the oligonucleotide primer pair HER2-neu) and oligonucleotide primers substantially identical thereto. The oliogonucleotide primers HER2-neu 2671F (SEQ ID NO: 4) and HER2-neu 2699R (SEQ ID NO: 5) have been shown to be particularly effective for measuring HER2-neu mRNA levels using RNA extracted from fresh, frozen, fixed or FPE cells by any of the methods for mRNA isolation, for example as described herein.

This invention includes substantially identical oligonucleotides that hybridize under stringent conditions (as defined herein) to all or a portion of the oligonucleotide primer sequence of EGFR-1753F (SEQ ID NO: 1), its complement or EGFR-1823R (SEQ ID NO: 2), or its complement or oligonucleotide primer sequence of HER2-neu 2671F (SEQ ID NO: 4), its complement or HER2-neu 2699R (SEQ ID NO: 5), or its complement.

Under stringent hybridization conditions, only highly complementary, i.e., substantially similar nucleic acid sequences as defined herein hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least about 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer EGFR-1753F (SEQ ID NO: 1), its complement or EGFR-1823R (SEQ ID NO: 2), or its complement or oligonucleotide primer HER2-neu 267 IF (SEQ ID NO: 4), its complement or HER2-neu 2699R (SEQ ID NO: 5), or its complement.

Hybridization of the oligonucleotide primer to a nucleic acid sample under stringent conditions is defined below. Nucleic acid duplex or hybrid stability is expressed as a melting temperature ($T_m$), which is the temperture at which the probe dissociates from the target DNA. This melting temperature is used to define the required stringency conditions. If sequences are to be identified that are substantially identical to the probe, rather than identical, then it is useful to first establish the lowest temperature at which only holmologous hybridization occurs with a particular concentration of salt (e.g. SSC or SSPE). Then assuming that 1% mismatching results in a 1° C. decrease in $T_m$, the temperatre of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at about 68° C. in 5× SSC/5× Denhart's solution/1.0% SDS, and washing in 0.2× SSC/0.1% SDS at room temperature. Moderately stringent conditions include washing in 3× SSC at about 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Oligonucleotide primers disclosed herein are capable of allowing accurate assessment of HER2-neu and/or EGFR gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying HER2-neu and/or EGFR gene expression levels in all tissues where previously there existed no accurate and consistent way to assay HER2-neu and/or EGFR gene in fresh and frozen tissues and no way at all to assay HER2-neu and/or EGFR gene expression using fixed tissues.

Over-activity of HER2-neu refers to either an amplification of the gene encoding HER2-neu or the production of a level of HER2-neu activity which can be correlated with a cell proliferative disorder (i.e., as the level of HER2-neu increases the severity of one or more of the symptoms of the cell proliferative disorder increases).

A "receptor tyrosine kinase targeted" chemotherapy or chemotherapeutic regimen in the context of the present invention refers a chemotherapy comprising agents that specifically interfere with Class I receptor tyrosine kinase function. Preferably, such agents will inhibit EGFR and/or HER2-neu receptor tyrosine kinase signaling activity. Such agents include 4-anilinoquinazolines such as 6-acrylamido-4-anilinoquinazoline Bonvini et al., Cancer Res. Feb. 15, 2001 ;61(4):1671–7 and derivatives, erbstatin (Toi et al., Eur. J. Cancer Clin. Oncol., 1990, 26, 722.), Geldanamycin, bis monocyclic, bicyclic or heterocyclic aryl compounds (PCT WO 92/20642), vinylene-azaindole derivatives (PCT WO 94/14808) and 1-cycloproppyl-4-pyridyl-quinolones (U.S. Pat. No. 5,330,992) which have been described generally as tyrosine kinase inhibitors. Also, Styryl compounds (U.S. Pat. No. 5,217,999), styryl-substituted pyridyl compounds (U.S. Pat. No. 5,302,606), certain quinazoline derivatives (EP Application No. 0 566 266 Al), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

Other agents targeting EGFR and/or HER2-neu receptor tyrosine kinase signaling activity include antibodies that inhibit growth factor receptor biological function indirectly by mediating cytotoxicity via a targeting function Antibodies complexing with the receptor activates serum complement and/or mediate antibody-dependent cellular cytotoxicity. The antibodies which bind the receptor can also be conjugated to a toxin (immunotoxins). Advantageously antibodies are selected which greatly inhibit the receptor function by binding the steric vicinity of the ligand binding site of the receptor (blocking the receptor), and/or which bind the growth factor in such a way as to prevent (block) the ligand from binding to the receptor. These antibodies are selected using conventional in vitro assays for selecting antibodies which neutralize receptor function. Antibodies that act as ligand agonists by mimicking the ligand are discarded by conducting suitable assays as will be apparent to those skilled in the art. For certain tumor cells, the antibodies inhibit an autocrine growth cycle (i.e. where a cell secretes a growth factor which then binds to a receptor of the same cell). Since some ligands, e.g. TGF-α, are found lodged in cell membranes, the antibodies serving a targeting function are directed against the ligand and/or the receptor The cytotoxic moiety of the immunotoxin may be a cytotoxic drug or an enzymatically active toxin of bacterial or plant origin, or an enzymatically active fragment of such a toxin. Enzymatically active toxins and fragments thereof used are diphtheria, nonbinding active fragments of diphtheria toxin, exotoxin (from *Pseudomonas aeruginosa*), ricin, abrin, modeccin, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin. In another embodiment, the antibodies are conjugated to small molecule anticancer drugs. Conjugates of the monoclonal antibody and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the antibodies.

Cytotoxic radiopharmaceuticals for treating cancer may be made by conjugating radioactive isotopes to the antibodies. The term "cytotoxic moiety" as used herein is intended to include such isotopes.

In another embodiment, liposomes are filled with a cytotoxic drug and the liposomes are coated with antibodies specifically binding a growth factor receptor. Since there are many receptor sites, this method permits delivery of large amounts of drug to the appropriate cell type. The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how and when to terminate, interrupt, or adjust administration due to toxicity, or organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and Hydration of Sections:

(1) A portion of an approximately 10 μM section is placed in a 1.5 mL plastic centrifuge tube.

(2) 600 μL, of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10–20,000× g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 PL) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step.

(9) The supernatant is discarded and the pellet is allowed to dry at room temperature for about 5 minutes.

B. RNA Isolation with Phenol-Chloroform (1) 400 μL guanidine isothiocyanate solution including 0.5% sarcosine and 8 μL dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5–20 minutes. It is preferable to pierce the cap of the tube containing the sample with a fine gauge needle before heating to 95° C. Alternatively, the cap may be affixed with a plastic clamp or with laboratory film.

(4) The sample is then extracted with 50 μL 2M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 μL glycogen and with 400 μL isopropanol for 30 minutes at –20° C.

(7) The RNA is pelleted by centrifugation for about 7 minutes in a benchtop centrifuge at maximum speed; the supernatant is decanted and discarded; and the pellet washed with approximately 500 μL of about 70 to 75% ethanol.

(8) The sample is centrifuged again for 7 minutes at maximum speed. The supernatant is decanted and the pellet air dried. The pellet is then dissolved in an appropriate buffer for further experiments (e.g., 50 pI. 5 mM Tris chloride, pH 8.0).

Example 2 mRNA Reverse Transcription and PCR

Reverse Transcription: RNA was isolated from microdissected or non-microdissected formalin fixed paraffin embedded (FPE) tissue as illustrated in Example 1, or from fresh or frozen tissue by a single step guanidinium isocyanate method using the QuickPrep™ Micro mRNA purification kit (Amersham Pharmacia Biotech Inc., Piscataway, N.J.) according to the manufacturer's instructions. After precipitation with ethanol and centrifugation, the RNA pellet was dissolved in 50 ul of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 μl of the RNA solution with 25.5 μl of "reverse transcription mix" (see below). The reaction was placed in a thermocycler for 8 min at 26° C. (for binding the random hexamers to RNA), 45 min at 42° C. (for the M-MLV reverse transcription enzymatic reaction) and 5 min at 95° C. (for heat inactivation of DNAse).

"Reverse transcription mix" consists of 10 ul 5× buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5), 1.25 ul RNA Guard 24,800U/ml (RNAse inhibitor) (Porcine #27–0816, Amersham Pharmacia) and 2.5 ul MMLV 200U/ul (Life Tech Cat #28025–02).

Final concentrations of reaction components are: 50 mM Tris-HCl, pH 8.3, 75 mM KCl, 3 mM MgCl2, 1.0 mM dNTP, 1.0 mM DTT, 0.00375. mg/ml BSA, 0.62 U/ul RNA Guard and 10 U/ul MMLV.

PCR Quantification of mRNA expression. Quantification of EGFR cDNA and an internal control or house keeping gene (e.g., β-actin) cDNA was done using a fluorescence based real-time detection method (ABI PRISM 7700 or 7900 Sequence Detection System [TaqMan®], Applied Biosystems, Foster City, Calif.) as described by Heid et al., (Genome Res 1996;6:986–994); Gibson et al., (Genome Res 1996;6:995–1001). In brief, this method uses a dual labelled fluorogenic TaqMan® oligonucleotide probe, (EGFR-1773 (SEQ ID NO: 3), $T_m$=70° C.; HER2-neu 2657 (SEQ ID NO: 6), β-actin-611 (SEQ ID NO: 7) that anneals specifically within the forward and reverse primers. Laser stimulation within the capped wells containing the reaction mixture causes emission of a 3' quencher dye (TAMARA) until the probe is cleaved by the 5' to 3' nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number of the sequence of interest with the starting copy number of theinternal control gene provides a relative gene expression level. TaqMan® analyses yield levels that are expressed as ratios between two absolute measurements (gene of interest/internal control gene).

The PCR reaction mixture consisted 0.5 μl of the reverse transcription reaction containing the cDNA prepared as described above 600 nM of each oligonucleoride primers EGFR-1753F (SEQ ID NO: 1, $T_m$=59° C.) and EGFR-1823R (SEQ ID NO: 2, $T_m$=58° C.) or oligonucleotide primers HER2-neu 2671F (SEQ ID NO:4) and HER2-neu 2699R (SEQ ID NO: 5) 200 nM TaqMan® probe (SEQ ID NO:3 or SEQ ID NO: 6), 5 U AmpliTaq Gold Polymerase, 200 μM each dATP, dCTP, dGTP, 400 μM dTTP, 5.5 mM $MgCl_2$, and 1× TaqMan® Buffer A containing a reference dye, to a final volume of less than or equal to 25 μl (all reagents Applied Biosystems, Foster City, Calif.). Cycling conditions were, 95° C. for 10 min, followed by 45 cycles at 95° C. for 15s and 60° C. for 1 min. Oligonucleotides used to quantify internal control gene β-Actin were β-Actin-592F (SEQ ID NO: 8) and β-Actin-651R (SEQ ID NO: 9).

Example 3

Determining the Uncorrected Gene Expression (UGE) for EGFR

Two pairs of parallel reactions are carried out. The "test" reactions and the "calibration" reactions. FIG. 7. The EGFR amplification reaction and the β-actin internal control amplification reaction are the test reactions. Separate EGFR and β-actin amplification reactions are performed on the calibrator RNA template and are referred to as the calibration reactions. The TaqMan® instrument will yield four different cycle threshold (Ct) values: $Ct_{EGFR}$ and $Ct_{\beta\text{-}actin}$ from the test reactions and $Ct_{EGFR}$ and $Ct_{\beta\text{-}actin}$ from the calibration reactions. The differences in Ct values for the two reactions are determined according to the following equation:

$$\Delta Ct_{test}=Ct_{EGFR}-Ct_{\beta\text{-}actin} \text{ (From the "test" reaction)}$$

$$\Delta Ct_{calibrator}=Ct_{EGFR}-Ct_{\beta\text{-}actin} \text{ (From the "calibration" reaction)}$$

Next the step involves raising the number 2 to the negative ΔCt, according to the following equations.

$$2^{-\Delta Ct_{test}} \text{ (From the "test" reaction)}$$

$$2^{-\Delta Ct_{calibrator}} \text{ (From the "calibration" reaction)}$$

In order to then obtain an uncorrected gene expression for EGFR from the TaqMan® instrument the following calculation is carried out:

$$\text{Uncorrected gene expression } (UGE) \text{ for } {}^{EGFR}=2^{-\Delta Ct_{test}}/2^{-\Delta Ct_{calibrator}}$$

Normalizing UGE with Known Relative EGFR Expression Levels

The normalization calculation entails a multiplication of the UGE with a correction factor ($K_{EGFR}$) specific to EGFR and a particular calibrator RNA. A correction factor $K_{EGFR}$ can also be determined for any internal control gene and any accurately pre-quantified calibrator RNA. Preferably, the internal control gene β-actin and the accurately pre-quantified calibrator RNA, Human Liver Total RNA (Stratagene, Cat #735017), are used. Given these reagents correction factor $K_{EGFR}$ equals 1.54.

Normalization is accomplished using a modification of the ΔCt method described by Applied Biosystems, the TaqMan® manufacturer, in User Bulletin #2 and described above. To carry out this procedure, the UGE of 6 different FPE test tissues were analyzed for EGFR expression using the TaqMan® methodology described above. The internal control gene β-actin and the calibrator RNA, Human Liver Total RNA (Stratagene, Cat #735017) was used.

The already known relative EGFR expression level of each sample AG22 1, AG222, AG252, Adult Lung, PC3, AdCol was divided by its corresponding TaqMan® derived UGE to yield an unaveraged correction factor K.

$$K_{unaveraged}=\text{Known Values}/UGE$$

Next, all of the K values are averaged to determine a single $K_{EGFR}$ correction factor specific for EGFR, Stratgene Human Liver Total RNA (Stratagene, Cat #735017) from calibrator RNA and β-actin.

Therefore, to determine the Corrected Relative EGFR Expression in an unknown tissue sample on a scale that is consistent with pre-TaqMan® EGFR expression studies, one merely multiplies the uncorrected gene expression data (UGE) derived from the TaqMan® apparatus with the $K_{EGFR}$ specific correction factor, given the use of the same internal control gene and calibrator RNA.

$$\text{Corrected Relative } EGFR \text{ Expression}=UGE\times K_{EGFR}$$

A $K_{EGFR}$ may be determined using any accurately pre-quantified calibrator RNA or internal control gene. Future sources of accurately pre-quantified RNA can be calibrated to samples with known relative EGFR expression levels as described in the method above or may now be calibrated against a previously calibrated calibrator RNA such as Human Liver Total RNA (Stratagene, Cat #735017) described above.

For example, if a subsequent $K_{EGFR}$ is determined for a different internal control gene and/or a different calibrator RNA, one must calibrate both the internal control gene and the calibrator RNA to tissue samples for which EGFR expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{EGFR}$ specific to the different internal control gene and/or calibrator RNA.

Example 4

Determining the Uncorrected Gene Expression (UGE) for HER2-neu

Two pairs of parallel reactions are carried out. The "test" reactions and the "calibration" reactions. FIG. 8. The HER2-neu amplification reaction and the β-actin internal control amplification reaction are the test reactions. Separate HER2-neu and β-actin amplification reactions are performed on the calibrator RNA template and are referred to as the calibration reactions. The TaqMan® instrument will yield four different cycle threshold (Ct) values: $Ct_{HER2\text{-}neu}$ and $Ct_{\beta\text{-}actin}$ from the test reactions and $Ct_{Her2\text{-}neu}$ and $Ct_{\beta\text{-}actin}$ from the calibration reactions. The differences in Ct values for the two reactions are determined according to the following equation:

$$\Delta Ct_{test} = Ct_{HER2\text{-}neu} - Ct_{\beta\text{-}actin} \text{ (From the "test" reaction)}$$

$$\Delta Ct_{calibrator} = Ct_{Her2\text{-}neu} - Ct_{\beta\text{-}actin} \text{ (From the "calibration" reaction)}$$

Next the step involves raising the number 2 to the negative ΔCt, according to the following equations.

$$2^{-\Delta Ct_{test}} \text{ (From the "test" reaction)}$$

$$2^{-\Delta Ct_{calibrator}} \text{ (From the "calibration" reaction)}$$

In order to then obtain an uncorrected gene expression for HER2-neu from the TaqMan® instrument the following calculation is carried out:

$$\text{Uncorrected gene expression } (UGE) \text{ for } HER2\text{-}neu = 2^{-\Delta Ct_{test}} / 2^{-\Delta Ct_{calibrator}}$$

Normalizing UGE with Known Relative HER2-neu Expression Levels

The normalization calculation entails a multiplication of the UGE with a correction factor ($K_{HER2\text{-}neu}$) specific to HER2-neu and a particular calibrator RNA. A correction factor $K_{HER2\text{-}neu}$ can also be determined for any internal control gene and any accurately pre-quantified calibrator RNA. Preferably, the internal control gene β-actin and the accurately pre-quantified calibrator RNA, Human Liver Total RNA (Stratagene, Cat #735017) are used. Using β-actin and the accurately pre-quantified calibrator RNA, Human Liver Total RNA (Stratagene, Cat #735017) the correction factor $K_{HER2\text{-}neu}$ equals $12.6\times10^{-3}$.

Normalization is accomplished using a modification of the ΔCt method described by Applied Biosystems, the TaqMan® manufacturer, in User Bulletin #2 and described above. To carry out this procedure, the UGE of 6 different FPE test tissues were analyzed for HER2-neu expression using the TaqMan® methodology described above. The internal control gene β-actin and the calibrator RNA, Human Liver Total RNA (Stratagene, Cat #735017) was used.

The already known relative HER2-neu expression level of each sample AG221, AG222, AG252, Adult Lung, PC3, AdCol is divided by its corresponding TaqMan® derived UGE to yield an unaveraged correction factor K.

$$K_{unaveraged} = \text{Known Values}/UGE$$

Next, all of the K values are averaged to determine a single $K_{EGFR}$ correction factor specific for HER2-neu, Human Liver Total RNA (Stratagene, Cat #735017) calibrator, and β-actin.

Therefore, to determine the Corrected Relative HER2-neu Expression in an unknown tissue sample on a scale that is consistent with pre-TaqMan® HER2-neu expression studies, one merely multiplies the uncorrected gene expression data (UGE) derived from the TaqMan® apparatus with the $K_{HER2\text{-}neu}$ specific correction factor, given the use of the same internal control gene and calibrator RNA.

$$\text{Corrected Relative } HER2\text{-}neu \text{ Expression} = UGE \times K_{HER2\text{-}neu}$$

A $K_{HER2\text{-}neu}$ may be determined using any accurately pre-quantified calibrator RNA or internal control gene. Future sources of accurately pre-quantified RNA can be calibrated to samples with known relative EGFR expression levels as described in the method above or may now be calibrated against a previously calibrated calibrator RNA such as Human Liver Total RNA (Stratagene, Cat #735017) described above.

For example, if a subsequent $K_{HER2\text{-}neu}$ is determined for a different internal control gene and/or a different calibrator RNA, one should calibrate both the internal control gene and the calibrator RNA to tissue samples for which HER2-neu expression levels relative to that particular internal control gene have already been determined or published. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{HER2\text{-}neu}$ specific to the different internal control gene and/or calibrator RNA.

Example 5

Patient Population and Tissue Acquisition

Patients. Eighty-three patients suffering from NSCLC consisting of sixty-five (78.3%) men and 18 (21.7%) women, with a median age of 63.5 years (range, 34–82) were studied. Thirty-nine (47%) patients had squamous cell carcinomas, 32 (38.6%) had adenocarcinoma, and 12 (14.5%) had large cell carcinomas. The primary tumors were graded histopathologically as well-differentiated (G1, one patient), moderately-differentiated (G2, 18 patients), and poorly-differentiated (G3, 64 patients). Tumor staging was performed according to the International Union Against Cancer (UICC) TNM classification: Forty-one (49.4%) had stage I tumors, 16 (19.3%) had stage II tumors, and 26 (31.3%) had stage IIIa tumors. All tumors were completely resected (R0 category), by at least a lobectomy as quality control. Patients with histopathological stage IIIa tumors received postoperative radiotherapy. The median follow-up was 85.9 months (min. 63.3; mar. 105.2 months) and no patient was lost to follow-up Tissue Acquisition. Tissue for gene expression analysis was obtained immediately after lung resection before starting mediastinal lymphadenectomy and was immediately frozen in liquid nitrogen. Tissues were analyzed from the following 2 locations: tumor and uninvolved lung tissue taken from the greatest distance to the tumor. 6 μm frozen sections were taken from blocks of tumor tissue and starting with the first section every fifth was routinely stained with HE and histopathologically evaluated. Sections were pooled for analysis from areas of estimated 75% malignant cells. RNA was isolated from tissue samples according to the methods in Example 2.

Example 6

Statistical Analysis

TaqMan® analyses yield values that are expressed as UGE. The ratio between UGE in tumor tissue and UGE in matching non-malignant lung tissue was used to determine differential gene expression. Associations between the two UGE variables were tested by using Wilcox on signed rank test. The Chi-Square test was used to analyze the associations between categorial clinicopathological variables. Hazards ratios were used to calculate the relative risks of death. These calculations were based on the Pike estimate, with the use of the observed and expected number of events as calculated in the log-rank test statistic. Pike, J R Stat Soc Series A 135:201–203; 1972. The maximal chi-square method of Miller and Sigmund (Miller et al., Biometrics 38:1011–1016, 1982) and Halpern (Biometrics 38:1017–1023, 1982) was adapted to determine which expression value best segregated patients into poor- and good prognosis subgroups (in terms of likelihood of surviving), with the log-rank test as the statistics used to measure the strength of the grouping. To determine a P value that would be interpreted as a measure of the strength of the association based on the maximal chi-square analysis, 1000 boot-strap-like simulations were used to estimate the distribution of the maximal chi-square statistics under the hypothesis of no association. Halpern, Biometrics 38:1017–1023, 1982. Cox's proportional hazards modeling of factors that were significant in anivariate analysis was performed to identify which factors might have a significant influence on survival. The level of significance was set to $p<0.05$.

HER2-neu mRNA expression was detectable by quantitative real-time RT-PCR in 83 of 83 (100%) normal lung and 83 of 83 (100%) tumor samples. The corrected HER2-neu mRNA expression, expressed as the ratio between HER2-neu and P-Actin PCR product, was $4.17\times10^{-3}$ (range $0.28–23.86\times10^{-3}$) in normal lung and $4.35\times\mathbf{10^{-3}}$ (range: $0.21–68.11\times10^{-3}$) in tumor tissue (P=0.019 Wilcoxon test). The maximal chi-square method by Miller and Siegmund (Miller et al., Biometrics 38:1011–1016, 1982) and Halpern (Biometrics 38:1017–1023, 1982) determined a threshold value of 1.8 to segregate patients into low and high differential HER2-neu expressors. By this criterion, 29 (34.9%) patients had a high differential HER2-neu expression and 54 (65.1%) had a low differential HER2-neu expression. FIG. 4 shows associations between clinicopathological data and differential HER2-neu gene expression status. There were no statistically significant differences detectable. FIG. 1 displays a Kaplan Meier plot of the estimated probability of survival versus the differential HER2-neu mRNA expression status. The median survival was not reached in the low differential HER2-neu expression group compared to 31.1 months (95% C.I.: 21.96–40.24) in the high differential HER2-neu expression group. To determine a P value, bootstrap-like simulations were used to estimate the distribution of a maximal chi-square statistic, since the threshold value of 1.8 had been chosen after examining the data. The resulting adjusted P value was 0.004 (Log-rank test).

The accuracy of HER2-neu as a prognostic factor was next determined by the Cox's proportional hazards model analysis. In univariate analysis of potential prognostic factors, high differential HER2-neu expression as well as advanced pT (tumor stage) classification, pN (lymph node stage) classification, and tumor stage were significant unfavorable prognostic factors (FIG. 5). In a multivariate analysis of prognostic factors (FIG. 6), high differential HER2-neu expression was a significant and independent unfavorable prognostic factor, as well as advanced pN classification and tumor stage.

Figure 2:
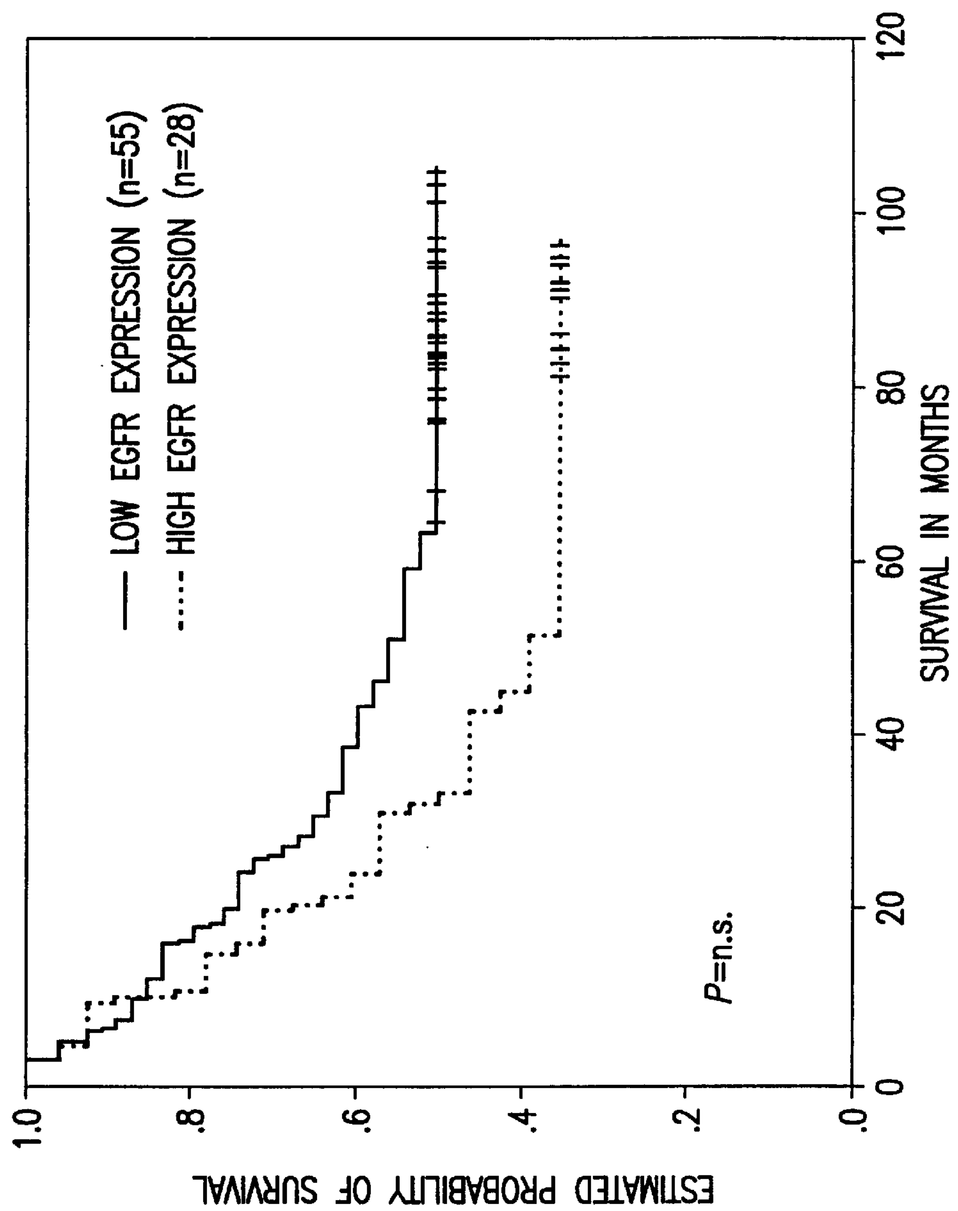
FIG. 2. Estimated probability of survival of curatively resected non-small cell lung cancer patients versus the EGFR mRNA expression status. A trend towards inferior overall survival was observable for the high EGFR expression group, but did not reach statistical significance. The median survival was not reached in the low EGFR expression group compared to 32.37 months (95% C.I: 8.43–56.31) in the high EGFR expresser group (P=0.176).

EGFR mRNA expression was detectable by quantitative real-time RT-PCR in 83 of 83 (100%) normal lung and 83 of 83 (100%) tumor samples. The median corrected EGFR mRNA expression was $8.17\times10^{-3}$(range: $0.31–46.26\times10^{-3}$) in normal lung and $7.22\times10^{-3}$ (range: $0.27–97.49\times10^{-1}$) in tumor tissue (P=n.s.). The maximal chi-square method (Miller (1982); Halpern (1982)) determined a threshold value of 1.8 to segregate patients into low and high differential EGFR expressors. By this criterion, 28 (33.7%) patients had a high differential EGFR expression and 55 (66.3%) had a low differential EGFR expression status. There were no statistical significant differences between clinicopathological variables and differential EGFR mRNA expression status detectable (FIG. 4). A trend towards inferior overall survival was observable for the high differential EGFR expression group, but did not reach statistical significance (FIG. 2). The median survival was not reached in the low differential EGFR expression group compared to 32.37 months (95% C.I.: 8.43–56.31) in the high differential EGFR expressor group (P=0.176).

Figure 3:
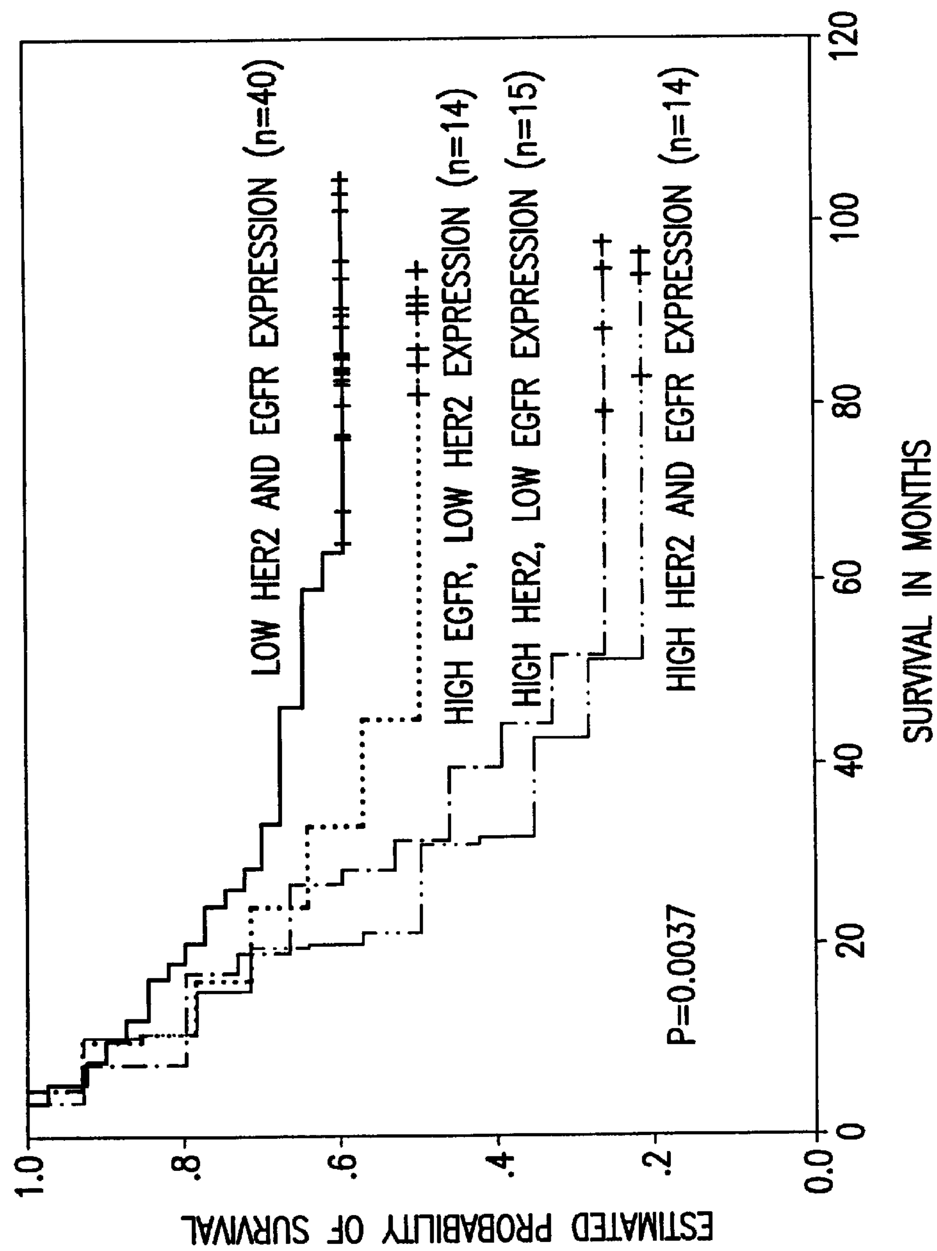
FIG. 3. Estimated probability of survival of curatively resected non-small cell lung cancer patients versus combined patterns of EGFR and HER2-neu co-expression in NSCLC. The median survival was not reached in the group that showed low HER2-neu and EGFR expression, compared to 45.47 months in the high EGFR expression group, 31.10 months (95% C.I.: 14.77–47.43) in the high HER2-neu expression group, and 22.03 months (95% C.I: 2.30–41.76; P=0.003) in the high HER2-neu and EGFR expression group.

High expression levels (above 1.8) of differential HER2-neu and EGFR were found in 14 of 83 (16.9%) patients. Forty of 83 (48.2%) patients showed a low differential expression status (below 1.8) for HER2-neu and EGFR, whereas 14 of 83 (16.9%) showed a high differential expression for EGFR only, and 15 of 83 (18.1%) patients displayed a high differential expression for HER2-neu. The median survival was not reached in the group that showed low differential HER2-neu and EGFR expression, compared to 45.47 months in the high differential EGFR expression group, 31.10 months (95% C.I.: 14.77–47.43) in the high differential HER2-neu expression group, and 22.03 months (95% C.I: 2.30; 41.76; P=0.003; log-rank test; FIGS. 3 and 5) in the high differential HER2-neu and EGFR expression group. Univariate analysis displayed high differential HER2-neu and EGFR coexpression as a significant unfavorable prognostic factor (FIG. 5). In a multivariate analysis of prognostic factors (FIG. 6), high differential HER2-neu and high differential EGFR coexpression was a significant and independent unfavorable prognostic factor, as was advanced pN classification and tumor stage.

Example 7

Tumor Response to a Receptor Tyrosine Kinase Targeted Chemotherapy

Five colon cancer patients' tumors were initially identified as expressing EGFR by immunohistochemistry. Patients were treated with Imclone IMC-C225, 400 mg/m$^2$ loading dose followed by 250 mg/m$^2$ weekly, plus CPT-11 at the same dose and schedule that the patient had previously progressed on. Previous CPT-11 dose attenuations were maintained.

Figure 9:
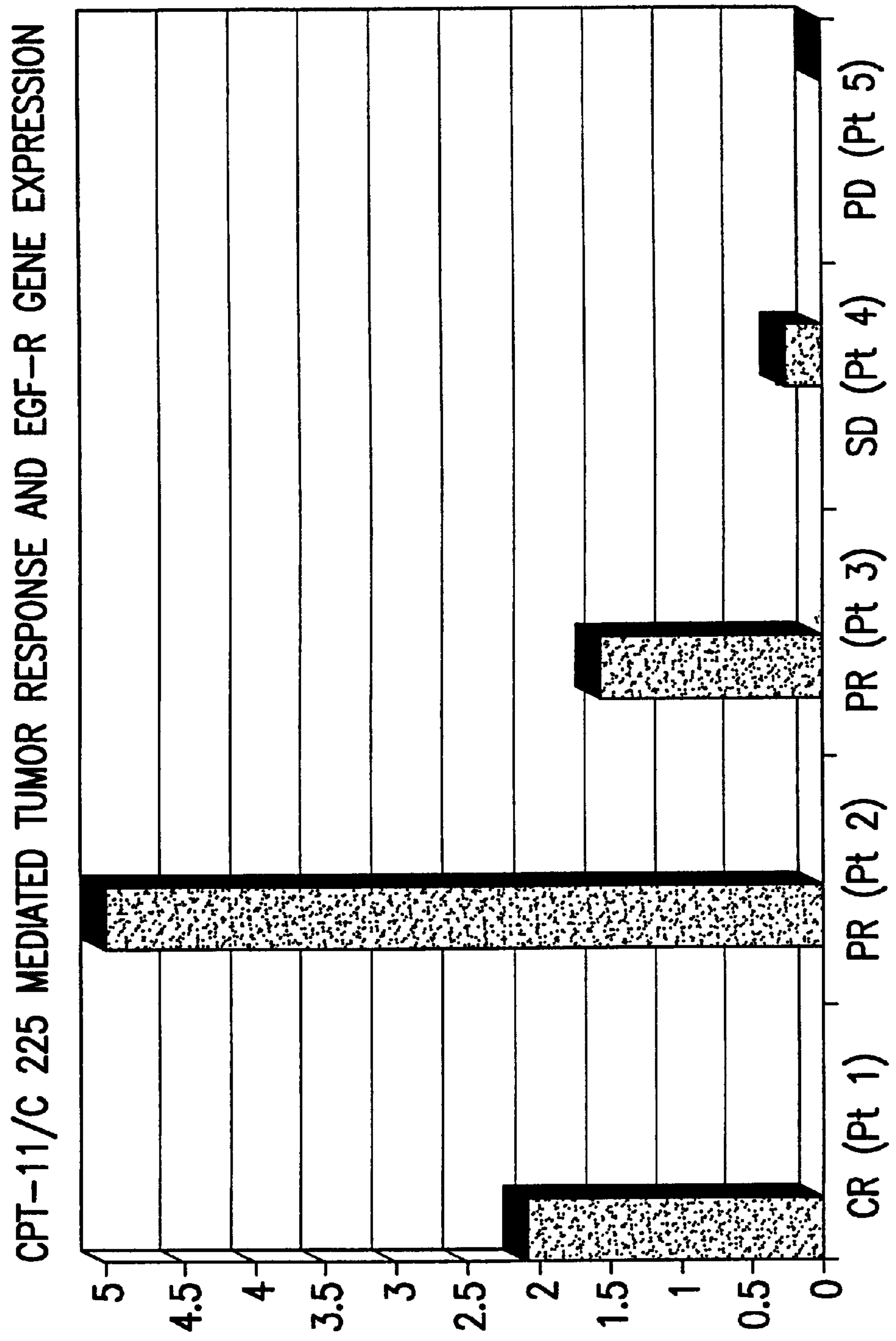
FIG. 9 is a graph showing the corrected EGFR expression values of 5 different colon cancer patients' tumors. The patients were on a CPT-11/C225 receptor tyrosine kinase targeted treatment regimen. Patient 1 was determined to have a corrected EGFR expression level of $2.08\times10^{-3}$ and had a completed response (CR). Patient 2 had a corrected EGFR expression level of $8.04\times10^{-3}$ and had a partial response (PR). Patient 3 had a corrected EGFR expression level of $1.47\times10^{-3}$ and also showed a partial response (PR). Patient 4 had a corrected EGFR expression level of $0.16\times10^{-3}$ and had stable disease (SD) showing no response. Patient 5 had a no EGFR expression ($0.0\times10^{-3}$) and had progressive disease (PR).

Using the methodology described in Examples 1–4, Patient 1 was determined to have a corrected EGFR expression level of $2.08\times10^{-3}$ and had a completed response (CR) to a a receptor tyrosine kinase targeted chemotherapy comprising CPT-11 (7-ethyl-10-[4-(1-piperidino)-1-piperidino] carboxycamptothecin)/C225 (an anti-EGFR monoclonal antibody effective in anti-cancer therapy; Mendelsohn, Endocr Relat Cancer March 2001 ;8(1):3–9). Patient 2 had a corrected EGFR expression level of $8.04\times10^{-3}$ and had a partial response (PR) to the receptor tyrosine kinase targeted chemotherapy. Patient 3 had a corrected EGFR expression level of $1.47\times10^{-3}$ and also showed a partial response (PR) to the receptor tyrosine kinase targeted chemotherapy. Patient 4 had a corrected EGFR expression level of $0.16\times10^{-3}$ and had stable disease (SD) showing no response to the receptor tyrosine kinase targeted chemotherapy. Patient 5 had a no EGFR expression ($0.0\times10^{-3}$) and had progressive disease (PR) showing no response to the receptor tyrosine kinase targeted chemotherapy. See FIG. 9.

What is claimed is:

1. A method for determining a chemotherapeutic regimen comprising a receptor tyrosine kinase targeted agent, for treating a tumor in a patient comprising:

(a) obtaining a tissue sample of the tumor;

(b) obtaining a matching non-malignant tissue sample;

(c) isolating mRNA from the tumor sample and non-malignant sample;

(d) subjecting the mRNA to amplification using a pair of oligonucleotide primers capable of amplifying a region of the EGFR gene, or a pair of oligonucleotide primers capable of amplifying a region of the HER2-neu gene, to obtain an EGFR tumor amplified sample and a EGFR non-malignant amplified sample, or a HER2-neu tumor amplified sample and a HER2-neu non-malignant amplified sample (e) determining an amount of HER2-neu mRNA in the HER2-neu tumor amplified sample and HER2-neu non-malignant amplified sample or determining the amount of EGFR mRNA in the EGFR tumor amplified sample and EGFR non-malignant amplified sample;

(f) obtaining a differential HER2-neu epression level or obtaining a differential EGFR expression level; and (g) determining a chemotherapeutic regimen comprising a receptor tyrosine kinase targeted agent by comparing the differential HER2-neu expression level of step (f) and a threshold level for differential HER2-neu gene expression, or comparing the differential EGFR expression level of step (f) and a threshold level for differential EGFR gene expression.

2. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor sample and non-malignant sample;

(d) subjecting the mRNA to amplification using a pair of oligonucleotide primers capable of amplifying a region of the EGFR gene, to obtain an tumor amplified sample and a non-malignant amplified sample;

(e) determining the amount of EGFR mRNA in the tumor amplified sample and non-malignant amplified sample;

(f) obtaining a differential EGFR expression level; and (g) determining a chemotherapeutic regimen comprising a receptor tyrosine kinase targeted agent by comparing the differential EGFR expression level of step (f) and a threshold level for differential EGFR gene expression.

3. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor sample and non-malignant sample;

(d) subjecting the mRNA to amplification using a pair of oligonucleotide primers capable of amplifying a region of the HER2-neu gene, to obtain an tumor amplified sample and a non-malignant amplified sample;

(e) determining the amount of HER2-neu mRNA in the tumor amplified sample and non-malignant amplified sample;

(f) obtaining a differential HER2-neu expression level; and (g) determining a chemotherapeutic regimen comprising a receptor tyrosine kinase targeted agent by comparing the differential HER2-neu expression level of step (f) and a threshold level for differential HER2-neu gene expression.

4. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor sample and non-malignant sample;

(d) subjecting the mRNA to amplification using a pair of oligonucleotide primers capable of amplifying a region of the EGFR gene, and a pair of oligonucleotide primers capable of amplifying a region of the HER2-neu gene, to obtain an EGFR tumor amplified sample and an EGFR non-malignant amplified sample, and a HER2-neu tumor amplified sample and a HER2-neu non-malignant amplified sample (e) determining the amount of HER2-neu mRNA in the HER2-neu tumor amplified sample and HER2-neu non-malignant amplified sample and determining the amount of EGFR mRNA in the EGFR tumor amplified sample and EGFR non-malignant amplified sample;

(f) obtaining a differential HER2-neu expression level and obtaining a differential EGFR expression level; and (g) determining a chemotherapeutic regimen comprising a receptor tyrosine kinase targeted agent by comparing the differential HER2-neu expression level of step (f) and a threshold level for differential HER2-neu gene expression, and comparing the differential EGFR expression level of step (f) and a threshold level for differential EGFR gene expression.

5. The method of claim 2, wherein the pair of oligonucleotide primers consists of SEQ ID NO:1 or an oligonucleotide primer at least about 80% identical thereto and SEQ ID NO: 2 or an oligonucleotide primer at least about 80% identical thereto.

6. The method of claim 3, wherein the pair of oligonucleotide primers consists of SEQ ID NO:4 or an oligonucleotide primer at least about 80% identical thereto and SEQ ID NO: 5 or an oligonucleotide primer at least about 80% identical thereto.

7. The method of any one of claims 1, 2, 3, or 4 wherein the tumor is a non-small cell lung cancer tumor.

8. The method of claim 4 wherein the primers consist of both the oligonucleotide primer pair SEQ ID NO: 4 or an oligonucleotide primer at least about 80% identical thereto and SEQ ID NO: 5 or an oligonucleotide primer at least about 80% identical thereto; and oligonucleotide primer pair SEQ ID NO: 1 or an oligonucleotide primer at least about 80% identical thereto and SEQ ID NO: 2 or an oligonucleotide primer at least about 80% identical thereto.

9. The method of any one of claims 1, 2, or 4 wherein the threshold level for differential EGFR gene expression is about 1.8.

10. The method of any one of claims 1, 3, or 4 wherein, the threshold level for differential HER2-neu gene expression is about 1.8.

11. The method of any one of claims 1, 2, 3 or 4 wherein the tissue samples are fixed or fixed and paraffin embedded.

12. A method for determining a chemotherapeutic regimen comprising a receptor tyrosine kinase targeted agent, for treating a tumor in a patient comprising:

(a) obtaining a tissue sample of the tumor;

(b) obtaining a non-malignant tissue sample matching said tumor;

(c) isolating mRNA from the tumor tissue sample and non-malignant tissue sample; wherein said tissue samples are fixed or fixed and paraffin embedded prior to said mRNA isolation;

(d) determining the amount of HER2-neu mRNA in the HER2-neu tumor tissue sample and HER2-neu non-malignant tissue sample or determining the amount of EGFR mRNA in the EGFR tumor tissue sample and EGFR non-malignant tissue sample;

(e) obtaining a differential HER2-neu expression level or obtaining a differential EGFR expression level; and (f) determining a chemotherapeutic regimen comprising a receptor tyrosine kinase targeted agent by comparing the differential HER2-neu expression level of step (e) and a threshold level for differential HER2-neu gene expression of about 1.8, or comparing the differential EGFR expression level of step (e) and a threshold level for differential EGFR gene expression of about 1.8.

13. A method for determining a chemotherapeutic regimen comprising a receptor tyrosine kinase targeted agent, for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of HER2-neu mRNA in the tumor tissue sample and non-malignant tissue sample or determining the amount of EGFR mRNA in the tumor tissue sample and non-malignant tissue sample;

(e) obtaining a differential HER2-neu epression level or obtaining a differential EGFR expression level; and (f) determining a chemotherapeutic regimen comprising a receptor tyrosine kinase targeted agent by comparing the differential HER2-neu expression level of step (e) and a threshold level for differential HER2-neu gene expression of about 1.8, or comparing the differential EGFR expression level of step (e) and a threshold level for differential EGFR gene expression of about 1.8.

14. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of EGFR mRNA in the tumor tissue sample and non-malignant tissue sample;

(e) obtaining a differential EGFR expression level; and (f) determining a chemotherapeutic regimen comprising a receptor tyrosine kinase targeted agent by comparing the differential EGFR expression level of step (e) and a threshold level for differential EGFR gene expression of about 1.8.

15. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of HER2-neu mRNA in the tumor tissue sample and non-malignant tissue sample;

(e) obtaining a differential HER2-neu expression level; and (f) determining a chemotherapeutic regimen comprising a receptor tyrosine kinase targeted agent by comparing the differential HER2-neu expression level of step (e) and a threshold level for differential HER2-neu gene expression of about 1.8.

16. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant sample; wherein said tissue samples are fixed or fixed and paraffin embedded prior to said mRNA isolation;

(d) determining the amount of HER2-neu mRNA in the tumor tissue sample and non-malignant tissue sample and determining the amount of EGFR mRNA in the tumor tissue sample and non-malignant amplified sample;

(e) obtaining a differential HER2-neu expression level and obtaining a differential EGFR expression level; and (f) determining a chemotherapeutic regimen comprising a receptor tyrosine kinase targeted agent by comparing the differential HER2-neu expression level of step (e) and a threshold level for differential HER2-neu gene expression of about 1.8, and comparing the differential EGFR expression level of step (e) and a threshold level for differential EGFR gene expression of about 1.8.

17. A method for determining a chemotherapeutic regimen comprising a receptor tyrosine kinase targeted agent, for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of HER2-neu mRNA in the tumor tissue sample and non-malignant tissue sample or determining the amount of EGFR mRNA in the tumor tissue sample and non-malignant tissue sample;

(e) obtaining a differential HER2-neu epression level or obtaining a differential EGFR expression level; and (f) determining a chemotherapeutic regimen comprising a receptor tyrosine kinase targeted agent by comparing the differential HER2-neu expression level of step (e) and a threshold level for differential HER2-neu gene expression, or comparing the differential EGFR expression level of step (e) and a threshold level for differential EGFR gene expression.

18. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of EGFR mRNA in the tumor tissue sample and non-malignant tissue sample;

(e) obtaining a differential EGFR expression level; and (f) determining a chemotherapeutic regimen comprising a receptor tyrosine kinase targeted agent by comparing the differential EGFR expression level of step (e) and a threshold level for differential EGFR gene expression.

19. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant tissue sample; wherein said tissue samples are fixed or fixed and paraffin embedded prior to said mRNA isolation;

(d) determining the amount of HER2-neu mRNA in the tumor tissue sample and non-malignant tissue sample;

(e) obtaining a differential HER2-neu expression level; and (f) determining a chemotherapeutic regimen comprising a receptor tyrosine kinase targeted agent by comparing the differential HER2-neu expression level of step (e) and a threshold level for differential HER2-neu gene expression.

20. A method for determining a chemotherapeutic regimen comprising a receptor tyrosine kinase targeted agent for treating a tumor in a patient comprising:

(a) obtaining a tissue sample of the tumor;

(b) obtaining a matching non-malignant tissue sample;

(c) isolating mRNA from the tumor tissue sample and non-malignant sample; wherein said tissue samples are fixed or fixed and paraffin embedded prior to said mRNA isolation;

(d) determining the amount of HER2-neu mRNA in the tumor tissue sample and non-malignant tissue sample and determining the amount of EGFR mRNA in the tumor tissue sample and non-malignant amplified sample;

(e) obtaining a differential HER2-neu expression level and obtaining a differential EGFR expression level; and (f) determining a chemotherapeutic regimen comprising a receptor tyrosine kinase targeted agent by comparing the differential HER2-neu expression level of step (e) and a threshold level for differential HER2-neu gene expression, and comparing the differential EGFR expression level of step (e) and a threshold level for differential EGFR gene expression.

21. The method of claim 18, wherein step (d) comprises the use of a pair of oligonucleotide primers consisting of SEQ ID NO:1 or an oligonucleotide primer at least about 80% identical thereto and SEQ ID NO: 2 or an oligonucleotide primer at least about 80% identical thereto.

22. The method of claim 19, wherein step (d) comprises the use of a pair of oligonucleotide primers consisting of SEQ ID NO:4 or an oligonucleotide primer at least about 80% identical thereto and SEQ ID NO: 5 or an oligonucleotide primer at least about 80% identical thereto.

23. The method of any one of claims 17, 18, 19, or 20 wherein the tumor is a non-small cell lung cancer tumor.

24. The method of claim 20 wherein wherein step (d) comprises the use of two pairs of oligonucleotide primers consisting of oligonucleotide primer pair SEQ ID NO: 4 or an oligonucleotide primer at least or about 80% identical thereto, and SEQ ID NO: 5 or an oligonucleotide primer at least or about 80% identical thereto, and oligonucleotide primer pair SEQ ID NO: 1 or an oligonucleotide primer at least or about 80% identical thereto, and SEQ ID NO: 2 or an oligonucleotide primer at least or about 80% identical thereto.

25. The method of any one of claims 17, 18, 19, or 20 wherein step (d) comprises the step of amplifying the mRNA isolated from said tumor tissue sample and said non-malignant tissue sample.

26. The method of anyone of claims 17, 18, 19, or 20 wherein, step (c) comprises the step of heating the fixed tumor sample the in the presence of an effective concentration of a chaotropic agent wherein the heating occurs at a temperature from about 75° C. to about 100° C. for a time period of about 5 to about 120 minutes.

27. The method of anyone of claims 1, 2, 3, or 4 wherein said tissue samples are fixed or fixed and paraffin embedded prior to said mRNA isolation and step (c) comprises the step of heating the tissue sample the in the presence of an effective concentration of a chaotropic agent wherein the heating occurs at a temperature from about 50° C. to about 100° C.

28. The method of anyone of claims 17, 18, 19, or 20 wherein said tissue samples are fixed or fixed and paraffin embedded prior to said mRNA isolation and step (c) comprises the step of heating the tissue sample the in the presence of an effective concentration of a chaotropic agent wherein the heating occurs at a temperature from about 50° C. to about 100° C.

* * * * *

```
                              SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1

tgcgtctctt gccggaat                                                    18


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

ggctcaccct ccagaagctt                                                  20


<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

acgcattccc tgcctcggct g                                                21


<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4

ctgaactggt gtatgcagat tgc                                              23


<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5

ttccgagcgg ccaagtc                                                     17


<210> SEQ ID NO 6
<211> LENGTH: 24
<212> TYPE: DNA
<213> ORGANISM: Artificial Sequence
<220> FEATURE:
```

<223> OTHER INFORMATION: Primer

<400> SEQUENCE: 6
tgtgtacgag ccgcacatcc tcca 24

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
accaccacgg ccgagcgg 18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
tgagcgcggc tacagctt 18

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tccttaatgt cacgcacgat tt 22

<210> SEQ ID NO 10
<211> LENGTH: 197496
<212> TYPE: DNA
<213> ORGANISM: Homo sapiens

<400> SEQUENCE: 10
ttctttttag cacagaataa caatccattg tccacatgta ccatggttta tttatccact 60
catccacatg aagacatctt agttgattct aagttaggga agttatgaat aaagctgtta 120
taaatattca tgagcagatt tatgtggaca acagtgttca actcatttgg gtaagtatca 180
aggagagaaa tcattggatc atatggtaag agtatgtaca cttttatagg aaactgctaa 240
gctgcattcc taagtggctg taccattgtg ccttcccatc agcaatgaat gagacttcct 300
attgttccac atcctcatca gaatttggtg ttgtcactga tctgaatttt ttccattgta 360
acagatgtgt agtggtatct cactgttgtt ttaatttgca atttcctaat gacatatgat 420
gttgaacatc tttttatatg cttacttgcc atcagtgtat cctctgatga ggtgtttgtg 480
tagggctttg gcccattttt aaatcaggtt atttatcctc ttattattaa cttttaagag 540
tttagttctt tgcatatttt ggataacaat cctttatcac atatttcttt tgcaaatttt 600
tctccagtat atggcttgtc ttcttctcct ggcattgtcc ttctcagagc agaagttttt 660
aattttaata aactccagct tataaattat ttatttcatg gattgtgcct ttggttttgt 720
acttaaaaag tcattgtcat acctaaggtc atctaggttt tctcctacgt tatctcctag 780
gtgttttata gttttgcatt ttacatttat atgtatgatc agttttgagt taatttttat 840
gaagtgtgta aggtttgtat ctacattcat tttttgcatg tggatgtcca tttgttccag 900

-continued

```
caatatttgt tgaaaagact atacttgctc tattgtattg tgtttctttt ttgtcaaaga    960
tcaattgact aaatttatgt gcgtcagttt ctgatctctc tggtccattg atatatttgt   1020
ctattctttc accaatacca catagtctag actactgtag ttgtatatgt cttgaagtca   1080
ggtagtgttg atcctccaat tttgttctcc aatattgagt tggctattgt gggtcttttg   1140
cttgcccata gaatcaatta gtcaatattt acaaaataac ttgctcgaac tttgactggg   1200
attaatctat aaatcaagtt gggaataagt gacattttga cattatggag tctttctgac   1260
catgaacaca aactattgat ccatttattt agttatttga tatctttcac cagagttttt   1320
ttgttttttt cttatagatc ttatacatat tttcttatat tcatacctca gtattccatt   1380
tcagggtgtt aatgtaaatg gtaatgtgtt tttaatttca aattccctta gttctttgct   1440
ggtatatagg aaagtgattg gcttttgtat gttaacgttg tatcctgctc acttgctata   1500
actgcttatt agttccagga gctttttat tgtttctttt ggattttcta agagacaatt    1560
acattatcag tgaacaaaca cgatttattt cttccctccc aatcagtatt cattttattt   1620
atttattgtg tgttattgca ttagctagga cttctaatac aatgttgaaa agcattggtg   1680
aaaggaaaca tccttgcttt gttcctgatt ttagctatag gtttttgtag ctgttcttta   1740
ttaagttgag gatatccttc tctattctta gtttgctgag aatttttatc atgaataggt   1800
gtaggatttt gcctaatgtt ttcttctgta tctattgata tgatcatgta atttttcttt   1860
atctattgat atgatctgtt gatgtgatga actacattaa ttgagttttc aaatgttgaa   1920
ccagtcttgc atatctggaa taaatcggag ttggtcatca tgtataactt tgttacactt   1980
tgttgcattt gattttgtaa tattttcttg agaattttta catctatgtt cataaaagat   2040
atcggtctac agtttctttt cctttcttgt aatatctctg tctggttttg ctattaaggt   2100
aattctggct tcacaaaatt aattatggag tcttccctct acttctagtt tctggaagag   2160
attgtagaga atggatgtaa tttctttctt aaatgtttga cgaaaatcag cactgatctc   2220
atctgggctt ggtgctttct gttttggaag gttattaatt atttattcaa tttctatagt   2280
ggatataggc ctatattgat tggcaatttc ttcttgtatg acttttggta cattctattt   2340
caaggaattg gttcatttca tgtaggttgt taaattcgtg ggtatagctg ttcataaatat  2400
tcatttatta tcctttcaat gttcatgaga tcagtagtga tgttccttct ttcatttctg   2460
atattcataa tttgtgtatt ctctctttgt ttcttagcct ggtgagaggc ttataaattt   2520
tattgatttt ttgaagaatc actttttggt tttgctgatt ttcttgctgg gattataggc   2580
gtgagccacc acactcttgc tcatttttc tatttttgtt ttccacactt tttctgcctc    2640
tgtggatttt acacagcatt ttgtataatt cgatttcctc tttttagcat agcaattatt   2700
ttagtcttta actttttaaa atcagttgcc ctagattttt ttctcccaac attttgggag   2760
gccaagggga gaggatcact tcaagccagg agtttgagac cagcctgagc aacatagcaa   2820
ggcactatct atacaaacat aattttaaaa agtccaggca ttagctagga ctgtgcctgt   2880
agtcccagct actcaggagg ctgagatgag aagatcaccg gagcctagaa atttgaggct   2940
gcagtgggct gtgatcatgt cacttcactc ctgcctagaa gacagttaga ccctgcctct   3000
aaaataaaca agcaaataaa taaaaagaaa ggaagaaaag aagagcaagg gcagcaaata   3060
gaaaatagta ataaatatgg tagctattaa tccaactatg tcaataatta ccttaaatgt   3120
tagtggtcta aatatactgc aatggactga atgtttatgt ctcctcaaaa tgtatatgat   3180
gaaatgtaag ctcccaaaat gatgttatca ggggagagtg tttttgggag gggattatgt   3240
```

-continued

```
catgagggtg gaggccttac aaatggggtt agtgctataa aagagaccac agagagctgc   3300
cttggtcctt ctgccatgtg agggcactgt gaaattatgg ccatctatga agaagtgggc   3360
ccttattaga catcaaatct gcaaatacct tgatcttgaa tttcccagcc tccagaacta   3420
tgggaaataa atttctgttg tttacaagta aatcatttta tgttattttg ttacagaagc   3480
ccaaaaagat gaagacatac accagatcac tccattctct tcttgcttgc atggtttctg   3540
aggatacgtt ggatgtaatt ctaatattct ctataggtat tttctttatg gctcctctac   3600
aggtaaggtg ttttttccct ttggcttcat ttaagaattt ttcgttaacc tttgattttc   3660
tgaagtgtga atatgttatg cctaggtatc atttgtttgt ttgggttttc ttggcatata   3720
tcttcctgat gttctctgaa cttccagaat ctgtgatttg ttgtctgaca ttaatttgga   3780
ggaatttttg gtattattgc tttaaatatt gcttctgctc ctttttctct ttctttgact   3840
tacagtattc ccattacatg taattatctc acagttcttg aaagttttgt tttgttcttt   3900
ttgttagtcg tttttctttc tgtttttcag ttttggcagt ttctgtttac gtatcttcaa   3960
tctcagaaat tctttcctca agcatgttca gcccactaat gtgtacttca aaagtattct   4020
acatttcttt tacagtgttt ttgatctcta gaatttttaa attctttctt aaaactttca   4080
tctctcagga attcaagact agcctgggca acatagtgaa actctatctc tacaaaacat   4140
tagccaggta tggtgatgca tgcctgtagt cagagctact caggaggcta aggtgggagg   4200
atcacctgag cctgggaagt tgaggttgca gtgagccaag gtcacgccac tgcactctgg   4260
attgggcaac agagccagac cctgtctcaa aaaaaagaaa aattccatgg ctctgcttac   4320
attatccatc tgatcttaca tgttgcctat tttttccatt aaaactccta gcctattaat   4380
catagttttt ttataattaa tactccgatg tgataatgtc ttagtccaat tactgtggtt   4440
ataacagaat gccacaaact gggtgattta taaacaaaag aagctgattt aggctgattt   4500
agaggctggg gagtccaaga gcttggtgct agcatctgat gagtgtcttc ttgcttcatc   4560
ataacatggg agagggcatc acgtgtgaag agagcttact cttataacat agccactccc   4620
acaagaatta acccaccgcc atgagagcca tgtgaattca ttcatgagga cagcgggtta   4680
agtttccaat atatggactt ttcggggaca cattcaaacc acagcagtta gttgtaacgt   4740
tcgtgtcatg tctcattctg gttctgatgc ttgtgcagtc tcttcaaact gcgtctttgc   4800
cttttagtgt gccttgcaat gtggaaatga tatactgggt aagaggagct gtagtaaaga   4860
ggcttctagt gacgtagtga caagctgtgg ggagagggag tgttgcacag tcctgccgca   4920
tgtcacagtc ttccagtgag cctgtgtccc tggactgtga acttcatgct tgcttctcag   4980
cttccccagc cccttagatg gtacagaact gttggagggg ggtggagttg tatatttccc   5040
ttgctctggg taggtcaccc tctgataaaa caccaggtta ggcctctggt gaaataattt   5100
ctcctgaggg cagaccttct attaataata gaatgttcca acctatttca aaatggttcc   5160
tcttctcctt ccactgccag aagcataatg agattttccc cctaatattc gtggtaagga   5220
cctagcagag ctccaggagg taacactctc aagtgtctca tactaccctg caccatgact   5280
gggctctgct ggagttctta atttgcagaa ctgcccacac tgagcctccc gcaatttctc   5340
aattacaggg caaactttcc cagccggcac tgggtccttg gaggtttctg tctgctggtt   5400
tcttcctctg gaggttgtgc ttctgtgttt gcctgtctct ccaatttggg gggcagtggt   5460
ttgcccaatg acctcaattc tctgaaagag ctaagaagag gtgttaattt ttcggtttgc   5520
tcagctttct acttgttgct agaatggagc gccaatagtg cctcctatag tgacatgtaa   5580
ccctcaactc tagagatgat gaagcatact aatgacaaag gagaaatgct tcagcagttt   5640
```

-continued

```
tctgtcagca cattacccct tgaaaaagct gcttcttcca cattctgcaa gagatgggtc   5700
tcaactcaga gctcaaggca aatgacttcc ttcaaggaga aggaataaac agtctcagaa   5760
accatgaaag cctgccccca ggagtgtccc tgaacctcag caggggccac acttaccttg   5820
cagaaatagg tgaggcatgc tcctggtaca aaatcccaat ggtacagaag gacaaattga   5880
aaaacaagtc tccctctaaa cccctgaccc cgagctacct agttctcctc cctagaggca   5940
aagctgttac cagattcttg tatctcctta acatatatcc ttagaagagc tgtcaagtga   6000
acacatgttt aagtgaaaac ctattttaga agtgcatttt cttaaggaac tttagggttg   6060
gaaggaacct gtgtcagtcc ttaattcaca acctccatta gtacttattg ttcttgcaca   6120
aaaatctttc tcaaaaaagc cctttccact ctgacatagc ttattctact tttacttagc   6180
tccaataact tataaaacat atttttgaaa gtctaaaatc tgccactatg tttttttttc   6240
ctaatcaatc tttactttga cctctaagcc agagaaaaca ggtggtcaaa tgccttttgc   6300
ctaagatgga acttagaata tttgaagacc tcagatcttc accctgccaa ataacgtgtt   6360
tctcctcccc tttcacagag catttggttt taggaaattc agagccacat tccttataga   6420
caagactaaa ctcttattca acatactcag aaacttcttc taagaggata accactcatc   6480
agaggaaaaa agtttctcat gtacagctgg caaagggatg gaaccatctg tgttattaaa   6540
attgacagac gcttatgaga tttattaagg gaaatactag agtcttagta catacttgct   6600
aatatagcat acatgaaggc tttatctata atttttttgg ccaagcagaa attttggtat   6660
tactcaccct aacaaatttc caagacatta tgaaatagaa ttttaggtcc tgacatcacc   6720
atttgtctca ggttttgaag cgttgctgga caagaggggt aaaacacggc tctgccttgg   6780
attcaaagtt ggcctctcat actagcaagt ataccttggt atcctggtca cttctcccgg   6840
ccacagcatc acattgctat aaaaggcaga tacaagtatt aaccagctca caggttatca   6900
gataagctta gtctgaccaa tgcttaacac agcaactggg ccactattgt cattcctgtg   6960
gtggtggcac acacacccag cctctgtccg ggccatggtc taggaccacc ctccacagag   7020
gctgtgagct agagccctaa ctgtgcaggg ccctaactat gccaggctac ttatctctct   7080
taagaggact tcattagtgc ctgctcggcc atacagtttt ttacttacca agtaacacag   7140
ttatcagcac actccaggta ctagccaagg actacaaaat caacgtgaat gtcagctttt   7200
gtatcaaaag ctcaaaggag aaactcaaac tttacataga tgtcccatga agatgttcag   7260
caaacccatt cttctctgtt ccctggaatc catcccagta ttgtgctatg tgtgtgtcta   7320
gtaattcttt acaaaaagct ctgtttcttg tgatgctatc agatcacatt gaagaatata   7380
caagccgtac tatgaaggct gttgtctcat atagtcctaa cgtagtgaga actgatgttc   7440
ttacatgctg tctttttggg cactcaaaga aattcctgta cagtcttaca aatcagttgt   7500
agcttaaatt gatttgtgtt gtgacttgta cacacaggtc acattccctt gacagaaaat   7560
atagtttaaa accaaatttg cagcccttgt taagtgaatg cacaggactt tattgtattc   7620
aggtctttta ttgtaagact cactcctgtc ttcattttat gttccactgt tgtgcttccc   7680
atttgccttt ctctagtttt gttttctgtg tttctacgga ctgctctcag cccaggtgtg   7740
caggaagcac acacatgcct gcagagcctt catggcctct gcattcaggg catgacttca   7800
acgcacagtg gctgtactga tttgttaaaa caaaggaaca gattacttct cctaattcac   7860
agggaagttc caggttgtgc gggcagtgag cagacctgtg tctgtctgcg cttgccctgg   7920
tgaaaaaccc caccgttcag gctgcagggt gcgagaccca ggcacaaaca ttttgctgga   7980
```

-continued

```
tgaggaggaa agatgtaagg ttgctcccct tcagagacag caaagggcag gtctgtagct   8040
tcacttactt caggattgtg atttttgaca gagccgagag atcagggttg ttgaaccagg   8100
cctgaaggtc ctagtgaatc tcgtgaagag aggaggggtc tggctgtaac atggacctag   8160
aggacatttt tactgcagga gaaggaacag tggggatggg gtggacttgc caaaggaata   8220
tagctcaagt tcctgcagcc caaaaaagct cagtttcttt tggccaaagc ttccgcgagt   8280
ttccctggca tttctcctgc gggagctaca ggggcagtgg gacacttagc ctctctaaaa   8340
gcacctccac ggctgtttgt gtcaagcctt tattccaaga gcttcacttt tgcgaagtaa   8400
tgtgcttcac acattggctt caaagtaccc atggctggtt gcaataaaca ttaaggaggc   8460
ctgtctctgc acccggagtt gggtgccctc atttcagatg atttcgaggg tgcttgacaa   8520
gatctgaagg accctcggac tttagagcac cacctcggac gcctggcacc cctgccgcgc   8580
gggcacggcg acctcctcag ctgccaggcc agcctctgat ccccgagagg gtcccgtagt   8640
gctgcagggg aggtggggac ccgaataaag gagcagtttc cccgtcggtg ccattatccg   8700
acgctggctc taaggctcgg ccagtctgtc taaagctggt acaagtttgc tttgtaaaac   8760
aaaagaaggg aaagggggaa ggggaccctg gcacagattt ggctcgacct ggacataggc   8820
tgggcctgca agtccgcggg gaccgggtcc agaggggcag tgctgggaac gcccctctcg   8880
gaaattaact cctcagggca cccgctcccc tcccatgcgc cgccccactc ccgccggaga   8940
ctaggtcccg cgggggccac cgctgtccac cgcctccggc ggccgctggc cttgggtccc   9000
cgctgctggt tctcctccct cctcctcgca ttctcctcct cctctgctcc tcccgatccc   9060
tcctccgccg cctggtccct cctcctcccg ccctgcctcc ccgcgcctcg gcccgcgcga   9120
gctagacgtc cgggcagccc ccggcgcagc gcggccgcag cagcctccgc cccccgcacg   9180
gtgtgagcgc ccgacgcggc cgaggcggcc ggagtcccga gctagccccg gcggccgccg   9240
ccgcccagac cggacgacag gccacctcgt cggcgtccgc ccgagtcccc gcctcgccgc   9300
caacgccaca accaccgcgc acggcccct gactccgtcc agtattgatc gggagagccg   9360
gagcgagctc ttcggggagc agcgatgcga ccctccggga cggccggggc agcgctcctg   9420
gcgctgctgg ctgcgctctg cccggcgagt cgggctctgg aggaaaagaa aggtaagggc   9480
gtgtctcgcc ggctcccgcg ccgcccccgg atcgcgcccc ggaccccgca gcccgcccaa   9540
ccgcgcaccg gcgcaccggc tcggcgcccg cgcccccgcc cgtcctttcc tgtttccttg   9600
agatcagctg cgccgccgac cgggaccgcg ggaggaacgg gacgtttcgt tcttcggccg   9660
ggagagtctg gggcgggcgg aggaggagac gcgtgggaca ccgggctgca ggccaggcgg   9720
ggaacggccg ccgggacctc cggcgccccg aaccgctccc aactttcttc cctcactttc   9780
cccgcccagc tgcgcaggat cggcgtcagt gggcgaaagc cgggtgctgg tgggcgcctg   9840
gggccggggt cccgcacgtg cgccccgcgc tgtcttccca gggcgcgacg gggtcctggc   9900
gcgcacccga ggggcgggcg ctgcccaccc gccgagactg cactgtttag ggaagctgag   9960
gaaggaaccc aaaaatacag cctcccctcg gaccccgcgg gacaggcggc tttctgagag  10020
gacctccccg cctccgccct ccgcgcaggt ctcaaactga agccggcgcc cgccagcctg  10080
gccccggccc ctctccaggt ccccgcgatc ctcgttcccc agtgtggagt cgcagcctcg  10140
acctgggagc tgggagaact cgtctaccac cacctgcggc tcccggggag gggtggtgct  10200
ggcggcggtt agtttcctcg ttggcaaaag gcaggtgggg tccgacccgc cccttgggcg  10260
cagaccccgg ccgctcgcct cgcccggtgc gccctcgtct tgcctatcca agagtgcccc  10320
ccacctcccg gggaccccag ctccctcctg ggcgcccgcg ccgaaagccc caggctctcc  10380
```

-continued

```
ttcgatggcc gcctcgcgga gacgtccggg tctgctccac ctgcagccct tcggtcgcgc  10440
ctgggcttcg cggtggagcg ggacgcggct gtccggccac tgcagggggg gatcgcggga  10500
ctcttgagcg gaagccccgg aagcagagct catcctggcc aacaccatgg tgtttcaaaa  10560
tggggctcac agcaaacttc tcctcaaaac ccggagactt tctttcttgg atgtctcttt  10620
ttgctgtttg aagaatttga gccaaccaaa atattaaacc tgtcttacac acacacacac  10680
acacacacac acacacacac cggattgctg tccctggttc aagtgtgcca agtgtgcaga  10740
cagaacatga gcgagtctgg cttcgtgact accgaccata aacccacttg acaggggaaa  10800
catgccttgg aaggtttaat tgcacaattc caaccttgag ctgcgcgggt tccaagagcc  10860
aggcccgtac ttgctgttga tgtcattggc ttggggagtt ggggtttggt gcccagcgcg  10920
gtcgttgggg gaggggcaag gcatagaaca gtggttccca gaccttgctg cacattggaa  10980
ttacctggga ttaaaaaaaa aaaaatcaaa acaaaaacca gtgtctggct cccgccccca  11040
gacattctga tttaattggc atggggcaag acctggactt gggatttttt ttaatgctct  11100
tcatgtgatc tgttgggcag ccagatttgg ggatcactag acggaagaag gattgttaaa  11160
gtctccggag atgttacttg ccaatgctaa gagctctttg aggacatctg gaattgttac  11220
aatattgcca aatataggaa agagggaaaa ggtagagtgt gattccaata ataaaggatt  11280
ccgcttttca ttgaaggaac tggtggaaag gtttcttctc tgctgagcct gcaggcccgt  11340
cctgcctgcc tggggtgccc gggagacgcg ggcctgctcc ggagactgct gactgccggt  11400
cctgttagtc aggtgtcagc cctgtctctg ccgaagagac tcttctcttt attttaaatt  11460
aaaccctcag agcaccacca aagcatcact tttctccctc cattggtgtt ctcattcttt  11520
gatgttactt gtttgaacac cactattagt agttggagat ttgttcctga gaaaaatata  11580
aataccactt aatttgcctg tttgtcccgc attcactcaa aacagaatgc tcctgaagac  11640
aagagagaga gtaggagaac agacgctatt ccattacagt aacataaaag actggatttt  11700
caggggcaaa ttattaaaat aggagatgag ctcttttaac agaaatttgt ttaaggcctg  11760
tgtctatcaa attcagtgga ttttattcaa gatgcacttt gtttagtggg agttttgttt  11820
ggttctggga catgctaact tctagacttg ctgctcttag aggtaatgac tgccagacac  11880
catttcatga gtcctaatcc ccacattaag cataagaggt gcacactctc ctcctatggg  11940
ggaaactgag gtacgaagaa ctaaagtgac tttcccacag ctggtgggag gcagacggga  12000
aattcacacc aggggcttcc aactccagat ccctctctca acttccaaac tccactgcct  12060
tgtccgagtt ctggtttcag gagatccaaa tcaggtgtgt gcaaatgtct aatgtcagag  12120
ctggcaaggg gaaagggccc agggagccgg ctcatgacga tgagcctgtc tgaagcttca  12180
acgcgggctg tccggcagtc tgcattcctg ccgagttcct cagccctctg ttgggtcacc  12240
ttccatagag gcagcttagt cctcagttca gtgagcatgg agtggagact gcttgagggg  12300
tgctgagcaa agccctgcct cttacaggat gaaggtgctc tccagaaggg acactggaaa  12360
gtattccaag gcgagtcgaa ttcccaactg agggagcttt gtggaaataa gcccgcccag  12420
ccccacttct ggagacgttc ccattcagta ggtccgagct gtcttaaaga gaaaccaaag  12480
tggggatatt aatggtatcc aaagtgagat ctaccccacc ctccctcctc aaaggaggtc  12540
agatcaagaa agcccaagcc cggcctggca attgggacct ttcttctcac tccagcccag  12600
ggtgaaggtg gacaagtcac tttgaccctt caggcttctg agctgttgtt tctgaattca  12660
gtgaatattt actgagtgca tagaatatgc tagatattct gggctaaagg ttgaaggggg  12720
```

-continued

```
ggtgagtttt aagggtttct gctcttgctt ccagattgct ttcaaatctg gaaaggacac  12780

cagtggtttg tgtgttagac ccacactgcc gtagcacaga atacaagaaa ctggctgaga  12840

gctccaatag gcttttaaca gtaatttctg gcttcacgta tttagtttca taactcatga  12900

tttttcaaaa acttctggtt tgaagacacc gattgccgaa agtccattgt gctgcataat  12960

tacacttggt ccacgtgaca gcactaacat gttctgaaat gtttttagaa gtagtctcag  13020

caaagatgaa ggattcctcc ctgtttgaaa agaaaatatt ctttgttttt tctttgatct  13080

aagctctaag actagcagct agcatctgaa actttttga cgagagtgac aaaccaactc  13140

taatattaaa ggcaattgat gattatgggc actgaaggga aggtaacccc aggctggtgc  13200

cccggaatag ggatgggtca caatgttgag gacatttcgc ctgttgcaga acccacctgc  13260

aacacagtgt ggcccttgcc atgtgacttg tgtgtgtgcc tgtgtgtctg tgtgtgcgtg  13320

ttttaatttt gacttcataa gtactctagt tatgagctta tttaacattg ggttttacta  13380

ataggggtat gtgttgagaa aatttcaaag ttttagaata tggttcaccc acatgttgct  13440

tccctgtaaa tataattttt aaaaccagat tctgggccgg gcatggtggc tcacctctat  13500

aatcccaaaa cgttgggagg ccgaggcagg cgaatcatga agccaggagt ttgagaccag  13560

gctgaccaac acggtgaaac ccagtctcta ctaaaaatac aaaaaaaatt agctgggcgt  13620

ggtggcaggt gcctgtaatc ccagctactc aggaggctga ggcaggagaa ttgcttgaac  13680

ccaggaggca gaggttgcag tgagccaaga tcgcaccatt gcactccagc ccgcgcgaca  13740

gtgtgagact ccatctcaaa aaaaaaaaaa aaaaaacaga ttctgttcct cagatccatt  13800

ccatttttgt tttcctttat cacttatgga catttgaaat tatggtaata aacattgtta  13860

gtctcagtta attattactg gtttattctt gaaccactaa tccatagaga atagagtgta  13920

aatcttaact tgttcctgta ggccatcccc attaaacatc atagtgtttt ctcattcgtt  13980

ctttttcgtt ttcctcctac aggaatgaat tttctaagaa aattccagca gttggctctt  14040

tggacgacat ctctagattg tcctccattg ggcccatagg cacaagctgg ccagtttgaa  14100

tttgggcaag aatccaggca ttggaactta ttcaaataac tagtttgcct gtaattttca  14160

ctttttcaga gtcatctgat aaagctttct tgctacacat ttagatagat acactcaatc  14220

cagttgtcta gaaagttccc tgagccagct gggagcagga ggggtagttg gggccaggaa  14280

tattgggggt gtgtttactg agcccctaga aagtaagtgc tagatttgac atttcaatcc  14340

ctgaaggccc tgaagttcag tatcaaatga ctggtcctgt ggactgagca tctgtgaatt  14400

gcatatgctt agagtaaatt ttactcctac cagtttcagc agcttgcttt agcaagcagt  14460

atggaaacac taacatgggg gagtagaatt tctctctctg atccaagttt tatctcattc  14520

tggtgggttt tcaaggagag actcggagtc caagtgtcct ttctgaatat atctggaact  14580

tctcattaac aaaagactca agttataatt taggggacaa ggcacccaat gagaatgcct  14640

tgcaggcagc cctaagtaca cctgcaatta caccattact agcgcggcag cacacatggc  14700

cctgacttag tttaaataat tacgtaagtc aaccatgatt gtttgccctt tgcatagaag  14760

ggcaagtatt ggtacctgtt acaacttagg ctttttttc tttatgtttg agccatgatg  14820

agtgatttac actgttgcat ccatatgttg agatgtaaga ataaattaga cttggtaatt  14880

gcccttaagt gtctggaagt caactgggga aagagagcta gagataataa gtgtgaaaca  14940

atgtcacaga atcaatgacg gaactcttcc caggacaaag gatgactttt gagttcagtc  15000

tttgccttta attctacatg gggaggagag cacgtttagc cacaaatgga agggattact  15060

catttgagct atttggttat atgattattt ccccagagaa taggatgtgc agggcattac  15120
```

-continued

```
acaagcagtg ccaatagcag caaagttctt gagagtgcta gtaattcaaa tggcaggaag  15180
agaaggaata aatggtaagg ctacctacag ttcacagaga gctccatcct cactgtggct  15240
ttggattttg tcctgtgtga aagagaagtg actgtgaact gacatgctgt gtttggtgtt  15300
ttagaaagat ggctgcagca gcggtttggg gaatggactg caggagtggc attggaaaca  15360
ggaaggttca tgactattgc cagagacaga ggatgaagca ggagcaagga agattcagga  15420
caggggactc cggggctgat caggaggcag aactggttga taagtatatg tagcagcata  15480
agaaagaaag aatcccagat tgacacccag gcttctcact tggaagcctg gatagatact  15540
gaatgcaatc acaaaggctg ggaagtcaat gggactgcag ggaagggaag ggaagggagg  15600
agaagaggaa gggcaggagg gtccaatatc aatattcagc ttttagatgt gttgagcttg  15660
aagtgctcag atggagaagt ccaggaggca gtagaatacg gtggtccaga gcacaggaga  15720
gcaatgtggc ttgagttgtc atttgctcac atatttccgt gtcagttact tgtcttagat  15780
cacagaacaa gttctcctct cacagtttcc tggctccacc tgtctcatgc tcaccgtcag  15840
catcgaaatt gagccacacc aggggttctg gataccagct tctctctagg tgaggctgct  15900
atagtcagca gctgattagt tgcagttatc agcaactggt aatataatat attgtgcata  15960
taagtgtacc agaagtcatg tttatatatt gctgcaaata ctcggaatgg ggatctcttg  16020
ttccctgctt aagaccacat cacattactt ggttttgtac gctagtggct gaaccaaaaa  16080
aagtaggaga tgattttttt tctttttttct taaagcagta gcttttgaac cttgaccatg  16140
ctttctaacc agctgagggg cttttgaaaa agagggtgcc ttactgtgcc ccagaccagg  16200
acaatcagta tttctgggga atggagcctg gcacacacac atttcttaaa gctcccttgg  16260
caattctgag gagtggatta catgttgtat gtagctcgta acgaaagaaa tcttgtcttt  16320
gctctcagac ccccatttct tactcatctc atgagctcct tcgagatcca gaaacagttg  16380
catatttcat tagtaaatca gttccagagt cacattttat ttcacaagtt agtccattaa  16440
aagtttcctg cagtgaggaa atagccagaa agaacactcc acccctcctc ctttttataa  16500
ctatagggtc tggctcgaca gagcaggagc atcgccatct tggacaagcc cctcattcta  16560
aagttcacct taataaaaaa ctgcctaaat tcaaactgca tcagcctaat ggctaaggtc  16620
agcatgacca taaaccacaa ataacatctc caaccggaaa cattcgaaac tcctcctcga  16680
ccagagacat gctagtcccg agataacccc cctccagcag ggaagatgcc agtctcggga  16740
taacctctct ctggccggaa agatgcctgc cccaagataa acttgcctcc tcccagagat  16800
attccaaccc tgccataaaa cttctccctc aaacaggaac attccaaaat tctgataatc  16860
tccctcaccc taaaaccaat atatactcct agtctgtaag agaaagcgct cttgaccaaa  16920
attcaccagg agtgcctccc aggttttaac taaagaaaac ctctctttaa ctgccaaaaa  16980
aaaaaaggga aaaaaaaaag ctttctgcag tggctttcag cgggcccagc atggcagcag  17040
cacctgagaa cctgttggag atgcacactc ttggacccca ccctggcctc tgagtaagac  17100
actggaaggg caggccccgg tctgtgcaca caagtcctca gggagattct gactgatgca  17160
tgccagattt tgagaactgc tgatatactc caggcacatc gcatgctggg atctagatac  17220
accaagggaa caaaataact gcacttgtcc tctgaggacc gacttacctt ttggaagggc  17280
tgagaaagag agacacatac aagatcactc cctgtaatgc aatgttttat aacagatgtg  17340
atttgggatt tcagtgggag cccaaaagag ggactgacta attcagcctc tgtgacaagg  17400
ggagtttctc agaaacagaa tgcttagctg ggcctccagg cacaggacag ggaatgagga  17460
```

-continued

```
aatacttgta ggccctgtgc tccttcagca aaaccctcag tttcttgtta tttttataaa  17520
tgcaaacatc ttattaaagt agatgctaag gcattagaat ttcctgcttt atttttctaa  17580
atgaccatga ggaaacctgg aatgtcaaag ataaagtgca acacattctg catttaaaaa  17640
ttaaaatgat cctttttaaa agtagcaacc agatgtgaaa aattggactg gagtccaggt  17700
tatagttgat agctttaact ttctccccaa cagcaacagc acaattttcc ctaaaatgtg  17760
ttatgaataa gtaaaatgac tacttcacat cctttaactc ttcctacaga aatctaagag  17820
agaaatgaaa caaaagtttg cacagttcta gacacgataa atacatgtga aatcacacaa  17880
ctcagaaaat gtcccttaaa ttaattgagc cattggtact tgtgaattag aagagacatc  17940
tatgttctga tccactgttg aaagctgtac aatgttacct atttatttgc agacatcctt  18000
tggaaacaaa taggtagatt tgcaacaaat aaagagtgga gtacagctgc tgacattacc  18060
ttgtatattc atgcctttat gtaaaaaaaa aaaaaaaaat atatatatat atatatatat  18120
atatatatat atacacacac acacacatat ggaggtaaag accactgctt gctttgcagt  18180
tgttttaaga gcattcatga aggattttat tttataagca gaaatgtgat atctgacgat  18240
tttaccacta catgcttgca ggccagtgca cagcagatga cgtcatgatt gttttagcag  18300
tcctatcgtt ttacttatga tgtcattaca accctttgct aaaatttctt tcctttactc  18360
caggttttgg ataaaattga tgcattgcac atagtctctc tgataagaca aactggcatt  18420
tgtatgtgaa aaactgtgca tgttttagtg tctctgctga tactcaaatt atccattatt  18480
ttagtgctgg aataaaaaca aaccacttag tgaatttgtg caggtcctta aggacaggca  18540
aaggtgtcct gagattttct gatcattgta taccaaattt tagaaacttt ttcaaaaaca  18600
tttttttaat ttcaaaaacc tggttttgtt tatttaccag caatcattga atacctgaaa  18660
gctttcagga gattttatta caatggtttc tattcactta caaaattatc tcctagttca  18720
ttctcataca ctgtaagcca ttgtaaatgc ttcaaattgt gccgaacaag ataaactaga  18780
caaactattt taagtttgtt ctagtgctaa cttgcaagat ctaatggctc caactagatt  18840
tttaaaataa agtatatttt aatatattat tagaaagtta agcaattatc tgtttatagg  18900
taacaaaaac cctggaaccc caatgtcaga tgtcatccac ttttgattaa gtccaaacat  18960
atgacagata aacaaaagat ggttggctgg gctcagtggc tcatgcctgt aatctcagca  19020
ctttcagagg ccgaggcggg cggatcacaa ggtcaggagt ttgagacttg cctgaccaac  19080
atggtgaaac ccgcctctac taaaaataca aaaaaaacag ctgggtgcgg tggcacgtgc  19140
ctgtagtccc agctactcag gaggctgagg caggagaatc acttaaacct ggaaggcagg  19200
ggttgcagtg agctgagatc acaccactac actccagcct aggcgacaga gcaagactca  19260
gtcaaaaaac aaaaaaaaag tggtcattgg agaattattg tgtcacctgt tgttttttaa  19320
tgtactaatt ttgagaggct tttaaataga gtgcactata gaactttttc ttggcttcaa  19380
tttgctacaa tgttaataga gaatcagaaa ccttatcctt atagatgttt cttgattttt  19440
ttaatttctg gtgacattta tgagtgagaa tagtgtattg ccctgttttc tttcttactc  19500
ccctttcttc ttccttcctt gctttctttc ttcttccctt ccttctttct cttcctcgct  19560
ccttcttttt tacaagctgt tatgaattag ccttcacaga gaaagaaaaa tttttataaa  19620
taactggaaa tgaaactttg caaaggactg cagatgaaaa actttgtcaa atgactgtaa  19680
aaatatacta tataattttc aaaagttaga aagtaccaaa cacactcagt attcatggtt  19740
atacaagtat gcatacacat gtattgctcc ctgaaaagtg gtgttgttaa gggagttttt  19800
cttagtacgc ggcttaacat atttttttct gtaatttgtt gttagttata atggggagag  19860
```

-continued

```
aaaacaggtt agagtctccc ctctcagttt caccttccat aaaacagcta aactagacga  19920
tcgtcagact ccttccagct gaaaacatct gtaaaattaa aaacaaatct aaatgtatgc  19980
aagatatgta tttaaacatg ctggtaataa gtgtgctgtc cctataattt agatgctaaa  20040
acattgatgt cataataata acaacacctc gcatttgtac agcacctcat agtttacaca  20100
atgccttaac attcttctct ctcagcctcc tacaacccca caggattggg atagctttcc  20160
agattgggag gtgagggacc caggctcaga gcgattctgc tgttgtccgt aatcaccagg  20220
ctggtgatca gtgggcactg ggtgctctcc tgctacacag cactgtctct caacatgcag  20280
gtcaaggtta cttattcctc cttcaagacg tcattgggtt ttttagctat ggatgcccca  20340
tcacttttag ttctatttgt gaatcaaagg ctaaataaag tattcctcaa aatttgttat  20400
acttctgtta ctaatgctta atgtccctca caatttctgt atatttctgt gtatttctgc  20460
tctgttttgg ttcctttccc aggtttcttt tttgttatga agtagttttt agactcaagt  20520
ctcttctgta tgtgttataa ctgcccattc cataagatac agggcagtga atttgtgagc  20580
cttgaaaata tttactttag aaatgagaag tatgactttt caacgttgtg tcatcaactt  20640
ctgtaaattt tccagaccta taaatacttg cagaaaaaaa atgaaaggag aaggcaactt  20700
gatttagcag ttgggtcagt tagcaatgcc tatggcaagc tgtagtaatt cccttacata  20760
gatttgtaag actcatttct atgatttaaa tgaaggcata cacttaacct ctttagggtg  20820
tgaaacagct tttacaaaaa gagacaaact taagaaacag tgtggccctc caagagtgtt  20880
cattttccat atcataccat ttgtaataag ctattctggc tgggatttac ttgcaagcat  20940
tggcttttaa gaagagatgg tttcacacat caaattattc acttggaggc actttctggg  21000
ttgaaggaat ggaatggaga gtgcggcagt gagtagatct ctcagtgacg gtgatgtgcc  21060
tctcccagaa gaaatttcaa aatgcagtgt tcattttcct ccacaagaaa ggaagaaact  21120
gttttgttat tgtttattcc taacatagtg gaaacttttc agtactctgg cagaaatttc  21180
ccaaaagcaa ttttctattt catgattata aagtagcaaa ggaaaaagtc ctgcactcca  21240
gctgagcaat ggatctccag ttgttatcta ggtgctgcag gtttagagag gattgccagg  21300
agaacacatc gatttttcag gcctgtgatg acgtatctct tgttgaataa gtaaaccctt  21360
ccagtaaaca gacagttagt atattgattt cagggtggct ttagccactg aacctgtaag  21420
tcttgcaaag gttacttggg caaaagcatc attattttac cttcagtcaa caaaaatcta  21480
cctggccaag gcagaacaga aagttcagca atttgatgaa gtgggacaac atgaagaatc  21540
aggtgagttg cctacttttt cacttcactt tccaccttta gagattcttg tttagatgca  21600
gagtagtgac gtgcctggtg tcagggagag agttgaatga gaaaagtccc agaagggcag  21660
aagacttggg tgattatctg agtccatctt tccttatcac atgacagagt tcttgaagtc  21720
ttggctagga attctaggct tttagattct ttgggcaatg gctactaaat gttcataatg  21780
ttgctcagtt gcaaaaacaa gacattcaaa ctatagccag ggagataagt agtcacgaac  21840
tcaaggccta aattctgctg atggagccga tgagaattgg gtgctaaggc aaagagagtt  21900
gccaatatta tattcttcgg ggttttttgt ttttattcgc attttggaaa aggaaaatat  21960
tagcattcct ctgacttaat attgagaaga cattgggcac tctttttcct cccacacttg  22020
tcttctttca ctaggtgaca agggaagagg tagcatgagg tggtggtcac aggtgagagg  22080
ggctgttgtg agcacaggca tgttgactgc acattggtca cctagtagaa gttttgcagg  22140
cttggtgact tctgaacact gttttcaagg ttgattttta gttgagagaa cctctaggta  22200
```

-continued

```
ccacgtaatg ttattaacag tagtactgat ctcacaatcg ccctatgtcc cattcacaag  22260
atgttctgcc aagccataaa aggcccagtt aagtttaaga gaagtctcaa aagtaacaga  22320
tgataactaa ttaataccca gtgattttga aatgtagaca tcaaacatac caattcagtg  22380
gtatcatcct tagaggcaga cagaggatga ttaaatcatt cagcccatct ctgtctgagg  22440
acgcagctta gcacagcatg gtggaggcta aatgggcctt aagggaaaaa atgatatctg  22500
aagatgcaat ttatttcaaa aagagtttgc tcccgtgaat tttcactctc tatgtagaac  22560
ggcaccagca cacacttttc ctgagccttt gcatgtgtgg caggcagcgg cctggcatcc  22620
tggggaactg aatgaggacg cagatgaccc ggacgtgttc acagtttgac acatctgact  22680
cccagatcag ggacagctag ctttgctggc tggttaagtt gatgattcca tctttgcctg  22740
gttctctgac tgtctcatgc tttctgttat tactattttg cagcagatat ttctgctcat  22800
ttttcaatca tatatgcatc ctggatggca tagagttgat tctcctaaca aatcagtgtc  22860
cctttgtatt tttttctggc cataagatag aatatatatg tcatttatta aaaatggaga  22920
aaatgttcag gagtttcttg actcagagag ggaaaaggga tactcagggc actttttcag  22980
ccaggaattt actacctttg cagggtaaag gggactcacc acgctggaag tcaaaataag  23040
ccaccagtgc caagtgttca aagcccttag aatcacaatg ctcttaaagc aaagtcttca  23100
acaatgcttg aaaacttcca ctggttctca gtatgtccaa aattgtcatg tctatgaatg  23160
attttctcaa tctgaaaatt tttatagcag gctaaagaat gagataggtc agtgtgattc  23220
tagaactaat cattaacatt caatagatga ctattttatt ctagaaaaag cagcaacttt  23280
ctatttactc tctattttga gggtaaattc tctgtaagta gaaaaagcaa aatgtggaca  23340
tgggactaac atatgaatat acaaagcaaa tgtaccgaaa aaatcttaag acctgccttg  23400
tggtgttttt tgttttgttt tgttttcatt aaagtgactt gttagcctct tgctccctgt  23460
gaagcacagg gaggtgacgt gatgtgcaca gggcagactc tgccatatgc cctggccttg  23520
aactcagggc cccctgggga ctgcagggga tgctggccat gctgagcaat gcctgtgggt  23580
gtcagtttcc tcatctgcag aatgagggta ggcctggtgc ttatttcata gggtcgcaga  23640
ggggattcag tgacagggtg gtgtagaggc tggagcgtgc cccatgtgtg cacgacagcc  23700
ttccaactag gggaggcggg cctgggctct caccagagag cctgtgttct ccatggctac  23760
atgactttgc cccagacgtc cttcccgtgg tctggaccct gggaagtcgc caagagccag  23820
acaggagaaa ggctccactt ggctctcctc tttggtgacc atcccttgcc tccatggcgg  23880
gactctcagg tgacatccca ccaaccctca ctttgcttcc ctggtgggtc tcactttccc  23940
tcaagagtgt tgctttttttg tttcctgcat agtcctgggc cagttttgat aaccctcttc  24000
atttcacttc agaaaccctg atgatttctt cctgtgctct ttttacctta ggacttttac  24060
tatgacgact gtgactggcc catttcttgt ttttttctc ttgctctgct ttctccccca  24120
tcatcactaa agcagacatg gcaatgatgg ccatgcacac tttccaaggg tccagctgta  24180
gatcttcatg gttccccagg tgcctggacc atcttgtgag gagggaggca aacacaccct  24240
gcctggagca cttggccctt tcggcaatgt tttggcttcc tcaagtgaga aaagaatgga  24300
tttgtattcc ccctctgcat tattgttttt gttttgtttg tttgttttgt tttgtattga  24360
gacagagtct cactttttttc cccaggctgg agtgcagtgg cccgacctcg gctcactgca  24420
acctccacct tccgggttca agtgattctc ctgtctcagc cccctgagta gctgggacta  24480
caggtgcccg ccaccacacc tgactaattt ttgtatgttt tgtagagaca gggtttcacc  24540
atgttggcca ggtgcccatt attatttgat ctggaattaa ctgagctact gcaggaattg  24600
```

-continued

```
cttgattcac tgatgactgg tgttgagcca gtacacaccc acacccaagg actgtgactg  24660
tcttctgagg tccatcctca gaaattcctg tctcttcacc tagtgtgtaa taaggcctgc  24720
gcgtgttata tggaactgta aaaaatgcgc caaccatctg tccttcctct ttatctgatt  24780
acttatcatt gttctctaag ttgcaagtta atagactgat cataaattaa tgcatgctgg  24840
agacttgctg tttcctacta gcagcatata aaagttattt ttaaagttgt tttaaatctg  24900
tgagtaaaaa taaattgctt tgctgcaaga aacaccaaac atggaaaagc taacggttca  24960
aagttaataa tttatcttat ggacatcact agtggcatag ttgctttaaa cagtgagagg  25020
atttaataga tatttgattt gcaagtggga tgaagggtgg tctaaccttt gtcctgtgtt  25080
taccttccat gagatcctag aggttgtaca gcacagtagt ggcatgtgac acacttgaga  25140
gtgcctgttc tgtttggaaa cctggaaact atgaagggaa gtggccttcg agcttaacac  25200
ataagacttg ggaggcaaaa ccttttattc tctttaaata ttcactttag gataagcatt  25260
tttttaggtg ttaggaacag ggaaaactgt gtggttagga aggaagaaag aagaaagtta  25320
actgttgtac attccctagg taatgttttt aagcattgtt attcactttc aaaacacatt  25380
ttatttattt ggacttaata ttttgatctt attttttcaa tttcttttaa tttaacagac  25440
aggatgagtt tttttatagt tgtattactt agaaattata ctaaaaatgg ccgagtgtgg  25500
tggctcacac ctgtaatccc agcactttgg gaggccaagg caggtggatc acttggatca  25560
cttgaggttg ggagttcaag accagcctgg ccaacatagc aaaaccccgt cttcactaaa  25620
aaaaaaaaac aaaaaaaaaa ctagccacgc atggtggcag gtgtgcctgt aaccctatct  25680
actagggaga ctgagacata agaatcactt gaatccagga agcagaggtt gcagtgagca  25740
gagattgcac cactgcactt cagcctgggt gacagagcaa gactctgtct cggaaaaaaa  25800
aaaaaaaaag gataaagaaa tcatactaaa aacaaaacag aatgctgacc accttataga  25860
aatagaaata gtggtttgct gtgatagcaa attttcttgt taacttttta tttttaaaga  25920
attgcacatt cacaggaagt tgcaaaaaat ctactgggag gtcctatccc ccttccccca  25980
acctcctcca gtagtaacat cttagtagca aagttttgta tatttatttt gatatcatta  26040
tctaagtttg acatcattat ctaatattaa cctaagccaa aagcccacta ttttaattat  26100
ctagtgatgc agtgttatag aactcatagc ctttcacagc attatttgga agttaatttt  26160
cttaagtgaa atgtttttgg tctttaaggt ttggaggcca tggaggcatg aggagaaatg  26220
ggatgaggga gagagagcta agatagataa agacagagat ggggagatcc actgattcgt  26280
tgaacaaacc agatacttcc ttatagtttt tggattaact tacatgagct aagtttatat  26340
tctgttcaga tcacaagtgg tcaagtttgt gtgtgtgtgg gggggggggg gtgggtgtgt  26400
gtgtgtacca ctctacccat cctatattta ttgtcctgta tttggtctgt tctgccttct  26460
ttattttcag gataggtgtc ctaaatgagg gtctttggaa agctggtgag gccatgttgc  26520
ccgtttcagg tgttccgtgc tcaaatgtat tcatttcttg aaaaattcag ggagtgcaca  26580
cttttgtaca ttttcctatg tgtatatgat accattatat aaatcttaaa aatatatatg  26640
gttcacctga atccccagcc atttggtaga gaagatagaa aacctacaga ggaggctaag  26700
attttattag aaaattcagc ttctcgacgg aggtattggc tttaaagtca aggcaatgca  26760
tctattcttt cttttgatat aactagctaa aagatctctt aaattcaaag tggccctcat  26820
cttactgtta ctgcaattta ctcttaatta caaattatat aaaaataggt tttgaaatac  26880
tgtagcgaca aagtaacata cctctgctcc attacacaga taaaacctct aaggaacacc  26940
```

-continued

```
tcctctctta acaggcatta accaactgca gaaactgcag aaggacaggg ctatttggga  27000
ataacacagc tcccttcctt gtctgttccc tcccattgtc aggcttctgt ggagccatat  27060
tcagagcaac atagggaggg ggaagagaaa atcaacccct tggtgaagga aagctcccaa  27120
ttcacagagc aaacatgggt actcttgttt gtgggagctc ccagggcctc ccagctcacc  27180
gagcattctg agccctgatc cttacactaa ttgtattatg caaccataaa tgatgtctgc  27240
tgtaccagcg gggacagttt attttaatag attggtataa cttggcagaa tcttatctgc  27300
atgtttcatc ttggattttt agctcaattc aactcaatag gcatgtgtca aatgtctact  27360
gcagactgag cactgaaaag ctgctgggta cagggttaca tggatagaaa acgtagcctc  27420
tgacccctaa ggagcctgta atccagatcc ccattctttc catcccattc tcccaagcaa  27480
gaatttacct aatgtggttt gcgagaattt aagagctgga aaggtggtca cgagaagccg  27540
gaatgggttc gctaaaatgt gtctatatga ttaagcataa cgtagctttg cagcactctt  27600
cacagcttcc tcagagcctt ccgcacgcgg tgtctcattt gaatacttgt gtgaggatag  27660
cctcataccc ctcagtgagc tcttcatgga gtgatgcagt agacagcaag cctcacactt  27720
ctatgctcac ggaagaccaa atttgccttg aaaaatcttt atagtctctt cacatttcta  27780
agttgacatc aaaaatcggt taccataaaa tcctaatagt tgaagagatg taatttcaat  27840
tatttggtaa acctgacctt cattgtcaaa gcaattagtc aactcagatt tactttctcc  27900
cagataatag attctgactt cttttttttct gattaaaaaa cttaacacct tcctcaggag  27960
atctatctca gttctgaatg ctgattctaa ctaagaagga tatttggcta catgctggga  28020
agaggggtac tgaggcacgc cgcgattcca ctccagcatt tccagttagt cgggtgcctc  28080
tgcactcccg gtgttccggc gcccagttag ttgtgtactc tgggctgtcc ctatactgga  28140
gtcctaaaac acttacgact gcagataggg ggaggttttt caaaaccttg gtctgaaaag  28200
ccatagaagg gagataggaa agcggggggg tggagccaca gtacattcag gtggatccgt  28260
ttttggaaat agtacaaact ggaggtgaaa ccctggaaat tgatctgtcg ttcacatgct  28320
tcatgccgag tccttgtgga cccacagaga cacactcgcc ccagtttgaa ggctgctaac  28380
ttgattctga ggacaccagt gaggtggtag tgtgcaaatg atgtgtgagg aaactttgga  28440
ggagtctcac cctgcctgga gcacgtggcc cctaaaacag cgcagcctcc caaagacaga  28500
agatgtggac tagtgagaag ccaggtatgg tgactgctgc tggatgaagc ttgtcccacc  28560
agaggctcgc ttgtttcatt gagcacctac tgtgtgcttg tgggatgcaa acacacgtgt  28620
ggtccctgcc ctcaggttaa taggcagggg tggaacagtt atgaaactgc tctaaagtca  28680
ttttctcaaa ctgggagtga caaatgtatc cacttggaaa agattgagaa ttttataaga  28740
tttttaaatt tttgtttatt cacattgagg agaatctaaa ttcttttgaa cttatgtata  28800
gatttcacca ttttatagta ataaatcagt cctcctgtgt gtgtgtgtgt atgtgtgtgt  28860
gtgtgtatgt aaacctcacc ttgcaatatt attattttaa atagccactt gcatcttaag  28920
gaaattaaga ggacaaaaga aaagctgctg ttttgtatgt atccacatat ttaccagctg  28980
cttccctgcc ggcaggtgct ctggttctgc actgcctgtt gtcccttgcc tgaaaatggt  29040
tgcctccaat attttgctca gttttctgat tgtttacagt ggcagaggag ggtagatctg  29100
gtaccagtta gtaattgcca gaggtggaag tctgtggatg aaatttgtat aacatggaac  29160
gttagttcca cagttaatgc tactcaattg gaacccatgg aaattatttt ttggtgaaaa  29220
gggcccatgc gttatgaaat ttgagatcca tcactttaag tgaatgtagg ccctggatac  29280
agtgggagct cagaagagca aatcagttgg tcaccttgct caacgtattt tactaagggc  29340
```

-continued

```
atcagtaagg ctttctatga cctgctcctt caatgcttgg ttgacatttg gggagcaaag  29400
ataaactaag gattctaagt tctgtcctgt gatgctgtaa ggggaatctc aaacctctag  29460
gtggaggagt gcagagatga ccaggatggt ggaagcctgc aggagagctg aacacctgaa  29520
gacacccagt gggaagacca ggacctttaa cgcccatatc tgctgctcaa gactggcaga  29580
gagaagaggg tttgtgatga gaaaaggtgg tgaaaggcac aaggaggcac agagcatgtc  29640
aggtcccata tcccaaaagg aatgtgcttg ggtgagggag agctcctcca tggctggagg  29700
cattcagaga ccaggcagtc gcttgtgggt ttgtgattag agtgaggttc ttttataaag  29760
ggagtgagaa gagaaggtct gtggatactt gagtgtatcg gtaattaaga aataaattgt  29820
gtacatccca tttctttcca cattttcctg ggctgtcaca gtggctgcaa agaaagcagt  29880
ccgtgaactg aactgtgatc ccagacaggc aagcacacca ggaatctctt ctcagctgtt  29940
gataatgagg gagcgctggg gagagaaatg gggtcctctt tgagtttcct ctgtgccgat  30000
acctttctct ttgttaaaac agctaattaa acactgaagc agtatagctc tcttactata  30060
cactggtagt catagttctc ttactgttct cttcactgac agttctctta ctatacactg  30120
atggtgacgc agaaattcag aattccccgc atgtgtcccg gtttgaaagc cactgtgctt  30180
tgctgtggat taggatcaga cagttgagtc ttgttccaac aaggaaagtt gcttattgga  30240
aagttttgct gcagggagcc ttgagttctg catcaggctt ggaagtgggc tctgtggagg  30300
tcagaaggag gatcccccac ccgcagcctc aagaaaaata tgaaaagtgg attatgcctc  30360
tgtagctata ttgcctataa actttctgca gaatgacagt attcatatcc tacatttttt  30420
caaagcgata ttaatcctga gacctgcagc taaagtcaag tagaatttag ggataattaa  30480
taggaggaag gtggggttgg aagatctgca tgattatagt cctctgatat aactggaaaa  30540
ttctttccat tagcaaggag ctttggttaa tataaaatgg acagattaaa cctaggcaat  30600
ttattttact cattgctgta tttttatttc agagctggtt gaaaatatta caaagtaata  30660
ttttaaagtg cttatctaaa ctcttactct gcattttatc attgggttat gaaatgactg  30720
gggaaagact tttcttgctt ttatttctca gtgtctactt ataaacatgt tttttgaact  30780
actgtttttg tgacaacatg ccttttttccc agaaaatctc aggttaacat taaataggca  30840
ctggatgttt atctgatctt gtttatagaa acacaagaaa attttaacct tgtatatact  30900
ttactcaatt aactaggtaa gaggtcattg aaacatttag aattccactc tacatttcaa  30960
taattatcag gtgaaagcta ctgcatctac atcagaagat gtttgtaatt tatttaagaa  31020
taaaattagc tatgcaagaa atagtatgtg gagtcctatg tggaaatcac agaaaccctg  31080
acaacttgat gatctttccg caagctaaaa atatcactct ggatcacagc agtagaggac  31140
tctgtaaatt taatctgtgt gtctcctgta aataagtgca ttagcagtac acaggtggtg  31200
tcagagtcag tgatgatgga tagaaattct acataaaatc caggctcagt ggctcatgcc  31260
tttaatccca gcactttggg agtctgaggc gggtggatca cctgaggtca ggagttcgag  31320
accagcctgg ccaacatggc aaaacctcgt ctctactaaa aatacaaaaa ttagctggat  31380
gatggcacat gcctgtaatc ccagctattc gggaggcgga ggcaggagaa tctcttgaac  31440
ctgggaggta gaggttgcag tgagccgaga tcacgccatt gcactccagc ctgggcaaaa  31500
gagcgacact ccatcgcaaa aaaaaaagaa gtaagaagtt ttacataaaa acgtggagtg  31560
agcccaaggt gccatttatc cagcccatac acatcgtacc atgtacagag tggacaccag  31620
ataaatacat tgactgcatg ccacaaacat atatatgtag gcaccgttgc attcaaatac  31680
```

-continued

```
acatctgcag ccctaacaca tctttatttg ctaacgagca tcaatgtatt taaaaacaaa  31740
catgtttaaa ctagtgaatg attagattat aatgatctta attcataagt tttctcattg  31800
gccttttgta tacttcaatt gtaataccta gaaaaacagt tatgtccaaa ggagtgaata  31860
ggccttatct gaaacaggtg agcgtgacaa gtgttttctt acttatttta cttttcagat  31920
aattcatcct taaagtacat tagtttaaaa gtactgttta aggaaacagt acttggatta  31980
aaacttgaat cattgttaag gaaaactata ccttaacttc atgtaatcac aattaaacct  32040
cttcatatag aaggatctaa gaattttctg cagcattcac cagcaccaaa aagctcagag  32100
acatatattt ctttctctgt atatgtattt taaattcaag ttagtataaa ttgacaggca  32160
ggtcagagta atatatgatc ttctgagtcc ccttagtaat taaaagaaat gattattttt  32220
gcatgaaata tgataaagtg attttaagtg cctgataaaa agtcttaacc atgacaacca  32280
ttaaagatta catcaaagaa aaataagttt gactttcatt taccttggaa acagctatta  32340
actggtaacc tcaagaaaca ccatgaagag tcagtttgct ccacacatgt cttgtaaaag  32400
tcaaataact ggtggttatc cagtaatgac aagaggtaga agttacatcc ttgctgtctg  32460
attgaacctt cccagagctg gcacaaggct gggaagacca taggtgctaa atgaggaact  32520
acttaaagaa agaaaatgga atttcacgga caagaaaatc catgtccatt tggttctgtg  32580
acccacatcc tttgtatcct atgctttttt acacttggta catggttgca agattgcccc  32640
tgttttctac ttatagttcc atgcagcatg gatgtgggaa aaagtctcct ctgcaaaggg  32700
ggttaatgca ggtcactcta cgtatgtgca cgaggtcgtt ataaagctcg aaaatatggg  32760
ctcaccaacc aggtgatttt tttaattatc caaccagaag acataacata taggggaatc  32820
aaaagaaatc tctgagtaaa ataatgataa caggtcaaac tttgcggtcc cacgtgaggc  32880
tggagatgcg tattgtcttg actttgcatc tacaagttta acaaatgatg ctttctcagt  32940
ttacctctgg aaatggaaat tagcattgca aatgacttca tgaggaggta gaagctatct  33000
gtgaatttcc tttcgctgtg tttacgatag actctcacgt ctagatgtgt catgtattat  33060
gttaaattgg tatgtcttga agttataaag cacagccctc tataagtata tatattccac  33120
ctctttcaaa tcggatggta cctatccttc aaactgctat ttaatgactg tctgctatgt  33180
tcaaggcact gctctcaatg ttaatacttg atgagatcgg gcgcgttcaa ggtggcatgg  33240
ccgtagactc aatgttagta tctgaaatat ggcctacgag ctgagttgtg aatcaagtta  33300
atagattttc ggaatgttaa ggtctaaacc agtagctctt aactgagaca atcctgtcct  33360
catctcacct gggagacatc tggcaatgtt tggagaacct tttggttgtc acactggggc  33420
atctagtgag tagaggtcag ggatggtggt aaacaagttt ttttgtttgt ttgttttgtt  33480
tttgagacag agtctcactt tgtcacccag gctggagtgc agtggtgtga tctcagctca  33540
ctgcaacctc tgcctcctag gttcaagcaa ttcttatgcc tcagcctccc aagtagtagc  33600
tgggattaca ggtgtgcacc actacactca gctaattttt gcatttttag tagagacggg  33660
gttttgccat gttggctagg ttggtctcga actcctggcc tcaagagaac cgcccccttc  33720
ttggcctccc aatatgccgg gattacaggt gtgagccacc gtgcccaggc taacattctt  33780
taatgcatag gacagccccc accatacaga ggaatcccca gcccagaatg ttaatagttc  33840
taaggttgag aaacccaagg ttaagccaag tcaacttatc tatcttcttt aaaattgcat  33900
aagaatgcag tcctgttctt cattcctctt gctttgcagt taatgatcct ttgcctggac  33960
tttctaagtg cccagaagag caacagccag catgcaggat ggcattcctg accagttgca  34020
cttggcctag cattccaacc tcacctgcct cagcttgttc aacctgaaaa cctaccaagt  34080
```

-continued gaaagcaaga gccacgtgaa gacgccttag ttatatgcac ccacccagac acttgctcag 34140
aaaggaatca gtggggccct ggccttagaa actggctcct tcactgctgt agaaacaaca 34200
taaatttaac ataaaacacg tgcttttctt ttttcttctt actttttcct gtcttggcaa 34260
tgcaaggatg ccattaggta aagaaatcct tcaccacact aatcctgcag agccagaaga 34320
gaaaccagct tgttctaacc cagctttgtc atggagagaa ggcagctgct ccagtctgaa 34380
ctattctttc ttttggtagc agcctgccca agggtgaaag tgtgtttaat agtttgaatt 34440
acacaagtga acagtaaatg tatgcctgtt tctgctttat gggactttga aataatgttg 34500
tttgtgccaa ggttttagat tactatacct aacaacctag aaaaagaaat gaaaaggaag 34560
ccttctgcca ggcagaggtc actacgggcc tggagctggg cacctgactc agcagctgcc 34620
cagatcccca gagctgagaa gtcaccatgc atttgtggtg cttcgagcga gttaccagag 34680
tcctggaaca gagcagcaca cctgcggggt gtccccttgg catttgggca gggcaggtga 34740
ccaagggtct tgttggaact gaagtccagc ttgaaaagca aatctggttg tgagctagag 34800
tccagtaaca cttgtttccc gccgcccccc gcataactcg tgtgtcctaa aatacaataa 34860
tttcttgaac ttcagtcact tatgcctata agcgggcata caacaggggc acaataaatg 34920
tttgttaagt gaatgaattc tttcagaact agatgggatc ttagtccaac tctcttattt 34980
aacgaggtcc acagaggttc tgcgattgtc taagaaagaa ggctgtgttc atggcctttg 35040
ttgtttacgt ggccctgtga ttctcttggc tccgtgaaag tcctgatgca gacattccgg 35100
ccatctagaa aggcatgcag acaagccatc cagctggcat gatcctgagt ccagctttct 35160
ttaaaagagc ttccaaaact gcttaagctt tgactgcaca aaacctgcat cacctccagt 35220
tgagaaactc aagagaataa gtaagttatg gagttggaga ccccagctta actactagtt 35280
ttaaaatagt gaaatcaaca ttttcaaatc tttgacttca ctaagattta ataaagttta 35340
ttaatcatat attatgagtt attgctctct ctttatgtct gtaatgcagt tgctcctctc 35400
tgtataaatt aataagtttt agagatccaa aatgagaatt ttaaaataaa ttacgtatat 35460
tttaatcaag tttaatttga ctatatccag ctaaacaatt gattgaactt cacttgcttt 35520
tctatgacag gttttttgtt cttagtaaaa gaccccagtt ttctcacttg tgaacagaag 35580
gggttagact tcatgacagc taaggttcct tccgtctcta acaaaagtgg cctgaagaga 35640
ggcttctaga ctatactcac ggtgggttct tgggacctca gagtcagctc catcacttaa 35700
gtggctgtgt gattgagtgg agacacctca atctctttgt gcctcagttt cctcacctgt 35760
cgagtgtcaa catgatggca cctaaagctg ttgagacttc agaaaggtaa tgtgtgaaaa 35820
gtgaaaagtg cctggcatcc aggaagtact caataaatac caactatttt attgctgcag 35880
ctgttcttat agatgtgatt tctagaacat tgccttctaa tagggtagcc atgggccaca 35940
attgttggct gttcggtgtt tcacatatgg ttagtccaaa ctaagatgtg ttgtgagtct 36000
caaatacaca ctggattgtg aagacttagg acaaggaaaa caatgttaat aaaatctcat 36060
tgataacttt taaattaatt acatgttgaa atgaaaatat ttgggacata ttgagttaaa 36120
taaaacagga gattaatttc ttctgtttct ttctactttt tttattagtg tggctactca 36180
aaaatgtgac attatgtatg catctcgtat tacatttcta ttggacagca gcgctctaga 36240
cagtactatg ggtagtatct gtggggaggt tctcagaaac atgtcgcatg ctcttttaga 36300
accttaaagt attcctagtc tcctctactt ccagcccttg gctcttgggc ctcagtcttt 36360
ttacttttgc ggctgtgttt ctctgaaggc ttggcattag tagattgaaa agaataacca 36420

-continued

```
tctagggaaa tgtgaattca gtttctttct gacattctgc tctctacaag ggatattat  36480
gtacacataa acctacttcc aaaataatga agtgaggcct aattccttac tcttcagaga  36540
gcccactgtg gaagtgtcac tgaccttgtg tatgggctgc ccttcatggc tctgggagtc  36600
attataaagg gcagcatttg gcgtggtgcg tcctaagcca gtgtttctcg gctctgttcc  36660
ttagacatgt gttagtgtta atagatgttc ttggaaaaaa aaaaaaaaaa cagcattctg  36720
aggtcaaaca tgctcagaaa gcttggaatc tgcactacgc ttctcgtaca catttcatat  36780
taaagatttt ggaaagtcct gcaatacaga gccctgtcta atattgccac aacccacaat  36840
tgctcaaatg taaatagatt tgagtttatt cacattcaga tcacctctta aggccccacc  36900
tcccaatgct gtcacaatgg caattagatt tccacatgag ttttggaagg gacattcaga  36960
ccacagcagg ggaaagcagg gtacttgctg ctttgcaagt gtgtccacat ctaattaata  37020
gtacagttct tactcttggt gtgtccggtg atattaaaaa ttaatgtgcc ttatttagat  37080
aagtaacata aaaatcacaa aatgtatgcc ttagatttat atgtatttat aactagtcta  37140
tttcctgaaa acagttgaga caccttgtaa aagttaccgg tacgataggg ccattccaac  37200
aaagctgtaa agtggtgata acacagtcat aaagaagagg agatagctct gggagaaaag  37260
gtggcccaga aaccagctct gagcctcatg gctgcaggca aggtctgcag gttcctggtc  37320
ctgattgcag gccatttgct gccttgagtg gtggttacac aaggccagcc ctgggggtat  37380
cacccagaac acctagtaca cgaatttcag tttagaggac gaagcattac tggagtattg  37440
ttatgcagga aaactttttc ctaaaaatgc cctgaaaaga gagtagccta atgcattcaa  37500
tcaaaatgtt tttaagtgga aaacatattg tgtgtacttg atctggcctg ctgcttttaa  37560
aagattaaaa ctgggactgg gcatggtggc tcacacctgt aatcccagca ctttgggagg  37620
cagaggcagg tggatcacct gaggtcaaga gttggagacc agcctgacca agatggtgaa  37680
accccatgcc tactaaaaat gcaaaaagtt agccaggctt ggtggcgcat gccggtaatc  37740
ccagctagtt gaggggctga ggcaggggaa tcacttgaac ctgggagccg gaggttgcag  37800
tgagctgaga tcgcatcatt gtactccagc ctgggcaaca agagtgaaac tccatctcga  37860
aaacaaacaa acaaacaaaa aaacactggg gccaaagaac tctgtgtgct gtatcaccta  37920
accacatttc atgacacggc tagagaagaa tcatgcaaat aaaaatttcc aacatgttcg  37980
taaactggga aagtatttca ctggggagtg agcagaaaag taatactata acctctatat  38040
ctagacaaat gtgaattcag tttcacatat aaatatataa gtgaaaaaat atataaatat  38100
aaataatatg aaataatggt tatctcacca ctttctacat cttttgtgaa tattttatag  38160
tgctcaaata tattagtgca ctagtatatg tacattacat taaataacta atcatttatt  38220
aggaggatgt gcttgttttt tgctaataaa gatgataata aaaaaatcct tagacccccc  38280
ctcggtttgt tttcagttag gaattaggga tatttataag aatatcttta aatgacacat  38340
gccttgctct gggacgaggc atctgcatgg gtgacacata tgtgttgtgt gtacaggctc  38400
ccagcatttc cagggccctg ctcagaatgt aggccttact gattcttaca gagttacaag  38460
cgctggtgag gttggcgaag tttaggtaaa cacagctggg aatgccccat ggcctctggg  38520
tgactttgga catcactgaa ctttaccctt agagatgcat acctgcatct tttttaccct  38580
gatagggcct tccatgatgc tttcaaagtg tttttgtctg cttttcggtt aatagacttt  38640
cacagtagcc aattgaatat attggttaaa tgcatctctt tatacacaga ctggattcaa  38700
actgaggttg tgtctctccc tggctgtgtg acgttgggta tgatccaagt gtcagattac  38760
tcaacttcaa aatgaggaca gagcctttcc cttctagggc tgccaggaac attgaatgag  38820
```

-continued

```
agagtgctgg cagcttagta caggtgttca ttgctcttgt atggtactgt ctgtggcacg  38880
gctagataaa atacagtagc cactgattca aatttcaact gaggagtaaa ataaactgaa  38940
taacttagaa aagttttctt cttttgaatg actctaagaa tttaaggagc atgtgagtgt  39000
tgatggctct aaaagggtaa cagagcccaa ctagctcagt tctcagcatg aaaatagtca  39060
tatggcacag actcagtgga gtgggtgcac ttcaataact ggaagcacag atgccctaca  39120
gcagcatcaa agatggcact ctaaactact ttcaatcctt taaaataaat ggaaacgcac  39180
atttagtatg catatgacaa cacgaaggac ttcgattttg ctgatgcaat acagttttac  39240
aggatttttt atactcaaat tagtaaaatt ctgtattgca tccaaattat aaattataat  39300
atcatctaga ttggacatag gaataacgac cactggtatc tgcccagaaa gctctaccgc  39360
ctgtttataa gctcctgcag gagacacaaa aagaagagaa tttgaatata acttgaaatg  39420
accgtaatct cctgccccaa ctcatttcat taccaaaccg cctctttctt cattatttct  39480
cctgaagcac aaatctatag agaactcagc tgccagtctc tcccactgca ctcagcagtg  39540
aaagggttag gcctaggctt ttcaaacaga ccagtgcttg tatcagccct taaacatctc  39600
tggagaagga aatgggatcc ttctttggta attcattttt gacagttggg gattaggtgt  39660
tctgtatctg gggggccttg ctgtcttctc tcctcctcct cccactgcag accctctcct  39720
cccctcccct ctccagctct ctgatgactg cttcatgctc cttccacctg aggactgcca  39780
gcacagccta ttgcaggaac agccaatgag gggctggctg tgctctttta tttataaaat  39840
tataaactca agcaaaatct agactatgtg tccccaagat cagaggagca caaatccctt  39900
gcttacagat tgcatggggg gcacattctt taaaattggt ccctgatcta gactctagcc  39960
tgagaatcat ctttaagttc agaatttcca ctcatgacct cacatctgtg ggctcccaca  40020
ttgtcttcca aaacacacat ggcatctggc atcaccttca cccccaccct cagagcctca  40080
tctccctgca ggtagatagt caaggcaacc tcttcactct tctgccaagc ctcctctcct  40140
cagctcttcc cttcctctct ctttttgaaa atatttttaa ttgtggcaaa atatacacaa  40200
cataaaattt accatcttaa tcatgtataa aagtggagtt cagtggcatt aaatacattc  40260
acgttgttct atagccataa acaccattca tctccagagc tcctttcatc ttgcaaagct  40320
gaaactctgt ccccattaag caatggctct gttttcctcc gttcccccag cccctggcca  40380
ccatcctcag ttttctgtct ctgtgagttt gattactcta agcacctctt ataagtggat  40440
catacaatgt atctgtcttt ttgtgactgg cttgtttcac tttccataat gtcttcaagg  40500
ttcatccacg ttgcagcata tggcagaaca tctgtccatt tccaggctga atggtactct  40560
tttgtacgtg tggaccacat ttcatttatc cattcatcca cgggagggca cttgggttgc  40620
ttctgctttt tagctattgt gaataacgct gctatgaaca tagctgtatg cctttgtctt  40680
ttaaagccca aatctgatca agtcactccc cagcttaaaa ccttccactg ctccccagca  40740
gtgggataaa ggccagtctc ccctgtaggt ctctcccgcc agccctgctc agtcttcttg  40800
cttgtcatcc ttggctaggc cttgcattgc catagccctc tgcctctgtt cacgctctct  40860
catcttggag catgagcctt ccatcatctc taccagatga actctcattt cttctttcaa  40920
aaaataaaaa acccaaaaaa cccagagatc ccaactgtcc tggtgtctgc atagtctgca  40980
gcacacgccc cctccatggc ccttcctcca taagcagaat cactcctcac tgttcctgca  41040
gcacctcctg tgtgcccaca cagctgtcct gcggtgggct gtgtgtgtga gtgtgccccc  41100
tctaggacct gagctccttc tggagggtgg gcacagcatc cattcattct gggaatcctg  41160
```

-continued

```
gtcggcacca tgctagaact tctgcaagtg agtgcctttg gtgctggccc atgggagagc  41220
tgttggtaag gcatactttt gcagattcca gttgctgctg aggttgttgc tctttgcaca  41280
agtttcttct agtcaccagt gaagtgacat gtgtggcagg catggcccag ggaggctttt  41340
tcataaagaa gaggttgaat ctttggggct gtggtttgaa tatgtccctc aagcttatgt  41400
gttggaaact taatcccaaa tgcaatagtg ttaggaggtg gggcctaatc acaggtgatt  41460
aggtcataag gctctgccct catggatggc ttaacatgtt tagtgaggca gtgggttagc  41520
tattgtgaga gtgggcttgt tagaaaattg agtgcagccc cctcttgctt gctggctacc  41580
atgctctctt gcttttctgc cttctgccgt ggggtgacac agcaagaaga ccctccccag  41640
atgctggcac catgccctgg gactttccag ccttcagaac cacgagccag acaaatttct  41700
tttctttata aattacccag tctgtggtat tctgttatag aaacacaaaa tggactaaga  41760
caatcttctt tcatcaagtt agggtaccaa cctttaaaga ctgccagtcc aaggttaaag  41820
gaaacttttc aagagcagtc caaacatgat ctggccctca gctactctcc agggtcatgc  41880
caccctatca cccactggct cacacagacg ctgaccactg cttagtttct caaactgaag  41940
ttttcctcct cagagctttt gcaaaacctt ttctttgcct ggaaaactcc ccccacaaat  42000
ctttagttgt aggttccttc tcatcttgca gaattattag tttgctcttc aaatagtctc  42060
tccagctaga ctatcaactc caggagggca gagttcttct tcgcttcctt cacccatgtg  42120
cccactgagt ccagaactgt atagcagttt gattgaaaaa atccacaggg tggaggatga  42180
gaggaccctg gatcccagcc tcacagcctc ttacttcacc tgtgtgattt tggtcaagtc  42240
ctttattctt cctgggcttt agttttccct tatctaaaat atgagaaaag ttcccctctc  42300
ctgggtattc tgggagactc atgtaaaagg cactgagcca gtgcagcaca tctatgacca  42360
ggaagggtca gcttcctgcc ttgcatgaga cacacattcc cttcttcatg cacagttatt  42420
catgagttaa atatgtattg agaagtgggt tctcaggaga tgatgcatcc acagcattgt  42480
ttgtatgcct ctgtctttga tgtccctgcc tgagtcgccc actttagagc ccttctgttc  42540
ttcagaaacc agacttttct ttcaatagtt tcagtaatca atcgatcaat caatcaacca  42600
atcaacagtg ataataatca tgagtgagcc cctgcccgtg ctggctgtgt cctgctgaag  42660
gcacactaag tgctgccctt cccagaagcc tcaggaagct tgcgaagctc aggtgcatgg  42720
atgcctggtg gaatgaggaa gggatgcagc caggtagaga aatgccctgc catcacttgc  42780
atcagcatct gtgaagagct ggccaggctt ttgctcacag tggttgacac agtcaaggag  42840
caagggcccc gtaggagagg ggagtcaagg gctccgggtg ggaatggagc tgggggctga  42900
tgctggcttc tggagcactg taatgtgact gagaaaggtg aaggagccgt tctgaaaaag  42960
aagaaggcag gagctcgcac agctcttgac tcatcttgac ttctttttcc tgcttcatcc  43020
aagcaggtcg actctctcgt gatctcagag acagagtgaa gtcatgagtg ggaggggagc  43080
acagaaaata agaccttgat tcccagcatt gggagactcc ctgctcccct gagtctcgga  43140
aaatagcacc cttcaaatgt tttagggatc cagatttgat gaagagatgt tattttggct  43200
tttagattct taggagagat ttgtctttct caggtcagga agaaaatgct gcccgctgca  43260
cattcttcgg gacagactct tttaattatt actagtttaa tgtatgtttt gcttagttaa  43320
ggaaaacccc tgtggtttct tgacgtgctt cagtattcta actcacagct gattcagttc  43380
agggggctgg ggagatgtcc tcgacctctg gaaaggaggg tgcatctcta gaaataaggc  43440
taagtatgcc actgacactg tctgcataaa cgtgtgtgat ctcaggtcca aaggatgggg  43500
cctggtctaa gccagggacg tgggaaatca ttttcctgtg gcaacttgtg aagaccattc  43560
```

-continued

```
tgtgaccttg gtgtctctgg gccttctctt agattttcta agttggctag tcagtggagc  43620
tgccatccct cctttgccca tgttctactc ccagagttcc tccaagaaat tgcggagcaa  43680
tgcctgtttc atgagagctg agtttgctgt gtcttccact tagaaacaac actgtggacc  43740
aggaggacac acagctccca gggccatcac cacacaaagt gaaggctggt gaatccgagg  43800
cttctagccc ttgccgggcc aggcccgcag cactccgctc cccaacccag ccgctgcttt  43860
gtcgcaggaa cctcagcagg gcagggtgtt tcctaggagg acatccgatt cccagccatt  43920
cctttcagtg aatcacctga gctcacattc tttttctttt tatttttgaa gctcttagcc  43980
aatctgcttc gcgatgaacc agttttgctt gaagcagaca aacccgattg tcaggagaca  44040
gtgatgattt cttcagtctc tgaggaagag ttttcatttt ccccaattcg caaaaaaagt  44100
caggtccctc cctccctccc tctccgtaga atattttcca tgtgtgttaa caatggctga  44160
gcgtggtaga tgccaggaat ttctgtcaac cctcaaagag gaaagccctg cctaatggtc  44220
tgcccgttct tgttcactcc ctgccccagg ctccccaccc gccttctttc tggaaggtat  44280
aaaggctcct gcttatacct ggcactgcac gcttcgctcc ctctgatctc ctgactgtca  44340
tgcccagtgt ctcagcctat cattctacct ctaactcgac cttgagtgac cttgagcaag  44400
tttctcagga ttccacctcc aagtcactct ccctttggga tatgcagcac taagttaagc  44460
ttgcctggaa aacatcactt gaagctggaa aaccactttt aacacagcgg gaaaagctat  44520
ttgttcagac aggagtgggg tgggtctggg cagagcactg ctctaacttg gccatgccgt  44580
ggcagcagct cctttaatgc cactttttcc tggcgcgccc gcggggcctg gagctcagaa  44640
agaggggaac gctccctcgt ctctcaacag ttgctccaga caggtcagca aacatggaat  44700
tcagaatgtt cattaaacac tggctgtgtc ttttgtgttc aaaagcaaga cactctctct  44760
gaaccatggc cccacagaga gtgcagaatg tgtgaaacct gccgggaagg tctggacccc  44820
ttgcggggca gtgggcagca ccgtgcctcc gttcacacca ctcacatggc tgtgcctctg  44880
cttccttctg gcatggctgc ttcttcctca ggtctcaacc atctccctca gatgctcttt  44940
cccatgtttg tggctacagg tccccgtgac ctgcagaggc agagcactca ccagcagccc  45000
agcctcgttg cgcacccatg tttgcatttg caggccctag aaccactcca agctccgtgt  45060
ggcgagatgc accctcctgc ccttcactgg ggagctgccc tcctgttcac agcggcacct  45120
gagtcacaca tctggagcca tcctggactg cctcatttcc ccgatggggg gtttccctga  45180
cttcatccat cctgtctttt gggtccccat aataactgac atgggtcggc ccgtaccagc  45240
ccctgtgaga agggctttaa ctgccttccc accccctgct catcttagag tctctctata  45300
gtgctgctga aagaatctct aaatcagtgg ttctcaacct cagccgcaca ttgagaatca  45360
cctgggaccc ttaaaaaaat cttaactctt ggtccaagaa ttctattaca atcggtctgg  45420
gatggggccc tacaggtatt tttttaaagc tctccagttg gtaatgcata gctagagttg  45480
agtatcgctg ttctaacgtg cagatctggt catgttacca gccttttagg tggtcttctt  45540
tggctttctc tatctaaagt tcaaaaccga acatgtgcgc attcagtgca cccattttca  45600
actgtgcatt aacacattca gcccaccagc aagatttatg aaccattttc tgctgttgta  45660
tataacatat catatgcata atggcatagg ttattgtttt cttcaaaata tatgagatgt  45720
gagtccttct acgaactgac tcacactgat tgcccaactt cctctctcga ggtctcatcc  45780
tctttccctg cagccgtctc cctcttgcac gcacacacac acacacacac cacacacaca  45840
cacacaccac acacaccagg gtcgatgcca tctaccctgg acttcatctt gaactccttc  45900
```

-continued

```
gagtgtgagt cattactcct ttgtgcacct ctgctttctc ttctcaagat gttcacctgc  45960
ttgaggtcag ttccttgagc gtcttccact tgccatgttc accacagtgc tcaacatgcc  46020
tgaatgcatg gatggcgact tctcagatcc tcagtctcct catctgggta ataaggcatt  46080
gggttggcgg gtccatctgg tttcttccag ctctgagagt gcatttgctc tgtgattcat  46140
tcgttccaca acacttcacc aattaaagag agggtacaaa aggtgaacat ccttggctcc  46200
cagcagatgc tcctcaaaac ctgaaaaatc agataggtga gggaagattg aatgaaaggc  46260
ctcttatgat tctgcagcaa ttttggtggt ttaagaactc tatggaaaaa tcatcagtat  46320
ttctggaatt gaagtaaaat ggatagtgag cctctgtgta tgtgaaggcc cgcatctgga  46380
acatgaaaga acctgtctga tgtgttctag tcaggaaagc aggtagccaa tactatttat  46440
agaatttaca gaaactgaag attttgtttc tactgatttt caaaatagta ttatgtctga  46500
ttttttttcct cagaaatata cttcctgctc ttctcaacaa actcatttga aaatatgatt  46560
agaacatgat agaattttac tcatttgcca actgcggttc ccatttcaca tattgttaga  46620
attctgcatg gtggctttgc cctttaacca ctaactgata aatgatgtag ttagctttta  46680
aatgtgtgga aaaatataat ttcaggttca accataggtc agaagtacac gtgttttgtt  46740
agtctatttg tctctcagtc atctcatgga aaattctcag cttttggtat ggaaataatt  46800
ttcttgaagg caatatttgt tgagtgactg acggaatgaa aaacgccagt tgcgtaagtg  46860
tgaaaaagat ctgggtgttt tcattggatc caaattccac atgagccaac aacagcgtgg  46920
tgtggaggct ggagcacatt aataagaaca gtgtcctaaa ttcaggaggt aatgctctgc  46980
ccatgccctg tgcagctcag acggtgtgtg cagtgcagta tgtaacccag ggcacatttc  47040
aggggcccac agggagctgc agcttgtaag gtggagtgca gccaacagag cagagagtca  47100
gaatccccgc agagtggttg aaggcacaag gatgcgcagc aaggaagaca gacttatagg  47160
tggtgcgact gccatcctct ggtactgaag gtgctatcat ggagggaggg aagtagattg  47220
accctcctgg ctccagagta cggaactcag acaaacggtc agaagcttac agggaggcca  47280
attttggatc aactttaaga agaatttttt aaaagctaga gcaatcctaa aatggaattt  47340
gctctttata aagttgcgaa tgcctcaccc tggaattgct taagcaaagt tgggacgggc  47400
agttgtgagt aatctccttt ccaatccata cccgcaatca ccagaaacgt ggacttccct  47460
gacactgagc acctcttaat taagcatctc ataagtgaac aaaacccagc ccttcaaaga  47520
agtcacttta tttatgtgtg ggtctgcagc ttggatttct tgataatgtt aaataaaact  47580
ccatctactc ttccacaaac acttcaagaa acctaagact tttggccaga gtaacaccga  47640
ggtttgagag aaaggatatg tgtgtgagag gtgtggtttc attagaacat attatttgac  47700
ttcatgttga atcaacactt ttgtgcaaaa tgcagtttta ccagcctctt tccttgtttt  47760
ggtcacataa tttaacttaa cattctcggt acttgatttt ctaacataaa atgggattga  47820
gaggggaatt ttgaagttcc catggtctgt cctctacatt ctgacagctc attatctctg  47880
cggtattgtt ctcacattta agtgaggtta gcggaggcag aggcctctca ggcctgaaga  47940
tagcctctgt tttcagggaa atactagact gtgagatctg tgacactgaa gcactaagtt  48000
catctcacaa aagcaacgtg ctctttttaa atggttgatc aaagttactt tcaaaaggaa  48060
gtgttagttt ttgttattag ccgaaacaag agctgcttta atgtagtata tttaaaatca  48120
tatctcaatt aagatgttat tcaaatacta tttgacccac caatctcatt actggatata  48180
tacccaaagg aatagaaatc attctattat aaaaacacat ggctgggcac agtggctcac  48240
gcctgtaatc ccagcatttt gggaggccga ggcgggtgga tcacgaggtc aggagttcaa  48300
```

-continued

```
gaccagcctg gccaagatgg tgaaacctca tctctactaa aaatacaaaa attagccagg  48360
cgcggtggca ggcacctgta atcccagcta ctcggaaggc tgaggcagga aaattgcttg  48420
aacgcgggag gcggagtttg cagtgaacag agatgaagcc actgcacttt agcctaggtg  48480
acagagcgag actctgtctc aaaaaaaaaa aaagaaccac ttgcatatac actattcaca  48540
atagcaaaga cgtggaatca acctaaatgc ccatcggtga tagactgcat aaagaaaatg  48600
tggtacatat ataccacgaa atactatgca gccataaaaa agaacaagat catgtccttt  48660
gcggggacat ggatggaact gcaggtcatt atccttagca aacgaataag aaaagaaaac  48720
aaaataccgc atgttatcac ttataagtgg gaggtaaatg atgagaacac aaggatacac  48780
tggggcctac ttgagggtag agggttgaag ggagagaagc agaaaaaata actattgggg  48840
tactaggctt agtaccaggg tgacaaaata atctgtacaa caaactacta tgacacaagt  48900
ttacctgttt aacatacctg cacatgtacc cctgaactta aaaaaatttt taaaaagatg  48960
ctatgcaata aaattctcaa ttaagaattt aacttggtaa atgttcattt aatgatctaa  49020
aaatatgtgt ctggatggct ctagcaaaaa aataaataat aagtttctca gagatggtaa  49080
ggctgaaata aatggggaaa aatctgaatt gtaatccttt ttctgttgga cctggtgttg  49140
gggtttcaca cttgtgggtg aatgtgggcc tcctgtgagc accagcacaa aagactaaac  49200
tgaacaaaag attaaatgtc acctctaaaa ttctgtgcaa caagacttcc agccacagaa  49260
tgtgcaactc agatttccaa gtaaaaacac accaggaagc agatcttaga tctctgttat  49320
ctccttggca ccagctggta ttcatcctca atgctagcta gagttgaaat aaagagtgaa  49380
agaactttct cttttattac ttaataaact tcctttttg agctgtttta ggcttacaga  49440
aaaattgagt ggcagtttca gggagttcca gcacggcccc tgtttctttc tcatggtccc  49500
tgcaggtttc ccctattatt aacgtctgtc attagcatgg cacatttgtt acaattaatg  49560
agccaatatt gatacattat tcactaaagc ccacaggttg cgttaggggt cattcttggt  49620
ggtgtacgtt cttcaggtct ggacaaatct ataatgacat gcattcacca ttactatatc  49680
acgcagagtc gtctcctggc cctacaagtc ccctccttcc ccacctgctc actcctcctt  49740
cccaccctcc ccaaactgtg gcaaccattt aacttttgac tgaatggatt tattcttatt  49800
ctgccttatt gtatgtacac catattttaa taagataaaa taatagtcta tagtagactt  49860
ctgtaaatac tcaatgaata aatacttgca tgaatgcagg aaaaatcaat cagtcttgca  49920
ggatttctta tgcgttacat cgtccttata agaaagcagt cattctcacc gagatgtgct  49980
gagcagatac tggacatgtt ctgacccaga taagggctgg gtggaagtag ggctggagac  50040
acagagaccc agtgccaact tccaggacct cggaagaact gaaggcagag aggtcctctc  50100
agtgtggact gggcctctgc tggcagccac cagcgggcac agagctgatg tgtgttatgc  50160
cacgtgggga aaacctacag acgattctga gaaaggctca cagggacacc ctctgcccct  50220
aaaagaacaa tttaactcta atttatttct gtcactctgc attttctgac ctttcccaag  50280
tgtacagttt tatatgcatt taactgccaa attgtcatgt gagattatat ggttatattt  50340
cattaatata ttctagtttg ttcagctgtt cttactgggt gaatttgtgt ggtttcctga  50400
catttttgtt tttagtagtg cctcagtagt tttatacata attacgtttc ccttctggat  50460
tatttcctta gtatctagtt caagaagtga aatcgctgga ttcttgtggt aaatttttga  50520
atttcacagt ataatgctga ttttctcaaa gtctcacatt ctaagaaagt ataatgaggc  50580
aaaacaaaca acaaacatct taagttgatt ttttcctagc atcttttcct tccatctttg  50640
```

-continued

```
cttgtagaat ctagactatt tcatgaaccc aagatataat cagtatcctt cttcagtatg  50700
gccaaagtga gtttctcatt attttacctc cccttcagga aatgactttt catcttgtgt  50760
tttgggagcc atagatggtt ctgggcagga aactggcttt ggatagaccc agcatgtaga  50820
tggctatttg gccttgctcc cagtataacg atgcagttcc ctgtgaaagg gtatgagtag  50880
gttttggggc tctggatacc gtgtggcctg aagagacaag ggctcaatgc caactctgcc  50940
tgtttccaac tgtgtaacca tgtgagcgtc aaaaatcatg gacgtgctct ggttaacact  51000
gagtgggagc tcaacaaatt attattttta attgttactt ggacatggcc aagttgacta  51060
cactttatgt tctgctacct gccagtctga aagtgacgcc acagaaggtg aaccgcatgt  51120
tgggagatgc tcctcatctg cttaaatgag gtgcaaacac agcccatgcg cctgctcttc  51180
atgactgtat ctgtaccagc aatatttgta ttggcaaatc acatgcccca gtgggaacta  51240
cttaagggga attcaatgga tttcattcct tttatgtaat tggccactta gtaatagacg  51300
tgtaggtctc ttgtgtggat aaggattctg ccttttatgt aagatatgtg ttgcaattca  51360
gctttcaggt cccagccccg ggaaggctcc aggccttcac aaactggccc acccacgaga  51420
aggaaagcaa ttgtccaaat gtgggtagct tttcttccca ctgttgtcag ctgcttccaa  51480
ttagcccccca tatacataat cccagtttgt gtctgtatca gtacaattct cccatgtcaa  51540
tgtgaatttt aagccacaga gggaaagggg acagagaata tgctttcatt cagctctcct  51600
cgtctcacac ctcttgccct gcatgcattt ctttgctctg attaaacgag cattttataa  51660
gccacatttg ctgtgtgaaa ggcaaagtct tccctcccac ggatgacggt ctccagggat  51720
gtgtgtgtgt gtgtgtgtgt gtgtgtgtgt gtgtgtgaga gagagagaga gagagagaga  51780
ctgtaaacat atatctctgt gaaacttcat tttccatatg tgaatttttg gaaccgagac  51840
aaatggaact tagctaaaag atgggaaagg tagactgact ctgacttaat ctacttaacc  51900
taccaggcaa tttataactt gatggcctaa tttttgcagc acccagaagc aagcctgttt  51960
cagcacggca aaggctcagc tgctaagtgg gcagcattgt tggaggtgag cagcttaggc  52020
tgactgttca tcaaaggacc aagcgcttga ggttcgctca tcgctggagg ccagagtggg  52080
gagggccatt taactgctca aggccatgga actctactgt cagtttcagg gaaatttggg  52140
accctggagc acaaaccaaa actccaatta accaggagag gaactcgatc cccaggagat  52200
aagtgaagag taagaagtct atctttagaa acaagagatg tccaaggcta gaaagatggg  52260
gaaggagggt ggaactgttc tggaagtggg tctcaatctc agcaccagca gctctcaaga  52320
ctttctagag aaggaaactt catttctgaa ttaaaattag tcttcaatga catggcaggg  52380
atttcggcac actctcttgc gtcataggcc actgtgttgg aggcaggagt gttggctttg  52440
gaggcataga gattaaaatt agagtaacac gtgagcactg aaaaggttaa acagtagaga  52500
catggaggac tcccgacccc catgtacccc tttcttaacc ctttaattaa gatcacagcc  52560
ctagaaatag cttgcaaaat aattaactac tgatcattta taccttagtg cttctgtgag  52620
catgttttct ctttcattgc tgctcatctg catggaaaaa tgtgcatggg tttctgaata  52680
taactccatg gtgcttgctt ccattatatt tgtgccattt ggatcataac tgataagcaa  52740
ccaaagagtc ccatattact gcacgttccc atcgctattt tatgtgaagg tggtcctggg  52800
ggctgttctg aattctcagt ttcctttttt cccctcccca gttctttgaa aatatcagaa  52860
acggacttgt ggcatctttg aaaagctact taaaatgtgc tgctgtgctc tgaacttgaa  52920
aatgtgcttt taatacaaag tttgtgcagc ccttgctgct catacgagat gaatcttacc  52980
atgtggtgga tgcccgtctc atgccaggca ctgtgctcta agcccattgg tttatttcag  53040
```

-continued

```
tgcttgaaat tggctttcga gagaggcacc acggttccct ttttacagga gaggaaacac  53100
cagaggatca gagatggaga gtctttctcc acaaactcac agaccccaaa ggcaagctca  53160
gggttgtcag cttccaaagt ctgcctgctc caggacctca tgttgcatct ccattctctt  53220
cactgagggt caaatggaaa gaacacatgg gggtcaagtt tcagaaaata agagaaatga  53280
agaaatatgt gcccggaagc aagaacgacc gacctcatta aactggctcc cttcacctcc  53340
tctcacatct ttttctgcct tttggccaag ttttctctcc cccgcatttc ctccttgatc  53400
tcgtttgaat cctcttccct ggtgaagtca tttaggttca ggctcttatt ttactttggt  53460
ccataattta gatcgaacca catgtgctga tgtgattgaa acgatgtgga attctctgga  53520
cagagataga attatggagg ggttagtgtg tgtgtttaag attaaaagac caggtgtatg  53580
ggaggaaata taatgaacaa aaaatagtat tttaaatgaa tactaaactt gcactcatgg  53640
aaaaagttct cttcccatga ggttctcgca aagcatttta ccatcagcac acgcagtttt  53700
tctcagtttt ctgagatggg gccatcttga atccaacaga caacacacag catcagccag  53760
actaacacaa aggacgtcat gggcatggac gtaaatactg gtgtcaacac taggtctgca  53820
cctcgagagg agtggagcaa aaggatggag tggcagatga aggtatgctg ttcagaaagg  53880
aggcagaaat gaaaggaaga ccatcagtgc gctccacagc ttgaggaccg tcctggaggg  53940
caaatgccag ctgctcactt ctgaaaagaa aaattccagt gaaatgagta cagtcattct  54000
taggattact cacttgatac tgtgtatgtc tcttcttggc ttctcatctc cacacaaaac  54060
cctcaggtgg taaaaatcta attaaaaaaa ttatataaag tcttgtagat ttattagcct  54120
gaacataata gatttttttt aagcacgtta agtcttccat ggactaaaag aaaacttgta  54180
aacctaagag aacctctatt tttgatatac aaaataatac atttccttaa actatgatct  54240
tgatactaga attttaatta aaaaatacct gcagtttata tgcaaagtta tagattaatg  54300
cttaaaaata ggttgtatgt agtatccaca ggtcatgttt gactgtcaaa tagatgtaat  54360
tttaattcat aataattgtg tcgtgttctt ccccactaga agccaattat gcaagcttca  54420
ccattcacac atggaaaata atttaatgga gtactcattg caatttcact tatccagaat  54480
tggctgttgt tctcagagca gcttgtgttg ccttgttaag gagaatatgt tagtatccag  54540
acatccagaa aggatccttt actgtttcag agtccatttt ccccactttt gaaatacaca  54600
cacaaacacc cattcatgca aaccaaacag agattgtaaa gtgattccac tgacatttat  54660
gcacttcttt tttctctttg gttcttcaaa ctctcagtca gtgcgcattt actcttaatt  54720
tagatacggt ttaaacctaa ttagaaacca gaagctcttg tatttccaca aaggattatg  54780
acagccccaa gaaaagatag tgaaaccatt atataacaag ataaaggctt cttaacaata  54840
caaggatgga ttttctcatt gatcttagcc ttctgaattt tagaaattgc catttcaaag  54900
tctaaaacaa aggaaaatca gggaataaaa gaatggtaag tagacacaaa cctactggct  54960
ccatcatttc tgttttagca aataacctgc cacatatacc aatagcccaa gagatgggca  55020
tgtccctgca tttcctggtc aaggtgacaa cactgcgtcc tcctggaaga ggtctgccac  55080
tcaccatacc acaaaccaaa tataataaaa tcagaaggca cactatagtg aattttttag  55140
aggcatgtat tgaaaagcat ctcaaaaagc attctcgaag cttccagaag tcaactcaag  55200
ttatctgaaa agtgacactt ttgatgattg ctcgcttaat actgggagag ccagatgaag  55260
attcctcccc acttcctcag atgtgcaact ctggaatttc ttagtgttac tggagattcc  55320
tgctgcattc tgggccttta atgcataaac actgagatgt tctaaggaaa ttactcccta  55380
```

-continued

```
gggaggagag gggtggacga ggagtaagct ttgctggtga ctcatgcgct gtgtggaaac  55440
tccctgcaca agtgagctgc gcagggtgag tctaaagggt taatgcactt tcaaaagcct  55500
ctaatttgtt attccagaag agtaatttac tcactagaag tatctgggtg gctactaaca  55560
catttgtgtc tttaaaaaga tcagttttat tttaagatta aaaatataaa gcaagagctg  55620
gaaagtcact aaaaactgac agccagtttc ccattttcaa gagtatttat taaaaggttc  55680
tggttgcaga aggaataaga aatggcttga gatcatgaca cagtgaatca tgttgtaaac  55740
atgttagcta tggctgtgaa ttcaaccagc gatgagttca agcgtcccca gaaggtgttg  55800
ggggaattag ggacatggct gtgtttcccc agagaaaagt ggccatttta ctttccctct  55860
tcactaacat gcttttgaca tgcatggcag agctgaaggc aaggggaagg ggacaacata  55920
gtaagtgact aagtggcttt tttttttttt tttttgccaa gtgaagctga gtcatatggc  55980
ctctgtcatt ccaaaactat tctctacggc tgcattcctt tcgctcttgc cttcctttag  56040
aaccctggag aaggcctcct gaagcctggc cctattatgt atcctgacaa agataaactt  56100
ttccaaaaag ctgcatgttg tttctagcac agtttttcct cgcagtgact acgtgatgaa  56160
agtaccatgc agaggaggtg tctgactgag gcgttcgtgg tgtgtgacag agtcccctgc  56220
acaggacagc cgcactcccc tcttgcgtcc tttcctccca tgtttgcaaa gcctctttcc  56280
ctgtcagcag gggtgttct ggcagttgac atttctgaaa actacagcct acatttttaa  56340
aaaatccagt aagtgaaaac taaaaaatta ataccgtggt cataatagtg tggcatttga  56400
taactaatga ggcactgtcg tgccagctat tattttcaga catttacagt cctttttttaa  56460
atacaaagaa atatttggtg tgaaatgttc cccgggagct ggtgcaagca gaggcgacag  56520
ggcaagggag cttgggttgt agcctcgaat tcctccggcc agggctaccg tcagcctgcg  56580
gcacacaagt aaatcaaata taaaaccaaa atttctgtaa gcaaatcagt ttctaactca  56640
ctgtaacgaa ttatctttcg cacatcacag aggcatctct tttcactgtc gagtttggtt  56700
tgcttggtta caaaaagggc agttcaaaag ctttggttgc tattgtgaaa gtcagctgaa  56760
ttccttccac cgtgctgggg tggggtgggg ttcacgcagg ttctcttttg tcaccagggg  56820
tgctgtggat tcacaagtaa gcaagaggct cctcaggtca agcctctggc tgctccctga  56880
ggtcagctgc ctagcttctc ctcctctgag atagacggga acaaagtctt tgatgtgtgc  56940
atttctcaag cttgacaatg atacagctac ataaaaaccc atgatttcat atagatattc  57000
caaaacgtaa aagtaaacca tgcatccaca gagacatgga attacagaac tggatgctga  57060
gctggtcact tgggaggcag gcgtccttgc cattggttta tgcctcagcc ccaccatgca  57120
gtggctggcc aggtgaccta ggccagtcct gcatcctcgg ctcctcacct gcctggtggg  57180
acagtgacat ctctcctgca gcactgctgt cagggtgagg gaggtagggc gcagtttcag  57240
aaaaccattg ggctgcacct gcgtgagcac agctgcagga gcaaaagtca gaaaggtcag  57300
caaaggattt caggagcaaa ggtcagaaga aaccctcaag gtggttgtgt ctgcaggaaa  57360
gtgctgtcgt ctcctgcaat gctttcaaga ctattcagaa gcacagtgtg aagggagagc  57420
cggagcccat ggggaaatga ctccagagtg ttccacgtgt tggaaggcat ctgttggaaa  57480
acggacattc aagcaaatag ttgcctgcat agacaacgca gaatgactgg gaaagcccca  57540
acaagttacc tactggtaaa tgaggtgaga agcttaaagt gagaacccca ttgctgcctc  57600
tttttcactt taaaaacatt taagttttga attatggtaa aatacacgta agatttacta  57660
ctgtaaccat ttttaagtgt acggttcagt agtgttaagt atattcacat tgctaaggaa  57720
ccaatctgct acttttgttt attaattttt tcctgagggg aaatattttt aaattttaaa  57780
```

-continued

```
atatttaatt gacaaataaa aattgtgtat attcaaggtg tagaacatga tttcatatgc  57840
acgtacattg tatactcatt accacaatca aagaaattaa cacatccaac ccacccatag  57900
ttgccattgt gtgtgcgcgg atgtgcgtgt atgtgtgtgt atgtgtgcac gtgtgcgcct  57960
gtgtgtgtct gtgtgtctct gtgtatacgt gtgtgtacat gtgtgtacgt gtgtgttcct  58020
gtgtatgtgt gtctgcgcac gtgtgtatgc atgtatatgg gtatgtgtgt acgtgtgtac  58080
gtgtgtgtgc atgtgtgtat atgtgtgtct gtgggcacag gtgtgcctgt gtgtatgtgt  58140
atatgtgtat gtgtgtacat gtatgtacgc gtgtgcatac gtgtgtgtgt gtgcacaggt  58200
gtgtatgtgt gtgcctgtgt gtgtgtgtgc atgtgtggtg gggacactaa aaatctctca  58260
tcaccttttt agtcaaaaga acagttgttt tggtttggct cttctgtttt aaaatatcag  58320
aacaataata atttcccaca gacaaaatcc tcaatcctca ccatccttct atttcctata  58380
ttcatcataa acttcatgct tgatgttgaa attgttttct gaaaatagag aatacaaaga  58440
ggagatttta aaatgtcagt ggcagcccca cactcctttt taatcttatt tcctgatatc  58500
ttgagtttac ttggacgtag agttttcctt gactatggtt atttctggta gtagcagctc  58560
cagattaggc aatggtttc ttcagagata gcttagagtg agccccagaa caaggtcaat  58620
gcgaagattg cttgtgtctg cgtgtccagg gcacagtgat cctcatcact agccgggggg  58680
ctccgtgagg atctgctcct ggtcgtttct gttctgtatc ttctctgcag cccttactga  58740
agccgttacc aactggcaca attcaattcc tactgtaccc atcatgcaca gatggctgaa  58800
gtattgagaa cgctccagtg accgggaggc aatagtctgt ccacatctaa gaacacactt  58860
ggaataacct tagagaagag agagagagag agaatgcatg gttagtaggt tatcaaactc  58920
ctatgacttt tcacaggaaa agccctcatc cacaccaact ttaggaatgt gtagaaagaa  58980
gggtcaggga caggggtgag tggtgggcag agcagttgga gggcacaggg aaaaggcatc  59040
tggtcatgta tttggagtag gaggtcttgc tttactattg aattgcaggg acactttggg  59100
aacagtgttc acttcttttt gcaaccattt cttcagagaa aagtcatgat actcaagtct  59160
tcttacaaag cagtttgagg ctttgagtac cagactgatt acagagatga gtatgaagca  59220
ttattgtagt atttttaagt gaaattcact aaatgcaaat aaacctagca aatgctctat  59280
ggttaatttt tttctaaaat tcagataatt aagacaattc attctcctga aactgctgtt  59340
catgtaaaaa ggaattttat cgaggtggcc cttgagtgcc aaacagcctg tcctcagctg  59400
caaaatgagt cgttgatgat cctccagcaa gggatacttt ttagctcgtg tggtgattgc  59460
tgcacacggg atatgtgcag caagtatctg ctgagctaat aataaacagc ctcagacaga  59520
aagacagtgg gcacaaggtc atgcttaaaa agaccccttg ttctactgca tcccagctcc  59580
ccaccatggg gcctcacagg ccctggtgac caagcacatc agacctggtt cttgctcagt  59640
cctgggagcc acagaaccca gcacgtactt tacccccaag accagactcc agcttggctt  59700
ttgtcctcct ctccaggatt ggtgacctcc taggtcgtga agctgtgatg agcaaagaca  59760
cactcctctc cattctccca acttcaggtc cctttgacag tgtcagcagg catttaaata  59820
gcagaccacc cacagcaggg ctggtagatg cagtgaactc aggaagatgc ctgcatagac  59880
tctagtgtta aagacagaat ccttacaagg aacccccata gttacctaac tgctgtctcc  59940
agtggtcata gaagtgtgat aacccactaa tcatcattct ctgtctctct gtctttctca  60000
tacacactta cacacacata cacacaacct tgttgcttaa ttttcagaga gtctactttc  60060
agaaaagcct tcaggaatac atcatgtaca aaactgagaa attacctgaa gtatctttaa  60120
```

-continued

```
atttagtaaa aagttgcatt gttttttgaa catcacactt gaaaagtaca tgaatacaaa  60180
catacttagg aaaaaaagct ttaattaatt taaaaaggag aacaatgcta tatgctgtat  60240
cccacctttc tctgaatgtt acattttctc ccctatccca ggctgcatct aagaaaactc  60300
agagggaata tgctatctat cttttccgag caatgaaagc tctgggtttt ttccttgctt  60360
ttcagggcac aatacttctc tttcttcctg gttagacagg ataagttctg agtcccctgg  60420
tatcatcagc ttacttcttc tctgttaaat attcacaaaa aatcactaac tttcatgcct  60480
cagcaaacct ccactgccta aaatatagtg aggtcattca tcttcggaca aattgcccca  60540
actacggtgg gaaaagaacc aatgtgttgg actatttatc taatttttgt ttagttcggg  60600
gatacaaata aatgcataga tacatacaaa catgcgtaca taatagcagc agcagcctgt  60660
gaaacattga caagacctgg agttggaaga ggactttgcc atcctccagt ccaacagttg  60720
cctgtcacag attagacgac tgggatgtgc gcaggcgatt atttgcaaac ggccctgagt  60780
cccccagttt atgtcttaat tcgcagccag ggctgattgt agaagcaaat ttgcaaacat  60840
gtgcaagaag aaatcacaca tcctagagct tggatttcct cgtttcttgc tatttctatc  60900
cgtagacaga accattgctg agctgttaaa tttgtctcct tcccctatac cagtcttgaa  60960
aaaggaaagg aagtggagca aagaaaaaga aattaataaa gccggcagat cctaggagaa  61020
tcttatttaa tccaagcttt gtaaagtttt gctttattcc atggcaacat gggtatacac  61080
atcccaccgg ctgtttcagt ggctcagagc aggtaaggcc tgtgccaaac gccgctagca  61140
ggaggaacaa cgtggagaca gccccagagg tggaacgttg gcccttctgt ggctccggtg  61200
tctcaggacc tccctaaagc ccagccctga cactgagcaa gtttccacca ctgttaggaa  61260
gaagtagaaa ggaatttgga gggttggtgt tactgttcaa gagctggaag gcttctgccc  61320
ccattcccat tccattaatt gcgtgaggta gagaactcat agaagatagg aacacatatg  61380
ctgatttcca aaattgcctt tgtatatttt cacgtgaaga ctttaggggc aaaagaaaag  61440
aagcaagcat tttgaatatg tgtttcaatt tgccttctgt tatataaaat tgtattttgc  61500
ctattctttt ttcattattc ggaaccttca agaaataaat taagttctct caaaaatgtg  61560
ttttttgaaa agaggactaa aacagatggc ctggctgtgt taaacacagg gaccagacca  61620
gcacccacct ctccacctgc cctgccttca ctggcagaat tgtgatccat catgttctct  61680
gttcaatgtc atcatccctt tcagagcatg ggtctcttcc tttctaggca gtcttaccag  61740
gatgcatggg tgtgcctgcg taggcacacg cacagctccc aaggactcta aaaaaagata  61800
tttttctgct tatatactaa taatatgtta gagatttatg tttcaaatta gtacagaatc  61860
acatggttct ctccaaatta tatttgagag agaaagaata gaacaaaatt tattttacaa  61920
aaatactcag tacatttagg gcatatacaa agatgttcca gaatgtagct tatctcttta  61980
aagacaatta acacagtttc tgggcaaggc aaggcaaaat attcagtaac ttagcaacac  62040
caacagaaga cagccaatat tgcagcacat ttttctcttg gattgggtca gagagtactg  62100
cagagaaaat ggagtagaga gacctgaaat actttcgcac acactgtggt cagtgcagcg  62160
tccactgtgt gccacagtaa tactagaaac tccctggtta ggccttggaa tccagctctc  62220
atttcgtatg tgacctgcag ggaagtaagt taaatgcaca cgttttatca agttcaaatg  62280
caaacttaat tttaaatgta tgcaacatca gtttaagcgt tgtagctatt actagcaatt  62340
gtacctatta ctagtctgta ctctgcacaa ctttggagta tactgcctac tcaaggtgga  62400
ttttagagct ctatttgtgg cattatatca cggacaaaag cacgttcatc agagtcagag  62460
gaatgtggtg caaatcccag ctgtcccact taccagctgt gggacttgag taagctcctg  62520
```

-continued

```
aagcagctgc acctgcattt tctggtgggc accatggagc tgtcagcagt gctttcctca  62580
gagggctgcg ggctggatga ggtttgctgg tgcatgtgaa gtgtcaatca ttgctctcat  62640
gagtggtgat gctgatgccg ttccctttttt tagggaagtg attttccctt acaaagttac  62700
caacagtttc atgttggccc atttttctat taattgtttc cactaatagg accaacagtg  62760
gtagtcccat cattttatta ctgcttgtcg tagcacaagc agttgcttca ttgtgtttag  62820
ataaatattg acggctgctt ttaacagtct gctgttttgt ctccttttga ggtccttaaa  62880
gtaatcctta aaaagatagt gcagatggaa agatgtctgg agtcagtgaa cctgccttct  62940
ttcctgtgtg cttgtcagtt tctaaaatgc catacacaaa ggactttcat gatttctttt  63000
taggtacatg attacagttc aattcacttc actgtctgga aaatttcctt ataatcagga  63060
tgaaatttct catgttagcc tttcacattt cactactttt agataaggaa ttctcaggct  63120
ttgctatatc tgactgctct tggaggctga gcttttggct aactacctga ctactttgtc  63180
gtttctcttc ccttggaatg aagcaaatat ctaacttctc actcattgtt tctgctattt  63240
taccatttag tcatctgtga tttttctaaa tactgaaaga cttccctcaa ttcaaactat  63300
gtgccggatc aaggaaaggg cagttggata ttgcagacag catagtgcaa ttgtgaagag  63360
tgtctgctta ccagccacgc tgccttgcac aagttatcaa gcctctcaac ccacttcctc  63420
aatctgtaaa ataggtatga gtgtaggacc ttcccagggg attttttgt gactatagaa  63480
tgattctcag aagactttca ggcagtatgt gggtgaggca catgctggaa aggcttctgc  63540
aggtgcagtg atcaatgctt ttctcagtgt gtacatccca taatacagac acgttaccag  63600
aaactcccta gccaggactt tgattgcagc tcacattttg tatatggccc atagggaaat  63660
gaagtgtgta tttttttataa agttcaagtg ttaacttaat ttggaattta ctatcaaatc  63720
tcagttgtta tgggcattta tagctattaa tacttcgtcc catgtgtccc atgaggaaac  63780
caaggaacag aaattaaagt tctttctgga gtcccctgaa tctcgttcct gttcttttgc  63840
accctgttaa ttacatagag acattcacag ctcttctgac cttatcagcg ttaaggaaaa  63900
cagaaaacca gcgtgctatt tgttctgtcc cttagtcaag ccttctcaac atatattttt  63960
cttccaagat tttgcatgtg cacagggatg cctatcctct acaagaaaca cattttaggc  64020
aaattataat taaaatgctg tttacatctc ttcaccttta gaatttaaag aatgatcatt  64080
tcttagattg catctcagac acacccttcc cctagtctgg agagggcgag gcccatgggt  64140
actgcaaaca gcctgacgtt gtcaggggcg gtctcaacgg ctcattcacc acatctgcct  64200
cgcgaaggct aagccatgtg ctgttacccc tgctgcgctc tggctcattc taaggtacac  64260
gctattaacc ttgtgagaaa acaaagaggc cagccccacc cttcctgctc actctgagtc  64320
acggtgaaaa tgtttcagga tctcgggttc gaccatgagt cctgtccagg tccaggagga  64380
aattcggaag gaccacatgt tcactctgag atcccacttt catttccctc ctggttgagc  64440
agcattaata ctctggctag atttaaattc tggctttctc cagttagaac tgaaagttat  64500
gacaatgtaa tcaaaataga atgtgggttt acagctggcc ccctggcctg gtttgtgaac  64560
ataaaacaga aacagaaagt gtaagtggtg acatcatatt ctctcattca atgtgaaagg  64620
ccaccgaagt ctttccagaa ttatttttga gaataatatg aatttttaaa aaatacctaa  64680
ttattttaaa tatcgtcttg cttgctcccc aaatacctac tgttttcaac ttggatatac  64740
gacatgatta aagaatatct aatatttggg aatgcatact ttaaccttat aaactaccac  64800
tgtaaataga cagactcatt aaagtgaaag gacattttaa atcaattagt aagcaaatca  64860
```

-continued

```
attaggtggc aaagacaaga ttatttttcc ttatggtagt tgaagaataa tgcttaacct  64920
gtcattctaa ttaccaagca cggtgttctc tttggaagat catttcaaca aaacattatt  64980
ttcatccaga atttgaacct tgagattgca tggtatttta gaaatctatt ttagaaatct  65040
ttggcaaagg ttactattaa aacaatcaca ttcatggaaa atcagtataa gagcaactaa  65100
aataactcac aataccagta aaatcacttt gtcatcttct taagactttt aaagagcatt  65160
tgtaagtaac tgaatagaag gccaaagggt gtgtaggtag cccagaccat cagtgggcag  65220
ccagggccag ggcaggggcc acggttgcag cctgcattct tctaaagggc agagcaaatt  65280
aaagttgaag caggagctaa aaaaaaaaaa aaaaatgttt caaagaattc caccaaccag  65340
aggatactac ctaggacagt ttgggcctaa cttatctgtg aaggcctcca gcttcctcca  65400
caccggtggc cacttttcat tcactctgaa cccttctttg tatggaggtc attttattaa  65460
ttgagctgtg accaacatga cagaatttcc tgttttaggg cttttataat atagatagtt  65520
tatatctaat ttcagaatat attcactggg gaatggactt agcaaccact accacaacaa  65580
tgcaacaatg tgttttggaa caaatttacc aatctgaatt tccccctaga ttaggtcaca  65640
ggaacattgc agctgatgta cagctatgtt cctcctgaaa cttggagaca catcctcttg  65700
agctgggtta taatgggcca cccaaagctc gagttcctgt aatggataca ctcaggcagc  65760
agaacctacc accgtagtga ggacagcacc cagagccctc agaggccatc acaagtgcac  65820
cacagctgcc ttctctggca cgctcagagc tacacagtgt actctgggat tggaactctt  65880
tatttttttt tcagttgatt tgtaaataag attgcacaaa aatccatgca catcaactct  65940
ccaaatcaga atttgctgag ctaaaaagag cattaaatta gatgggctgg ctttcaaggg  66000
gtgggggtgc aatagtggaa ctctgcacaa cagttcttta caaagagaca agcaagcaca  66060
tcgcgtggaa atttccattc aactggaaat gtccaagcct gtttacctca attaattgtc  66120
cttgttcact tgtccagcct agcaattgtc cattagtaat ttgttataaa tgagacattt  66180
ggtattaaag catctctttg ggatactggt atggtttatt ataacattct gttagtagtg  66240
ttgtacaagc ttgagatgta ttaatacgaa atccaagctg catgagggct ttatttttca  66300
agcctacacc ttgctgaaat tctgaattaa aatatgattc tcagtacaaa tgaataaatc  66360
aacagaaatg gtaacgcatg tcaaatattc ttaaaaccca agaaagcctt gtaacttcct  66420
tcaatctaat gggaaatgca ggcaaataca agactgatgt ccttgagttt tattatcaag  66480
actcaagggc accagtaaaa tctagtttca ttggttggaa aaaaaatcct gataagcact  66540
gttaggcata ttaactttaa tgattacaat ttttaggaca ctctgtggcc tagacttaga  66600
aacacaacta atgtccagaa aaagattcct ctttttattc catcatctga taggcctatt  66660
tttacacata cacaccaacc aaaagtagcc aagcaaacaa aacaacatac tcacacccct  66720
tcgcctatta tcatctaggt gattttcaat gctcattgca atgaaaccta cttattgtgc  66780
atggcaccca cccccactga ggaatactgt agtttctttc cctttgaact tcattagtag  66840
agcacatggt tcattcactc ctgaagagtt cttcgtatgt cagaatatat atactacaac  66900
ataatttcca tcagagctct gaccacccgc ttatctattt tcataatgcc tgccactcca  66960
tcattagctg ttgtcatgta ggctatcaat aaatatatga caaataaaac agttagggaa  67020
tgagggaaat tgactagcag ccaaagacct aagccatcct ctgcttggac attagaaaac  67080
tgagttcact acagtcataa gatacacaaa ggcagaatgt aagccataca aaaatccatg  67140
tcaatcccaa tatgtgagta caactattga acaccatgta ctaatggatg agttggtaaa  67200
tcattcaatg tcttcatgag gtcaattaca gattattatt tagaccccaa agattccaaa  67260
```

-continued

```
gatggtattt cggtcagatc ttcatccttt gtaagcctag cagaaaatat ggcagtttta  67320
ttgactacta ttctttgctg ggtgtggtat ttttaaactg agacatcagt gtgcctagca  67380
cagggcctca agcacacaga aaaattcctt gataataatt aaataaaatt tcagcaaaaa  67440
atatcatctt aaggctgtga aattatcttc ctgtgtggct aaaatagtga ataaaattca  67500
gcgcaatata aatcatagta caatttcatc actaaatttt ctgatcttga tcttgtcatt  67560
ttacattgga agtaaaaatg tgtcctcctt tttttctctg acagtgaaaa gtgtgtgtgt  67620
gttgtgtgcc cttttgcaca ccctgcctca cacttgctgg tctaattcct tccagcatga  67680
ttatgatata attaaatgac agaaatgttt acttccaagt ggaactaagc cagggtaact  67740
cagggtaggg cagctgcttg caccgaaaga ccaagactgc tagagaacta ggaaacaggc  67800
ggtgcaagaa ctccaggctc tcatggaaga gcgggaggct tctatggggc tgcagaaact  67860
ctttggtgct tggggaaaaa atgggttaaa tgctcttaaa aaagaaacct gggagaggta  67920
gtttccagat gcaggcccgt cttttctttt aaacagaggc agctccgaag agctggacat  67980
tgaaccctga gcaggaactg gaggccgtca gcgcagcttt gtttggcgag cggagctttg  68040
caagggtgta atgctgcacc agggagacgc tatctgcagg gaccggtgac gccgtgggtg  68100
tggaggggga ggcagtggct ggccctcttg gggtaaggta cgcccaggaa cagtttagaa  68160
taacgtgcgc gagtcaaagg gaagaagaag ctcctgcaga ccttctgggc actgtgcagg  68220
gtttgctcct gtccaccgtg ccgtgttcct gtcctggggt atttgggtgt gtggcgtgtg  68280
gggaggggag aaggagcaag gcggcaggga ggggatgagg accaccctgt ccatgggaca  68340
ggccctgggc cccgcacaca ccccaagccc cgcgtcccgc gtcctcactg tcctgggaca  68400
ccccccaccc caccccaccg ccacagccca gagcggtgcc aggaagccgc ctcgacgcag  68460
ccgtatcttg aggctccagc cccatcccca gggtaccacg ccacgtagag acactatttt  68520
tcacttcgtg tttgtcactc ctaaagcatg tgtgctagct gcaccaaccc tgggatgcct  68580
cggtgcatag ggtttatgtg cgtcctcctc cttccctctg agctggtccc ccgtggggaa  68640
ctgctgccca gactgacctg cgtccttccg cacgtgcagg aaaatgtcca cgtgcacttg  68700
tcagggtggg ggccacacgg gcaccaccac tgatcatctg tgggatcgag ttactgccca  68760
tgcagatccc acgtgcaggg cccagtcgct ttggtgagag agtggacgct gtggtgactc  68820
cacggtctgt ggctgtgctc aggaggacag agaggggaca tcctgagatg gtttgggcag  68880
cccgcggatc ctgtgcatgt ccccagagcg tccactttct ccatggagca gtggagtggc  68940
gttgctgaga cagaaagttc aggttctcca ctccccatgc agcccccact cccctgtctc  69000
cggccaggca cgcgtctggg gtggagactc ccggtgcccg gggccctcca gacctctttc  69060
cccaccccag ggagcaggcg ggtacttcta ttccgtttgg cttcagaagg gaaaagagaa  69120
cgtaagttca gggagttctc gtccattcct ctcccgtggg ccgggcaggc agcagggaca  69180
gccttcagga gccaggaggg gctcgagctg cgaggccctg gaatgaggca ggcatgggct  69240
gaggctggag ggaaagcccc gctaaggctg ggcgggggcg ggaaaactta ccaccagggg  69300
actcgagatg gggaaggaaa ggtcagaaga ggagaggcca ggcacggggt gtgggcggcc  69360
tgcagagctg gagcaggtgc tccgcccaga gccaggcatg cacactcaga gtaggtggcc  69420
tgtgcagcgg ggaagagggg cgggtcggcg tgctgctgaa gatgcaggag ctgcggcctg  69480
ctctgtgcgt gctgaaggtg tggtgagaag cacttacaaa aagaaatgga ctgtgttagg  69540
attgcacatt ttactttgtt tctcccaaat acgtgttctt tgaatttttt tccttccagg  69600
```

-continued

```
gccaggactg gagtgatggt tgagacaggc acgcactggg tcttgtctgc atttacattt  69660
tgagattttg ttcagcatgg attttatggc gttttttgt ttgtttgttt gttcgttttc  69720
aaaatactgc acggtttatc gtgaagacag ggtcctttgc tgccgtctta agttttgggc  69780
ccaagaacgt gccccaccct aggcccgggc ctgctggctt catagctctc atcattccca  69840
cggaacctta agacctgagg acagaaagga aggaaacaag cccagtagtc cgtgaaaatc  69900
cagggtcccg ccactccagg tgtctgcagc agagctgaac acacgtaggc tcttgccagg  69960
aggggcattt gtatgtgctg agcattcctt atattctcaa tatgacgcct ttgaaagatc  70020
tgtggtttgc aaatatttac tctcagtcca taacttatct ttccaacctc ttaccaggct  70080
cttttgctga ataaaagttt taaattttga agtctaatat atttttaatt tttttatttt  70140
atggatcata ctttttgtgt caggtttgag aagtctgcac caaagtatgt cctgtggttt  70200
tcccttaggt catcttcaac aagtttcata gtattttgtt tagatgtaaa tctgtggccc  70260
attttgagtt agtttttgca caagagttga ggtcaaggtt cttttttgc ctgtgatgtt  70320
cagtggctct ggcaccattt gttgaaaaca tgatagccaa tgtcaagact taatagttat  70380
aataatcagg agcttttgtt tctttttgtt ttgtttttag taactgccag tcactgcttg  70440
tggtatacat acacaatgga atactattca gtcttaaaaa aaaaaaaaga aggaaatcct  70500
gtcatttgca tacctggagg acattatgtt aagtgaaata agccaggcac caaaagaaaa  70560
acattgcatg atctcactcc ttcatggaat ctaaaaaatt gtattcagag aagcagagag  70620
tggaatggtg gttaccaggg gctgggaagg tgtgagcttg ggagatttg gtgaaaggac  70680
atagaatctc agttagacag gaggaataag ttaaagagat ctattgcaca tcatggtaac  70740
tgtagttagt gacaatgtat tgtatacatg aaaattgcta agagagtaga ttttaagtgt  70800
tctcaccaca ccaaaaaaag gtatgtgcag taatacagtc attaattagc ttgatgtagc  70860
cattccacaa tggatacata tatcaaaaca tcatgttgta taccataaat atatactgtc  70920
tctttatgta aatttaaaaa taagataaaa taaatgttat tcacttgtcg tggatgtggt  70980
ggggacaggt gtgggatagc cctccctgta caactaggac ccaggggtga tctagtgaca  71040
ctagccattt atcaggacgt atgggtgcca gtcaggatga taaagcttcc ttttggccac  71100
tatactactt agaaatgccc tgcaaaaggt gcacatcaaa gattgaaagc tcaatcctgg  71160
attttaagtg cttcaaaagt gcacttaatt gccacatttt tgtcaaacat tttcccaggt  71220
agtatttttc ctcatgtaaa acaacagcaa tttaatttga acagaaagca ttttgaaaca  71280
tacttttggc agggttcctt gcagatcaga atggaaatga ttaacagggc aattatcaat  71340
catggacttt tggcggcaga aggaactgta ttgtttggta cagtctgggc cagggccaca  71400
caccgtaacg gagatactct attctgtgga cggttggagg gggctgtgct gagcagggta  71460
actgcatctt ttcctagact gttcacactg ctgccacgaa ggagtcttgt ttagactgga  71520
cctggctttc ttcttcgcaa tgagtgttgc agactcccga caaaggccag gtggtaaagt  71580
gtggtgtctg tgagcgagag cctgagatgc ctgagctgac ctgtcctcag ccacctgcca  71640
tcgtgcagag gtgagagcag cccctgaatt ctgcccctcg gtctctccat agctaaagca  71700
aaaccatcct tccgtgctcc caggacaagc aggctattac caaatcaccc actaaccctg  71760
ggcgaggagg ggccatcact gcacaattca tcagtgtctg tgacaggaag agattgtttt  71820
agactggttt tttttttttt atttgcaagc ttttttctct ctccaaaacg tgctgtcagt  71880
gtgttctaat ttactctgta aggaattctg gagctaatca taggctcaca aaaagcagca  71940
caggaaagtt tcccagataa catctatttc agtggctttc aaacattttt gaccttacca  72000
```

-continued

```
aagtaagaaa tacattttaa tatcatggca cacatacagc tgtatctaaa ctttcataat  72060
actgccttta cgatatcact ctgatattgt ctattctttt ctgtttattt ttctttttgt  72120
tccttgttat gctggttgtg acccactcca gtgatttcac aatgcaggct gggtggtgtc  72180
ccacagtttg aaatcccaat ctagggcctt cctctcactg tacaaagtag gtaactgggg  72240
acattagtgg atcagtgatc aaaccaaagt tatttgatct taccaagtga tatcaggatg  72300
agaaagctgt tagagtgtca gatatgtgaa ggaacttggg tcattcctga tacctcaaag  72360
agaaaaaagg tagtccttga acacctccta cttgtaaagg atgcacaatc ctacatgccc  72420
ctccctttcc tttcctcccc tctgtacccc acccctgccc acattttctt cataagcagc  72480
tttggtgttt tggcttgttt gtttcccttg tctcctacct gtgactttat agccttttgg  72540
agactcacag caatagttgt atttaaactc agtgggtggc atccaaggct aaaaaggaga  72600
ttgcctagac acaaaaccac ccaagggaga aagcaggaca gcatcttact atgattgttt  72660
cttgtttctt cctgtctcat aaggattatt acccagggtt ttcatttttt tcatttcatg  72720
gttcatttc gctccagtgt agacatacaa tagaccactc gtccctgtgg ctccgggcag  72780
cagcctcatc tgagaccctc ctgagacatc tcgtgcaggg cagccgtagt gtgtggcttc  72840
cccagggctg ctctaacaga tcaccatcct tgccatggct taagaagctg cagatttatt  72900
tgcttacagc tctggaagcc agaagtccaa aatcaaggtg tcagtagagt ctctctctct  72960
gaaacctgct gaggatgatg cccctggcct ctccccagcc tctggtgttc ccagcagccc  73020
ttggcattcc ttgccttgta gatgcaaaac tccgatctcc acctctatcc tcacagtgag  73080
ttctcctgca tgtctgtctc tgtgccttca cattcctctc tgtgtgtctg tgtttccatc  73140
tccttatgag gacacccatc actgaatcag ggcccactct ataccagtaa gacctcattt  73200
caactccatt acatcttcaa aaaccccatt ctcaaataag gttacttcac aagtgctgga  73260
ggttaggact tgaacatacc ttattgaaca atccaactga tgacacatag taatttatgc  73320
actcgttctt ggagacgttg actttattta gtagcattaa ccatggcaat gtcaccagca  73380
tcgctgacag cctgaagcat atgatctcca gaatgtattt caatcatcat gttcacttcc  73440
ttggtattct ttagacaata actcagcctt gaactccagt aaagggtttc cctgggattt  73500
tcttcttgac tcactccact gtggcctccc tcatccagga ctgtaacaga cgcctgacgt  73560
cagtggtcta gacctctctg ctgaatgtca tctttggtga atgtcttatg agaaaacaca  73620
tggttggtca ctcttagaag ggcatgaaag cctgtctgca gtataaccaa aacaggcaca  73680
tggcgaggca cactgtgcgc atgtgtgtac aattaatatc atggttttaa attattttca  73740
ggccaagggg agatctttgc tgcatctact gaagaaagcg aatctttttc ttcctgaaaa  73800
aaaatggcta cttattagtc gaatttgtgt tttaaaaata tgtgaactaa tataatgcag  73860
acatgcatta atgtttaaat atactggaag tttttggtaa aatgaaaccc attgtctctg  73920
ttgattactt tgatgagtca agaagtaaca tcctgggaat gattggccag tttaaatgag  73980
tgcctcaggt ttttggaata caagaaatca agaggaaggg attagaacat ataggttagc  74040
aagattggga tcctaaaata cagacccaaa tgaatggaac aaaatcaggg aatttattaa  74100
taacagggtc aaggccaaat cagtaacaaa tatcctgagt ggaagaaagg tggtttaaca  74160
aatgccccta tgaaagatag agattggctt accatgatga gatgtaagcc caagttatga  74220
ggttggcaca caaaaccaca aatgtcatag cttaaaacaa cacacacttc ttatctctgt  74280
ttctgtgggt cagggtctgg gttctcaggg actcacaaag tatgttttca tctggagctc  74340
```

-continued

```
caggtcctct tccaggctca taagggttct tggcagaatt cagtttcttg aggctgtagg  74400
actgaggtcc tggctcctag aggccaccct ctccataagc agttcttagc atggccgcct  74460
gcttctccag gcccagtggg aaagcatgtg cctccaggag ggctcagtcc attcttcatg  74520
gcttttacct ggttaagtca ggcccactca ggataacttc attttgtatt aaatcaaaac  74580
cagctgattt gggatgttaa ttacatctgc acaacttcaa ctttgccata taacctaacc  74640
atgggactga tatttatcat gcatttgggt caagttgcat taagagatat aataaagctg  74700
gacaagcttc tgttgattag aagagttcag ttacaaggct acacttggga ggaatgttta  74760
caaactggaa tggtcagagg atggggaaga cacttgagaa aagtcaagtg acggatgaag  74820
gcaaatgtgg atatttatct gggagaaaac taagaggagt tataatagct gtcttcaaat  74880
atttaaaggg cttttattag gaagaggaat ttggcatatt ggattttgcc ttcagagaag  74940
tggagtcctg agatgctctt agccattcat tccagcctcc agggctcacc tgctgtcttc  75000
tgtccaggtt ctcggtagca gggcagtaca gccccatccg tgatcttcca tagtcaggca  75060
tattgtcaca ctcagtgagc ggagagtcaa ccgggaggaa ggcacagttt ctctggaatg  75120
acctacggaa tggtacgctc aaatgcaaat tctccttccc ttccccagtc cttgtccttc  75180
agatggtaat ttaggagctg aaggtcaggg caccagcagc ctttggaagc ctacaggaca  75240
acagtcagcc tggctagaaa aaaaaacaat gtcacaggca tgttgtgttt aatcacatga  75300
aggatatttg cattgttttc caactgatgc cagcagacac attgtcagtg gtatcatgcc  75360
tggggtatca gagttgacat tgggttgccc cttctctgag gcattcatgt aaatcctttt  75420
aagtttataa aacctccatg tggctcctgc atgcttcatc atttgcatgt gtctcttttt  75480
ccaggggagg cagcatgggg agcaggatgc tggtgggctc caggtgcaga gagcagggtg  75540
ggcgtcagac cccaggtcca ctgtgcacgc cctcttgtag agcccgttcc gttgtccatg  75600
agatgaggag tgttcttatc tctaaagtat tatcatgaaa acctaacaat gtagaaagac  75660
taaagcacat gggtggtgct tcataaatag tatttctccc actttctgaa aactcctgct  75720
gaagtaactg cacaagaatc cttgaacatt tagaattctg gttttagcca taccataaag  75780
tcagtagtgc gtggtggaat tctgctaacg aaaattgcga aggatcaagg cagagtacag  75840
agctggtgtg tagcgggtac cttctgtctg ctggcactag gtattttaca cattaaatca  75900
gctcgttctc acatcagctc ttttaaaaat aaggaaatga ggagccacag tggcccaact  75960
gatgcagtgg cagaagtaga atttgagctt gtgcagatgt gcctccgtgt tttgtctcct  76020
gagcatgctg ccccaagttt gacaatacca agatttgtac tggaacattc cctcccatcc  76080
ccacccccta gaagcccctc ttcctccctt agatttgaca catagtttga aaccactatt  76140
aactacctta tgagagccac tgtttgtgaa gtgctgacta tgtgccaggt cccgtgccgt  76200
gcaatttttg tgaattatct cgtgtctaca gtgcctcaca atttctctgc tcaatacctc  76260
catgttactg ccgaggaaag ggaagctcag agagagtaag taatttgctc gagttaaaga  76320
gctggccagg acagccaggg gcttgcaccc cggagccttc atccactaca ctgtcagctg  76380
gtatctcaac cagccattac aggctgtaaa aaaattatat aagatagtct atggtaatgc  76440
agaaaagtga ggttattttg ctccctttcc ctttgaagaa aaaagccctg gaaagacata  76500
tcacttgagt atgggaaaaa atgaagctgt ggcttttctg tgagtcaatt ctttcctggc  76560
agcttcttgg aataagacca agtatagcag cagagttttc tgttttaatt tgagctgcag  76620
ggtgactttt tttcttctat gctttcatct ctctgtggct tcttttgcct cgttaatttc  76680
atgccctgcc caggcgggct actgtgctgc ccagtcaccc gggtctgggg cggccaccgc  76740
```

-continued

```
tggccagcag gcaggccctc cagaggcaga ggtggccacg cttaggtcgc tcccgctgtg  76800
gaggcggcac acttgggtgg cagcacagct gtgatgtggc ggcagctggc agccccatgg  76860
gaaagatgtg tgaagtgtgg ggtttgacga cccatgggag aacagacttt cttcctcttc  76920
ttgttttccc ttcaaagccg tgagtcaacc tcaaattctc tgtctttttt ctccaccccc  76980
tcgtgcctct ctccctcacg ctctgcatct ctcattgcaa gcttgcattt ttttgcacac  77040
aacactatct taatatttct cttttctgca ggcaggaaat gagaagtcat ttttcagggt  77100
cattcaggaa gtcatccaga gttataatgg cccattatct actggtcaga gtttacttag  77160
gctttcacta cttccactgc ccacttgaaa cagggaaaaa tattttcccc ccgcgctgtg  77220
agtgtgctat ttagagctga ccacaagcgg ggggaagaga ggatggctcg gatgctgcat  77280
ttccactgag aacacaaggc tggcaaagct tgtctgctgc ccagcaagca cttcaggctc  77340
acaccatttt aggttcactt taagtagttt ctcaattgtt aaaaaaaaaa caaaaaaaaa  77400
aaaacctgta ctctgaggat atgcttataa tcccatagct aacccagaat ttcttagaga  77460
actgatcaac atcagcagtg gcacttactg aaaatgcaca ttctcaggcc ctgcgtaggg  77520
cctactgagt tagaatatta gagagcaggt ctcagaaaca ttctatccgg cagtcttatt  77580
ctatgcaccc gaagggataa gagccatgct ttcatgaaac atgggttgtg tgtaaaatgt  77640
ttaaaaggta tggcaaaatg tgtttgattg gcaccaagga tttctggttc ctcctagaat  77700
cattaatcaa actttgaagg agaaataaga gagtcggcat tttcttgcac attctttgtg  77760
atgttgtgat gagttggaaa cttcccgatt gggtttatta gagcatgaac acccaggcac  77820
ccagcttcta gccagccctg tcaggcagag tctcctcgaa gatgtggaaa ggactgacca  77880
acagctgagg cctacaggaa cctgagcagg caaggggaga ggcaccccgg aaccaggagc  77940
aatggccttc ccaccctccc tcgtcctctc ctcttctcct tttggagttg caggccacag  78000
aaaggaagtg acatgagtca ctttgggcct tcttaattcc ttcatcaaag gcagcacagg  78060
tgtgtatgtg tgttggtggc taattgaggt aggcccacag aggagataac agatggacat  78120
actatttcct ttcttccatt ctgatataat tcagggtata aacacacaca cacacacaca  78180
cacacattct cacttctttg gcatctacca cacctgcccc agtgcccatt tctctcccac  78240
ctgaataaaa agcccccaca aagcctgagg tacatggaaa ggagcagtgg tctggctccc  78300
aggagtgtga gaagcagcca tgttttcaga ggctgtattc cacttggact tggccctacg  78360
ctgaaggtag gagcggatgg gggaggcccc cttcgcacaa agagccccat gaaagagtgc  78420
acagtccagt ctataaaaca gacgcagaaa atgtgtgtag gacttcttcc tgaaaaagag  78480
cgtggtgcgt ccagtacctc catgttcatg gaacttccca gtctgcagtt taccctttttg  78540
tgcaactccc ttttggtaaa gccctggtca cacttctggt tgttcagatt atacagggat  78600
aattccagag tgattttaaa gtcaactgcc aggcatccgc acttgcaaat tagatgcctg  78660
gcacatgctt gtgttaaggt aataattcat tacaatacaa attacagggg agttcctctg  78720
ggcatgcgac ctttcccgtc atttggcttt ccctgtgatt atcaggggag cttccatcgt  78780
gctgctaatg ggaccttaac catgtgtcaa cccatggctg taatgctgac actgttttct  78840
ttctggaatg aaaggccttc gcaattgaaa ccaaaatgtt atccaactca gtcctgtccc  78900
tttgacgatg aaaacatcaa gttctggaga ctggccatcc agcctccctg cctcatctcc  78960
cacgccctcc atcatttttt gtctctactt acttatttat ttggctgtat tttacgtaca  79020
tcatgcaaaa atattcctct ttgtaaaaag tataatgatt tcaggaaatt agagggtaaa  79080
```

-continued

```
aagcaagaac catgctttca ctccactgtc aagagttgtg gaagaatcct tccagcattt  79140
tttctgtgta ttttacatac atacaaatat atgtacaaat aaaggtcgat catttaggtt  79200
ttgtttatat ttttgtatat atgagcttat gtcattcata catattgttt tgcctcttgc  79260
ttttttttaa cttaatttta ctttgcttga gagctttttg aactgaagta cgtgtaagtc  79320
agcctatgca tgtaatggct ccctcatctt ctgtgaggct gtcactaaaa aggggattta  79380
gcttgttctg ggctttgcag cccgtacact gggcactgtt catacgtact tctctgtgca  79440
cgcaaaggag ggcttgctag ggaggcctgg cagagggtgc cattcaaata ggattttcaa  79500
tggaggaatt tttaaatttt cagttatttg aataagtttt aatatatatc cagaacccca  79560
aatcatcaag tttgttttct tccacatctg tccttccatt tctgaactat tttaaggcca  79620
gtcatgtctc atccaagaaa tcccatcctt tcacacaaca ctatctccgt ttcatggtta  79680
tgaatctcta aaagcatgat ttttaaaaca taatcacaat gctgtcatcg aacttaaaaa  79740
ttagccataa atctcttatg ttacccaaca accagcctac tgacacatct ccagttgtct  79800
caaaaatgtg ttttccattg tggtttgtct gaaacatgat ccaaaagtca gacccacctc  79860
tcacctttcc ctaacctgcc ggagcccatg tttctttcca gccaggcttg gagaccacca  79920
cacgggattt gcttcttggg gcctccctct aaccagctat gcaggatgcc ctctttcctg  79980
tcaatacaag ctgctcaaag gactcattca gttcaaattc acctatgtga gcctaggtga  80040
tgctacttat ttatttattt atttatttat ttatttattt atttatttat tttgagatgg  80100
agtctcactc tgttgcccag gctggagttc agtggcataa tctgggctca ctgcaagctc  80160
tgcctcccgg gttcaagtga ttctcctgcc tcagcctcct cagtagctga gattacaggc  80220
acgtgccacc acgcccagct aatttttata gttttagtag agacagggtt tcaccatgtt  80280
ggtcaggttg gtctcaaact cctgacctcg tgatccaccc acctcggctt cccaaagtgc  80340
ttcatgtttt caggagctgt acgtgcattt ttagttttga tgaccaggtc ctttttctgt  80400
tttttaaaga acttcaaatg atctccaggg tacacagcgc ttgtgtgctg atgaaaaagc  80460
tggcagtaca aaggccacca gccaaggtca cacagccaaa aagcccctga cctcgggccc  80520
cttcccagac cctgggtctt ttgctgccac atgaatcttc ttcaaggtcc tatgtgtaga  80580
ttttcttgac ttggccatat tatttaggat tcagatataa taacaaaata gatgttaaag  80640
cataacatga aggcatttaa aagggtagaa agcacatgat ttactaaaac cataaatctt  80700
atgacctgaa agtttcacct aatctcttaa aaaataccgt actaaaccct gattgaaaat  80760
cagagctcag acatacagcc tgagatgcca aaaaatggcc aggcttgtct gttgagaaag  80820
ccatatgtaa ctaactgttt ggaaattcaa aatatatctt atcattttaa aaacatcttt  80880
cttctaaaga caatcatctt ggcttcagga atgaggctag taaaaagtga aatactccta  80940
cttgtggaag aaatcctcat tttaaccatg aagaactgaa aaatgcattc tgatgttgat  81000
ggacccaacc tatatttggg tattttatga tgtacacaat atacttttgt atatgagatt  81060
gttattaaat gtgactttgc tttttcaaga catacaatgt tcctccgggg gtcaggcact  81120
gtgtttagca ctttgtcctg acctcatctg acttctcagc tgtccctgag aggtaccagt  81180
gtgcaagatc gctgagttgg caagtgatag tgacaatatt ttcaccccaa tttctaattt  81240
aaagaccccg atttctagtt ttgttttgta ttggatttgc acaatttcac gttctgaaag  81300
aggatgccct caactttgca aaatgggcct tttgaatgaa aaggatcagt catgtcagga  81360
aaagcgctac aatgatgaaa tatgataaat aagtcagtct ttcatctgta attatctact  81420
atggggtaaa aagtgatgaa aactaccatc ttgaaaggtt ctggtgatag tggttcctaa  81480
```

-continued

```
tgcagtgaaa gatgtgtaag tcaaagattt gtaaccagcc agggaatgag aggcgaagcc  81540
atagctggtg gcgggggcca catctgggtg tggggaggcc acagttgggt tgggggtggg  81600
gcctgcagtt atccacaccc ctcccacctc ccttcgacag tacaggcttc ctggttacct  81660
tccagagagt aaggccaggg agagttgaat aagttgagaa atgtcatgtc gaagctattg  81720
gtggaaagag ttccattaat tgacaataca agtccctact acattctaaa atctggtcct  81780
gactagtggc aagccgggcc caggagtagc acttaaacaa tggcaggctt gtgttgctgg  81840
caggatactt cagcctcaga ggagctgtgt gcagctgggg agactcacac tcagaggatt  81900
tcaaagcaga gggcatctcg tagagcaact tatccaaacc ctgacccact gtaaacacac  81960
acacacacac acacacacac acacacacac acacacaccc tgagagagag aaagagagag  82020
agataactaa agagagagaa ctaaagtttg gcaaaataat acatgctcta atgaaggttt  82080
attaatgatt aatctactcc tagcatttcc tagtccactc tatctcctta aaaaaaaatt  82140
ctggttgcag cccactaact tgattgtaca gctgcttaat ggatagcagg ctgtaatttt  82200
cagagaactg tttaatgcgg gctacctctg ttcttccatg ctgcttgtgg ttcctgctct  82260
gctcaggaca gaatggggag gaaaacaggc tctgcggcac aatattggca agtgaaattt  82320
tgtaaaccgg ccctcccttc cttttgcatt tggtctgaaa attcaattag atgctgagtc  82380
ctacaatgta tttgagaagc ccaggagtgc cctagaggat gagactgggt ggctccctgt  82440
caggttgaac atttgcctta attactttgg caagatttgc atcagtggta ttagtccctg  82500
cctcacttgg aggcctgcac ttaagtggcc acattcaggc tccaatttcc tggtgatttc  82560
atagtgtagg gcacttgcaa tcaaaactag gcttaaagcc caaccctctt acattttacc  82620
cacccccaca aatgcagcaa ataaaatgac tctgattttc attccctaga cctcttttct  82680
atatttatta cattattgtt aagacagttt ttgaagaaag ctgttttatt taacaaaata  82740
gctttatgga atcaacttca tatatcttct ccgccagatc aaaacaagct cgtagtatta  82800
gatgtcaccg agcaccatga caggcagatg aacatcatcc ctgtgcccgg ctaatgatag  82860
ctcggcctgc cccggcgtca gccgctcctg gcagggccag cgggcggtgt gggaccggca  82920
ccgtatctcc agcaattcgc agataacaaa tatggttctg atgatgttac taaagatctg  82980
tccctttcaa gattggatta gacattagga atttggaggg ctttttattg ctagcatttt  83040
taagaataac caattagagt attgattcta aagtctgaaa gccacatgga cagagttcat  83100
gtaattggct actttatgtg cctcttccta gattgccctg cattttcaaa acaagagcct  83160
ttctatttta atcaaaagaa tccagaatga aatgaggctt tgaaaactca gcctatgttt  83220
gtcttgattt ccttaactga catctagaag aaaatatgag ctcaggggtc cgctgggttc  83280
cttccagcgc ctaagcctgt aagctcttcc tgctggaacc aagctttaaa tgcacttgtc  83340
agtcatgtcc catgagaata gatactgcct tccatgtttt tttgttctga tttccgtgtt  83400
tgaaatgatg aaaatcattt ttctgtgctt tttaaaaatg gaattgcttt tgtgttggga  83460
attgtgctgt tcatttttac tctacctcgt tttggaatca ctaatgtggc caatttatag  83520
ccaaaaatca gtatcgtaga gtgagcaatg aatggcatgg tgactgtgtg agcgaattca  83580
tgccctccct ccccaccgct cgccccgcgt ctcagtcctc agtgatggta aacagaatga  83640
ggaccttctc ccgaccgtga tgcgcctcag ccctacttcc cttgtccttt cctatcataa  83700
aatcttcttt catagaaatg gtcatttctg ttcatatctg tggactgtaa ataacaagga  83760
agtcattttt gaggtgaaaa ctgcacttag actcattcca attttgatgg aaacttttag  83820
```

-continued

```
ctggtggatg gcattttgtt ttgtcttagt tttgcaagga gttatcttaa tttagggaga  83880
tgaaactagt ctgtgatccg aggtctcact tccatacatt tctctcgggc agtgtggctg  83940
cctgaatcat gcctggatgc cacaggtgct tagccagctg gtcctgtcgt aactgtcact  84000
ggtagctcag ggagtgcaga ggtgccagca gacactatga aattggcctc gtaaagcatc  84060
agttatgttg tgatggtggc aaagctgcag gcgagatggg aagtgcagcc actgagaact  84120
cacagtagag cgtgtgtaac gtaaaaagat gaaacccatt gtacacagct gtgtactgcc  84180
tccttgaagt caaatttccc ccattaccaa ggaaaagttt tttctgaagg gggctgcttg  84240
acaggatgac atctggtgat atcatttatt cctttggaaa tcaatctgtg gaagtgagtt  84300
tccactgact gatgaggaga aaaatgaatt ggcttcaccc agcatccagc ttcttatcct  84360
gggagagata gctcttggtc tgtcatccac gcagctgcct ggtgcaagag ccaagtttgt  84420
gcagcctgca gagcactctt cctgagctgt gggctgccag gtcgggggc agggggggcc  84480
tcactgtgca gcctcctgcc acccactgat catctgggga gactggccta tcctgtcagg  84540
agacgcagtt gcccagacgt tttcaagggc ctaagatgta ggcagttgat ccacagattt  84600
ttggagagtc cttgagttgg agattacagg tgacctcaga ggagggagtg agaacatctg  84660
ggtcatgggt ttctactagg agtccacagt gaaaacaaga agaggaattt acgacaagac  84720
agtccagcaa cttcctttct aacttctcct ttcacatatg ctggatactc caagactttg  84780
catttacatg gacatcacag atccactttg agagaagtag ggtaaaaaga aataaataca  84840
tagtgcttta ggtgtatttc tatacatctt aattgatatg ggattacatt ttcacttgtg  84900
tttactgtac agactctaga cagatcctgc tcttttgcag gtaaaacaaa tatttcttaa  84960
aacctagaaa gacccaaaac aatttaacag aaacattttg gaccattttg gaccttggca  85020
gttaggcccc agtgcagcag cggcaaccat aaacctctcc ataggtgctg aacccaggtg  85080
atccctggca ccggcagcct tatgtcaggg ctctcttatc gctggttttt atttctccta  85140
ataaaagtga ttaaaagatt catcttttaa agaaagcaag gacacagagg tggattctcc  85200
ctgacgctag cacagctcat gcccaagcca ctcctgcagg gctctggtct aagtgcaaaa  85260
gctggaaaag ctgcaggtcc cgcaagacac agagcaaccc tgcaagccag gtcaccttcc  85320
ctcttctctg ctgtccgact ggccctccac catgtgacat tcaaaagctc aagttactta  85380
acctctcaaa actcagcatc cttttctgta cagtggggaa gatactggac tgttgtgagg  85440
attaagtgag gagagtggcc caatgaggtt gacagttatt actgtcattg tcattatttg  85500
ccttctcaca ggcaggcgtg ccacagtcat tttactgaag ctgcttcagt gggtcctgaa  85560
ttaggccctg tcctttggga gagacagtcc tggttcaaca cacagctccc tgcccagggc  85620
agcttgggag tgtgggccag tttcgccttt agaaccacaa ttctctgata tgtgcaatga  85680
gagaattaat tatagactca aaggattgca tgcagacaca cacagataca aacacataca  85740
cacaacacac agagttacac acagacatgc tcacaataca cagaaataca cacagacaca  85800
cgcacacagc acacagagat acacacagac acacacacac acacacacag acatacgcac  85860
agatgggcac acacagagac acactcacag agacacacag atacacacag gcacacacac  85920
agagagacat acacacagcc cacagggata cacacagaca cacagagaca tacctacaac  85980
acacagagat acacacagtc acacacagag agacatacat acaatacaca gagatacaca  86040
cagagacaca gatacagaca cagacagaca tacacacaga cacgggcaca cacagagaca  86100
cacagacaca cacaggcaca cacgtgcaga taaggtaata ttagctagtt caggaggaga  86160
aagagataaa gataaagtaa tattagctag ttcaggagga gtgaaagaag ccttgttttt  86220
```

-continued

```
ctccactttt tatagaagag aaagtgaaga ttcgatttga ggtgagttca gcacaaaagc  86280
gtatcccagg ccctctggct ccaactgcag ccctttctac ctcattccca gaccccacct  86340
aagccttttc tcttcaaaat cttctcaggc acactgatac acatacctca gatttttaat  86400
tctccggttg tgttcaccag gtgcttggtc atgattaaga attccgtgat gtgtacccca  86460
tgtgtttaaa tttgctgctg agttaacttt gtggcggcct gtggactaga cctctgcaca  86520
tgcaatgcag aacggcaggg ccagatttga aatcctgcta tcttttcggc tgccttgtaa  86580
aaataacatc aggcgatggg gatacgatgc cagaggtcac ctgtgataag ttctgtttat  86640
ggccatttta cttctaggaa gacaggaagt gtcaggatct cagggatcta ggaagccaaa  86700
atgtttttcc actctgaaat aaagtgactg accaggagtt cccggccacg cagccctgtg  86760
ggaactgccg cacggccact tttatgaagt ggacacgtgt tggtcccact gaaaagaaac  86820
tccccaccca tggctccctc acgctgcagc agaggccctg ccacagcacc tgtcagcccc  86880
tgccagcttg caggggcgca ggcgcagagc ggtttgtgcc cttgctggag ccagggaagg  86940
gcacagggtc cctcctggag tcatgggagg tgcagccgag gttctatatt aaaatacaga  87000
ggctagcaca tgtgcttggg gaatgcagct acagtagtgg aatgaaagtg ctgtccgttc  87060
cttacccccc cagctcctca cctgtcctcc acacgcatat ccctggctcc ctttccctag  87120
taaggagact gaattgaaat tgtggcttgc ccgaggctgc atacctgtgc tctttctgaa  87180
gcccaagtca ctggctctag aattctaacc tgtgaggaag ccactgagga tgtttgtcaa  87240
aatacatatt tctgtgcctt gccccagttc cacggcccag gaatctgcag ttttcacaag  87300
cacccccagg tgattctggt ggtgtctttg cacttcttca aggcagtact gcctggaacg  87360
cagaatccca gcctcctcta tcctccttgc ctaatggcct ggatgctctc agatctacag  87420
gggaagggaa ggtcacacag tcatcgcaat agtaacctca gctgataaat cctcccccat  87480
aaaacttatt ccccagtgtt ttttaatagg aaacaataaa actgtaacca gcccaaatat  87540
ccatcaaaga gaaaatggag aagtaaatca tcgcacattc acctggacca gatctattgt  87600
aaagccaata atactgaagc cccttccaag gccctgggag tcctaacagt gcactggcag  87660
tgtctataat ttatattatg aaatttgcat aaggaaaaca ttttgtctca tttgtgcaat  87720
ttctccttct aaatatacgt gtcactttgt acctgatttc tataagaccc aggacctaca  87780
aaccctgtgt ctgcccctgc agccacccag ggaaggactg cacagcagca agacagattg  87840
ccatggagca tgttgtgccc aactagggac agcgcagata gattctgtaa tttgcctaac  87900
aatgtctata ggatgatccc atttgtcaaa aaaaaaaaag aactgggctt tattgatgtc  87960
acctaaatgc acctaaactt ctttttttgcc ccatgctctt ctgtactctt gatctttccc  88020
caaattttta aaaacatgac actcattccc ttatttttcc tacttagaaa agtgtagatg  88080
gttttatcat aggaagttca aaaaaattaa aatataatga aaaatactca aatagtgcct  88140
cacaacagta actactgcta acataaataa aatccatatt tcctctcata cagaccccag  88200
agttgctttg cctgacagtg tagttgatgg agaaaataat ctttatcctt agcctccatc  88260
tggttgcaga ccataaagac agggaaaaaa tgagggtgtt ggtagcttcg ttagaaactg  88320
aaagctcact gatttttttca aaacctaaat agcctgtgtt tctccaaata actaatttgc  88380
agccttcggc agccaggact ggcagggatg gggctagggg gactggggag aactgctctc  88440
tcctgagggt ggtctgaccc gacagcacgc atgaccttcc cacagtcagg aactgctcag  88500
agacgtgatg gcaactccat agaatgaaat actcttcagc cagtaaaatg tatttttgga  88560
```

-continued

```
taaatatttg ctttaaaaaa ctttactata tgttgttaaa tgaaaaaaaa accttaaggc  88620
atcagaaatt atgtgcagta aaatctcact tttgtaaata aatatacctg tttactacgt  88680
atgcataaaa agaatcctga gaaatataag tactgtatgc atattgttgt taagtatttt  88740
ttctgtttgc ttatctataa ttctaatttt gcttcaaaga acaagttact ccggcaatat  88800
aaaaataaaa taactaattt gtcttgtcat caaacagata gtaagaacag gcaaacctgg  88860
ccctccacac tgccagcctt ttgtgattca aggcttcagt ttcctccact tgttaaaaag  88920
attcaacaaa gtagttgaaa tagtatgtga accagtaaac cctaaaaggt gtccagtgtt  88980
gtctgtgagc taattaagtg atttgattct gactccccga gtcttctgat ttcgaagcag  89040
tggggagtca gacaggagcc tcaggtggcc tctcctgaga ggccctggaa agtgatgaga  89100
acctggcctc tggcagctct tcataaacgt ccatgttttc cctctactct ctcactcttt  89160
tcccagggcc tcaaacagaa gatgaaaatc aatttctaaa acagccctct gtgtgctctc  89220
tcgtatctct ccttttcaca catcgtggtg gtggctttct ctgtgttcct ctgttgattc  89280
agtctctgga attaacggat caggattcca tgcccagaat gctacaaaga ctgtgcttga  89340
gttctcccac atctcactca attacacaga agtttcagat tatgtaacag atgctgtgct  89400
gggttaggca gagccatctg acttgttttg ctttatttta gaccatgaga tgggtgagtt  89460
tttcttttta atgccacatt cttttaagaa ttaaaaacct ccacttggct gtcagcattg  89520
gaaatcagag tgatggtgca agccctgatg aggacaatgt ccttgtctat gaaaaggtga  89580
aatcattgct tgaaatcgct aagcaggaca tgcagtccca gatggagggg ggaattcggg  89640
agctggttgg aaaagagtat ttggcacttt gcagccttga gaggtgcaga agagacaccg  89700
aggggttcac caccagagcc accattgtca gagaggcgtc cagctgtgtc cacctgggac  89760
tctgccttca gggcttcttg cctggctggg agctgcacag gcagactcct gggacggtgt  89820
gccgacagct ctgggcaccc ccttctagga tctgattcct gaggaatcac aatgtggatt  89880
tcacaatcac ttccagtgtc ttttgccaac ctctgtgaac agatgtgcaa ttaaaaaaaa  89940
aaaaagaaag gggcccaatt ctcaacactg taagtggaaa ctttttaatg gaaaaggata  90000
ggctaatgaa ttgaatttga aatctgagac agaaccgatg catcaaatgt gctggtgttt  90060
acagataata caagggggc tgcatcttat ggtttcaatc cttttttaaa tttttgttct  90120
gagagaccca gccagcagac tgccgccagt cttgtcagag atgtcagtgg tggccactct  90180
gaatggaaag cagcatctct cagcatctct gaggcactgc tcctcagcgg agactgtggt  90240
ggctttgcct ttcagcacgc atcctttcta cgatgcctga cagtgcccag ggaatgggca  90300
gagctgggag ctctgaagcc ctttcaccta aaccaccctg ggtcacctga cctagttttc  90360
ctcccaattt taattatgtc aggcacttca caaaggcctc cttggggaca ccatgagctc  90420
actgtcatca gattgctcca atcacagctg tggcttgcac acaaccgcca tctctgcccc  90480
agcagatgct gtgtgtaaac agttgtatta attacatctc aaaaacatgg ttcttgccag  90540
atcctcagga tttgggtgca gcctctgagg tgggtgggag gccctcgagg gagaaatgtc  90600
tgcaggaaat tcttccccta cgagaggtct gttttctaag ttatctaaga gctactgcag  90660
ctgtttactg cagagtgacc ctgctcaaag ctgtggtcac ccaaggcttt gaaaggggac  90720
ctccacttcc gccctgggtg gagcaccgtg ctggagaccc acgcctgcca aggcctcatt  90780
gtcatctcca cacgccgtcc ttggggtggg ccactcctgg gacacgcaga caggaagccg  90840
gccacctgag ccactcggag gctctatcca gagtcagctg ccaagcctca cgtcacacat  90900
cactgttagt cttggagggc tggcggggcc ctgaagtcaa ttgaacactt ggatgacagg  90960
```

-continued

```
gaacttgcca ctgccagagg caatatgctc cattttttg acagttccaa caatttttct  91020
ttaaactgtc ataaaaaatt gctgctgtga ataccagtgt cggcgtccct gcctcacctt  91080
tacctggtgc ttttccacca cacaaaactg tttctcctcg tgctggcctt gggcttgcag  91140
acagctgatt cttctcctcc cgcggctgag cagcctcctc cgagcaaccc tctgacaact  91200
ctgctccttc tgacaacctc tgcaagggct gccagatgtg aacaaggggc ccgggcagaa  91260
ggtatccagg aagactggaa actcgaggaa gcctgccctg tcctgtccac cagactttac  91320
gcttgcgtca ctgggctttg ggacctaagt cctcgtcatt tgttcctttt gcagttccta  91380
ctgttctcag cacttccttc cagcttactg aggtacactc agatgtgata tgccatcggt  91440
acagacacag ttctgctcca gcatttcccc gtgttctttc tgtcgctcta tttactgaat  91500
taccgtgagg atgtggagcg aggctgagtt ctgtatttta acaccatttt aattctcacc  91560
tactgagaaa tccatcctct tatcactgtg cttttttaa cctgtcacga atccatgaaa  91620
tcctatcagc cagcctgcat acttcctttt aaggtgcagt tgaatcagga gaaacttgcc  91680
gcacatgctg cgtccgggca cagcattggc tgaggctgct gccctgacct gtccgctttg  91740
tagtactgcc cagctatgaa acaggttagc cacacatgac ctgcatttag gagtaacaag  91800
tctgtctgta catgcacata cagcaacttt tttaaactgt ctatattttt tcctgagata  91860
ggtatttata atatctccat cttctttccc attttgaaac ttagaacaag tttgcctgtc  91920
aacagttctc cacagcatac tgtgtattct aggattttct aaggttgagc aacggaggtt  91980
cagcaatttt gacttaattt cttcccatcc cttttccacg cagcccagaa gccttggatc  92040
acgtggtgag gggaagaggt tgtgctatgt cgggaaactc tgtatcgaag ctcggctcag  92100
atcatgacat tctcttgact aaaaccctca gtttccatca aacttgtcac tctggcatta  92160
aagcctgtca ctgtgtggct ctgaaaacct ctctgaacgt gttccctgcc tctgccctgc  92220
aggtccctgt gctccacaga agcccactta tgtgacccac ccccactcat caccaccttc  92280
cctcacccag agcctcagct ccccactccc acctgtaaga cccctactgg aaagattccc  92340
acctgcccct caagattaat ctccaaggac atttccaaat tcctctcccc atctctcagc  92400
cagatggctt tgctccctcc aggaacccca gccaccttcg acctccagca gggcactcca  92460
ctccacattc tcctggtctg tctggctcat cttacctgag ccatgctctc caggtgaagg  92520
actatgtcta actcaactct gctttaaaag cagctaacac attgctcttt gcatattgtt  92580
cactcactaa gttgaactgg acttggacat gcacactgaa ctgcagcgtc tgctgcttct  92640
tggtggccca gctcgtcaaa agaataagat ttcagcaaaa caatgtaaca attttttta  92700
ccaaaagtaa tgttaacaat atatggtttt cccctgatgt ttgcgtcaaa atgctttttg  92760
gaaaaaacat ttttcaactc tttagggtca gaattaagca atgaaattta tataccacat  92820
gtataatgtg tatgtttatc taagtatctg ttcatttata tatcttaaat agaaatttta  92880
aaaatttttt taaaactcct gataaacatt ctcaggaggc acactatgta actgttggtt  92940
gatataccta gctagatggt gaaatcagat tttgtttaaa gcatggagga gagggaaaaa  93000
ttaaatcttg cagattctgc agtccttaac atctttgaaa gaggaacatt tcagacaatg  93060
taataagaag gccacgtgct ttgacttctg tagattttaa aaatacttct gtatagtttc  93120
ttcttccttt gaagaagttt ggggagtttg ggaagatgga gaaagatata agaatagact  93180
ccccatatgg gtcatgaatt atctttttgc atcagaactc ttagtgcagt ttcagtattt  93240
tcttcctcag gagggtgagc tgcttccgaa tgtcctcccc ttctttgagg catcctctgt  93300
```

-continued

```
tggtgaactt tgagagcatc catttatgaa gttgatgacc tttcccagtc tctgcaagcc  93360
cttcagtgtg tgtcctctct gagcaaatct gaattgtgtg cttaatacat ggaaagggat  93420
ttgggagggt tgctttttaa actgatttct taattaatat tatggtttag ttaactagac  93480
agtctcattg cagaagtgca taaccataat atgtcttcaa atatatctcc cttcctaaca  93540
ccctgtaata tacttttgta aagataccct tacagaatgt gatccaccat ttatgaacct  93600
gcagcattgc attcagagac taagtgaaaa gctggcagat tttcatttaa agcacaagct  93660
aaggaagaaa gctggtctag aaggagctac agaagggtaa tgcttaggga gggaatgatg  93720
tgcctgtggg tggtggtagt taaatctaac caaagaatga tgtcgtgggt gtttggatat  93780
tggatggtcc acattgggcc acattctttc aaacataaga gtctgtagaa atatgacctg  93840
taaaagactc ttaaatattc tggaaactgt ttcttccttg tcacatcctt atatatactt  93900
gaacctatgc ctaccagaca tgacatgtga ctattcatac agatttcatc atctctggtt  93960
taagaataaa ggatgctgca tagaaggctc acatctttta attcacaaga ctgaaactgt  94020
tctgaaatga cattgtttct aaaaattcat tacttgcatt atattcattt ttatttttcc  94080
atgccagaag ggtagaagtt cctgtgctca tattaagaaa cagcaatgtc aatcgaggcc  94140
caactcaaat ccaatttata ggagttataa agggcgtgtg cctgttttgt ctagaagcag  94200
tgttgggcag cactgagtag gatagaccac ctgttgctac cgataaagga gcagcttctc  94260
gaatgctcct gtctggtagg cactatcccg agtgctttgg cccctcatcc acaatctgtg  94320
tggcaaaagg cattgcaggc aattcagtga ggagaccgag gcatggagag caagtgccat  94380
ggaattccct aaggccgtgc agggagcagg ttgccaagct gggttgaaac cgtcctccgt  94440
aggctcccaa ctccgccgtc gctgctactg tgctggatga tgcctggtag atgcagatgt  94500
ggagccccat ggattctgag acaggccggg tttcagtcct gccctagctg cctattggct  94560
ggatgacctt ggcaagttga ctttcgtgag cctcatttgt ctcatctctc aattaagaaa  94620
acctagagcc tatctgtggg ggttatctga aggattccag ggatgcatat ggcactgtct  94680
accgcatgcg gtaactgttt cacaaatgat gaggagcgat ttatgttctt agtggaaata  94740
tgtcggcgtg tgaagtccca aagctctgcc ctgcctggct tgatccagtg cctaggcact  94800
gcccctcttc cctctctcc caacccactg taagaggcta ggctgcctca gtaactctga  94860
ggggcattga ctcttttcat ccaaaaattc atgttactgc cccacatttt ttctgttgtt  94920
ttacaacgca gtaggaagtg ggcagactgt caggaaaagt gatttatagt catgtattgc  94980
ttgtgctttg gcttcatttg atccaatgca gatcagctgc actcagaaaa ctactcaagt  95040
gaaagagaaa aagtaactga agggggaaat ctggatgagt aagaattcca gggataggaa  95100
tattaatagc aagcttttttg cctgatatag tcactttatg ctgcaggggt gccccttttat  95160
aaagtgcttg tacaatggat gtttgctttt gattttggat ttggagtcta atgaatgttc  95220
taaattatta ttagaggagc ttgcggttgt tacatgtctg cctttattgc ttatttttag  95280
ccatctcccc tgatgtcaaa tgctcaggca agaatgatac attcatttat aatgtggctc  95340
cttcagaaat ataccacata ccttttggtg tggtttgtgg ctgagaagag tggggaatgc  95400
acaagtggaa aactgcagaa agattatgcc ttcatcactt caagtatttg agatgaaact  95460
agatcatttg ctgttgcttt ttattctcat tctaagtgct tttcaaagtc agcgctaaga  95520
ttttaaaatg gttttctgtt gttggcagag agggaattac tctattactt tctgataaaa  95580
cagagtcttt catgatcaaa gagaaccagg ctctagtagt tccagtatcc taacgtggac  95640
actaattgtt tccctccttt tcttcatgaa aacagcttct gcacaaatga tagccttgtg  95700
```

-continued

```
aactagccat gggcacaact ggagaagcat ttagggagct ttagtgcaaa ttgagaccac  95760
ctacacatct gactctacag ggtttgacaa catccagggt gaatcacaaa acatcagtct  95820
aatcagggct tatatagaaa gagtgaaaga actctgattt catcctaaag attatttata  95880
ttaaccattg ttccaaatgc attaactatt ttaatttagt tgttttgatt gttaaaaaaa  95940
acacatctgt ttggtagata agacataatt taagacaaat gttctatttg ataagctttt  96000
agaaacaact tatttttatt ctttcctgtg agataactca gatgtggaga atgtgacaaa  96060
attttaagca taacatgaga agggctgaca cacatagatt tctgtgtgct tacttgaaaa  96120
caacaaaatt taagaatttg gtataggagt tgtatcaggt agtgcagagt ccccaggaga  96180
cctagagacc caggtctggg agcctagcgg caagggctga atgtgggatg acatcagcag  96240
aaactcacag ccactgctat tccaaaaacc cagcagcagc tcagtgcagg gcagtgctga  96300
tagtacagtg cctgcaatcc tggagtggat ttggatgtgt caggtacgca cacgctcact  96360
gctcccccag cagtacgttg aacagtgtgc gtccaggtgt ctgtagggcc cctcgcccta  96420
actcacaaaa ccattctggg tcagaagcca ccaatattgt catcatcctc ccttttctga  96480
gaaccctagt aagtccctcc agtggggcaa gcccaccttt tcccttcatt ctgtggcaat  96540
atgccttcat ttcctaatca gttttgccct gctcattcaa tgcaaaatgg atctgctttc  96600
cttgggcacc aatatgtcca gggattgttt atcaatcttc agttctgttt cctttacata  96660
tccctccaaa aatcaggcct gcactgcctg tgcactccac aatccacagg cctgaaggaa  96720
atgttatctt tgatgtagag acttaaagta aaactcttca aattaattat ttcatgcaaa  96780
aggctagtcc tgactctaat tctaagacat gtctcctaaa ctctggaagt ctgatgtatc  96840
ctattatcaa catttatcct taatgtgatg gtttatcatt tatcctcaaa gctgcattgt  96900
aaaatgtaca ctgtaaagtg tacattttaa agtcggtttt aaaaaatcat atttagagat  96960
cctggtaaaa atctatcaag tcaagacatt accttattac ccatggaatt gtcttcaact  97020
cttacagttc aaatattcct gaattggctt tcacaataaa catcctaaat atgtaagtag  97080
aaacatatat attgccaact ttgtgccttc ccaagcaaaa ttaaaataca ggaaaagtca  97140
gtttgttttg cccataaata aatatatgtg tgtgtgtatg tgtgtgtata cacatacaca  97200
ctcagaaaag atagaagcag cagcatattt tggcagcatc tggtttattg gaactcaaac  97260
gttctgattg tgcatacaga ctagttaatg tggtaacaat tatgtatttc ttccctgctc  97320
cttgccttct ttccctcccc agttttttttc ttcctgatag taggtgtgta ctttttttcct  97380
atttccattg gcaagccaca tgacaagcaa aacgatcact cgaagaatat tgttccctca  97440
atcaagaaaa atgcccattg ggttttgtta tttgatgtta tttgatgaca gagacctatt  97500
gtttttccat ttttcttttt ttgttttccg tggcacctat ggaattaagc aatataaaaa  97560
atctattatt tcagatgttc acgtctaatg aatttcatgt gaaatactgg cagtataacc  97620
ccaaatagag gaaatttgtg aagagtggat gctgcagggc atgagacatc tgcacagagt  97680
tcatctcttc cagcatcttg catgtcccaa gcactgccct gccaggcaga gaatgctgca  97740
gatcacggca gtgaattcca gttgttcaga gcacatttga cttccaaatt ctcaaggcca  97800
cagatttgag gacagaacaa tatttgcatt tgaaattgga agattatttt ttgcacaagt  97860
gcctatatgc tatatagagt ttgcccactc tgcattatct tccccctgtt cccccgttat  97920
ctggcacaag ctattcaaaa gacacgccta cttgtaaaat aaatggtttg caaactaagg  97980
aaaatactta aatctcatgt aaatggtact atactatgta taaaaatgtg aagaaacaca  98040
```

-continued

```
gaacagctca tgaacacctc cactgctgta taaaagaacc atcttttttc tggctcctat  98100
tggatgcctt agaaaaatct gtatttcctc tttagttatt gtgtttgaaa gatgaagttg  98160
agacaaaagt tctattcttt ttaagttggc agaacttctg aaaggtgatt tttagctgca  98220
gtgtgactca ttccaaatgc agaaatctct gaccctgagt tagtctattt gtcatgcaag  98280
agcctagaaa agccctgagt gataagaaat ggccataggc cattcccaca gaattttcaa  98340
caaaaataga atcatgctta tgttctagtc atgacttaga acttataact catgttcgga  98400
actgtccatg ttcacgcaca ggggccgtat cactccgcca gagctgccct gggtgccggt  98460
gtgcagaggg gtccgagagt gactgtctct tcctctgttg tcgaatgtgt gggttatctc  98520
cataaatggc tgccatgagc atccttgttc acacattttt aggtacttga gtgagtgtct  98580
gtggaataat tttgggaagt gaaatctgtg gtcagaggtt tgtgagtttt acatgctaca  98640
ttttcagaag ttgagaaata gcagtaggct gaaggcaagt cgccatgcct ggaattcatg  98700
aacactagtt gaaagaactg gcgtgagtta gtcatgacag gagagatggg gaagggagtt  98760
gcaggtagga gggccatctt caaattctca aagtatagtc actccaaacc aaaattcgat  98820
ttaatctgta ggactccatt ctcaaagcac agtcactcca aaccgaaatt cgatttaatc  98880
tgtaggactc caggtggcag aataagaggc aatggatggg tggaagcgaa acagggccaa  98940
agtttgactt catgtgcaac ttcctaagga gtgatttgaa ctccacaaac atgaactaag  99000
cacctcaaca caggctgggc aagttgctgt tcttttggag cttacatctt agtggggaaa  99060
gagaaatgcc tatgtaaaca tataaatcag caggatacat tgtgaggacg gtcattgctc  99120
agtgagactg caatagagtg atacgctgga gggggctgca agggagaagg tgggagggac  99180
agcatttagc agaatgagca gcacagtccc ataggaagaa gaatttattg cctccttagg  99240
caaataaatt cccaaacctt gaacatcaga aaggaaatag attaatgtgc acagaggatt  99300
aaattatgtg atctgcaaag tcatttaaaa tctatttcca cataaaacat attaatgcaa  99360
cctaaacaaa aggggtctgg ataccctcat cttcttccca agcatcaagt ctttctatag  99420
ttaaactgag atgcttttat tcttggaaaa ttttaaggac tatctacagc aatggaagaa  99480
tcgggtgttg ggatgtgttc ccaggtaata atgactgcag gctgatttgg cccttgaggt  99540
gtggcctcat ggccctctcc aaaaaaaatc aaggacctgc tacaaagcac aaagccgact  99600
gcaatgcttg ctgcttactg gttagggcag ctcctctttg ccagcgacca agcagaaagc  99660
aagacaagac aggttctgaa gcagtaattc aaagccttcc tcgctttccc atgtgagtca  99720
ttgctagtca gaatattacc tttgcagaga ggcttaattc caaatttgct cttaaaggga  99780
tatcctctcc tggtttaggt ataaactttt gactcacagg acaaattcta tcattccttt  99840
gggcctagga ttgcatttat ttccatgaca aaagggcctg tctggtgttt cagcaaatga  99900
aaacaaaaat ataaagccca tctccttttg aatgagctct aaaacagttc tccactggac  99960
ttcagaacaa gagggagctc tgggctgctg gctggttgtg catttgctgt gggttccctc 100020
cggcaggcga cctctccgcg ctgagaaggt tatccggata accaagtaag aaagtacatg 100080
aggaggcaca gaaagaaaaa tgtgagagat aacagcataa acacacagtg tatgttgtta 100140
tgaggcatca catgatgaga tactgctggg gagggaagaa gtgaggagat tcctaggaat 100200
cttatgagaa tttccagaga caacaagttt tgagcttttt tttaatttag aaaatttacc 100260
ttatttttaa aagaatatgt aacatatccc atgctataaa attctagaca tagtagattt 100320
aaaacagcat aatggaaaat ataaatatct attttctttt cctatttatg tattctgtgc 100380
cagtaggaat gtagccaaaa agagagaaaa ggggtctctg cagacatgga tgtctctgtg 100440
```

-continued

```
acttgatcac tgctaaccca agaagataat aaagcagaag catgtatcca ggttgctgca 100500
gccaagcctg cccggtctgc ggggcgtcct cacacatggg gcagctctcc caccccacac 100560
actgggaaag gcggacagag gctgggcaaa gcccccaatt ttcgttggca ctgaccccga 100620
tgatttatag gcctttgttt cccatgttaa atgtcttacg atcattaaat tatttatagc 100680
tcaattagca tgtgtccaaa accaggaagt tcataggaga ctgtgtgact gggaattaag 100740
gagcaaagca actttccagt ctgtgattta ctgggtttcc attctgtttc ctgttcggat 100800
ccggaagtag aatttcaaat attgcttttc atgctttatt tgggaccgat tttagccccg 100860
ctctcctttc tcttgccatt cgctggccat tagccaccag cctctgcaca atgaccagct 100920
ggcccctggc agatcttggg cccaggtgtg aagtcgctgg agaagcattt cagggccaag 100980
atgggagtga tttcattttc cattgacact atgcagaaat gaaggggatt caagtgcctt 101040
cagaaaagct tccttccagc gaatggagtt ttgggggttt tccagacttg caactgcttt 101100
tattcttgga agcatcattg ttgctttttc ccccttcca tttatatccc aggaactgat 101160
tcagaaacca tagaaattgg atttggaatc gctgaatgct agcagacagc tgactgcact 101220
cttcccaaga aaccctgcca gctgggttcg ggtatcgcgc ggtgtgtgct ctctctgcct 101280
ggcccgctga gtcctctaac tctaatggat tccttcttac accaaagtgc actagaacta 101340
aagtgttttg cttcattctt tagacatttt gtggtttagg gctcaatcag ccagggtatg 101400
atttgcaatc cacagtaacc ggtttcagag cagctgccca gcgaggcagg tttcatctcg 101460
cttgctagac gttttgtttt tttttttttc taaacctcac acctttttatt tattagactt 101520
ggattccagt ttcctgagcc tgtttgtgcc actgattaga caggcttgaa gcagaaccca 101580
ccaggcttcc tgaataaaat gcagcagtga ttgtattagg gggttttaaa ttgctcaaaa 101640
tactgtctaa aaaacactaa aaatcatgtt actttctaga ttgaataaaa tcctatagaa 101700
atgaattcct ggacttgata tgtagcaagc tggcattggc tcgggagtga gtgggctcag 101760
ttaagtgagc taagatgaga tggtgcacag gcgagcaccc acctgaggag tgtttggatg 101820
ttatgatagc cagctcctct gtaaagacct gtccttctat gtcagcagcc cagcagataa 101880
atgacgtgta aataccacat ttaggagggc ttatgatgat gccaattaat ggagaccttt 101940
ttgaaacagg aaggaggtga aacatattcc tttgcttcta catcactgtg tgccaggcac 102000
tgtttacagc atctcgttta accagcagtc accacctgac ggatggctga tgtggggtgg 102060
ggtcccaggg tgggattgcg tgatgggctt ggggtctctg gctgatgggt gccagagctg 102120
ggactggaac tcctggcgtg actgaggcag acacctgggc tacccagcct cacccacgac 102180
gccctcacta agtgacccac aggactcacc ggaagcaggg cagcaaggtc cccctacaga 102240
ggtccccact gcaaaccgat acccagctta gacagcagtt ctgcagtcgg cgtctcaccc 102300
cttcgggtct cattgtgact cactttgata gccacacgat ttaagggtgg ttcagtagtg 102360
atttgatgag tgctgtggct cagggtcatt cccctgccca agcatttcaa attccagaag 102420
ttcatgccct gcatggtggg tgaaaagtct caggccaacc atgagcacac agcagccagg 102480
cgactgaggc agctgcccgg ggtggcacgt tgctcaaacc catcatttgg agtcaaaaca 102540
aacagatgat tagctggggt ggtcactttc aatcaagagt tttcacatcg cctagacatg 102600
gcctcagaat caggcctggt gtggccaggg gctgatctca cagtagacag gaagtgtggc 102660
ccgagggcca tggctgcccc ctcagaaggc cctgtggagt ggctggccga gcctcagcag 102720
cctcctgtga agcgaggaag ggtcttcctg ccggcctctg gagatcagta tgggaatgca 102780
```

-continued

```
caagtaggaa acgctggatg ggaatccctc tgccctgtga taccaaggca gtgagtttgt 102840
agactatgga attgctgtcg gagggctctg taaccggcca aggtcacaca ggtagccatt 102900
ggtagagcag ggactggaat cccagacccc caacttccag gactgtgcac ctttctttat 102960
cccatacagc cttacagtca agtgccagtg caacacctga ttcccaggtt ccagcctttg 103020
tcttttataa tgggaatcaa ccttatcttg acgatccaga gatagtcatc aaggaagatt 103080
aaattatccc cttagactca gagtgaccat atcattttcc ctccacacaa ggacactttt 103140
gagaatgaaa aggaggagat gtctgtacca gacgctggat gacaggcacc gacaggctgt 103200
ctgccagggg agcagcgatt cctgtatgtt gtagaaagtt tttcaaaagt caccttggaa 103260
agaggttttg ttccttaacc ttctgttaaa taggaagctc cgtgaatgaa aacaactccc 103320
ttccctaaac attctagtaa tgacccaaca ctgccaagcc tgccagctct gcctcatggt 103380
cgtgttgact gtgtgagact atgtgagtgc ctgctacaca gtacgctttc agtaaacatg 103440
gtattgcctc gataatccca caaaaatgtc ctattcaaat cacctggcac ccaggaaatt 103500
tccttctttt ttttcccagg tgaaatatac agttgaaaac acctgacagc aattcccctc 103560
tcccatgtgt ttgcaggatg gtggttttgg ttcctccatc tttgatgtgt acaagtgtga 103620
tgttttcccc ccacagacaa gtaaaccaca ttctcttcac attcccaatg ttttgtcaat 103680
gtacctcctt caatagagga tcgataagga aaaaaatcat tgacaatctc aattagattc 103740
actatttcat ccaaaagcat agcttagaac tctagttttt gttcaacact cttgccctat 103800
gagtgcacag aactttaatt ctgatacaaa catccctgaa tgtttagctt tgacagagat 103860
tccaaggtga tttgataaga agcagggctg tgtttggcgct ctgggagttt ttgatatggt 103920
ttcaagcccc atccaaaacc cacagacctc tagaaagtag gtgcctgcct tcctgcagca 103980
gccctggagc ctgctggggg ctttgagcag ctgctgccaa gccaggcctc acccgacact 104040
ctgatgggca cggccatggt ggcaggggct tggacgctgc caggtgactc taacttgtgg 104100
ccagggtggg aagcactgct ccacagaggt gccaaaacca ggttccttcc tgtgttctca 104160
catttcacag cctcaatgta aaaagtaaga catgggcact ctggaatatt acaaaaatat 104220
agaaaagcat gttatagtaa ataaaaggct cacagaattt tgtcatttag gaacaatgat 104280
tattaatata ttagtgtgtg tttttgctca ttaacagtat atcctgagat atttcctata 104340
ccatttaata ttttaaaaga tgtttacact ggccacagta gctcatacct ataatcccaa 104400
cactttagag ggcaaggcag gaggatcact tgaggcttaa aaattagcca ggtgtagtgg 104460
cacatgcctg tagtcccagc tactcaggaa gctgaggctg gaggatcact tgagcccagg 104520
agttcaaggc tgcagtgagc tataattgca ccattgcact ccagcctagg tgacacagtg 104580
agaccctgtt tctaaaataa ataataaata aattaaaaca tttaaaaata catgatgttt 104640
aattattaga ggactcaatt ttatatctat gtatacaata atttttaagt ttcttaatat 104700
tggactttta gtaccttttt aaaaatacta tttttaaaaa aatctgtatt tctaactttt 104760
tataacaagg aacctttggc tttgagatga ctggggaatc cattctttcc tatagtatcc 104820
atgtccaatg gacttaaagt attaatcaat gtgtttatgt tttgttattt ttctggcatt 104880
acaaaaaatt ctaaatatat tgttaccgcc tgtataaata tcagcttttg agagaaggac 104940
attgtgtaga aataatgaaa cactgcaact tgtatttgta ttattctttt tttttttttt 105000
tttttgaga tggagtctcg ccctgtcacc caggctggag tgcaatggtg cgatctctgc 105060
tcactgcaag ctccgcctcc caggttcaca ccattctcct gcctcagcct cctgagtagc 105120
tgggactaca ggtgcccgcc accgcgccgg gctaattttt tgtattttta gtagagacgg 105180
```

ggtttcacca tggtctcgat ctcctgacct catgatctgc ccgcctcagc ctcccaatgc 105240
actgggatta caggcattat attattcttt aaattcacat gagaatttag tatggcttca 105300
aaaaatacca taagttaaaa tatcaccaag actctgttca gacaaaagta tcagaaaagt 105360
gagccaggca ctcacatagt ttatagttta taaaagtgag acaggcatga tctcttaacc 105420
tcactatagt cctgtgaata aggtttattt acatttcatt ttacctgcca ggattattgt 105480
aaaaacgcca agcacattgc ctacacaaac taaatattca gtcaatggct gctattttca 105540
tgagttcgtt ttaacatata tttattgtcc tctactggat ttaagaagtt atatttatta 105600
tcatctaaga ttttagctat tccttctctt aaaaatagat tttataatca atggcagtaa 105660
gggagagtaa ctcgcagttc tctgaatctc aaggggttcc tggaagcctt cctgaaggta 105720
tagtgaaatt tcagcttcac attcccatcc atgagctccc tgcaaatatc ccggtctgct 105780
ctcaggaccc agtgacttac ctatgcagag gctgtagata gcacctggag cttcctgtgt 105840
gccctcctca aactcagcca atgccgtcat acagtagcag gcaggtgtct ttgctgggta 105900
gttggactgg atgtccctgg gattgcagaa ctggaatggg gagtgacatc aggaaactat 105960
aatcatcagg acaacatggt ttgccataac tttaagtttt aagcgaccgc agattatgcg 106020
gagagagatg catgcccaca gccatgcttc ccatgtaact ggagaggggt ctgaagtttg 106080
aaacaagtgt tcctaggcac gggttacagt gtttgttatc atcatacttg atttagaatg 106140
gggcacaaca tgtggattca tggtaactgt tacaacctta ctcattttaa tacctgaaaa 106200
catgctttcc ccatgctggg aatcgaaaga ttctcctagg aaaagaaagg cttgacaaca 106260
tcgattcaaa aagggcatgc attttcctca tttaaataac tctaatgtgc aagtagatcc 106320
cctgacctca agctcagaag agtccaggcc ttcacacctt ctctgcttct gctctggggc 106380
cagctattga gattcctgtg cccacgcaat gcgcacatcc cacccctggc cgctgtccac 106440
aagaaatcca gttgcaccaa gcaccccact ttttgcacct ctcatttatg tactcctaag 106500
agcctcacca caactccctt ctaaaaacat gagttcctga ctgggaattc gatgctgccc 106560
aggcagcttt gctcagaggg agcagccttc tagaaatgtt tcaagtaaac tttcaagtat 106620
aactaaattc aaaaaaaaca catacacaca cacacacaca cacaagtcaa aggtgtgtaa 106680
tttggccaat atcacaaacc aattagccct ttgtaagtgg cacccagatc aggacagctg 106740
accataccag caccctagaa gcaccccgtg ctgcctcctg ggacagggct accaccatcc 106800
taaggccagc acgatgggcc agctttgcct gctgttgaat tttgcttaca tagaatcctc 106860
cagtaggtac tcctttgggt caggttcttt cactcaacat tatgtgttga tatttttcca 106920
tgctgtgctg caaaattgta tttcttgcat tccataactg ggcagttcca tcataggaga 106980
ataccacact gcgttcgtcc attctaccgc caatggacat atgggttctt tctcttttct 107040
tgcagttaca agtttatgaa tattgtccca cgtgtccctg gtgaactttt gtttgcattt 107100
ctgttgggta cctcagagtg gcgttgctgg gtcagagggt actggtcgct ttagtagctt 107160
tgaaagatat tgccaaaaca ttttccagcg cagttatagc aaattataca ccaccagcag 107220
tagaaaacat ctcctaattg ctcacagtaa acccccaaag attgccacat acatcttcca 107280
tatcaattac ttaactattc agcaaatttg aagggaaata tatttaatct ttttattcaa 107340
atagtttata aagtggaata gagatgtggg taaaagttgt cttgccacct ttttagatcg 107400
107400
gtaaaagttt gttgaatgca ggcaagaaaa gatgagaaat aatggtaccc aatgaaagac 107460
atagcagtct acaaggaggg gcatttcccg gggtgggggg gacccacact ctgtaactcc 107520

-continued cacattcaat tagcatgtta taggtaagct gcagaaaacg aggcagcttg tcaaagagga 107580
acggctcttg gccatggttg ctgccctagg aggatatttg atactagcag agctggggca 107640
accctggagg aaaccacctg gaatgatggg agaactcctc cagggaacat ggccctttaa 107700
tagatctctg ttataaaaaa taatcccaaa gcagccacca gggcatactg ctgcgatcaa 107760
gtcctaggcg gtattccctt ctgcgccata gaccctgtgc agagtgccct caacgaagga 107820
gcaaggaaga ccaagtctcc cgagggtttg catatgtgta tgtgattctg cagtcatggt 107880
gaatgacaca gtcagggctg cggaaaagca ttggtaaagt gtatatttga ggcttcagaa 107940
gtttgaaaag gctagatttc ctaggccaaa acactgaaaa tttgcaatta gaacttcagt 108000
gctgatgctg ggaagactgg agttagtttg agacatgcac ctgtgcagaa ctgggccccc 108060
agaaaaggag aaggaaggga atccagacca gagtagggcc tgacaccact cagactcggc 108120
gtgtctataa attagaattg cgttacaatt acactttgac attttagtgg tttttaaagt 108180
gcccagcaca agttaatttt tcattaatga atcctttatt cataaaatgc ttagatggag 108240
attacccttt tgagcatttt gccagtgctt ctgaaattaa tggggacctc ctgttggagg 108300
acacagtctg ttgcaatagg tgaccactgc tctgaatcta tgtcacctct ccaggaccac 108360
gggcacaacc atcacctgag gcatgttgga gatgcagatg gtcaggccct cctagaatct 108420
cagaatctgc attttagcaa agtcctgggt aattcctatg tccattggag tttgagaagc 108480
actggtaatc tcaaatactt taaaagatta ctagagtaag ataggctcag taggtacctg 108540
aaggcaccat cccaaagacc agagtggtag aagcaggtgg accagcctct gaacacattt 108600
ctcccccact ccccggctgt gtggaaggtt gccacctttg gggtagtcat tcaacaaaca 108660
cgtgtcaact gtccactatg tgtcaggcca ccactgggca ctggctgtgg ctagctggat 108720
agacaccatt tctgccctcc agaaatgtca tgtccactgg cacatgacaa gtcactaagt 108780
cattcagagc catgggtgac agctccaggg gccgacaaag gagctgtgat ctcacagatc 108840
cacagagaag tgtcccaggg cgggcgggaa ccaggactgc acagggaggg gtgaagtgac 108900
acataagaag tcagcccatc agcctgaaat gctcccccaa atcttcccat tcagtgtttt 108960
ctcagtagca aactcgtggg aaaattggtt attttactta aaaaactcat actagaaagc 109020
tagtttaact ttaaaaataa attttaaaaa catttttatt aacaaatcct acctttcctc 109080
caaagtcaag gagaaaagaa tagaagtgaa caatggacca agtaagccta aaactctgct 109140
ctttcccctg ctcattttac agttcaagtg ccattcaatt tatcctggca agaagaggaa 109200
ggcatcatca agaccttaat tttctaatac atctgatctg agaagaatgt gaaagctata 109260
aaattaattt ttgatcaata actacaggcc ttttgagaga gtgccctcct aatgaattga 109320
gtacctattt ctccatacac agtgtctatc atgacctaca aaccctttc ccatgaggtg 109380
taacagagag agattacagc cttggaactg gatgtcagac tctcctggtt taagacaata 109440
agccatgaca tagagcctga aaccaacaca atcttccgag tggttccaga aacatatagg 109500
ggataatgtt ggctctgatg ctgtacatcc ccaacaacca tcaactattt ggaaactaga 109560
atttcagcat aattggagtt ggtgttaccc tagcaaatgc tgtgggaaga gagtctcact 109620
gtgtatcttc tcctgtttaa agcctgaatt tgttcagaat gtaatatctc tgtttagcca 109680
ctctactgaa actgatctag gaaatgttca aaaaaaggta tcccaaggat ccctttgtag 109740
ctacatctgt gggattcccc tcgctctggc gtggcctggc ccctctgcat ttgacaatac 109800
ggtcctatgc ttttgtcttc ctgggctgcg tgaacccacc ctgccctggt tcacctctcc 109860
tcttgaccca tccttatcag tgtcttgaaa ggtccttcta ttggaggaca cattctgttg 109920
cagcaggtga ccactgcccc aaatctgttt cacctcccca gggccatggg cacaaccatc 109980
cctggagtgt gttagagatg cagttggcca ggtcctccaa aatctcagaa tctgcatttt 110040
tgcaaagtcc tgggtaactc ctatgtccat gagagtttga gaagtactgg tctcatgagt 110100
tcctgacata caaatagtgc tgaggccagt atgctgactg ggtagccaga tacaagtgaa 110160
aaccttcctg ttttttgcaa acctggatgg acccgaggcc gctgacgtgg gccaggacaa 110220
gctactcttt ttcagtgttt ctgttgcatc gctgtgtctc tctgtgatca ggtgctgccc 110280
tccctggcag gaggactgca gacaggatga ccaagagcac tctacacagc ctgctctcca 110340
gtgttggggg acgccaccca ccctcgtggt tcctgttcat ctgcctacac gtggagggcc 110400
caagagggct aatatgtgac tatctccact tcctggtacc ctgtgtgaat aacttcactt 110460
actaaaggga tgttgagcaa ctttattaat aatgaagaaa gcactttggt ttgacaaata 110520
atcactccat tttttcattt gaaagttaac tcttgttagt agagaaagca atgtattaca 110580
accacaagga cgtttacatg gaaatgaacc atctgcaaag catcccccat tttcctttta 110640
aatcagccaa tgggtggtgg tgggagaaat attcaccaga gtatttaaca tctatccccc 110700
ttcctagact gtcagctcca tccgggcgga gactgttggt atctccacag cacacacagg 110760
gcctggcaca catccggggc tcagtgagca cttgctgaat ggtgaacaga ttagctctcc 110820
tgggaacgtt gttgacacat ctcataacac tggtttggag tggagggcat tcatcgggct 110880
gcatattcct atttttaatt gtattctcca ctggttacag cacctacagt tataaagaca 110940
ttgttaacat tgcttatagg aagacatttg atggaaatga gtccaaaggc attacggtta 111000
gaaactggcc aggtgtcatt tttgagagat tagataactg ttttccggta gagtgaattg 111060
cctgtttgtt gcaagttggg actttgctgg gctggtttac agggccaagg ggaaagagat 111120
aagtggatct tctagtgaga ggtcatctgt tttgaaagcc tggaagattc catgaactaa 111180
atccaagtct tacaacacag ggaagtgtgt catactgtgc agggatgaag tctccaattt 111240
agcatgaaaa caagagctcc tcacactgtc ctcttcagaa agcccataca atccaaactt 111300
ctgaatgctt agctgcttac aaccatacat agattgaggg ataaaactct gatatggaag 111360
agaaggtaaa catttttttgg cagacattcc caggaaaagg cggctctctt ctctcattgc 111420
tgctgctctt tcagaatcca tttcaacaga ggaggagtca atgggagccc cgtgcctctg 111480
gcagatatca tatggcgttt cagtggcatt gtgtgttacc cttcttaggt aacagctcag 111540
ccattagaag aatgtcctac acaccttctc attttctgtg atgagaggaa tgtgaggtac 111600
tgcccttcga gagctgtcat ttgtcctagt agccagcagc gtgactgtgc tgtcttctgc 111660
tctgtctccc tgtcagcctt ctgcccagcc accaccacta tagttttgtt ctctccattg 111720
gaactcctgg ttcagagaat taccataaaa aacagacccc tagacataca acactctatc 111780
acataatggt gactttgtct tctattttgg attactgagc tttcttgggt aacttccact 111840
aaatcgaagt taatattaga agaacttcct cttactagaa tcgaaaagca tttaagtgat 111900
gcagtcaagt ttgtaccata agtaattcag tcatttaaca aatatatatg gcctctgtgc 111960
gacagtgacc ttgactggga atgaagctgt cccatgtggg gcctgttctt caaaggcagt 112020
tccctgctgc ccagttcagt ccagtggatc tgggcatctc tctttaatcc gcattagggg 112080
ctctttactg attcttcact atccaaaaag acttggaggg gagacctgag cccacttctg 112140
gaaggaaatg ataacaattt atttagataa tctttgtgca acaagtcaat tcactgaaga 112200
gatctgctct ctaggagcct ctgtgacccc accataactg ggaaggctct acctctccag 112260

-continued tcttcgggcc acatttctct ctggcctgct gtcttcccag cactctcagc cttgctcatg 112320
gagcactcta gtcctccgtc gaccttggcc tttggtaacg tgatttttca cctggcagct 112380
cccatctggt ctcactccct ctttttgtcc agtctgcatg acacagcctc acatcgttag 112440
tgttccctca ctcccctctt actgcccaac ctgcaaagtc catgcctggg ccagtgcagc 112500
atgtgtcctc aatgggctgc tggtggcagt ggggggaacc gcacagccac gctgtgtgct 112560
gctgaagaaa tgcacagcct cctaccctcg ccctcaagag gcagccatgg ctgcgcattt 112620
ctgcccttct gagctccgct cacttttggc agcagccgtt ccaacctgca tgggatcttc 112680
actctctcac agatgtgctg actcctcctg ctgcctcccc tctctgtgcc ttctcactct 112740
ctgttccctt tgccctttct ccccttttct cctctgccta cctccaagcc atccatcaca 112800
ggacagctca agcatcagat cctctgggac actttcctta gttgttcagt ctgatgaggt 112860
gtccctcatc ctctcttagc tgaaaatcag cagctgcctc aacttctttt ccagcatgtc 112920
tcatgagtat tgccacaaca gcatctgtca caatgtgggg tagtggctga cttgcttttc 112980
tgccattcaa ctgagttccc tcagtgctgg ggccagcgtg cagtgtcttg tattcagtat 113040
atagctgatt aattgatgaa ttgattaatt aatggttcac actagcacag tgcaaccttc 113100
aatgcaaaga tctcatcaaa ataattcaca tggtgggata ttttagaagg atgaccaggc 113160
tagtttgtag taagaaaaaa tcaacaagac taggtcagga attctttttt tgtctacagg 113220
cttgctatag aagatattga aaatcatcta cctaattacc tttattttat caggttgtgt 113280
attaaatatc acgtctgggg gaagaaaatg tgatatgtga ttacagacct ttcctggtac 113340
aacatagtac gtttcagatt aactcaaggt attgtggtga tattgcggtc aaagccaggt 113400
gattaaagag tcattctttg aaacaaatat ctgtgcaatc aattaagaaa ttaatttgca 113460
aattttattt gcttagagta attgatatat cattcctttt acaaacaaat ataaagaaaa 113520
cttaactaaa aatactgcat atctctttca gattatatat cccagaaagg atatattttt 113580
ctcctttctg gtcttccttt ttggtgtagc atctgtagga aatgcatttc ttcatagcta 113640
agtgtacctc cttgtgaaat atcttcagag tctactggtg cacataagca attgctggca 113700
gcagcttgag ggtctccatc tcacatttat catatgcctt attgcatgag gctttgcaag 113760
aggaggtcta gagctacaat atctcatgga tatgaatgtc aattcaaatc ccagtggcag 113820
tttatgaggg ggaaagccta gaagagaaga aacctagagg aatcaagcag gaggggagag 113880
taataaaaga ctagagcagc aggtttttct taactcaaac tagaattaaa tctctgtgtg 113940
tgtgtgcatg tgaatgtgcc cgtatgtgca tgcatgcacg tgtgtaaatg gatgtgtgtg 114000
tgtgtgcatg tgtgtgcaag taagtgtgta tacgtgtgtg ggcatgtatt gtgtacatgt 114060
atgtgtgttt tatgcatctg tttgcaagta tgtgtgtatg cacataaaag tgtgaatgta 114120
catgtgtgct tggtgtatgt gtgtgtatta atgtatgcgt gtagttctag agtctagtta 114180
gagaaagtgc ataaagaaat agggaaatta acaagaaagc tatagcttaa attataggaa 114240
aaacttttct ccctatcagt catggtttta aaatgttcag acttgatatg tttcccagtg 114300
ctattgtcag aaaatgtccc tatgacattc catactactt caatcaaatc taaaaccttt 114360
gttccaacat gttttattga tatgagtata tttcaaattt ctaccaggtt tttggagagg 114420
tattttggcc ataaaattga ctaaattatt caaaataaaa aatgaataag cctgggccaa 114480
ggcttggaga cttgcttaac tcagttctta aattttcaga ttttcaaaat tacaaattta 114540
agctctaaaa tcatggtgct gtgtatgata ttctttgatt gcaacttatg gttgaaaaac 114600
tatagagggc tttatgctaa gagttgtgga tcttaggatt ttcatgaaat ctgcattatc 114660
atcatctgca agtttagatg gggcataact gatccaaagg atggatccct cgggggcaat 114720
tcaactggct gattccagcc aagatgacaa cagtcaggat ccgttccctt ctgatcatcc 114780
attgggtgcc ctgatttcct ctacagccct agctgaaaga ccagacacta tctcaggctg 114840
gctgccccac atgccttgct ccacaccaaa ttcacagtct ataaacctga gcctccagtg 114900
ctcctactac catactcact cgaacattcc cgattctgac ctggagatgt caacagctac 114960
ttgatgccac tctcttctat ctttctgtag ctaagccatc cccaagtttg tcgattcacc 115020
ctctttaacc cctgtcgggg tgtccattgt gccccttcac cctgccatct ccctggtgca 115080
ctgttttgca aagttcagca tacatgagcg tcacctggga accttaataa agtgcagatg 115140
ttgattcagc aaatctggga tgccctcggg ctgcatttcc agcaggctcc tggggatgtc 115200
cccgctgctg tgctgcagat gacactctca gtggtgggac tccaggctct gctgtcgcct 115260
cctaggggtt tctccacact ccctggaggc ctaatgggcc cttctccaca tggcagtaag 115320
atctgttttt gtgtttgtgt ttcaagttgg gagaaggaga ttatttaata ctaaaatgtg 115380
caacatggga ttgagaaaac taattattag tcataagttg agtatgcaac attgaaacca 115440
catgctttaa aaaattataa gaaaaaatca tagtatttga aagttacaag ctattatggc 115500
taactccatt tatctcagtt agagaagaag agtcacctgt caccagggca ctgccagaag 115560
ccaggctcat ttccaacagc actgggtgct ccagctttgg ggtgccagct cctcccataa 115620
agcaaacaca tacctaggga tgatatttct ttgcaagggc tctgccctac agcttgtaca 115680
tctcaagaag ttatgtaatt aaactgtctg ttttgagaaa attgtagatt cacacatact 115740
agctgtaaga aatgatgcgg ataaatccag cgtaccagct ttccccacgg agacgtcttg 115800
cagcgtcaca gccaggatga ggcattgacc caggcgaagt ccagagcacc tgtgcgctac 115860
agggcccctt gcactgtgct gtcacagaca cgcccacttc cagatgccat ctaggacccc 115920
ctccaaaaag cagaggcatt cttaaaaaca cacatctgca catgttcctc ttcatttgaa 115980
tctgtcagtg gcttctcagt gcctttcaaa tgaaatctaa agtccttaca agccttgcag 116040
caggaacctc tccatcccac ttcccctcac actctcagct tcatctctgc taggctctgt 116100
tcagccaggc agcctttcac agtccctctc ctcctgccct gccaggaagg tcccctgccc 116160
ccaactcttc cccacatgtg gcggggcccc gcttgtcctt agaagcccag ctgaactgct 116220
tcctgaagga acccctccag aacctctcag accaggtcag gtttctgcac tcttagatca 116280
tccccatggc ataatcacag ttgtgatgtt gtgatgattc agtgaatgtc tgtctcccca 116340
ctggatggta agcttcctga gggcaggaac agcattggtt ccagtcaatg ctatgtccca 116400
ggactgttcg tttttgcaca tactaatcct aaaaggacga tgacaacagc aaccacttac 116460
atgacctaga tgctcttctg ggtgttgtgc aaatattaac aatttaatcc ttgcaacaat 116520
ccacgaggga ggcattcttc tactcccact taacagacaa ggacagtgaa gctagtaaag 116580
agaagtcatt tgcccaaggg gaccccacta ctgttggcag agctgggtgc aaacgcaggc 116640
ttgtgaagcc aggacccatg cattcaaaga ccatgccagg tgcccccact gcacacctca 116700
tccccacata ccagtgaggg ggagagaaat gctcctgcac tgcctctgat taactgcttt 116760
cctagaagtc acacatataa aagggattta attctagtgg gattgaatct caatagtttc 116820
cttattaggt tgatttctgt taatagttta agtactggat atacatgaat tagaaaatct 116880
agattattag caaatgcaaa ctataaagta ttttataaat gttatcttgt ttgtcagggg 116940
atgagtgaga tattcattat acaaaaagta gtgtggattt tgaggtagaa ggtttactaa 117000

-continued

```
ggatcatacc gtagtatgaa atagccacaa acattcagtg aaaccaaaca cccccgctta 117060
acctcaaact aacactaaat aataaggaat agacttgggg gcagtgcaag tgtatttcta 117120
atggtgaaaa ccattcccca gtgaaaacta atgtaccatc tagttaataa gagctcctct 117180
gacccacgca catcaatact tacatcccaa tggtgatgtg acattttggg ttttgtattt 117240
cttttgcaaa ttgagctagc atttttgatg agtggcaggg ctctgctacc caacctttgg 117300
acagtttcca agcataaaat cacaattcca gataattctg tcacaaagat ctgggtctca 117360
ttaggaagga gaggaagctg ggagatgatc cagtccaacc tcccccaaac caaacatcac 117420
ggccttctca gttgtttcac caaccatcta aatgttttag taattctaaa aattgatgcg 117480
ctttttccac gaaaggaagt gttaccacat tttccaagtg ggaggcatct atatccttac 117540
tccttcatcc tctccttccc accccctcac cccccaccac ccacacaaca tctgcaattc 117600
ttaaactaaa gcacaaattg ttacaaaagt taattgcact ttcaaaggaa tgcttgtata 117660
gaaactttct cggcttcaag gaaaaataat acgctttgaa tggctgttca acagcataga 117720
aattagctga gtagaaggca ctcatatagc cattaggacc aatcctttct gccgccaaca 117780
ccccccttat aaagacttga cagtgggcca gaataaacaa cttcaggatg aattcagttg 117840
agacacaaag tacacacttc cagtttttcc cttctctggt tactggcctc aataaccagg 117900
cagtcaactt aaaaagaaaa acaaaagctt gcttcagatt acagattgca gacttcttat 117960
aatatgtcca tttcaccagg ccccgctctc agccccggga aaggccactg gaaaccacct 118020
cacatggtag ggccttgcgg gagccagtaa taaccttatc tccgtcaaca tgttctgtca 118080
gattgaatgg ggcagccaga gaagccagag ttggcacagg aaccaaaaca aaggcttccc 118140
atcctcctgg agtgagcggt tgagcctgga ttggtgctta gacctataat gggtgcaagc 118200
agcgttcatt catagtggct ttctagaccc agggacttgg ccccagccct gctgctccac 118260
tcctcttctt gcttcattac cacgagtctc ctagaccacc gaacgatgcc tgcatttgaa 118320
agacacttct gctgatcaaa gcagctgatg tgtccctttg cggttcattt ctaattgtcc 118380
ccaaggagga gaaattcaaa tagtttatta ctgagagtta aagaaatcca ctgaaatatt 118440
ctttggtcta aaattactgt catggcggag cagcttcacc ttagtcattg cccttaaata 118500
tgaaagctat ttaagaaagt ttgcccttaa atatgaaagc tattttaaaa agtttaatga 118560
aagaagagaa tcacaaaaca ttttcaaaaa gcaaaagaaa acctaagaga aaagttgaaa 118620
gtaggaattt tttaaagaat atacgacgtg tgttctgtga ctcacccctg caagttattt 118680
gtgtgtattc ccttgcatag taattaataa tgaagcaaag catggcaatg atatcttttc 118740
ttgtctagta ttctagaaga ctccatgttt ttggaaaata tcactctagt tagatctcaa 118800
atatattcaa tcagaaaatg ggttttctac aagattctat atctgtagtc aatagcaaat 118860
ataattctat taagctagta ggatgtgata ggaaactaaa acctagggga gaccaaagca 118920
aggaaaaata cttcctcatc caaacttgag agcaatttac cgtcaggcct actattaata 118980
gatggaatac agattccatt ttcattactc aactgccata ttcattatta cactgtacag 119040
aaaagggaat cacatctgtt gaaaacttat atatgatgtt catgcatgca ttccagtaat 119100
tcaacaattt ttatttatct ttttattgct tgctaatttt tcaaaataat aagctaaaga 119160
aaacaaaatg tttgtgctgt tctcagatga catgttatct ctttaaagga caaaatgtgc 119220
tgtgaaataa tagaatgctt tcagcactca agtgtgagtg agtgctcata catgagagaa 119280
agccgtgggg actacagaag ccaagaagca gatctagctg ggaggccttt tgcagaggat 119340
gtagttgtgt ggagaggcca cacacgtgga attcccagga gggctgtgga ggcggggaat 119400
```

-continued ctgcaggaaa gcactggggt gagaaacgtg atgagaaaca attattgtct taaaatatct 119460
gcagggctgt aaggtagaga agcaatacgt tgcatctgtg ttaagtcaaa caaaattatc 119520
aagggactgg tttcagctta acataaggaa caattatgtg atagggttgt caataacaag 119580
agtagactgc ttcttcacac actcctagtc actcagaatg gtccaggagg agtggacaac 119640
catttggtag agtatgggaa ggcaggggcc ctgggtggga gtggtgaggg tagggagtga 119700
gtatcccaat ctagaagtaa attgtgccca gcacggagct gcaacactgc cctgcacaca 119760
aacacacaca aataacaatc cccagcccct gcatttccct ctccggtttc aggaccttgt 119820
atcttacttc aattccttta tttagctgat gatgaaatag gaagagctta gcactaagaa 119880
aatccttttg gagtttggcc ttgggggaaa atgaatcact ccaaccaggt ctgtcttcta 119940
gaaagtatag gatgaaaggg ctcctcatca catacttcct gacctcctgc taggcctttc 120000
cctaaaacag gggctggcaa agcacaacct gtgggtcacg cctagcctgc cacctgtttt 120060
tgcaaataaa gttttattgg agcatgacta tatgtatttg cttacagtct gtggctgcgt 120120
tcacactatc ccagcagagt tgaataattg ggacagggac catatgatgg gtgaagctga 120180
aaacatttac tctctggctg tattcagagg aggtttactg agcccttctc tgagacatgg 120240
caagcgctgc ttcaggctca tgcttcacta gattcaggcc tggggcagta aagagccagc 120300
tcaggatagc actcccgact cactcatttt ttcaggcagg ggagccatct aatgtcaagt 120360
gcctacgtgc aggaactggt ctgttaatta gcagctctcc tcatggaagg gataatatat 120420
tctagaaaca ggagtgcggc cctattgcaa gaatgtcctg agccaaaatt aagattcttc 120480
tatggcagaa acttggctgg ggcttctcct gagttaactt ggtagttgtt agtgattttt 120540
gagtcagttt ttccttgtca acgaccccag gaatgagttt gggattacag ggtagccagg 120600
gaaagggaaa gcttcacgcc cgcccccggg acaaggtctg tcttcacact gctacatccc 120660
ttcacccact ttaaaatgaa acttaaaagg aggatttcag ttgagtagga agtgagaaga 120720
gggctcattt taaaacaagc gttaaatgaa aacccacaca cactcagagc acacaaatcc 120780
aaccacgctt acaaaaccat cacagagggt caggcgaggc ccttttctaa atgaaaaaga 120840
acaggggtgg agactgttct gagagcatgc tgggttccct gaagggaatt ctcagctgta 120900
tgtgccccgc acaggatccc tgctagacac aaggccagct gccttccttt caagccgcag 120960
acgcatccct gtgtccaggc gggctggtca gctgcggtca gcaccagctt ccccgctcca 121020
tggtgaggtc atcacaacat gtgagcagga gggcaggccg gcaacctctg agtgcttaga 121080
gaaagggacg ggattcctcc tgtgcaaccc ctctagtctc actcagactc aagtctgact 121140
aaggggccag gtgctttgac cagggactct cccctctcac ttccctccca ggagtcacag 121200
gtacatgagt ccttgtttta caaatgaaga aaacagaccc aacatgatta agatgttgcc 121260
ttcatagggg tggcaccagg attccaaacc atggactcca ctgagcccag tgcccactga 121320
catgtgccag taacagtgca gctgcctgtg gttctgtcga ctaaactgcc ggcagaggct 121380
ggctttccac cttctttttt tttttttcac tcttcaaaca ctttatgaca tgaacataaa 121440
ctactggctg catcgttctg ctgacaacat gacatgtttc tataacttga aaaaagcaag 121500
cagtggactg ctcattggta aaattgagtc agtaatcttt taggaaggtt atttttcttc 121560
cttttactgc ttctcatctg ttccccgcag taaagaggac aagatgacga cgactcaggg 121620
aacacctcca gcctgaagca gcaccatgcg agcttagacc ttagggtcgg cttagaaacc 121680
acaggcgggg cggcttgggc ccctcggaca ctccctctcg aagctgcttc tccccaagct 121740

-continued accccaaagg cactgagcgc cctctgcccc ccagcaattc aattcactgg ctgtcctgct 121800
cctgtcagta ctgagagttg catgtttgac cctcggggga aaagtccaga ggccctgggg 121860
tgtccagcat gctctgaggt ccctgctgct gaccccttgc gctgtcagca ttcagagaca 121920
ttcacacagc acagcctccc aggctaacag ctgtcatgga acagtggagc agctagacgt 121980
ggccattctg tggcccagtg ctgcagaggt caaagggaca agcgcaggga gcatctttgc 122040
tttcagaaaa aaaaaaaaaa aaaagaagca cactggtgca ctgacctgct cctggtgtct 122100
ttgtgattgc tcttttcttt cgatttttgg ttgtcttttt ttttttgaaa gaggggcttt 122160
tatgcttttt tcctaatgtt catgggtaaa ccaatgtaaa tgtgtgtatg tttatagaga 122220
tggctttaaa tcgcaattct gcagtagaga ttgatttttt aaaaaacatg ggtaaaaatt 122280
gaagaaaaat tttaaaagaa catttaaacc atcttgggct aggggtggat atgcaccacc 122340
ccacggaagc caaacaaaat ctctctgcag ataaacattt gcaaaaagaa tttccaatcc 122400
caatttttga gtcagagatc ttttatttcc ttgcaaatta catatctgtt tcaggatttt 122460
tgactataag aagaatgaat gaagatgtgt ttcttacaga taactatgaa caaaccagga 122520
aggataataa cttgtatccc ccaattcgaa tccagaggat gggaaggcat aaaaaaaaga 122580
aatggaagaa actttatttt tagtggtaaa tggtgggact atgtatttta cgtatggtga 122640
agtcaccaag cccaacactt ggcacttgta ggcaaggtag tcttctaatc tgaatgtgaa 122700
gtattatgtt ttcatttgct tggtaatgag gaatattggt gctttcgtcc cagttctcga 122760
gctgactgac ttctctttct gacgtgtgtt cctttagcac acctctacac tgcatggctc 122820
tgagatgtcc tgtgactgtt tcatgtgtaa agttgcctcc ccaaaggact cacatattcc 122880
ttcagggcag tgagtacttc tgattcatcc ttagcagcta ccttcgcgct actttactag 122940
atatgttgta gttgaattaa tgaacaaaag aacaagcaac tttggtgcct ggtgtgcatc 123000
tcagagcagg gtggagtgag cctggccaaa gggtcatcat gcaacctctg tggctgactc 123060
catctggcca cggagcttct cagccatgct tggtattcac atgacttcta gggcgacagc 123120
tcaaccagca aataaacagc ttcatatggg aaatattact cagcctttgt catcaaggag 123180
tgagtcacgg gcctgaactg aatagaagat agaggagaaa aggtgtgtgg actgggtgag 123240
acagcgccca gcgaggtgaa ctcccggcag ccctgcctgt ctttacctgc acatcacctt 123300
gctagggtgc cttcggttgt gagggcctgt ctaggaagag aagagttgca ccctggcagg 123360
cagcactgag ctgtctcatg caaagctgag gaagaaagag tgagctgccc agtgagcctg 123420
ctggggtggt ggaggctggg ctgggctgtg cagtctgcag cccccagcag cccttggcac 123480
ctttctactg cctggtgctc accagctctc cagtaacaaa gagggacgtg aagtcagagg 123540
ggaagggagg tagcacaggg cagtcttgac tttgaacaaa gagctggctt cctgaagtca 123600
gctggccggg ttttgaagcc gattttccag cagtgatctt tgatgccaac cccatttagg 123660
aattctgtat ctccccctac cttctaccag atgtctctga gctcaccttt ggtgataatc 123720
atgcaatctc cgtcatcccc acgtccacac tgccccattc tgtcccaccc cgggttctgt 123780
ggtgctgtcg gctccccagc gagccaggaa gggagaggcc agctctgctg gggctcctgc 123840
cgccctggct ctgcactgcc cttctctggc aggtctgagg cgccactgga ggagccacac 123900
ggccctgaag cagcaaggca gatgccctgg acacagtgga ggcacagagt gcaagcaccg 123960
gcctggccca cagacttttg gaggggaagt ggtattattc agttcaaaag tatgcctgtg 124020
tgtaaagaga gagcccctga acatgagtaa gcaaaagtct cagcgcagag attagacaag 124080
tagaatgctg gcccgagagg aggcgtttac tcaccctctg tctaggaagg aaagccaggc 124140

-continued

```
ccagcacgct cactgctatc tatcctctca cacagaggga ttttgaatcg aagccagcat 124200
cctgtccttt ctccaatgtc ccctgctcag gagtcaggac tcagcaaggc ccaccccagc 124260
cacacacaga tacagttcca ggactcagaa ctcagcgagg cccaccccag ccacatgcag 124320
gtccagttcc aggattcagg acacagtgag gcccacccga gccacatcca ggtccagttc 124380
caggactcag gattcagtga ggcccacccc agccacacac aggtccagtt ccaggactca 124440
ggactcagcg aggcccaccc cagccacatg caggtccagt tccaggattc aggacacagt 124500
gaggcccacc ccagccatat ccaggttcag ttccaggtaa atcatctgcc ttcctccgtc 124560
caaaagcctt gtttcctgtg tgtccttgtg tttaaaatgg aaacgttatg agaaactgcc 124620
tgccagggca aagggtgctg cccggcacac agtagggact caaaatgaaa ctattgtatt 124680
gaatacataa cagatcaacg ggtattgctt tctgaaatct tttttagccc aattttgttt 124740
cttatagtcc aataacaggt caaattcatt tctgatttac tagccattca gttgcccata 124800
aaaaatggaa agtgatttaa gattattagt ttaaaaacca atgaaggtaa aacagttatc 124860
attgaaggca cataggcaga aatagattgc aatagttgct gccatgtgaa gcctcagtgt 124920
catgctccat atttagagag atctatgatt tctgaggccc tttcatgtcc atgatctcag 124980
tactgctcac aactgccctg tgaaattcgc cgagctggcc ccatgtcaat cagagtacac 125040
tgagcactga gacccagcat gttgagataa ctggctagag atcatcccat aatggtacca 125100
tcacaatctt cacactgtag aagtttgatg atgtcactgg aagcatattc cacagtccct 125160
tgtgaactgg ccttcctgtg atcagaagca tcagtgaact cccaagaggg tgggaactcc 125220
caagaggtat tctcactcta cttagtgtat attttacaaa tcacaagctt ggctttggat 125280
tcttttaatg gctagaagga gaatcatggg gttggaagtc caccagtttg ggtattctgt 125340
tccctaactc aaaataaaga gatgttattt tcaagtcttc tgcttgttaa cttaattaga 125400
gatacatgag tttgcagctg tgctgggcat gccgcagctt ggcatgttta gtccagaagg 125460
catattataa tgtacatgga agattgtcag aaattcaaaa ggactttttg agtatcacat 125520
gtgtattttc aagttccaat atagattcac attcagtttg acaggtatct ttggatgcct 125580
atcagttaag aactatttat tagttgtgga ataaaatagg gtaaaataag gaacaactga 125640
ggaaaaaaca taaaatttgc tttgtgaata aaagttgtct tcaaaattat gactttttcc 125700
atcccacaaa agttttgatt aaacccacaa tgaaaattta aataagtgta tttactttgg 125760
tttaaccact tatttcatta tgactcacaa ctataggttt tctagtttcc attattacaa 125820
actattgtgt ggtttaaatc aatttcatag actagtctag ttctatagtc acaatttata 125880
aaattttttt atgtggtaaa ttgagtgtct tcatagatgt acatgattat ttctcaattt 125940
ttaaggaatg tattttttaa gatagccttc tttagccttc tttaacactg atttttgtaa 126000
atttttttaca gattttttta aatttttggt aattttttag cataaagtaa tacatggtca 126060
ctatggaaaa cataaaaaca caaaaactat gaagagtaaa taagaaaaac acccagaaat 126120
ttaccattca gaaaaggtca ttgttaacaa cacggtgtat cttcctcctg tcatgcttcc 126180
gtgcatttga gcacatttga gatgtgtata catgttcact ttgagatttt agtatagcaa 126240
aagaaatgac cggtcctgat tcaatgaaac ctctggcaaa ctcgctatat tttccttaca 126300
tatttttaag ttcatcctat aaatgaacta tccattcatc ttatttgaga ttttcttaaa 126360
tctttcagca agaaagcggg aaaaaaatcc tcctctggcc tttaaagcct aattaaatat 126420
atgactaagc tagaaatatt ttataatgac caaccagaaa gtggcaagga ctgtcactct 126480
```

-continued

```
tcccatacag cccacctcct cctctatctc cctcaggcac acggaaacga gaaaggcaga 126540
gaaacccagg acaagtcatc caagactttg gtcacatggc catccattgc tttcacaaca 126600
aaaatataaa tccaacatgt gtgtgtgcat ttcataccag taggtccaat aagctatcta 126660
tatatacaca tatgtgtaca cacacacaca cacatcctta cagacactcc ccagcttact 126720
acagtttgac ttaagatttt ttgactttac gatggtgtga aagcaatgca cattcaatgg 126780
aaaccatact tctaatgttg aattttttat cttttcttgg gttagttgat gtctgatatg 126840
ttactttctt gcgatgccag gcaatggctg ggagccagag ctcccagtca gccatgcaat 126900
caagaggcta aacagctgat actatacagt ggactgtgtc accagcattt tggggatatt 126960
gtgttttgtg tttttgaatc ctatcatgtc tacaaaatgc cattttcgac tgctattttc 127020
aatttagggt gggtttatca ggacataacc ctatggaaag ttgaggacca tctgtatatc 127080
tggtagggaa agatggataa caaattcata ggcaaataat aatttcatga ttattattaa 127140
gttattccta cttaataata agtagtgatc actgccaggg agcagagaat gcaggataat 127200
gtgacagatg taatggtggg tacttaagct aatgtagttg cagaacaggc ttttctagag 127260
ggtaggcctt taagcgtacc tcgaagatgc aaaggaagca aagatgcgaa gatctgggct 127320
ggggatggaa gcagagacaa cttggaggcc aaggggagag actgacaaca gcccagctca 127380
tacctcagca gcctttaatg catagctaag aaaacaacaa attaaaacaa ttatagttta 127440
cttagacgat tctaagtgtc taagtggatt tgggcaaatc tggagaaact tgttctaata 127500
ctgtgtctta ataagtaata tagatttgcc caggcttgtg ggcagagtgg tatacacccc 127560
ataatagcag aggaaggcca cagggcctac cctacaaaac cagaggcatt taaaaactta 127620
aaggaggcag attgctttta ttttcagtta aaataaagtg aggagtttct caagaaaaat 127680
aataacgaga ccaccggccc gccctagatg tccaacaaga atgcacagat aacttcgtat 127740
atccactttc ctgaacctgc ccctgacagc caagtggagc acaacaacag agatgaacct 127800
caaaactact gtgctgtgac ataaggcttg ctcaagagga cagtgtggtg tgagtccatc 127860
tatgttctaa agcaagcaaa gctattctgt agtgaaaatg gatcaggaca gcagttgcct 127920
ctggtgtatg ggggcaggga tcgactggga ggggcatgag ggatgacagt tagggtttcg 127980
atcatgacag gaattcagat tactccagca tgtgcatttg ttaaagctca tcaaatgcta 128040
cacttaagat taatcctctc acagtttgtg gatgttacct taaaaacaac aatgatgact 128100
gcaaactaat attgaactct ggttagtgat ataccaatgt gaagtatagt gatatctcta 128160
ctttacttta aaatgcatcc aaaggcagac tagaggacca tatctgacag acagaaaaat 128220
agatatgtga taaggtgaat gtagtaaaat gctaacataa ggatgtttgc ggtacaattc 128280
tttcagcttt tctatacatt tataaatcat aataaaattt taggacaaaa agttagtgct 128340
ttgaagtcct aagtcatagg gcctgctgct cttgatgcag tagaatttgt cttcagattt 128400
gcaaagggta aggcaaacca ctagcatttt gtatggaact tgatgcaaat acttttaatt 128460
gtctggtttt caaatgtata gacttaaagt aatatcaact ctttctttga atcaactact 128520
gaaataccta gtcttaaata aatattttta tgtaatcctt aaagtactat gtattcattt 128580
ttctttcttc tttcttttct ggtttgataa atattctata aagtaactgt gtttaatggc 128640
caacatttga gtaagtccat atgcagatcc aaacatctca gtttagacaa taacttaaga 128700
caatatagag tggctgacat cccctaacgt gggtccagat gcatgttatg ttatgtttct 128760
gttgcattct caatagttaa ctttaataaa agaaagtcaa aagcttatat attttttcaa 128820
tcttcaaaac atttctggga ggttgtctta gttaatttta tgttgctata cccatatcac 128880
```

-continued agactgggta atttataaag aaaataaatg tatttggctc atggttctgg tggctgggaa 128940
gtccaagagc atggcattgg catctgcttg gcagctggtg agggccttca tgctgtgtca 129000
atctatggtg gaaggtcaag agagcatgca tgtgaggtgg tggggaagag aaaaagcggg 129060
tttaactcat ccttttatca gggactcact cccgtgatag ctaacccatt cttacatgaa 129120
tggcattaat ccattcctta gggcacagct ctcatgacct aattataata cctcttaaag 129180
tttccacctc tcaacactgt tgcattggtg attaagtttc caataaacgc actttggaaa 129240
acacattcaa accacagcag agatcaacgt tattgtcacc attttcatat ttgaggaaag 129300
catggcacag agagcttgga gaagtacttc aaggtcaccc aatgaggaag tggctaaaca 129360
aaaaccttat cttaaattaa ttaaaaacct cttgctcttt gcagttttgt cttaaatcta 129420
cctaatttgt gactgtaatt tttaagtaat ttactcatat aagtggtctc acattaaatt 129480
ttctcattgc tttatatttc taacatgaga tatttggtat aaggatggaa ccaagatcat 129540
accttgtttt aattagaaaa cctagaccaa gtcattgtga tcctcatcct agatttcagt 129600
taaatgctgc tgtctccttt tgggtatgtg acaggggaaa gcctcagaag aaacaacctt 129660
atgtgttttc ttttgatact ttagtaatta acccaggata gtattcaaga ttgacatgcc 129720
ttatattgaa tcaaatagca tatcaactgc cttcttattc tcaagtatag acatgttggg 129780
taattgggca tttaagtttc tttgcaattt tttccattat taacaaaatt aatgagcaac 129840
attctgcata aggtctgttt cctcagaata cgtttcccaa agtggaatca tcatgacgta 129900
gaatttaagc atacttactt gtttaaacaa attgtccagt tgcttcccaa aatgttttgt 129960
gaattaagat ttacatcaag aatatgtaat gttgttactg tctcccaaat acaggatctt 130020
tttctgaata taaaagttat acatgctaat tgtagacaat gaagggtcat tatcctcata 130080
gataatgaag tgcttctaat acttgtgctt ttattcattt attcaaaaag tgctaaataa 130140
gccctgaagg ggcttttggg gggtcatttg gggcttattt agcacttttt gaataaataa 130200
ataaaagcac aagtacagtt tttttaaaat actgttttct ataatagatt aatcttaaat 130260
ggcatgtttt cctttatttt actgacaaaa gttacttact ctgtgattga ataataaaaa 130320
ttctttggtt cagctgagag aaacttgcaa gctgacgtcc ttgattattt aaaatgaaag 130380
cagctgcctg ttttcatctc tctgcatcct gaggaaactc ttctgcaacg tgttccagcc 130440
ctaggttcta gctgaccctg ttcatctgtt tggcacgagg ggcccaacta acacttgcgg 130500
ctacctggac gacagccaat ctagttggaa tgagagttag aggccatagt ctgtcagctg 130560
ggaaagcagc ttttattcca aggtgtgcca accgaaaggc cacatgttat tgtcacaacc 130620
tggtacctac atcagtgctg acatctttaa gaaccttaga attgggaaat cagtttagcc 130680
ctatctgcat gtgtagccga caaccacaca attgttccaa cttgaggttg cattcagagc 130740
aacctcattt cccccatact cctgaggaaa agcagaccag agacgctggg tcaatccaga 130800
gttatggttg gaaaaatgat ggaataattc tgcccctggt gataggagag agggactcca 130860
tcttgtcaac tgtcatggtt cccatgtgaa agctatcatt atcactgaaa ttgaatgaga 130920
acacagaagg gaagaacagg gaaatcccca cagagttaaa gaggatgtga agattgcttc 130980
atgtttaatg tttgtgtaag tgctttgggt tggttatgtg ctgtctgaac atgtgctcat 131040
ttccatggct cattgagagg gcagacagtc caatgatact ctttagaatc attcccatgg 131100
ggaaggaaca aagaagcctg taaaatagaa atgcacatgt aaaaagcatt gaagaaagtg 131160
ccagtgtatt gattttggcc atggtttgtg ctctaccacc tggttactgt gattgcagaa 131220

-continued

```
gtgcctttgc agatgaggaa gaacctggcc aaggctcaat ccaacatcca aagccagagg 131280
ccatatttct tcactcttaa gataatttgg gttcaaatta tagtcccttt acacactctc 131340
tgcctcaaaa ggcccaagac tctcttttgt tatgcttgcc taaacatgcc tttcaaagaa 131400
ctagttctgt aaatacaact ttattataaa cctctccttt gcttttaaaa atggatcacc 131460
acgtccattt ctatggtcca actttgtccc ttaatttaaa attttttctt ggattaagtt 131520
tgatgccttg aaacattagg aactcaagca tacaagattg tatgctggtg gtgagggaag 131580
taactgtgcc tccgcctgtg ctgggtggat caacatggag tgtggacgag catagggatg 131640
tgtgggtttc tcactagctg agagtgtttt taaatgttgt attttgatgt ttgttatttt 131700
ctgaatattc tacagttaga cctttgattt attctttgat gcattcattt gaataatatt 131760
tttaatctcc agccagttag gtttttaatt tacacttttg tccctgattt taggtgtagt 131820
gttgtgtaca ctactgccca gtgtatgtta tgtttgtaaa cattcattgc acgcacaaca 131880
atgtgactca caatattttt gagaagtaaa aagttcatta tatagttatt aactcaaccc 131940
tacagttata ttcgtgaaat accttgtgaa atttattttt tgcctactgg agctcttaca 132000
ggttaatcct gtcttcaaga ttttcataga attttcatct accacccacc cctttaaatt 132060
tcaacatttt tttattttgg cattttaatg caattcaatg cattataggg acaagctatc 132120
tcttattatg aattgcacct tatataaact taaagatctt ttatcacaaa tttctttgct 132180
gtgtccttta gtgagaattt gtattatcag tcactaaagc tcactaagtt agtaagcttt 132240
gcgcccagat gacctgggca ggaatgggtg agtctctgtg tggagagagt gaagaaactg 132300
ctacccttaa tacctggacc ttgagggatt gttttatttt agtttttctg catttctcag 132360
tatttcatgt gatatctgtc tttttcttcc agtttgccaa ggcacgagta acaagctcac 132420
gcagttgggc acttttgaag atcattttct cagcctccag aggatgttca ataactgtga 132480
ggtggtcctt gggaatttgg aaattaccta tgtgcagagg aattatgatc tttccttctt 132540
aaaggttggt gactttgatt ttcctacaca aataaaattg gagaaaatct aagtggagaa 132600
aggcctgggc agaattccac ttgaagtgtg tttatttttg ctatggcaat gacaagtctt 132660
acagagctac aaacgagagt tttatgagaa agccatttta ccagctaatg tcaagtaata 132720
actagaaaag gatatcaaat agaaacaggc taatctggag ttccatgtca tcatagacac 132780
tgacgtttat ccctgaccat tacctcagtc atgatgtgct gccatactcg ctcttaaaaa 132840
cttttttttaa aagccctgct ttgcaccatt tgcctattcc cttagtgtaa atactcctac 132900
tatagctgat ttcaaggtac caagtttcac tcagctggtc acagaattct tatttcacga 132960
taggcgctaa tgaccccata ggagccagct ctgaaggctt cagagtttca ctgaattttg 133020
gatggggttt acttagcctt cttctgtttt tcttttacct ttccttttta aataagaaat 133080
aatgcaagac agatacaaag taattctttt taatttccat tttcactgga gagtgttgaa 133140
ccccgtgagg catgagagca cagtgttcca gaacaatgct tactgctcat tatcacaggg 133200
gtcaaaggct aacgtgcagg gattgttgca gatcgtggac atgctgcctc ctgtgtccat 133260
gactgcaatc gtctacctat tttacagttg ttgagcactc gtgtgcatta gggttcaact 133320
gggcgtccta gggctccctg gacccatttt agaccttgag ttcttgagtt cctcaaaaga 133380
gaaatcacgc atttatgttt tctcttctta gaccatccag gaggtggctg gttatgtcct 133440
cattgccctc aacacagtgg agcgaattcc tttggaaaac ctgcagatca tcagaggaaa 133500
tatgtactac gaaaattcct atgccttagc agtcttatct aactatgatg caaataaaac 133560
cggactgaag gagctgccca tgagaaattt acagggtgag aggctgggat gccaaggctg 133620
```

-continued

```
ggggttcata aatgcagaca gcagttccga tggctcccag cgagcttgtc actcaattcc 133680
acctcggaga aggcttttat ttttacccag tacacgtgca ctgagtgccg gctgtgtgta 133740
agatactgca ggggaagtta ctgagaagat ggcagatact ggaatgggaa gatttaagcg 133800
gggtaccagt gtttacatgg acatgaaaaa atactgagag atagtaagaa atcgtaaaga 133860
ttctgagtaa aagagagtat gaccaaacaa gctgagcagg aatcgtgaat ctatgtgtgt 133920
aggcagtgaa taaactgcca gtcttattac ctggacctca aggataaaag acatacagta 133980
aaaatcaacc cacattgagg acagtttcga gagtcgcgct gctacacaga aagccctgtg 134040
taagttaagg atagagaatg aggtgttcta gaactttgaa tttttgtgag caggactcgt 134100
gaggttcctg tgagaggaaa caatgaagga tgatagaaaa gaagggaaat tgattttaaa 134160
aaactggaga tagcagtgat tgtgcctcac tgtgcagtgg gtttggggcc aggaatgtta 134220
aattggtaac ttcatttaac gcccacaacc tttcttcaaa gtaggcactg tacagatgcc 134280
ccttgactta tgatggcatc ctatctggct ggaccccgcc gagggtgaag gcgtcattag 134340
gtcggatttc agggctaatt gaatgtatat tgccttcaca ccatggcaaa gtcgaaaatc 134400
tgtgttaaat catgctaagc cggggactgg ctgtgctctg ccatcgtaca aataaataaa 134460
tggaagtcaa gtaactccct tgagggcccc agctagtgaa tggagaggcc agctatggcc 134520
accactctct gccccagggc gctcaacgcc cctcctgtgc catgcagttc tgacagggag 134580
gcagtgctgg taggaaaggg gtgtgatgaa aggggtgccc agcagaggga gtcatatccg 134640
gagtgacagg agcccaacag gggtgcagcg ctggaaccca agccagcacc tctggtcatg 134700
gctcctcagt tcaccgccta taaaattgtg tggttccccc acaccccttg ctgctcagag 134760
cagccgcgca catgcttgtg ctgtgcgtgc ctcctgtgag atggcctggt acaccggttc 134820
ctacagtgcg cctcacacgc tgtctcggag ggaggcagcc tgtgcgggtg cctggacctc 134880
cgagccagac cctctgggtt cctgcctggc cccgtccctc agcagccaga tggctcggga 134940
gcacattctc caatccctcc gtgtctctgt ttcgtcatct tcaaaaatgt ggatggcata 135000
gctgctaaaa aatggtgaca tacttcctag gtggtgcaga aaattaagtg actgtaggaa 135060
caggcctcag cagctccttc cacttccttg gtatgattgt tttttaaacc aaggctggga 135120
ttgtatagat gcagattagt taatgtgata ccattaatag ctaacctagt gcctgctgca 135180
gggtgagcct cccctaagcc accgggaagc ggctcctgca gcctccctca cgtgtgctgg 135240
ccctcctctg gcagtcattg cctgtggtgt gctgaaggcc cagctctgac tgtgcctctg 135300
tgctctcctc gccccgcccc ctgctctctc tcaggtcttt ggtctgttgt ccgagctgcc 135360
acagcagcct ggacatccct gttggtgttt ccagccctgt cctctcctga gttccatcca 135420
cctgtgcatg gctttttcat gagtgttttc acggatggtt ctgctgtcat ctccaacctg 135480
ataaacaaag caccacgatt cagcccttat gaccccaagc ttccttcctc agttccttgc 135540
ttctgtgcat ccactgaaga agcctgttcc actgtttccc tgcactgggt ctcctgtctg 135600
caggaagcct tcagccctca cttccacact cctctaagat gtgtgcctgt gcccttctgg 135660
ggaagctcat tttcctagca gcctccagga tcttcagggg tgaatccctc ctttcccacg 135720
ttggtactct gtacacacaa catgcccatt ccctgcctgg ggagctgggc attgcttcat 135780
gaatcagagg tcaatttttt ctctattaaa gtcacagatg ctcattgcac cattgtgaga 135840
atgaatgaag atagtgctta taaatcagcc agcaaggtac ccagcctcac tgtgtcaggg 135900
tctccctggg catgaggtgg ttagagtgtg tgacatgtct gtccccaagc ctgtcagctc 135960
```

-continued ccagatcgaa gccagtggat ctcattcatc ctcgcagcgc ccacagcact tgcacagggt 136020
tttgtacaca taagtcattc tgtcaatgtt catgtttaat gtcatcagtg gaacactccc 136080
actttgtaaa gacttgaatg tgttcatccc tgacttttcc acatcttgtt agttcttctt 136140
tggaaacagc tgtacagttt caccatcctg tgcatccctg gagtctacct gtctctgtca 136200
tacattcaga ttcttcttgt ttcgtgtcac tctcatatcc ttttctctaa tgaaaagctc 136260
cgcctgggca tgcaaggtgg agccctggat gccagcccct cacctggcat ccagggctgt 136320
agcactcagg aactgcctcc ctgccctgcc taccccctac atcatgcgac cattccagtc 136380
cagccaatca gccccttggg acccagctta ccacatgcat atcatttatg ctgtgaccac 136440
tgactaaacc attctcttcc ttcctcccca tatttctaaa tttctaatca ttgctcaaag 136500
cccaattcag agaaaaccct agctcctcca tggcaccatc attaacaatt ttatctggcc 136560
gccccccggg aagttcactg ggctaattgc gggactcttg ttcgcaccat ggcatctctt 136620
tagcagaaca taaatgcgaa gagcacatgc atccttcatg ggaatttaaa ggagctggaa 136680
agagtgctca ccgcagttcc attctcccgc agaaatcctg catggcgccg tgcggttcag 136740
caacaaccct gccctgtgca acgtggagag catccagtgg cgggacatag tcagcagtga 136800
ctttctcagc aacatgtcga tggacttcca gaaccacctg ggcagctgta agtgtcgcat 136860
acacactatc tctgcctcca gctcctatgg gggacagctc tacagcactg gggcagggga 136920
gagaagccat gtttagtaag tcacattaat cagaaacaaa aagtagtaag caaaatatct 136980
gaccactaga aaagcatgta tttaccacgg acatagagat cgtttttttg tggcgggtgg 137040
cagcccagct ggttggcagt gcaggccacc ggaggcagat cccctgcagg gacagcagag 137100
cacttgtgtc ctgagaagag ctgctgttca tggggctggc agcaccaggg cctctcctag 137160
cctgccctgc tgacactggc cagactccta catgcttctg agtctccaga ggctacccgg 137220
ccctcctgaa gcaccagggc tgaatccacc cccagctgag ggcatgaaca ctgccacatg 137280
gagtcacaca cacagctggg cactgccatg gagaggaagt ctgtccatgt ttccttgaat 137340
actggtggcc tggtccctgt cccattcccc agtgaggcag cctgtgggga agcctggcag 137400
ggaaccaggc gcaggtcagc gtggcgccct gactcaggcc agcactgatg gggggactctg 137460
agacgcaagc tcacactcac ccagctcccc tgggctgcgc ccgttcctga tcgcttggac 137520
tttctgttct ttagagtaag aagtgatcac catttcctgc ttctttgttt ctccacaact 137580
gtgcagtgga tgcctgtttg ttttctgccc tcagaacaaa aaaaaaaaaa aatagagctg 137640
acgtgaatct tcaaaatcat caactacagg gctttggatt tttgtgtatt tgttttattt 137700
tcattttatg gatggattgt gatgaaatgc ccgtaataca agattttcca tcttaaccat 137760
tgtaagttac aatgtcagtg gcattataca tccacatggg tgtgtggcca tcaccaccgt 137820
ccacacacag aactctttta tcttgcaaag ctgaaactct acccattaga cagtaactct 137880
ctgctctccc ttccttccca gcctctggcc ctggcaggca acagtccact tgatgtctct 137940
atgaatttga ctgctctggg gctctcatac aggtggaatc atgtagtatc tgtccttttg 138000
tgtctggctt atttcaccta gcaaaatgtc ccgaaggttt atccatgctg tagcacgtgt 138060
taagaatgtc cttcctcttc atggctgaat aatattccat tgtatgttga cactacattt 138120
tgtttgtcca ttcacctatc tacagacact ggggttgctt ccatcttttg actgtttgaa 138180
taatgctgct gtgaacatgg gtattgaggc tctttgtttt atagacatat tattccacca 138240
gatacccatc ctgacaccta ctatgtttgc aagaaactga aagctttatt ttacattgca 138300
aaatttcata ttatgagatc aaggttagca tttcctcagc tgtctggtgg acaatgggga 138360

-continued

```
ggttaaactg tgcacatttt attttttttt aatgaacctg gaacggttat ggggccagtg 138420
tttgccatgg atcaggtcag gcagcccaca atggcaggtc tccatgttct gtacaacaac 138480
tgtgggaaag acccacagag aaagtgctgg aaaggggaat gatgggtagg ttcatgcagt 138540
aaaaagattc aaatactaca gggcattgaa ctataggcca atatagcatt gctttaagaa 138600
taaacaaaaa ataagacagt aagaataagc ctagcaaaat caaaagtcta taaagaactg 138660
acatttcaag ccaataagag aataattcct tattcaataa attgtctgga atgacttaac 138720
tattaggggt gaaaatatca aagtgagaga actataaagg gtttttaaaa aggaattagg 138780
tatgttgggt tagtcgcatt ggagagtgca aattcaccat cgacctgata cctgaaattt 138840
cctccttacc atctagaggc aagttgggaa tgctgccagg ctcctgtggt aaaggaagct 138900
cctctcttga ctggtgcttt atggctacac gttcctgctc agaatggatc tcatttagtc 138960
ttcaccaaaa aaaaaaatct catgagatga tttaagtgtt ttatggacaa gatgtctaaa 139020
actcagaaaa atttcacagt gtgcctagct tttatgttta tgttgaagtt gggcattaga 139080
agttagaatg aatgggttta cttcagagaa aattaaatcc atcacccact ccttgtacta 139140
tgaattccaa atacatatta aatacatata ataaaatatt taatatatat gtaagtgcca 139200
gaaggaaaca taaatatgaa tattttgtaa tatcaagttg aagaaaagcc aaaatctgac 139260
atcataaaag aaaactttca agtaaaatat gttaatggct accaggaaaa tattgtgcaa 139320
tgtctgattg ccatgaagag ggttaatatc cttgctatat cactctgtga agtcatcttt 139380
aaaagactaa gaaaaagatg aatctcttaa taaaaacctg gcccagaaca tgagcagcct 139440
ctctctctca ctctcactgt ctctctttct gtcacacaca cacacgcaca catacacaca 139500
cacacacaaa tatggccaag aaataaagta aaatgttatt tctaatgtaa taagtaggtc 139560
aaaatagaaa aagaaagcat cacaccttcc tttgcaaagt atttgggttc cttttgcttt 139620
taaacacctg ggtcagctgg ggtgtcgaga aacagaaatt ctcacgttct gcttgtgggc 139680
atatatgtta ataaaaccaa gcttggcaat atgcctgcaa tatgtatcta aagcttcaaa 139740
gtatgtatag ctttgaccaa tcaatatcac atttcggaat aagagaaaaa gaaataatga 139800
aagtgaaaat cataagagat gtagaaacat attcttatac aagaattcct tgcagcctta 139860
tttataataa attttgtgaa caaattatat atctaaaaat aagagattgg ttgaaaaaat 139920
tatgcagcag ccatgctatt gataatcatg ttagatagaa gcatatttaa aggcatggaa 139980
aaattgccat gttttatatg ggtttttaag gttataacac aatgtatagt gggattccaa 140040
ttcctgtata tacatagact tatatgtcta tattgattaa ctctggatga gtctcatgtc 140100
ttctttttgc tttcttctat tatccatatt ttatacgatg tgcctgcatt tctttttttgt 140160
aacagatggt caatactaga atcataaaca gatcttgttt gtttattggc aaatgtttcc 140220
cgttagaaaa agatgcattt ttcttttaaa tatttttatt ttatacaatg attacaagct 140280
tataatagaa atttgaaaat tatatgtgag tacagggtaa aaagttgaaa gaatgggatt 140340
gcacgctaca gatctagctg cttttagcac gcctgcgtag gaccttgctt tctctagacc 140400
tctgttgcag tctctctgcc tacctcctca caacgtccat cccccgcggt cactgtcgtg 140460
atgccagcct ccccggcctt catgtctcta aggagcacca gcgcggcaat tagcgccctt 140520
tgccttggtg gtattctggc ttcacagtca catgggagat caatcgtcag cttttctgtt 140580
tgaaatctaa attcttcctg actgcagggg acctcgggac ccatgaacac ctctagttta 140640
ctatgtcttc acagtaaaag atatctgcat gactggactc tttaacaaat ttggtggtta 140700
```

-continued acctactctt tctatataga tatagcactt cgaccttcag acttctcaat actgataaaa 140760
agaaaacacg acagatgaca ggaaaacctt tgcagctata atttgtaatc ggccaattat 140820
aaaaactgca aaaattgacc agatagctaa ggttttacac agtcatgaaa gtgatctgca 140880
ctgttaacat ttcaccctct gtgcaccatt ctgtgcttct ctctggtttg gagtctagaa 140940
ggttttattt acaggctatg acttaacaat cccagaacgg ctgacacatg cagtcactca 141000
agactggaca cagcaaggaa gtagtgggtc catgccaaag gctcagccag acgagacact 141060
ctagctgtgg caggagatgc cagggaatgc tccaagccta agcagattgt aaacaaggaa 141120
cctcaaattc atgaaaaatt cttgcttatg tggcccatgt cagtaattac tctctgcctc 141180
agtttccgca gctgacatgt aaataaaagc agttcatggt tcatcttctt ttcttatcgg 141240
ggtctcaagt gattctacaa accagccagc caaacaatca gagaataagt tgaaaagatt 141300
gtcttcattt attgaatgtg cttaactcag gcccgggaaa gggcgtcatc agtttctcat 141360
catttcactg agatatgcat ctattacttt tacatttcag gccaaaagtg tgatccaagc 141420
tgtcccaatg ggagctgctg gggtgcagga gaggagaact gccagaaacg taagtcagtg 141480
aacagcctca gacccatgtg tgaccgcccc tctcttcctt cacttgctta ggtgattgga 141540
tttgttttcc ctctgaagac tccaaagagt tactttatta cagggtcaga tgtgaaccag 141600
taggtgaagg acagtcttgc aaatctcacc gcatgcagtt aatccagggt gggctatttt 141660
gggagcttca gcctatcaca aataagtgaa catcagcagg ggctgggcgc ggtggctcac 141720
ccctataatc ccagcacttt gggaggcgga ggcggtcgga tcacgaggtc aggagatcga 141780
gccattctgg ttaacacagt gaaacctcgt ctctactaaa aatacaaaaa attagccggg 141840
cgtggtggcg ggcgcctgta gtcccagcta ctcgggaggc tgaggcagga gaatggcatg 141900
aacctgggag gcggagcttg cagtgagccg agattgtgcc actgcattcc agcctgggcg 141960
acagagcgag actccgtctc aaaacaacaa caacaacaac aacaacaata agtgaacatc 142020
agcaagtacc ccagccctgt cctctgaaca cagcacactt tcccaggaat ggaagacttg 142080
ctcctgttga cagcagtcac cagacttctt gtttcctctc cctccctggc tttctttggt 142140
acccacctac acagaagcct gagcacgggt tctcatgggg acttttccat gtggaccctg 142200
ctttacgatg gagagggcca ttctcctagg tatggttgtc tggctcagcc tctcagtggc 142260
caaggaacct ggggacatga gctcaaaaac ggacactatg tccttaagct gaattgtggg 142320
ggggctgtta ggcccttcta aacactactt cccagcaggt atttttgttc tttgtatgtg 142380
ctttctgcat tgcccaagat gcatctaatt atttagcagg tctcaaagtc tagacttgat 142440
ctcatgagtt ctcttaagtg attaaaaata aatcaggaga aaaaagaggc aatcagaaaa 142500
gggcatggtt tgacttagtt tgaatgtggt ttcgttggaa gcaaatgtgt cttcactttt 142560
tcatgaaaaa gtctgcaagt gctctgcgac atccctggga aatgatccta ccctcactct 142620
tcagctcaca gggaaccttt gctctttttc agtgaccaaa atcatctgtg cccagcagtg 142680
ctccgggcgc tgccgtggca agtcccccag tgactgctgc cacaaccagt gtgctgcagg 142740
ctgcacaggc ccccgggaga gcgactgcct ggtaagatgc cctccagca gcctccctgg 142800 agcaggctgg ggctgcaccc gccccaccca caccaggaca gaagacttcc tgtgggggag 142860
ctgtcaatta gcatttgtca taacagacag gatattgccc tctgcctggt gacaaagtat 142920
ctttagtatc ctgcctccac cactcactga gaccttggga aaatgatggg actaccatgc 142980
ctccatttcc ttacctgaca atgatgcata acaaagtctc tcccagttga atgcttaaat 143040
gatgagatgc ctgtgatgtc cgtcattagg acctgggcac agaacaagca ctaaatacta 143100

-continued catgcaagta tttgtcatga atgtgccttg ttgccagcag cacactctct ttattgtttg 143160
acttcggcta tacctctaga gacttgacac tgtgaggtcc ctaagagacc catggagagc 143220
cacacaggtc ttgctggctg gggctgggtt agggcctcct gacacggatc cctcggctcc 143280
tccaccactg ctcaggcacc tcctgagctg caccctgccc tcaaggggtc ctgaagtact 143340
cactgtcgcc ccattgctcc agaaagtgcc agcagaagcc ttgctgcccc agcgggctct 143400
gagcagcact ggagggtaca ggtcagaagc gtcttggaag tcctggagac gccaaggctg 143460
gtggatgtga ctcctggagt gggagctggt gtgacgaagc ccttcctaag actaaatcca 143520
gagcactctg tggtttcaga gaagattcct aaattccaga gtttggaccc agacccagga 143580
attgtgactt ggttggcctg agctgtttct aatgtgagcc ccagggagaa gactgtgcgt 143640
ggggttggtc ctaggaaaag ccctcgctgt attgggtctg gctcctttac acggcattgt 143700
tctagcaagg ctttctgcca ttcagcaata cattataaaa tataccctca attgtacttt 143760
ataagggaag cccaatgtcc tttataaggg aaattaaaca taatttcatt ccatagtcac 143820
cgctataatg tgtgaactcc atcatctata cgttagtaaa cagacgtatt tttatcataa 143880
tccataaatt atgataggtg ggacagtgca cctaagaaaa aaatggactt tttagagaag 143940
ggtctttctg actctgcaga gggcgccagc tgggttttcc cacactagtg gaacactagg 144000
ctgcaaagac agtaacttgg gctttctgac gggagtcaac accgtgctgc gcttcctccg 144060
tgtgtggcgc tgagtgtact tacctcactt gcccagcgtg tcctctctcc tccataggtc 144120
tgccgcaaat tccgagacga agccacgtgc aaggacacct gccccccact catgctctac 144180
aaccccacca cgtaccagat ggatgtgaac cccgagggca aatacagctt tggtgccacc 144240
tgcgtgaaga agtgtccccg tgagtcctcc tctgtgggcc ctctaactgg tcaggcatcc 144300
ttgtcccgct ctgtctcctg ctgagccctg gagtatccca tcttggagag tctttgggtg 144360
gatgtgtttg ccttgcttgg aggaggcgac cctgtgcccg tccaggcaca caggcgaggg 144420
gaggggctgg cttgctaccg aggagcgggc aggtggtggc catctccacc catgggggct 144480
gctcagtgca cagggcagat ctgggtggcc aggccacctc acaggagaaa cacctgctgc 144540
tcagccctca ccactcatcc agcagccaca gccgtgggta ttcagttgtc tgctgggcac 144600
aaagccgtgg gcatgccact gtttagtgct tgtgccaagc aggtatttaa tacaccgaaa 144660
tcagagagtc tatcagaaga cctgccttct tgagtggtta aaattctagt gaaagttatg 144720
cctcttagga gtattgcaga ggttttgttt ttgtttttat tttgttttgt tttaatggtt 144780
tgggtttgag ttttgcttgt ttgtacttac atttgtactg gtggctccag ggtttaggga 144840
aattgtgaca taaaataatt cctgacagag aaagcaaaac tttgtctaat gaaagagttt 144900
tagaagccac tcttgatctc tagaagggga gattaactga gaaaaaaaat tgaaagaaca 144960
attatgaggg ggagatttta ccctgccaga tttgtgtaca tgaaaaattt tacattccgt 145020
atggaaaaaa aaaacacaaa ataataagcc attataaggt aaatgacaaa caaagctaaa 145080
gaaaaatgtg ccacagtgat gacacagata tatctttgag atagggctta acagagcttt 145140
aaaatccata ggaaaacact tcgagcctga gataccaaga gcagatggtt cacagaagaa 145200
tcatcaatgt cctataaata tttttgagga tcttcttggg gaacttaaaa caggaacagg 145260
ccaggcacag tggctcattg gctcatgcct ttaatcccag cactttggga gactgaaggg 145320
gctggattgt ctgaggtcag gagtttggga ccagcctggc caacagggtg aaacctcgtc 145380
tctactaaaa atacaaaaat tagccgggcg tggtggcgca cgcctgtaat cacagccgct 145440

-continued

```
caggaggctg aggcaggaga attgctttaa cccaggaggc ggaggttgca gtgagctgag 145500
atcacaccac tgcactccag cctgggtgac agagcaagac tccatctcag acaaacaaaa 145560
aaggaagaca tagagctcct aaaaataacg cagaagtctg ctattaatac aaatgaatta 145620
ctttaaaggt gagagcaggt ggaggagagg gctgaggtgc ctgctgggac gcaaaacagc 145680
tggcccctca agggacccag tgtttcctgc catgatgaaa cacctgtatt gtccacattg 145740
cggcctagaa tgttattaaa ctcttgaacg ggattccttc tctatttgca acctttcatt 145800
ctttgtcctt aaagtaaata aagccaaagg aggatggagc ctttccatca cccctcaaga 145860
ggacctggac cgcctgtgtg aggcccgagc acctggtgcc accgtcatca ccttcctttc 145920
atgctctctt ccccaggtaa ttatgtggtg acagatcacg gctcgtgcgt ccgagcctgt 145980
ggggccgaca gctatgagat ggaggaagac ggcgtccgca agtgtaagaa gtgcgaaggg 146040
ccttgccgca aaggtaggaa gcccgccggt gtgcggacga ggcttgttct cggctgctga 146100
ggctgggctc tcatgccacc tccaaaggaa cacatcttcc tcttctcatt aaaaaacaac 146160
tatacatatc gtttctttaa aacagaagat aaagctgtaa agctaggtta ggcaatggga 146220
aggcactgaa ggttgtgacg gggtgggggg ctctgatgag aacagtcaca gagccagccc 146280
cgctcagcag ctgccaggtg cccagccctg gggagaatcc agggaaggca gagctggaag 146340
cagtgcagct ccaagcggcc catgggaaat aatgaggaga acgcaaggtc agtgtgaggt 146400
gacagggatg gcatctccta caccgccgta gccccaaagt gtactatagg tcctggtgtc 146460
ccccttccc gcctgcactc tccccagccc cttcagtgtt tgttgagtga atgaaggatg 146520
atgtggcagt ggcggttccg gtgaccggaa ttccttcctg cttccctctg cctgtggatc 146580
cctagctatt cttaatccaa caaatgtgaa cggaatacac gtctctctta tctctgcagt 146640
gtgtaacgga ataggtattg gtgaatttaa agactcactc tccataaatg ctacgaatat 146700
taaacacttc aaaaactgca cctccatcag tggcgatctc cacatcctgc cggtggcatt 146760
taggggtga gtcacaggtt cagttgcttg tataaagaaa aacaaaatct gcctttttaa 146820
ctggtagaga ttggtgatca ataatcaccc tgttgtttgt ttcagtgact ccttcacaca 146880
tactcctcct ctggatccac aggaactgga tattctgaaa accgtaaagg aaatcacagg 146940
tttgagctga attatcacat gaatataaat gggaaatcag tgttttagag agagaacttt 147000
tcgacatatt tcctgttccc ttggaataaa aacatttctt ctgaaatttt accgttaatg 147060
gctgatgttt tgatattttt caaaagtgca gtttctcctg caggcaaaag gggacacgtt 147120
aagtccaggc ttgggtcatt cactgcggtg taaacacgct ttctccctcc cgcccggccc 147180
cagccagctg ccttggtggc ccataacccc tgagggtaga gggaggggac aggggtaggt 147240
gacaggcagc ctgggcctca ggcttttgaa actggacgcc agagccttgt ggggccacgg 147300
gcaagcctcg ggtctatgac tgccgcctga gctccgcttc cttcctctct aaaatgggaa 147360
gattagacca aaataacaag actgttttaa ggttggaatc aaataaggaa aatttgtaaa 147420
gctccttgta tgtgatacca gatccacaat tggcagataa tcgcagcagg agcctcttcg 147480
gggtaatcag atacgcggcg cagcaggggt ctcagggcca cagccagggg ggcggcggga 147540
gacatgcgga atcgcagcgg aaggcgggag gcagctgtga actgtggctc ggcctgcgtc 147600
cgccctgcgc atgtacactc agagaagatg ataatgaaaa agaaagcaaa tccaattttc 147660
ccacttactg ttcatataat acagagtccc tgagagtcta gagtaatgtc tcatacaaaa 147720
aagaaactcc tacgtggtgt gtgtctgaag tctttcatct gccttacagg gtttttgctg 147780
attcaggctt ggcctgaaaa caggacggac ctccatgcct ttgagaacct agaaatcata 147840
```

-continued

```
cgcggcagga ccaagcaaca gtaagttgac cacagccaaa gcctggtaga ttacatttgc 147900
ctttttagtt ggaaattagg cttaacagga gagttgctaa gatagggcac agagctcctg 147960
catctctcgc cggcattccc aaatgctatc tcacatgagc aggcacaggg agcaagactg 148020
cacgaccact ggcacaggct gtccgctaaa ccacagactt ctcagcgctc gccagtgctt 148080
ctgcttctgt gtccactcca gatcccacat tgcacttagt tgtcaaatct tttcagtcca 148140
tttctaacct atattagctc ctgtgtcttt ccttgtcttt cacggccttg acacttacaa 148200
aacgtgtggg tcaggtactt tgcacactgt ctaaccatgt ctgttcagct ggtgttttct 148260
caggatgcaa ttgaggttat gcacatctta tcacagggac cagagagact ttttagcacc 148320
actcttcaag aatttccact ttttcagctt tgacagtgga atagacatgc aggtgctcac 148380
acacaagcat ctttaatatg gtaatggtaa tcatcagttt agtggtgtgg aggaggagat 148440
gggaatctct tagtgaaacc cgccttggaa gcagcctcgt tatgagaact gctgccccta 148500
cttgactctt aaagcactag ataatactgt gcaacattaa agagaataag agtgcgtgaa 148560
atatgcattg cctcccataa actcccttgg ctctgaatct ctgatactaa atatgtggct 148620
accgttgctt cccagaaagg ccttttttgct ctgaattctc tggaatgctt tctttgacca 148680
agattcttat aaaaataaga gatttagagc aattttcttg gatggctggt atgagccagt 148740
tggcttagtt gtagggattt aaacaagata agggttactt acttttcaca tttaatgaga 148800
agtctggtga ttccagctcc tactgagaca gggtggccac acgttccagg gtgtgactca 148860
ctgaggcccc agacctgccc tgcaaggaaa acctggctct gccctggtgt cctggcctcc 148920
ctgggcatat gtgggggaga attcctaatg gtattggtta caggctccta tgcgagacca 148980
ctcatctgtg taggagaaag gaaaaagatg ggggaaagaa gagcagcagg gagaggagaa 149040
gcctctggat gatactctaa ccccctgcca tccaacacct gaacatcagt ctcttcatcc 149100
agtgctctca gctggcccag cccccagcct ggggtcagat gagagcttcc tgcaaatgca 149160
gatctctttc ctgtggctcc ttctcaatta cagacagctc ctccacaagg tgcactctgg 149220
ccttgtgctc cctccccaaa ccagcccagc cctcccagcc tgcatcatcg tggtcctgta 149280
ggggctagag gttctcacac ccatcgtggt ctggcagagg ctggtggttc tcacacccat 149340
cgtggtccgg caggggctta gtggttctta tacccatcgt ggttcaggag gggctagtgg 149400
ttctcacacc catcgtggtc tggctggggc tagtggttct catgtccacc gcgtgctttc 149460
ctgctcctcc aggtggctga ggacatcccc ccttcggtct gaatgacttc catccagtca 149520
tctgatatac acattggacc acccaatagc atcctagtgt catgttggat ggtgaagaaa 149580
atgccacagt tactgctttc agggcctcac aaccttgggc atagcttttt ggaggaaggc 149640
cccacttccc aggcatccct cccagacctg gtcagaggcc cctgctcttt gcttccatgt 149700
tgcccacact cactgtgctc ttcacaccgg ctcaaaatga tctgcttacg gggttgtgtc 149760
accaccagat caagcgtcct ggagaggagg aaacatattt aacctgcaca gaatttggga 149820
cagagaacct ctagtgtttg ttcaataaat atatgaatgg atagagggac aggttgggtg 149880
gtggatagat ggatgaaccc acacctttga agtgtatttg gctgtttgag aggttagaat 149940
atgttctcaa tttccaggca aaatgaaaat ggagaaaata taatgacatt aaggcatttt 150000
attcatcctc cccatctgcc actgggttaa agatactaaa taaacaagga actatctttt 150060
gcctggagga actttaaaaa cacctgcagt tttcaaaagg tgcagtgtgt gcctcccaca 150120
gcatgaccta ccatcattgg aaagcagttt gtagtcaatc aaaggtggtc tggagaaaca 150180
```

-continued

```
aagttttcag ggatacattg tttttataat ttttcaccac atgatttttc ttctctccaa 150240
tgtagtggtc agttttctct tgcagtcgtc agcctgaaca taacatcctt gggattacgc 150300
tccctcaagg agataagtga tggagatgtg ataatttcag gaaacaaaaa tttgtgctat 150360
gcaaatacaa taaactggaa aaaactgttt gggacctccg gtcagaaaac caaaattata 150420
agcaacagag gtgaaaacag ctgcagtaag tcaccgcttt ctgtttagtt tatggagttg 150480
gttctaatgg gtcctttatt tgtatttaga atattgaagg gctattccca tttaaattac 150540
ttttttcagt tccttaagaa gcaaattaaa atcttaagat tcctaactgt gaaattacca 150600
tgtgaattcc attaaaactt tttccagatc attaccattc aatgggatga atttaccctg 150660
aggtttaggc taccaattat ttgtaatgta agtaactaaa tttagtatta gttatattac 150720
cttttagttg taggtcactc tctgctcatt tcagcctgta aagactacag ctacacacat 150780
acacacacag aggaatggaa tgagcacttt acatcaacac ttcctgttct ggctctagag 150840
cctcagcttt tgaagctggt gagagcctgg cctgtgctgg gccttggcca cgggcagcgt 150900
cagctttgag tcaagtgctg gtctggcctc cctagctttg agcctctgtc aattccctta 150960
atctgtttag gctttggctt cctcatccat agaatggaga tatgaatgat tcctacgccg 151020
tagtgctttg agagaattca gtgaaattcc tgtgtgtaaa acccttccat ggtgcctagc 151080
acacagcaca cagccaatgg cccaatggct cctatcagct gtgggatttg tcatcagaac 151140
accaccagct ctgctccagg ctgccctggg taccatcaaa acacaccctg tgcccagcag 151200
cacctgctcc tctgcacacc tggttccttc agcaggggca gtggccgtgg gagcacagaa 151260
aacatggagt cccatctggt ttaattgatg ccattgccaa aggggaggac tcacggcacc 151320
ccctctcggg tgccagggtg cctggctccc accaggagga agacctgtcc tccactgtca 151380
ggcacatttc agtcttccca gcagccagca caactacttt gtccttccag tcacggtcgg 151440
cctctgggaa gcccagtctg tgtcctcctc cttcaggggt agccagcatg tctgtgtcac 151500
ccaaggtcat ggagcacagg gcccctcccg ggaaggtgcc gtctcctccg gcccctcggg 151560
tccctgctct gtcactgact gctgtgaccc actctgtctc cgcagaggcc acaggccagg 151620
tctgccatgc cttgtgctcc cccgagggct gctggggccc ggagcccagg gactgcgtct 151680
cttgccggaa tgtcagccga ggcagggaat gcgtggacaa gtgcaacctt ctggaggggt 151740
aggaggttat ttctttaatc cccttgcgtt gatcaaaaat aaggctccag gttgttgtta 151800
tagctttaca ggcattctgt ttgattttct cttcctttta ttctttgccc ttggcttttg 151860
gaggttttgg gttttctgtg gggagacggg aagttgtttg attgcgttat ttttggcaaa 151920
tttaagcaca ataggaaata agcaagtatt attgcctaat ataatccaat aatttataga 151980
atctcttttc ctggaagtat cttaaatttt tctaagctac aaaaagttcc taagacaaat 152040
gagacagtca tcaatggttc atctagccaa caccgtggcc atttgggctt ttctttgtag 152100
tgcccgattc ctggtgtgtg aaaataaatt aacacaaatt atattgccaa gttaatatct 152160
gttttatgtg cccccagcat gtgttgaaca tcaaacagta ccagggactt taaatatacc 152220
cacggacaaa gaaataattc ataatgatgt ttgttgaatt tagttgcaat caataaaaag 152280
tgcagtttgt gaatgctctg aggttcttga tattgatgta aggctttgaa cgacaaatga 152340
ggacaaaaca taaataggaa agtaaaactg aaggatagag gccaaggcca tgttttagaa 152400
gatttaaaga aaaagggaaa tttggtgagc accataggaa ttacagatgg ctgtaggaat 152460
tcttcctgtt ttactctctg ggcatggacc acagcttgga tccagaaata tttaggagca 152520
ggataagagg accaagttca attctatagg aatcctttag ctgataggct cagaacaaat 152580
```

-continued

```
cacataattg atagtgctgc ttcaacttca agtaaggaat attgatgcaa tccttacagc 152640
tacaaatgga cagtggtctc atgttttcag ttttcaagtg tttcttaaga ggcaaggtga 152700
tgaaaacgcc cacgtgggga gccccatgtc cttccattag tgtagagaaa cctggtgtcc 152760
agcagcacct gctccctctg caagcccagc ccccttcagc aagggcagtg acccagagaa 152820
gaagcacaga agacacaacc ctgtatcaca ttttgtttaa tggtgccatt gaccaaaggg 152880
gaggatgaaa ggcacacact tttttgttgt tttttgagac agagtctcac gccatcaccc 152940
aggctggagt gcagtgatgt gatctcaact cactgcaacc tctgccccct gagttcaggt 153000
gattctcctg cctcagcctc ccaactagct ggaattacag gtgtgcacca ccatgtccag 153060
ctaatttttt gtagttttag tagagacggg gtttcaccac gttggccagg ctggtctcaa 153120
actcctgacc tcaagtgatc tgcccgcctc ggcctcccaa agtgttggga ttataggcat 153180
aagccactgc acctagccaa ggcacacact ttggagaata aacactcctt gttcgctgct 153240
ggagggtaga actatgcttg actactaggc agagtccagt cttactgaca aacagccgta 153300
catctgttct gtcttttcaa tcaaacatca gcttcttgct taacattgat gtgtacatct 153360
tgagggatgt caaaatattg taagctaagt ttttcatacc tgtgttccac actcaccatt 153420
tttagtaata accattgagc gagttcattc tccctccttc ctttttctat cacttaatct 153480
aaaattatca tttttccagc ttaattttga taaccatgaa tctggtatta gaggcaggga 153540
acacctcctc aggactatct tttcttttat catttggctt gcttacccaa tatgcaaaaa 153600
ctatgctgta gaaaaagcag aaaagatatc ttgattatga atgaagctcc tgtgtttact 153660
cagagagaag atgacccagg attcagttaa caaaatcagc tgattatatt actatatagt 153720
cctggagtcc caactccttg accattacct caagttattt ggaattttga agaggtgatt 153780
tgtgttcctg caataatgtc tcaggggtgg gctgacgggt ttcctcttcc tcctctcagt 153840
gagccaaggg agtttgtgga gaactctgag tgcatacagt gccacccaga gtgcctgcct 153900
caggccatga acatcacctg cacaggacgg gtaagagccc cttgctgcta tccacgtcca 153960
tttcatggga agggccttca cagaagccga acagtgatga tggcccaggg catcctgtgt 154020
gggcaggacg gccatcagag ccacttccca gaggagacgg caggcgctga cagcgctgtc 154080
cgggcagggt gtcggtgaca ttagcacaca cattagcctg cgatgaacat tcactctttc 154140
tgctgacacc cccaacctta tctaagctta tcaaatcctc acatttaacg gaggctgttt 154200
tcacctggtt tcccccatcc ctgacctagt cagcattgct ttatcgcttt catcaaacat 154260
cctcaaattc ttaacattag cttgtaatta attgaagaat ttttaaagaa attgctagca 154320
aaacttttta aactgcacaa ctttgtatct atatgttcaa taacatatag atacaatatt 154380
ctttacaata atcttttaaa gaatatgagt gagaattcgg gcccctctca caccaaatgt 154440
cctgatgttg ttaattctca atgttattat atagggagct ctgttttctt gtgagcttca 154500
acagccagtt ctaaatctac taactgaaaa catttttttag acattctcta aattgggcag 154560
aagatgacag gactgtgttt tgagggatag gctgccagcg tggctgctta caaagtaaag 154620
acttggttta taggtttgca tggtgttggg ttaaatttct gtcattaaaa taattggcga 154680
tattgacata gtcatctaat tatgctggct ctgggcacac acagcccttg agtggacaaa 154740
accaacatga gagaacttag ccaaggggaa agcctttccc tgctggtttt atttctgcta 154800
cttctgaagt gtggggcaca caacctgagc agtgctttta tttgagtccc aatgctttta 154860
tttgagtttt gcaaggttat tccaagtttt acaaatagaa ggtagcgtat gactcagtcc 154920
```

-continued

```
ttgatatgcc aaccactgca cagagacttg ccaccttcct gtcactggag aaacactcat 154980
gtgggttttc ttaaatttgc ctccctctga gcttcccttt aacttcaact ataatatgca 155040
agaaagacta tctgaccata aatacacatt tgggccaatc aagatggttt tgccaaggaa 155100
agatgcccac aatggttaag cagaatgcaa taatgtagag aatatcattt ctttcatgct 155160
ggtgtatatc atatgcattc aaaaacaggg agaacttcta agcaactaac agtgaccata 155220
tcaagcaggt gcaatcacag aataactggt tttctccttt aagaattttt ctatcatttg 155280
gctttcccca ctcacacaca ctaaatattt taagtaaaaa gttacttcca ttttgaaaga 155340
gaaaagaaag agacatgcat gaacattttt ctccaccttg gtgcagggac cagacaactg 155400
tatccagtgt gcccactaca ttgacggccc ccactgcgtc aagacctgcc cggcaggagt 155460
catgggagaa aacaacaccc tggtctggaa gtacgcagac gccggccatg tgtgccacct 155520
gtgccatcca aactgcacct acgggtgagt ggaaagtgaa ggagaacaga acatttcctc 155580
tcttgcaaat tcagagatca aaaatgtctc ccaagttttc cggcaacaaa ttgccgaggt 155640
ttgtatttga gtcagttact taaggtgttt tggtccccac agccatgcca gtagcaactt 155700
gcttgtgagc aggcctcagt gcagtgggaa tgactctgcc atgcaccgtg tccccggccg 155760
ggcctgtgtt gtgcaatgct gcacatcaca acaggagggt agggggacaa aagagcacag 155820
gtcctggcag ctgccacagt ctccaggggc ttttgcgttt ctctccagat ttctaaggtt 155880
aacatgggga ttagctgttt tgcaatgaat aaaaggtaac attgcctgga atgttgctta 155940
aagacacttt tttaaagcta gttgattgtt aagctgttgc tacttaaatt aaaactactt 156000
tgggccagac gcagtggctc acgcctgtaa ttccagcact ttgggattcc aaggcaggca 156060
gatcacttga ggtcaggagc ttgagaccag gctggccaac atggtgaaac cccacctcta 156120
ctaaaaatac acctgtagtc ccagctactc aggaggctga ggcaggagaa ttgcttgaac 156180
ccgggaggca gaggttgcag tgagccaaga tctcgccact gcactccagc ctgagcacca 156240
agagcgaaac tctgtcgcaa aaaacaaaaa caaaaaaaaa agctactttg actggaatta 156300
gcagaagcac tctgattgtg tgtatcttat ttactggaat aataaagctg tcaatcaaac 156360
tggatcccac tcaacaatca gaaagagaag ttgagctgtc atatagtagt tcacacttac 156420
ttctgtttct caaaatcctc agctttgttt ggaactgtta ctcattcttt ctctgaatcc 156480
atctgtatga gttgtgtgcc cttgggcaag ggtcttacct tctctgtgcc tcactttctt 156540
ttctgtaaat tgggataata atgctgcata gctcacagga tttttatgac catgagttaa 156600
gatatgtcat atacttaaaa tggtgcctgg aaaatggtga atactgagtc aatgatagca 156660
tcattgatgg tgggatggtg atgaggaggt gggagtcaca atggtggtgt tgatggtggt 156720
gatggtggtg aggaggtggg agtcacagtg gtggtggtgt tgatggtggt gaggaggtgg 156780
gagtcacaat ggtggtggtg atggtgttga tggtggtgag gaggtgggag tcacaatggt 156840
ggtagtgatg atggtgttga tggtggtgag gaggtgagag tcacaatgtt ggtggtgttg 156900
gtggtggtgg tggtgaggag gtgggagtca caatggtggc agtgttggtg gtgaggaggt 156960
gggagtcaca atggtggtag tgatgatggt gttgatggtg gtgaggaggt gagagtcaca 157020
atgttggtgg tgttgatggt ggtgatggtg atgaggaggt gggagtcaca atggtggtga 157080
tgagggtggt gatgatgatg aggaggtggg agtcacaatg gtgtcagtgt tgatggtccg 157140
atggtgatga ggaggtggga gtcacaatgt tggtggtgtt gatggtggtg atgatgatga 157200
ggaggtggga gtcacaatgg tgtcagtgtt gatggtggcg atggtgatga ggaggtggga 157260
gtcacaatgg tggtggtgat gacggtgttg acagtggtga cgaggcggga gtcacaatgg 157320
```

-continued tgtcggtggt gatggtggtg aggaggtggg agtcacaatg gtggtggtgg tgatggtggt 157380
gatggtggtg aggaggtggg agtcacaatg gtggtggtgt tgatggtggt gatggtggtg 157440
aggaggtggg agtcacaatg gtggtggtgt tgatggtggt gatggtggtg aggaggtggg 157500
agtcacagtg gtggtggtga tgagggtggt gatggtgatg aggaggtggg agtcacaacg 157560
ttggtggtga tgatggtgtt actggtggtg acgaggtggg agtcacaatg gtggtggtgg 157620
tgatggtggt gaggaggtgg gagtcacagt ggtggtggtg ttgatggtgg tgatggtggt 157680
gaggaggtgg gagtcacagt ggtggtggtg ttgatggtgg tgatggtggt gaggaggtga 157740
gagtcacaat ggtagtggcg atgatggtgt tggtggtgag gaggtggaag tcacggtggt 157800
ggcgatgatg gtggtgagga cgtgggagta acaacagtgg cagtgacggt gattgagaca 157860
tgatgatgat ttgtcaactt tctaggaaaa caatcatata atctccaaca gtgatatctt 157920
aatatctttt ccaaaagtat cagatcatat tataagggcc aagtttccag aataatatca 157980
gacataatga cagtggacat cagagcttgg catctaaagg taatgggaat agctctaatg 158040
tctcagcgtg aaaaacaaca tttgctatta gtctgagata ctaattatct agttaaggaa 158100
gtactcacct atacctagtt tttaactgtt ttttaaaatc tggaattgat tttgaatttt 158160
aacaaatatt tccctgggaa caatgtaaga ttcttcatat tttcgccttt gggtatacca 158220
acatgccagc tctgttggcc actttgtgag ctcgatgaag catggtataa aagatgcttt 158280
gctagtgttt cacgtaatct atttctataa gcaattttgg agctaagcct ctgaaacaga 158340
attatattat ctgtatagaa taaatgtttt atcttccccc ttttctttct tctggaatag 158400
atgtgcatca gtatctctgc atcaatatct ctatatcagt atctctgtgt cagtgagcat 158460
atgttgctgg gcttagggga ggtccagaaa gtgattgggt tttggcattt tcaatacact 158520
tactttgtat aagaaatagt ttgccaaata tagaaagagg ggatttagtc aagatttaaa 158580
ttaaaaatgt tagtggtcat ttttctaatg tctttctatt ttttcccagg tcctaataaa 158640
tcttcactgt ctgactttag tctcccacta aaactgcatt tcctttctac aatttcaatt 158700
tctccctttg cttcaaataa agtcctgaca ctattcattt gacatatgga attttataaa 158760
tattttcttt agtatgtgtg attacattcc tgattctgag ccttttttaga tgagtatata 158820
gtttgatata atcttgttat tgccacctgt gtcttctccc aaagccatta attatatagg 158880
aattacacga tagaaatggg tttaattttt aaaatacggc caagtgttga tgagagggaa 158940
aatttttttta atttctttca ctgagtattt atgacgtgca caacattcct gaatatattg 159000
tctctctcat ttctcagatg ggatgtattg ccttctccat ttctattgtt aaagaaacac 159060
ttacaggggt ttctttaaca acttgtgaac agcagcatca gagcccagac tacagcataa 159120
gcagctgctg attccaaaag ccctaccttc caaccgggca ggtgcagcca cccagacgag 159180
ggggaggaac cctggaggaa tagctatttc tttttttttt ttgtcgagac ggagtcttgt 159240
tctgtcaccc tggctggagt gcagtgccgt gatcttggct cactgcaacc tccacctccc 159300
aggttcaagc aattctcctg cttcagcctc ccgagtagct gggattacag acacctgcca 159360
ccacgcctgg ctaattttttg tatttttagt acagacaggg tttcaccatg ttggccaggc 159420
ttgtcttgat ctcctgacaa gtgatccaca caccttggcc tcccaaagtg ctgagattac 159480
aggcgtgagc cactgcgccc agcaggaata tctattttta aatggaactg tgttttcata 159540
gtacacggtg aggagaaagt tgctttgaaa tctttatcct aataaaccaa ataatatgaa 159600
aatttgccta ttttaattat atgtaacaaa gtttagttac tgctataatt gcaaatatgt 159660

-continued ataaattcct taccaaaaaa aaaagaatca agtgggagcc agagaataat ttttctgaca 159720
gaattaaata acatgctata gctgcttgag ttcatactca atagtcattt ctgcagagtt 159780
accgagggcc tcatcagcgt cagcaggagc ccctcgcctt ctgacgctct cacatccttc 159840
tctcctgcag ccccgtcctg ccactgtcct tgtccagctt ctcttcaagg gtcaactggt 159900
ctacctttcc ctacaagtct gtcacagctt cttgttagca atccctatgg ttgcccaaaa 159960
gcattttcag agcctgcata agactgcatc ttgtagaaaa tttgcagttt caatctgccc 160020
tccctctgcc gggtgttccc attgtattgc attcagcagg cagggagaga ctgctattag 160080
gtctgttcct gagtgactgc tttctgtctc agactgtttg gtgtctgtag gaggtagtgg 160140
ggtgggcagt aacgaggtct cctgtatatt ccacccctac gaagcctgtg tgtttggttt 160200
atgaactaag ctcaaaagca ccacaggggt aagactgcag tacatgacac catggaaaag 160260
agggagcacc cagaccccca aattaagaag agcagtgtag agaacagaga cctggagagc 160320
agagatagaa actgttagga tcagattata gtgttacacc agggctcccc aggcctctca 160380
catattgaaa tgtacttgtc catctttctc caggccagga aatgagagtc tcaaagccat 160440
gttattctgc ctttttaaac tatcatcctg taatcaaagt aatgatggca gcgtgtccca 160500
ccagagcggg agcccagctg ctcaggagtc atgcttagga tggatccctt ctcttctgcc 160560
gtcagagttt cagctgggtt ggggtggatg cagccacctc catgcctggc cttctgcatc 160620
tgtgatcatc acggcctcct cctgccactg agcctcatgc cttcacgtgt ctgttccccc 160680
cgcttttcct ttctgccacc cctgcacgtg ggccgccagg ttcccaagag tatcctaccc 160740
atttccttcc ttccactccc tttgccagtg cctctcaccc caactagtag ctaaccatca 160800
cccccaggac tgacctcttc ctcctcgctg ccagatgatt gttcaaagca cagaatttgt 160860
cagaaacctg cagggactcc atgctgccag ccttctccgt aattagcatg gccccagtcc 160920
atgcttctag ccttggttcc ttctgcccct ctgtttgaaa ttctagagcc agctgtggga 160980
caattatctg tgtcaaaagc cagatgtgaa aacatctcaa taacaaactg gctgctttgt 161040
tcaatgctag aacaacgcct gtcacagagt agaaactcaa aaatatttgc tgagtgaatg 161100
aacaaatgaa taaatgcata ataaataatt aaccaccaat ccaacatcca gacacatagt 161160
gattttaatt atttaagagt agtttagcat atattgcttt atgatttaat taaaaatctc 161220
caaaatatat gccaaagaag tagaatgaga aaaatgtata tttctctttc acttcctaca 161280
gatgcactgg gccaggtctt gaaggctgtc caacgaatgg gtaagtgttc acagctctgt 161340
gtcacatgga cctcgtcaag aatgaccaca ctgctgtggg tgaagatgct ttcctgcatt 161400
tctgactgtc ctctgtcctg atcaagtttc tatggctctg ggccagccta ccctcagcca 161460
gggtttctgc agagactgcc cagctggttc cacgtggctc cacgtgccaa ctttgtcctc 161520
agtggaggga aagttggaca cacagtgctg gggctgctcc ctgctccgcc gttgctcgat 161580
gcatggcctg cctctgaatt ccttggttcc actggttttg ctgggtcctt ctgtgcctct 161640
agctcctctt tttttctgtc cacttacccc attggtccca tcacaagcct gtgtgtgagt 161700
ggcctttctg ttcgatgaca acctccagca taggggagtg tttctccttg ctttctttcc 161760
cagacacact gcccagcaaa ggcaaaaggg cttccttcaa catcagctct ggccagtttg 161820
ccagagcaaa gccctgagaa aagcaaggtt gaaaagtctt attcaaactc accaggaaag 161880
agtggtgtta ctctcgatgg cgtctagcca ggaatcatgg aattatacac cgagcacctg 161940
tttgccattt tggatgtttc caaacatgaa ccaaacttcc aggcccctct gccatctctg 162000
gtaacattta caaagtccct tcctcaccac tgcccttcct tcattttggc atgctcctcc 162060

-continued gcccccgagt tgacagccat agctctctct cctgccacca gtgtcacatg atcgaggaag 162120
aaggcaactt caaaaagact gggtcccctt ccactcccat ctcttcagtg agctgctagg 162180
acacccagca gaacttcccc actccacact gcaatctcag ggatcttagt cacggggctt 162240
tccaccatgt ctccacctgg aaaccagtca tggccattcc ttcttacatc tgctcttttc 162300
catctttttc ttctcctcct gttcacccgc ccttactctt gtggcgccct atggatatgc 162360
gctccatagc aaatgattct ttatatctta cggtattcta gtgagctggc acatgtggct 162420
tctggtttcc tctctctgga actagacatg acctctgtgg gagggaggat taaatgcacc 162480
ctacagtctg aggctgcatg atgacatcac tcatcacaat gatgctttct atgtctgaat 162540
cctattcctt tataacccct ttcaagctcg ttcagagagt atttcacaca atccatgtgc 162600
tcatcttaaa agccaaggac ccagaggagt ctcagcattg ccaaaaagtc ccttcaccca 162660
gcctggccag aggcagtgcc tggtccatgt gtatggacta tggcacttca attgcatgga 162720
aatactcttg gaatgaacaa aataccaatc catgaaaaag cattattgaa gtctaagtta 162780
ttttttgaat catattttgt taatcaacaa attgaaaaat actcattata tggagaggtc 162840
cagataaagc ctcaatttta aaaaatgagg aaaagtgtgc ctggtagggg actggggaga 162900
gcttgagaaa gttggaaacg ttgccttaga agcctgtttt ttctcctttt agaagctaca 162960
tagtgtctca ctttccaaga tcattctaca agatgtcagt gcactgaaac atgcaggggc 163020
gtgttgagtg ccaaggccat ggaatctgtc agcaacctca cccttccttg ttcctccacc 163080
tcattccagg cctaagatcc cgtccatcgc cactgggatg gtgggggccc tcctcttgct 163140
gctggtggtg gccctgggga tcggcctctt catgcgaagg cgccacatcg ttcggaagcg 163200
cacgctgcgg aggctgctgc aggagaggga ggtgagtgcc agtcctgggt gggctcagga 163260
gccctcgcac cccgacagga acaagggcca gccccgagaa cgggccatta gcagttgtgt 163320
atgttagata cataattgta ttatgatgca gaaagaatct ctgaatgtgc agttataccc 163380
agttggtgac atgttggtac atccatccga ggaaatggca atgtttctag gctgcaccct 163440
tcaatgtcca caaagctgtg tggcatctgc ttaggacccg gtgcctgtgt gtgcatagga 163500
gggaggccag gaagcctggc tgttgatccc atgctggcac tgtggcgaag gcgagagatt 163560
cctgctttgg aaaacaccat tgtccacaca gtggctttgt ccatgatgga cttcgccaca 163620
gcccagtcct gtgctggaag ccatgttctc tggaaagagc aacccagcgg ctcataagca 163680
taagcgcgtg tgatgtgccc caaccaaacg accgccatgc acaacttccc taccggagtt 163740
ttcaatccag ttaataggcg tggaaacaga catagaaatt gtgtttgttg aaaggtagct 163800
gttcagttaa agaacacctg tatcagagcc tgtgtttcta ccaacttctg tcaagctctg 163860
tagagaaggc gtacatttgt ccttccaaat gagctggcaa gtgccgtgtc ctggcaccca 163920
agcccatgcc gtggctgctg gtccccctgc tgggccatgt ctggcactgc tttccagcat 163980
ggtgagggct gaggtgaccc ttgtctctgt gttcttgtcc cccccagctt gtggagcctc 164040
ttacacccag tggagaagct cccaaccaag ctctcttgag gatcttgaag gaaactgaat 164100
tcaaaaagat caaagtgctg ggctccggtg cgttcggcac ggtgtataag gtaaggtccc 164160
tggcacaggc ctctgggctg ggccgcaggg cctctcatgg tctggtgggg agcccagagt 164220
ccttgcaagc tgtatatttc catcatctac tttactcttt gtttcactga gtgtttggga 164280
aactccagtg tttttcccaa gttattgaga ggaaatcttt tataaccaca gtaatcagtg 164340
gtcctgtgag accaattcac agaccaaagg catttttatg aaaggggcca ttgaccttgc 164400

-continued

```
catggggtgc agcacagggc gggaggaggg ccgcctctca ccgcacggca tcagaatgca 164460
gcccagctga aatgggctca tcttcgtttg cttcttctag atcctctttg catgaaatct 164520
gatttcagtt aggcctagac gcagcatcat taaattctgg atgaaatgat ccacacggac 164580
tttataacag gctttacaag cttgagattc ttttatctaa ataatcagtg tgattcgtgg 164640
agcccaacag ctgcagggct gcgggggcgt cacagccccc agcaatatca gccttaggtg 164700
cggctccaca gccccagtgt ccctcacctt cggggtgcat cgctggtaac atccacccag 164760
atcactgggc agcatgtggc accatctcac aattgccagt taacgtcttc cttctctctc 164820
tgtcataggg actctggatc ccagaaggtg agaaagttaa aattcccgtc gctatcaagg 164880
aattaagaga agcaacatct ccgaaagcca acaaggaaat cctcgatgtg agtttctgct 164940
ttgctgtgtg ggggtccatg gctctgaacc tcaggcccac cttttctcat gtctggcagc 165000
tgctctgctc tagaccctgc tcatctccac atcctaaatg ttcactttct atgtctttcc 165060
ctttctagct ctagtgggta taactccctc cccttagaga cagcactggc ctctcccatg 165120
ctggtatcca ccccaaaagg ctggaaacag gcaattactg gcatctaccc agcactagtt 165180
tcttgacacg catgatgagt gagtgctctt ggtgagcctg gagcatgggt attgtttttg 165240
gtatttttttg gatgaagaaa tggaggcata aagaaattgg ctgaccctta tatggctggg 165300
atagggttta agccccttgt tatttctgac tctgaaactt gcattcaatt cactccacca 165360
agttatctca tctttgaaat ggcttttttt aaaggtgcct agaatatgat ggcgtgcagt 165420
ctataaactg ttgcccacct tctgtacttt ctctcagaat aattcacatt cttctccagt 165480
gtctgttgat tgttactttg tggaataagt tcttggaaaa ttccacaaga ttattgttat 165540
cttcttacta ccaattctat tgaactttct ccaccttctc tgggccttcc ccagccagtg 165600
gtgggaagat gctggctgga gtctgacaga gcctcttcta cactggcctg ggcttgctgt 165660
gagttggtgg aaacctttgc tcttgtccca acacagagca agtgaaagag gaggtcaagg 165720
ggctcaggca gcggactagg gaagcagaat cgaggaaaag gaaaaatggc tgacttatta 165780
cctcaaaact ctagagaatt tagttgatct tacagccaag aaggacaaaa gccagagagt 165840
aatatcctcc gcctcatgtc taacccacag aatacatagc aagtaaagag aacatgggcc 165900
tttataaaaa tgtcttaaga tacaattttt taattggagg aaatctacag tttaattttc 165960
tctgggcagc ttttcttcct tttattatag taggggaaat cccatgttga tatacttcta 166020
aatgaaagat gatgaattga tataatacaa taaaaaatct gtaaaattga tgatatactt 166080
atcaagaaaa attagctttc attttaacgg tttacaaatt gagtcaagtc ctagtaacaa 166140
aatgttaagt ctattaacat aaccacaaga aatacaggaa gacgggcaat ctgtgaagcc 166200
tttcacttac aatctctggc ccctcacctg tgctgtgtag gaaaatcttt gtgcacaatt 166260
tgcttcctta attcattttt tattcattca acacattcta ataaattata caaaatcatg 166320
ttgaaatgtg aatttcagtg gtatttataa atgcagtgtg aggagggttt ggatgtattc 166380
taagacaata gttgtgcttt gggaaggaag cagtgttcac tgaaaagtgc ccccaggacc 166440
ttttaattgg aggaaatatg cttctgtgga gttggaaatg gggtagaaga tagataaggt 166500
caaggcttaa aagttaagtg cacccaacat ctgaagcgtc catgggcctg gcatggtggc 166560
tttcgcctgt aatcccagca ctttgggagg ctgaggcagg aggatccctt gagcttagga 166620
gtttgagacc agcctgggca acatactgag acccagtctc tacaaaaaat aaaaaaattag 166680
ctgggtgtgg tgtctcatgc ctgtagtccc agccactcag gagatgggaa gatggcttga 166740
gtccaggaga tctaggctgc agtgagctaa aatctcacca ctgcactcca gcctgggtga 166800
```

-continued caaagcaaga ccctgctcaa aaaaatagtt agatataaat attaatatag atacctatat 166860
atatctgaat atagatatct atatatactc tgtatatagt tatttagata tataaatata 166920
tatgatatat atttagagag atatatattt agagagatat atatttagag atttatatat 166980
attttatata tatttagaga tatatatctc taaatatata tctctctcta aatatatata 167040
tatctctctc taaatatata tatatcccta aatatattaa ataaataaaa gaaataaaag 167100
aaagctcagt ttggcctcct gcttgtcctg tctcctcatc ccctcttccc cctccatcat 167160
tttatttcct tgccccatgt ttcttcactg cggccatgtc ccccctcctc tccaatgatg 167220
gatgtcatgt ctgctgcagt cagagggcga caagcctgga gtgttccctg aagcctgtgg 167280
tttgtggttt gtcctgcagc tcaggctgcc caggcctcac cagcaatcct ggcgggcagg 167340
gcaccacact gggatggaga gggggaagct ggaggaggca ctttctggta aagaaagcaa 167400
aagccagcag tgcccaggcc aatttcaaca gggagttaaa tagcacctta atcctgtggc 167460
aggacagctc atggggccat gtgtgctctt agaaagactc acatgcacgc atgcacggca 167520
gcaatgactc catactcacg ttcccctgca gacaccaggc ccccacagcc ggcacacaca 167580
ctgcagcccc agttccatgt tgctagcagt ggcttagtga atgagtaaag ttcttaaaat 167640
gcaggggaca cctgcccttc attcataagg ctggacgtac acctctcctt aaggagttca 167700
agagctagtg gaatcccaat tcatacggta gagccattca cagatgagag agacaagcca 167760
gaaggaagga accaaaagtc atgtcagcag ttaggacaaa ataacaggct ttcaaggtca 167820
caaagcctca gggacactcc tgcggtggga ctgggctagg agccatgggg gctccaactg 167880
tgcgctctgc ctgccagcct gtgggtgctg gggctccacg aagattgttg tggaatacca 167940
agcatgcttg ctgtaggtca cggtgcacgt ttactacttc caagacaaac agccgagaac 168000
aaagctcgct ttagcttctg cgtacaccga acgggacaca cgactgaaca gcgttcccat 168060
tgtgcctgct gggtggggag gaagtgatgg cccagtgggt ctatcagatg ttagtaggat 168120
ggggcctggc ggggctccag gctctgtgtg gccgacaccc acgccccccg ctctgctccc 168180
cattcccagc cccaggtcag ccctgcgagg ccctgcagca gatgggctgc tcaaactgct 168240
ctggtttgca gatttttctt ccctctcaaa tgaatacaat atgttttcaa gtctcaacca 168300
gatcttgaga aaataggaag agccagaggg tttctttggt gttatggttg tacagcttcc 168360
cagactccgg gggagagatg tgatttgtgc tttctggcaa tcccatggcg tattaaattt 168420
tcataggctt tccagtttaa atttagggta ggcaatggaa gggaacgcaa aacagatttc 168480
taggtgtact gtgtgtgtgt ctcccacgtc taaagtctgt taactggagc acccaacagg 168540
ccccacaggc tgccttcaca cagaggacct ggggcgcctc cgacccattg ggtgagcag 168600 tgggccatgg agggagccag ggtcaggaga cctggttgtg ggcctgacct gaccctgctc 168660
agggtggcct caggtgggcc gttcacctcg tcagcctcag cttaccctct gactacagtg 168720
acctcagaca aaatacgctt cctggccctg tccagttctg actttttata aacaagcact 168780
tatccaagtt aaagggatat tttcaatatc tactgagtcc acagatatta aatatctcct 168840
ctcttcttta aaattgtggc attatcttta gaatataaaa ggaaaataac acacactctc 168900
cttgaaaata gagagcctaa acactctgca ggaaatattt aaagctatag tttttgtttg 168960
tttgtcttga atgcaagtgg cctggacttt gacttgcttt gagtctttga ccttcatgac 169020
ttcagtacag ttcaaccctg acagttttga agtaggtatg tgcctagatc tgccctagtc 169080
cctgctggaa tgttgaagaa gcaaaggtcc aggccctcag agcacttgcc acgtacttgc 169140

-continued

```
caacagatac ggggcggaga cttgagtcaa cgtaagagca agtgtgtgcc gggtgatccg 169200
acactgcaga gcgccagcta gaccctaagc gtgtgctagg ggctgaccaa gccgttcttt 169260
cctcaaaaac ttggtgggga gggtattttt aaaatcacac aaatatttaa gtacagatta 169320
tgatgactgc ctcaaagcag tggctcttca gcttcatcaa gcttcagagt ccagagggtt 169380
tgttcatatg gaaggctagg cctgtctcct gcatttcacc ctcttggcct gggggcggga 169440
cccaagaatg tgtggctcta aaaggttccc aggcaatgct gaggctgctt tctgaaggaa 169500
aaactgcaag ataccaggag agtttcattt agattgaaga gtcgaggaag gctcctctga 169560
gaaagagtct gctaaggaag gaggaggtgg gttctgggga cagaggttct cccgtgggta 169620
agggtggagg gaagctctcc tggggagaag gtgggcagga ggaccagagg ctggagggag 169680
gagggcagtc agcctcgggg cttcccagga acagggacgg ccagggcagg gtttagggca 169740
aggaaagcgt gtgagcatat ttgtatttta gtaaatattt acagtttgcc ctccatgtct 169800
gcagtttcat atccatggat tcaatcaacc acaatgaaaa acgttgggga aaaaaattgc 169860
atcggtactg aacatatacg gacttttttt cttgtcatta ttccctaaac aatacagcat 169920
aacaattatt cacatagcat ttgcactgta ttaggtacta taggtaatca ggagatgctg 169980
tagatgggag gatgtctgta ggttacacac aaatgctgtg ccactttata tcaggggctt 170040
gagcatcctc acattttgat atttaaggga ggtcctggaa ccaattcccc agatactgag 170100
ggtccactgt ctgtgtcccc tcgccccacc ttgcctttgt ctcctgtctc ctatctccac 170160
cctgcctccc gccagcctgt tgctcctgac ctgcccgggc accctggagc agcaccctat 170220
ctcagagcct ggctcagtgt gttcacttct gcagagaaac taacttgccc aagtccacac 170280
tcaaaacata ggcattgctg agatgtgaaa agcagctgtg gatgctttct gctacagtct 170340
gtgtgttctt ttccatatct gaataaaagg tcaccaccat ttgtatttta aagagaaaga 170400
gaatttatgg gtggaaattg gggattccct cattctcagt cagacagaaa agagggcccc 170460
attgtgtgcc tgattgcaaa taaatttagc ttcctcagcc caagaatagc agaagggtta 170520
aaataaagtc tgtatttatg gctctgtcaa aggaaggccc ctgccttggc agccagccgg 170580
aattagcagg gcagcagatg cctgactcag tgcagcatgg atttcccata gggagcctgg 170640
gggcacagca cagagagacc acttctcttt agaaatgggt cccgggcagc caggcagcct 170700
ttagtcactg tagattgaat gctctgtcca tttcaaaacc tgggactggt ctattgaaag 170760
agcttatcca gctactcttt gcagaggtgc tgtgggcagg gtccccagcc caaatgccca 170820
cccatttccc agagcacagt cagggccaag cctggcctgt ggggaaggga ggcctttctc 170880
cctgctggct cggtgctccc cggatgcctt ctccatcgct tgtcctctgc agcacccaca 170940
gccagcgttc ctgatgtgca gggtcagtca ttacccaggg tgttccggac cccacacaga 171000
ttcctacagg ccctcatgat attttaaaac acagcatcct caaccttgag gcggaggtct 171060
tcataacaaa gatactatca gttcccaaac tcagagatca ggtgactccg actcctcctt 171120
tatccaatgt gctcctcatg gccactgttg cctgggcctc tctgtcatgg ggaatcccca 171180
gatgcaccca ggaggggccc tctcccactg catctgtcac ttcacagccc tgcgtaaacg 171240
tccctgtgct aggtcttttg caggcacagc ttttcctcca tgagtacgta ttttgaaact 171300
caagatcgca ttcatgcgtc ttcacctgga aggggtccat gtgcccctcc ttctggccac 171360
catgcgaagc cacactgacg tgcctctccc tccctccagg aagcctacgt gatggccagc 171420
gtggacaacc cccacgtgtg ccgcctgctg ggcatctgcc tcacctccac cgtgcagctc 171480
atcacgcagc tcatgccctt cggctgcctc ctggactatg tccgggaaca caaagacaat 171540
```

-continued attggctccc agtacctgct caactggtgt gtgcagatcg caaaggtaat cagggaaggg 171600
agatacgggg aggggagata aggagccagg atcctcacat gcggtctgcg ctcctgggat 171660
agcaagagtt tgccatgggg atatgtgtgt gcgtgcatgc agcacacaca cattccttta 171720
ttttggattc aatcaagttg atcttcttgt gcacaaatca gtgcctgtcc catctgcatg 171780
tggaaactct catcaatcag ctacctttga agaattttct ctttattgag tgctcagtgt 171840
ggtctgatgt ctctgttctt atttctctgg aattctttgt gaatactgtg gtgatttgta 171900
gtggagaagg aatattgctt cccccattca ggacttgata acaaggtaag caagccaggc 171960
caaggccagg aggacccagg tgatagtggt ggagtggagc aggtgccttg caggaggccc 172020
agtgaggagg tgcaaggagc tgacagaggg cgcagctgct gctgctatgt ggctggggcc 172080
ttggctaagt gtccccccttt ccacaggctc gctccagagc cagggcgggg ctgagagagc 172140
agagtggtca ggtagccctg cctgggtgct ggagacaggc acagaacaac aagccaggta 172200
tttcacagct ggtgcggacc cagaaagact tctgcttttg ccccaaaccc ctcccatctc 172260
catcccagtc ttgcatcagt tatttgcact caacttgcta agtcctattt ttttctaaca 172320
atgggtatac atttcatccc attgacttta aaggatttgc aggcaggccc tgtctctgag 172380
aatacgccgt tgcccgtcat ctctctccga cagcagggca gggggtccag agatgtgcca 172440
gggaccagag ggagggagca gacacccacc cggcctgggc aggtcctcct cattgcttgc 172500
atccgcctgg ttagcagtgg cagtcagtcc tgccgagtca ttcgtgaggc gctcacccaa 172560
ctccaggcag atgtaaaagg tgacctacaa gaagacaaac aaaaacatct ggagcgctct 172620
tatgccagca tctgcccttg acaccaccag gcaggctgtt gctgggagcc gtggtgcttg 172680
ggtaagctcc ttcccatggc agagctcctg ggacgcattg tagaagcagg gaccacctcc 172740
caggataacc agatagcagc acaccctgca cagccccttt tactccagca tcatcgggca 172800
ttgatatctc agctgcagcc acaggcggcc cccagcaccc caggaagtgg ggagcgctca 172860
tgcttctctg agcacaaaaa tcactgaata tttttgccat tctcatggtc ataacccggg 172920
ccacagagta gaacactcct atcactgttg ttagacagtg gtcctgggag agggtcttgt 172980
gtgcctcgga tgccagggcc tctttttatt gggaggtgct tgttatttct gtgtgtggct 173040
gcatttgttt cccaagactg ccacaacaaa tcatcaccaa cttggtagct caacatagca 173100
cagctttatt ccctcctggc tctggaggcc aggtgtctaa aaggccatgc tcccacaatg 173160
gttctgagga ggatccttcc tgcctctctg gcttctggtg gctccagcat ccctgggctg 173220
tggctgcacc tccccatgtc aacctccgtc ttcacaaggc cttttcctgt gtctctgcaa 173280
ccacaggccc ctctcctttc tcttaataaa gataccagtc attgagtttg aaaattgcta 173340
agagagtctg ttgtaaatct tcttagcaca aaaaaaaatg acagatatgt gaagtggtag 173400
atatattaat tagtttgatt tgatcactcc gctatgtgta taaatgtcaa aacaaacatt 173460
gcactccata aatatatata ttaaaaaaga tcccagtcat tgcatttagg acccacccta 173520
aatccaggat gatttcattt caagactttt aactagattt gcaaaacccc atttccaaat 173580
aaggtcacat tctgcagttt tgggtagacg tgaaatgtgg agacactgtg caacccactg 173640
tcttggggag ggggtggtca gcctggggca gatgttgctg ggtgtggagc tacatccact 173700
catgccctga cctggaaccc agacctgctt ccccagctct cctcctggtt atctgaagca 173760
gggaatggag agcactgccc tccttgccca ggcagtctct atcacctggt tttagtttct 173820
tcttagcaca tattgcccca gaatatctgg ttggtttatg gcttacttga gtttgtgcct 173880

-continued

```
acctgtccca accgggaggt gagccctggc tattccccaa acccggccct gcatgtggga 173940
gctgcccttc ctccgttcat cagaggggc caacagtcca cagctgttct taatcatctc 174000
ccagtaaccc ccagctccac aaaggtgact ccttacatgg tggagaggtg gtcgggccat 174060
ccgtgtgaaa tgtgtatgtg accgttttcc ttaaggggca cgtagtcttg gcaggtttcg 174120
ctcaatatag gatgagctca ggactccagt ggactgtgga ttcagatctg gattctggcg 174180
cattcgccgt gtgaacgggg gcacgttgct ggcctgtctg cgcctcgtct cccgactgtg 174240
gagtgtgttc tgccccttgt ctttctggga ggtagggagg gcagtgagcc ccttcgcatc 174300
gcccaccaca ggcccagcac atggctgatc cccactgagt gttcttttcc tcctttgatc 174360
ccctttggct gacctaggtt ggagcagcca ctaaaatata cccagaaaca tcttcctaat 174420
ctacatctgt gccaaccctc attccctggc gcagcatgac catcacatgc ccgccattgt 174480
tcctgatctc tgctgctcat gacctgctct ccagcgctcc ttctcatgct cacattccag 174540
ttggcctgac ctagataagt ggaggtttat ttgaccccaa aaattagcct tctacaaacg 174600
aatataatag tgtccattac agagaataaa cttagtgcgt gtcccattta agcagaagtt 174660
actgaaagcc tgagtttaag tttccagggc ctgaaagttt tccatgacag ttttctgcat 174720
aatattacct acaatttcaa tctgttattt aaagccattc ttgtgtttgt tgtactttga 174780
ttagctttat tttgatttga agtcctttta cattacgggc agttaacgct ttgtctctgt 174840
tagatttgct ttttagttca caagagaaac ctcattcctc tgtatttgaa tagttgcaat 174900
gatggaacag ctgtccctgg agggaaatga aaacagtgat tccccaaatt gtgacaatag 174960
aaatttgctc ttgggttact tacaatgtat ctgagtatta aaaaattttc tttttaaacg 175020
tttgaagtaa aactacccag aaacacttag tggctgacca gaaactaaac tcctggcatc 175080
ctcaaaatgg gatttattgg cttataaatg tcctgtgttg actcacaaag gcacaaacta 175140
tctaggtaag ttttcttcta aatgttgatg ggagagctgg ccactgttat gcaagtttca 175200
ttgtcctgac taaactgcca aagagattac ataaaattat atcaactaga caaaaggaaa 175260
aaggaaaaaa aacagaggtg tcttgggagg aatccatatg agaccagtag accatgagag 175320
agacatccct tgccatctac aaggaaaatg gattttgttc tccatatgca aaaccatctc 175380
aggagcttgc ggagacacca cttgcttact agccagaaag agcaggtgcc tcctaaattc 175440
cccacacagg agctcacagt ggctttcatg cactgggatt aagttagact taagaaagcc 175500
tgtctactct tcctgggatt tacaagccag ctagtaaatc ccagaataaa tcacacggca 175560
cagtcatcca aagatcccgt catccgtgcc gtttggaaag ccctgctcct gtgccaccct 175620
ctccccgtgg agcctcccat gcccaggact gcagagtcct gccattcaga ctgcaactca 175680
tctcacattc ttccaaacta tttggacaac agagctttct catcacctaa tgcagattac 175740
agtctcacag aattgagtgt tcaggcagac actgatgtgg ttctgtagta cagcaaacaa 175800
tatcagttta cagtcctgag gccaggcctg gtgaacaacg cacggtagcg gtggggcagg 175860
gttctcagaa tgaaactggc ttacacatgg cactctctga ccacaactgt ataagcacca 175920
aactacactt agttccatct atgaggtaaa atttaatgca gatgaacatc aaagaaaacg 175980
tcaaaggctc ctttttacaa gtacgtgggc tacttaattt ggtccaagtc cattttaaaa 176040
agccctaggt gctttcacgg ctctgctact gacaagaagc cccagtgcct gtgagctgct 176100
aatgggaggg agaggaagat gagctgagtg ggccgggcta tcccgtccac accgggagac 176160
agggaaggag actccaagct ggtggtgcca gcacattcca ggccactcag gcctattcct 176220
aggtgccagg tcacgaaaac cacgctgaca gatcgtgctg tgtgcgtgtc atagcacaca 176280
```

-continued agcaggactg tgagagagtg aaagtgacac tgggtggagc actgaggaag ggccacagtg 176340
tgttggtgga gataggctgt catggagaag agaccctggc ttgctctaca ttgcttccaa 176400
tgcaactgca aggcaggtcc cagagggctc cggccttcgt catccaggtt tgctccctcc 176460
cctcatggct ttcccatcct cagatgagga ctcggcagag cctacccctg ctgactaact 176520
gtggccccag ggtggtgact cagccctgca cctcctgatc ccgtctgcac tgggccagag 176580
aggatgactt acccagcacg ttcacatcac acagctttgt ggattcctag gtccaaggac 176640
cagagatttc agttatgtga gttatttttt ttatttgttc ttgcgtattc cacaaagggt 176700
cgcagctaaa cttaacctaa tgatcacttt agtatatcac taaaaagaca aagctcacag 176760
tgctgttgaa gcacattcat catctttaga cattttgact agttatttct taagcattta 176820
cctgctagtg ttaagcatca catgaaatac atatagaagt aagacaaaat ttcttatctc 176880
cccaagtttg ccaacaaata cagagcagga agggaagcag gtcagagcag gaggcgcagc 176940
tatagtgagg ccaccatgca aggcacaggg agggtgagct ccaagtttga atggaatggg 177000
tctgtcagcc aagcccctg gctctgggaa gatagcagtg aacaagccag atggcccctc 177060
accctccaga gccgtgagtc ctgcagacca aacagcgtga caggtccttt ccctgtccag 177120
gaggcctctg tgggtgagag ttggctgcgg acagggcgtg aaggcacttg agggtgggga 177180
agtgactctg actgggagat gctgaggaca gggaggaaac caccagataa gggacactgg 177240
ggaggagggg tggacccctc agggccaagc acatggagcc tcatcacaaa ggcaagatgg 177300
tggccaaatt caaggtcgct gcaaaaggaa tggagaagag agaatagatt tggcatttgg 177360
aggaaatggt gacaatcatg agcacctacc cgggactctc catgggtgct atctctacat 177420
aaactcattc caccctctga ttaatccatt ctacatatgg ggaaacaaag gcatgcggtg 177480
tttacgtcac ttgccaagat ctcaggattt gatccaggtg gcctggttcc atggtgcagc 177540
ctctcagcct gcatggatgc ccagctcag agcatgactc tcaggacagg ggtcccagca 177600
gccctccctc cctgagcagc agggtgcccg tgctgcacca cttctgtcta ggaataggac 177660
attctgacac tttcctgcct cttccgaggt ctagcactta ctctatgcct gcctgggaag 177720
gtggcaagct ggcctgagga acagactctt ccatttttta gggagctcaa ggccacagat 177780
gctctgagat ctggagtcca gagacaggag cggaggcttc tcctggtgac cactctgctt 177840
aaaaacttca tcagatccgt agtttcagag cccccctgaa ccccatccct tacctctacc 177900
agttgcaggt gggtctctgg ggtggggctg ccctccccac cagcacccca agggctaaaa 177960
ggttgagggg agaacaccat catttgtaca gggggatcct ggaagatgag gcctgagaaa 178020
gccctgcggg gcccctcacc ttctccctag ctgtggccaa gagtgtctgg ccttgcctgc 178080
ctcaggacca gcccaaagtg gaggtgagag gtgagcccca gcccccaggg gaagggtgat 178140
ggtggtcttg gtctcagcat ggttctggta gaggtgggtt attttgaaga tgatgaacct 178200
taagcctctt tctgatcttg ctttaaataa atacttctga acaacagcaa caacagaata 178260
gtgttgatag gaaagccctc cactccacca gaaccacgcg gccttctcgt cctcccctcc 178320
tccacttcct tcctaagtca ctgctccatg agctcttcca caggagattt acaaaacaga 178380
acacaaacaa tccagttcct gcctctcact ctgaactcct cccaagactc gtggggtgcg 178440
gcagcccctg ggaacaccca gcccttcaag gtcaaacaca gcccccgccc ctcactctgg 178500
ggtaccctgc cagaataagc cccgacagcc atgtggagca gagccttctt ttttgtaagt 178560
ggaagttcca ggctggcttt tcaaatcccc ttttaacctc agtgctgtat ttcaaaattc 178620

-continued

```
attccagttt tcctgtagta attaacaaaa ataaatattt taatttcaat taaagtgagg 178680
gtctcggaga agaagcagga actgagtttc ctgagaggcc ccgctgaggc tttgttgata 178740
tttcttcctg cgacctctgc tcggaccctg ggagctcaca ggccgtatcg cagctcttat 178800
ctttggggac cagttaaagc ataactgcgc caggcacaga gttgtccttt caaatgtgcc 178860
ggcagtggga cggagaccca tgcgtcaagt ctcctctaag ttcacatggg attctctcct 178920
tgtcccaaag ctgtctctga cttaaaaccc tccaactgat tacctgaatt ccagaatatg 178980
tcctgtgctc tctgcccttt cccacgcctt tggtgaagac cggtgttctg aggaaacaga 179040
cactgtgtag aaatggctca ggtcctttaa agccctggtg tgaggagtgg ggaagggctg 179100
ggccagaggt cagctggatt tgttagattg acagagtgac gcggacttcc ccagaggcac 179160
gggaccaagg tgcatgctca cgctgtctca tgctctcaca cataatgtgt gtgtgtgtgt 179220
gtatatatat atacacatat acatatatat atatacacac atatgcatat atataaaacc 179280
ccaagcagcc tctggcttag caggtgcatt tcccagcagg gcaattaaag ccatggtccc 179340
agtagtggtc ttggggtctc agggtatttg gtctgtgcag ccacatgctt cagtctctgg 179400
accccaggtc atctaacgag gtggtcgtgt ggggactggg atagaaaagg tgtctgcacg 179460
gacgtgtgtg aaagggctgg cacatcgcca gtgctcagca ctgtcagctg ctatcaccag 179520
tcattcaatc attcattcat tcattcagtt gttcattctt caacaggccg ttttaaaaat 179580
gtgcccagta taccaaaatc tccgctaagc atttaaagag gcagaatgaa agttagcagt 179640
ggtggtgaaa cgaagctggg aatgtgctct gagggcctcc ttgtgggctt aatgaatatg 179700
tagaaaccac gcattttaaa tagagaggga gaaagggaga ggttcctggt cctctgcatg 179760
gggacttgtg tgtggctctt tactgtaggc ctgtgccact cctgctcaac agctaccaca 179820
gaggacgcct tcaacaaatg tgaagaacga acaaaaggta caaatgtgaa gaacgaacag 179880
ggtagaaaga aaggagaaag caagggtgag ggtgagaaat caagggacag agaagagaga 179940
agaggagata gcctgggagt tcacacagcc aagaaggtag acactcagtt gaaccagcaa 180000
gaggctgagc ctaactctcc ctttcgaatg ggcaggagtt catgatattt aataaacaga 180060
ggccttgctc tgtaagagac agggtaccag gcagagagca agtcagcatc gcaggagtca 180120
aacgaggcag acagcggggg cagggagctt gcctctgaag gagacccagg ctgccagagt 180180
agcagggagt ctgggccagt cctcttttgg gaagcgcttc ctcggcttct gcccccccctc 180240
tcctctccct ttccacccac catcctgaca taatacttcc taatctggaa gtgttgtcca 180300
gagaagaacc tgctcatttc ctcttaagta ggcagggaag cactaacgtc cagcagcatc 180360
ggaaacccgt aggagcgctc tcggcagtgc agggtgaggg gacagtccat gtagtcatga 180420
gacgtgggtg tcaggcaagc gtctcttttc caaaagagaa aaacattaaa ggcctcacaa 180480
acggcgccca aagactaatt ctgcatagca tctttgcgag accctaggtt cttatgatga 180540
ctggttttgc ctgagaaaga aaaaatttta attttgcttt gacatgccaa ttcaacaaat 180600
cattttcaca taatattcat gcaaaaaaaa aacaatttgc cagaaaactt gggaatccat 180660
ccacatctac agcttttccc tgcagtcaca ctacagtggg atccctccat acaggagcgg 180720
cagagtggag caggctagag atgcctgttt gtttctgttt gctgcaccgc agcaagcatt 180780
tctgtcgtgc ccactctgta ctagaaagta catgaacatc agccataaag ggaactagaa 180840
aggtggccca ccctcttggt ggagagagaa gagagtgtgg tagaaacaat aataagaagt 180900
ctgcagaact tgacccctcc cagcctctcc cacctgccag cctggccctt gcagagagat 180960
gcaggctgcc attcttaggc caaagcctgg gacagttggg ctcagcaagg taggcatccg 181020
```

tcaagcaagg aggagcaggg gtcagcagtg accccagcag ccagcaggga gaaaggtgca 181080
tgtgacaagg acaccagagg ccgtgggtca ggatcagcca gggtcagggt agcatttcta 181140
ggaattcact ctgttgggcg ctgtgctggc tgcttctcac atattattcc tttcttactc 181200
tcagagcaga gatttcaatt gcagcgagat tgtggaggca gccagggagg tggggagggt 181260
ggtgtcttct aaaagcattt tcagtatcca tgtggtttca gtaataataa taataataaa 181320
ccagtgaaaa gtaaaacagg acaaaaatct tcataggcag tgaaccatat cagagagtcc 181380
aagaaagcac aatgagagtg tggcttaaaa accctgaacg acattccttt gcaccagctt 181440
ggtgaggagg gcatggtccc cgccaccccc cacccccact ttgcagataa accacatgca 181500
ggaaggtcag cctggcaagt ccagtaagtt caagcccagg tctcaactgg gcagcagagc 181560
tcctgctctt ctttgtcctc atatacgagc acctctggac ttaaaacttg aggaactgga 181620
tggagaaaag ttaatggtca gcagcgggtt acatcttctt tcatgcgcct ttccattctt 181680
tggatcagta gtcactaacg ttcgccagcc ataagtcctc gacgtggaga ggctcagagc 181740
ctggcatgaa catgaccctg aattcggatg cagagcttct tcccatgatg atctgtccct 181800
cacagcaggg tcttctctgt ttcagggcat gaactacttg gaggaccgtc gcttggtgca 181860
ccgcgacctg gcagccagga acgtactggt gaaaacaccg cagcatgtca agatcacaga 181920
ttttgggctg gccaaactgc tgggtgcgga agagaaagaa taccatgcag aaggaggcaa 181980
agtaaggagg tggctttagg tcagccagca ttttcctgac accagggacc aggctgcctt 182040
cccactagct gtattgttta acacatgcag gggaggatgc tctccagaca ttctgggtga 182100
gctcgcagca gctgctgctg gcagctgggt ccagccaggg tctcctggta gtgtgagcca 182160
gagctgcttt gggaacagta cttgctggga cagtgaatga ggatgttatc cccaggtgat 182220
cattagcaaa tgttaggttt cagtctctcc ctgcaggata tataagtccc cttcaatagc 182280
gcaattggga aaggtcacag ctgccttggt ggtccactgc tgtcaaggac acctaaggaa 182340
caggaaaggc cccatgcgga cccgagctcc cagggctgtc tgtggctcgt ggctgggaca 182400
ggcagcaatg gagtccttct ctcccttcac tggctcggtt tctcttaggg accctcacag 182460
cactaagggg tgcgcgtccc ctgtcaggcc ctcgaatgcc ctcccacagc caggcccctc 182520
tgaggtttca ctctggcctg ctgggctcct agcagccacc aacccatgat gctgggccct 182580
gaaaacacac gcagacctgg atgagtgagg ccactgggca caaccagggc tcccagctca 182640
ccagagcagc ctgggacaca gagggtgctc agaaacctac cagagcagcc ctgaactccg 182700
tcagactgaa atcccctgtt gccgggagga ggcgccgggc ctgggggacg ggtcctgggg 182760
tgatctggct cgtctgtgtg tgtcactcgt aattaggtcc agagtgagtt aactttttcc 182820
aacagaggga aactaatagt tgtctcactg cctcatctct caccatccca aggtgcctat 182880
caagtggatg gcattggaat caattttaca cagaatctat acccaccaga gtgatgtctg 182940
gagctacggt gagtcataat cctgatgcta atgagtttgt actgaggcca agctggcttt 183000
tattgttagt taatttacat tatatcctct gacatgcaag tattttcttt cgagataatg 183060
actaatgata atgtaatcat tgctgtctat ctattgtact gagaaaacac ggcagaggaa 183120
atcgagtcca gctgccgtcc aaaagtcact ggagattgca atgagctcgt ctggcagggt 183180 gggggtatg ggagggaaag agcttaggaa acggctctcc ctgcaaagtc caaccaaact 183240
ttaacgttaa ccaaaccatt aatgttgcca tgaatttgaa gtgaaccaga gggaggtggc 183300
agaagaagct taatggggaa tagttccggt agagaaatga ggcttaagat gaactaccct 183360

-continued ggcccttatg tgtcagagag aacggcttga caaacacaca ctgaggatgt ctgcagggat 183420
aaaagaagaa agggagatga cccttgcttc tcgctctcgg gaggaccatc tggtccggcc 183480
ctggggattc tctgtttcct cttctgaatc ccagtgttgc ccagcactgg cctgtaccca 183540
tcctcacgag ggccgctctc ctcacccggc cctaggtccc tgccctgtcc tgagcctaca 183600
ggggcctccc atgttgagaa agtgttgctg acacattgtc tctgaccgct gtgccaggca 183660
ttttctgctg aattaccgca cttggtcctt gaatttcacc cagcaactta ctgaaaggct 183720
ggaacccatg aacctacccc ttcactgagg aaaatcagtt accccagcca tctacagcga 183780
caggagcaag ggaggagtcg cctcacctct ctagaaatgt gtatttgagg agaacactat 183840
tgaaatgaat ttccaagaat aatctagtca gtattacaaa agcaaaatta tttgggatat 183900
cgtccttttt tacttagtat tttttctttt tcctatagca ttattaactt tctgattttc 183960
caaatacata cacattttta aatttcctga gtctttatct cttctgttaa aatgtaagat 184020
ttatgataca aaggcagaga tttgtgtcca tgaataagtg aagtttggtg tgcacctgtg 184080
agctgagcca cctcaattaa tggaacagat aaggaaataa aggtctgctg atgcattgtt 184140
atttacagcc attttcagaa tgtatctcct ctccacgagg gaactgcagg gtcctgcccc 184200
aagccattta ttttgtcctc aagcagcccg cccctcccac tccaggcaca gcccggtctc 184260
ctgctggtct cccctcttcc cacttgctcc ccctcatcta tgctccagac agaggccaca 184320
tatatttttt aacttttttt tttttttttt tgagacagag tcttgccctg tcacccaggc 184380
tggagtgcag tggtgcagtc tcggctcact gcaacctcca cctcccgggt tcaagtgatt 184440
ctcctgcctc agcctcctga gtagctggga ttacaggcgc acaccaccat gcccagctaa 184500
ttttttgtat ctctagttga gacagggttt cactatgttg gccaggctgg tctcgaactc 184560
ctgacctcat gatctgcccg cctcggcctc ccaaagtgca tattttttaa ctttatcaga 184620
cttttcattc tctgctcaac atctttcttt ggtcctccag gtatgttcag ataaaacctg 184680
agcacctggc catgactgat gggttgctgg gccatctggc cctggcaact ctcccgtcca 184740
ccaggtcccc ctcccgtcac gctccaggca tagcctgtgt gtgccagcgc aatgcccaca 184800
ctccatgcac aagtggaagc cctctcaaag tcagtggctt agtgccttga tgtggtcaca 184860
cccattctca ggaagtccgt tcccactgaa aacattgtgt gttttcaaca tcattgaggc 184920
tgccacggca gattataatc actggcctag gcagcccact ggaactacca gaccatgagc 184980
ctgaattttt tgtttaaaaa tcatatcctg ttttctctac tctctagtct ctagtcaagg 185040
tgaattattc aatttaataa attaggggcc tagtgtgttg taccaaggag ctaaaaagag 185100
agaactcgca acaccttcca gcccattctc cacctaacac tggctatact ggctctcctc 185160
tctctcgctg tttgttccaa aatctaataa cctgtcttcc cactagaatt catcatacat 185220
gtttaaaaac ctagttaaat agtagttaaa ctgactgcat agatctggaa atgagacagt 185280
ctttctttta caaatccata tagactatga gttgggggca ggggatgaca caagaatcta 185340
ttttcttgcc cccaaaccat tgctttcctt ccaatgttaa gcttgtattc tgtgtattaa 185400
ttcaggtggt tccgtttggg aatggcctct gttacccaga gatgggaggg ccatcagaac 185460
tcggggttgt ctgaaaaaac actggttcta aaattatcac tgctttcact tgtttttaac 185520
catcatagtt gtttgatttt gaaggaaaaa catgagggtt tttattctat gcttgttata 185580
tctatattgt ggtttcgtat tttttagatt ttagtacctg acattttttt aacttttatt 185640
ttaggttcag ggtacatgt gcaggtttgt tatataggta aatttgtgtc atggggggttt 185700 gttacacaga ttattttatc acccaggat taagcctagt acccattagt tatttttcct 185760

-continued gatcctctcc ctcctcccat cctccaccgt cctatagacc ccagtgtgtg ttgttcccct 185820
ctaagtgtcc atgtgttctc atcatttagc tcccacttat aagtaagaac atgcggtatt 185880
tgattttctg ttcctgcatt agtttgctag ggatgatggc ctctagctcc atccatgttc 185940
ttgcaaagta catgatctca ttctcttttg tggctgccta gtgttccatg gtgtatatgt 186000
accacatttt ctttatccag tctgtcattg atgggcattt aggttgattc catgtctttg 186060
ctattgtaaa tagtgctgca gtgaaaatac gcatgcatat gtctttatgg tagaatgatt 186120
tatattcctt tgagtaatgg gattgccggg tcaaatggta gttctgtttt tagctatctg 186180
agaaattgcc acactctttt ccacaataat tgaactaatt tacattccca ccaacagtgt 186240
aaaagcattc ctttttctcc acaacctcac cagcatgtgt tgggattttt tttttttttt 186300
acttttcaat aatagccatc tgactggtat gagatggtat ctcagtgtgg ttttgatttt 186360
tatttcttta atgatcagtg atgttaagct ctttttcata tacttgttgg ctgcatgtat 186420
gtcttcttct aaaaagtgtc tgctcatgtc ctttgcccac tttttaatgg gattgtttaa 186480
ttttttcttg tgaatttact taagttcctt atagatgctg gttattagac ccttctcaga 186540
tttgtagctt gcaaaaatgt tcacccattc tgtgggttgt cttcactctg atgatagttt 186600
cttttgctgt gcagaagatc ttcagtttag ttagatccca tttgtcaatt tttgcttttg 186660
ttgcaattgc ttgatgtgtt ttcatcatga aatcttagcc cattcctata tccagaatgg 186720
tattacctag gttgtcttcc agggttttta tagtttgggg ttttacattt aagtctttaa 186780
tccatgttga gtttattttt gtgtatggtg taaggaagga gtccagtttc aatcttcttc 186840
atggctagct agtcatcatt tattgagtag ggagtccttt attcattgct tttttttttt 186900
tgtcaacttt gtcaacgatc acatggttgt aggtgtgcag ccttatttct gggctctcta 186960
ttctgtttca ttggtctgta tgtctgtttc tgtactagta ccatgctgtt ttggttactg 187020
tatccctgta gtttaaagtc aggtagcatc atgcttccag ctttgttctt tttgcttagg 187080
attgccttgg caattcaggc tctttttttgg ttccatgtga atttttaaat tgtattttct 187140
agttctgtga agaatctcat tggtagtgtg ataggagtaa cattgaatct ataaaatact 187200
ttgggcagta tagtcatttt aatgatattg attctttcta tccatgagca tggaatgttt 187260
ttccatttgt ttgtgtcatc tctgatttct ttaagcagtg ttttgtggtt cttattgtag 187320
agatctttca ctttcctggt ttactgtatt tctaggtatt ttattctttt tgtggcaatt 187380
gtgaattgaa ttgcattcct gatttggttc tcagcttgac tgttgttggc atattggaat 187440
gctaattatt tttgtacatt gattttgtac aactgagtct tcactgaagt tgtttatcag 187500
cttaaggggt tttgggcaag actatggggt tttctagata taggatcatg tcatctgcaa 187560
acagagatag ctgttttcct ctcttcctgt ttggatgtcc attatttctt tctctcacct 187620
gatttatctg gccaggactt ccaatactat gttaaatagg agtgttgaga gagggaatcc 187680
ttgtcttgtg tcaattttca aggggaatgt tttcaacttt tgcccattca atatgatgtt 187740
ggctgtgggt ttgccataga tggctattat gttgaggttt gttctttaaa tacctagttt 187800
attgagaatt ttaaacatgt tgaattttat tgagagcctt ttctgcatct attgagatga 187860
tcatgtggct tttgtcctta gttctgtttg tgtggtgaat cacatttatt gatttgcata 187920
tgttgaacca atcttgcatc ccagggatga agccgacttg attgtggtgg cttaagcttt 187980
ttgatgtgct gctggattcg atttgccagt attttgttga ggatttttat gtctatgttc 188040
atcagagata ttggcctgaa gttttctttt tttgtggatc tctgccaagc tttggtatca 188100

-continued

```
ggatgacatt ggcctcatag aatgagttaa ggaagagtcc ctccttctca attttttttgg 188160
aatagtttca gtaggaatgg taccagcttt ttttgtacat cttgtagaat ttggctatga 188220
atccatctag tcttaggctt tgttttggtt ggtaggctat ttattactga ttcaattttg 188280
gagctcatta ttggtctgtt cagggattca gtttcttcct gaggttttta tttttatcaa 188340
atggaactta acctttttca tttccaattt ttttatgatc taaaaatgtg cagtttacag 188400
ccctgttcag aatctgcatc ttcctcattc tgcagataca ggtccctcag agcaggtgac 188460
tgagtgtgta tcctgtctgg agcataatac ttatgctagt agagttactg ttgtctttat 188520
tgttaattac caaagtttac cacttatcag tcacttacta cttgctgggc attgcactaa 188580
gcatttcagt tgtattatct tgttgggtcc ttacagcaat cctgtgaaac agatactgct 188640
attaccccac tttatagaga ggtagactga ggcttccagc attgaagcaa attgcccaag 188700
actacagaaa tgtaggtttc taaacatcaa gaaacagtaa ccagtaatga tgactaaagc 188760
aagggattgt gattgttcat tcatgatccc actgccttct tttcttgctt catcctctca 188820
ggggtgaccg tttgggagtt gatgaccttt ggatccaagc catatgacgg aatccctgcc 188880
agcgagatct cctccatcct ggagaaagga gaacgcctcc ctcagccacc catatgtacc 188940
atcgatgtct acatgatcat ggtcaagtgt gagtgactgg tgggtctgtc cacactgcct 189000
agctgagcct tggtggctgc tcttagccaa acagctgagg cctttgcatc cctggagaaa 189060
tgtcatcaca ttacttaagg caggcacaca aatccagaaa catctgtaaa taccccttca 189120
agcattcttt taaagacact tcttgactca ttgggcagta tgacctgaca tttgcccatg 189180
tttgcaagca aataaataaa actaaagtct tccgcaagcc attacaccaa aatattctat 189240
tcgctgagtt actcaatgaa ataccgagtt gccctatatt ttgaagcctg ttaccagaga 189300
gactgaatgt ttttaaatgc atggcagtga gtaacaacat aaggctaata gagtcaacat 189360
ttctgctttg acttaaacct tttaaaccag tggatttatg tgaagtctct gcagtgtggc 189420
atttaaacat ttcaatctaa ataagagtgt gtaatttgat tgatgctatt attctaccag 189480
attcacgagt gcagtgggct ctggaggtag cattacatgc atgggatgag catttgcaaa 189540
agaaagttgt atagggaata tgacagagcc aagttaatgt aaatattaat gcctttctga 189600
actctaggcc acagagttga tcttttttaa cttccttggt ttgggctaag gaagctgtga 189660
tccagagaag ccacgtgatt tgtctaaggt cacatagcag tctggcctaa aatagcttga 189720
tatgctgtgg atggaaaata aatgtgatcc ctcaagaggc atgaggattt ccaggcagta 189780
gccatacctc caaattgttt aatctggatt tagattgttg ggtagtcaca tgcagcagca 189840
cagttaacag tgtgtcctcc tgtggaagtg gccagcacag ccagccctct cacttgcatg 189900
catgcccacc agccttctca cttgcatgca tgcccactgg gtatgtgctg tactggagac 189960
gccggggggta ggggcccagt cccaacccca aattctttaa agcctatttt tctaagttgc 190020
atctggtttc ctacctgaag gaatgctaag ggtggatgtt gagtgaggac cttggtgcag 190080
ggcaccctgc agtcaggata gttcatggag agcaattgta cagacccaca ctgctccatc 190140
ccctcaggcg taacacagga tgctgacccc aggaagagtg ggcgtagaaa aactagaggg 190200
cattattgtt attctgattc aaatgtacag tgctggcatg gtctttaaac agtaaccagt 190260
actagctggc caagacagaa aagtctacca caaagacttg gttctttcat cacttatttg 190320
actggaagtg tcgcatcacc aatgccttct ttaagcaatg ccatctttat catttcttcc 190380
agtgttctaa ttgcactgtt ttttctcatt ccttccccag gctggatgat agacgcagat 190440
agtcgcccaa agttccgtga gttgatcatc gaattctcca aaatggcccg agaccccccag 190500
```

-continued

```
cgctaccttg tcattcaggt acaaattgca gtctgcgctt ccattgggaa gagtccctct 190560
aatgagcatc tcatgtcact gtgttctgtc acatgccagc ctggcctccc tgtgtcccag 190620
atcgcattat taaaccctcc agcgcattag agcaagcctc agtaaggcgc aggccacatc 190680
gtgaactaag cagcatccgt gagtggggcc cacccaactc catctccccc tccccgtctg 190740
aactctcctc tggtgctcgt cctcactgtc cggctagcca aagcctcagc tgggtctaag 190800
agagaagcat ggtctattgg gctttggtgt caggcagacg tggcttcaca cccctgactc 190860
tccacttctt cgcatcaccc aggcagccga tccacctatc tccttccata acacaggaat 190920
accaaaacca agctcacagg attgtctcaa agattcaata aaatatgttg caaaatacgc 190980
tccctaacac ctcacagcaa ggtgcacaaa tcgatgaatg ctgcagcttc ttccctttct 191040
gtttcctcag aagctatttg aatctcatgt aggggctttc aagcatcaaa ggatggttca 191100
tgttttattt taaggcaccc acatcatgtc atgaggggag gcagctataa tttagagaac 191160
caagggggat ttcattataa caaaattggc aaacacacag gcacctgctg gcaatagacc 191220
cctgctccta tagccaagaa gtggaatagc atctctacgg gccattctaa tagcctcaaa 191280
atctctgcac caggggggatg aaagaatgca tttgccaagt cctacagact ccaacttcta 191340
ccgtgccctg atggatgaag aagacatgga cgacgtggtg gatgccgacg agtacctcat 191400
cccacagcag ggcttcttca gcagcccctc cacgtcacgg actcccctcc tgagctctct 191460
ggtatgaaat ctctgtctct ctctctctca agctgtgtct actcatttga acaaattgaa 191520
ttttagggaa aataaccatc tagtgaaact cacatggaaa tgaagtcaat tttaaccaaa 191580
tggtaaaatc aaaatcaaaa taaattaagt gtattaatta ttttgttgca ttgcaacaac 191640
ttgattgtaa gccttttagg tccactatgg aatgtaatta aatcaaaact aaacctagtt 191700
gctctaaaac taacgattaa gacaaaaatt aaacaccttc acaatatacc ctccatgagg 191760
cacaccacct gcattcagga aaagtggatg agatgtggta caagcattcc atgggcaatt 191820
ctctgtttct ttttccagag tgcaaccagc aacaattcca ccgtggcttg cattgataga 191880
aatggggtat gtatgaacac cttataagcc agaatttaca gctctccact atggctctat 191940
tttacatgga aaatgcctta acctaaataa ttttaaccca gataatcttg agttttcttc 192000
ctgtgtgggt ttttccctgc acggctgtca cgcctcacag tgccgttcaa agcgtgactc 192060
ctggaccagt agtagcatcg cctggccttg ttagaaacgc catttttcag gccactgccc 192120
cagtttgacc aaatcaggac ctctgggggt ggcacccagt agtctatgtt tgagccactt 192180
tccaggtgat gctgatgtct gttgaagtgt gaggccgtgg tctagaccgc actgtgccat 192240
gcagaaacca ctagccacat gtggctactt caacttaaat gttaatgagt taaaatgaaa 192300
taaaatataa aattcagttt ctcacacatg tgaagtgtcc agtagccaca cgtggctagt 192360
ggtgaccgta ttgaagagca ccgctcatag cacacctccc tcactgcgga aagttctgct 192420
gtacagcacc cagcaacagc cctgctgccc aaccctgcag cctgtggccc aagtagcacc 192480
agcacccacc agggtgcaag actctcaagg cctgcccaac ctactaatca gaaccagcat 192540
ctcaaggaga tctcgggtga tttttgcaaa cactgaagtt ggggcagccc tgaccggagt 192600
aaccttccct catttcctcc tgcagctgca aagctgtccc atcaaggaag acagcttctt 192660
gcagcgatac agctcagacc ccacaggcgc cttgactgag gacagcatag acgacacctt 192720
cctcccagtg cctggtgagt ggcttgtctg gaaacagtcc tgctcctcaa cctcctcgac 192780
ccactcagca gcagccagtc tccagtgtcc aagccaggtg ctccctccag catctccaga 192840
```

-continued

```
gggggaaaca gtggcagatt tgcagacaca gtgaagggcg taaggagcag ataaacacat 192900
gaccgagcct gcacaagctc tttgttgtgt ctggttgttt gctgtacctc tgttgtaaga 192960
atgaatctgc aaaatttcta gcttatgaag caaatcacgg acatacacat ctgtgtgtgt 193020
gagtgttcat gatgtgtgta catctgtgta tgtgtgtgtg tgtatgtgtg tgtttgtgac 193080
agatttgatc cctgttctct ctgctggctc tatcttgacc tgtgaaacgt atatttaact 193140
aattaaatat tagttaatat taataaattt taagctttat ccagatactc ataacctgct 193200
aacacacaca catatacaca cacatacaca tacacacata tacacacacc acacacatac 193260
acagacacca cacacatacc atacacagac acatacacat gcacacacat atacacacac 193320
acctcaaata catacacacc acacacacat acatgtatac acacatacac acaccacaca 193380
tacaccacaa aaaccccaca cacatacaca tatacacacc acacacacca catacacaca 193440
cgtatacaca catatataca cacatacacc atgcatacat acacaccaca catacataca 193500
gacacaccac acacacgtac acacaacaca caacacagac acacacgtac acacactaca 193560
gacatgtatg cacacataca cacacaccac acatacatac acacagacac atatacacta 193620
cacacaccat tacatacaca cgtacacata caccacacac accacacata cacacaccac 193680
acacacatac acacgccaca cacacaccac aaaaaccgca cacacataca aacatataca 193740
cactacacca cacatacaca cacacaccac acaccacaca cacacataca cacaccacac 193800
acaccacaca tacacgcacc acacatacac acacgtagac acaccacaca caccacagaa 193860
acacacatta acacaccaca tacacatatg tatgtgcata tacacaccca caccccacac 193920
acacatgtat aaagatttag atatatataa aacatacgtt atatatatgt tgatgtaata 193980
tctaatatct atatatctaa tatgtagttt attagctatc taatatctat gtcatatata 194040
tcaaatcttt atatataaaa atatgtagaa atctttatac atatgttata tgtatataaa 194100
gatttagata tataacatat gtaagttata tatatgttag tgtaatatct aatatatagt 194160
ttattggcta tctaatataa tataaacaga ttatcaatat tataagctat tagaaaaatg 194220
caagttaagg cagatgatat acctctttca caccaactca cacaccaact acacacacac 194280
atacacacag acacacacga cacacaccat acacatgtac acacacacca catatacaca 194340
aacgtacaca cacaccacac acacatacac accacacaca caacacacat acatacacat 194400
ccacacacca cacatgtaca cacaccacac acacacatac acaccacata cacatatgta 194460
tgcacacata cacaccaaca ccacacagac accacacatg cataaacata tagacatata 194520
cacaccacac accatatgta cacatgtaca cacacaccac atatacacac aacacacaca 194580
aatacacaca ccacacacac accacaaaaa ccccacacac acaaacatat acaccccaca 194640
catacgcata tatacacaca cacatacaca ccacacacat acacaccaca cacacaccac 194700
acatacacac acgtacacac accacacaca caccacagac acacaccaca catacataca 194760
catacacaca ccacacacac gtacacacac cacacacaca cagacacaca tagacacacc 194820
acatacacac ccacaccaca cacacacaac tcataccaca catacataca caatagacac 194880
atacacacca cacacaccat acatacacac gtatacacac accacatata cacacacgta 194940
cacacacacc acacacaccc acatgcacac accacacaca catacaaata tacaccacac 195000
acacatacac cacacacacg gtgcacatac acacacatat acacacacca gacacacata 195060
ccacatacac atcacacata tatgtataca tgcatacaca tacacacaca catacacaca 195120
ctctcctcaa ggcagtttat cctctgagaa ctttaaattt acaaaagaca catatgtcca 195180
ttactttgag aaggacagga aagaacccac tttcttttgc agcaacagca agagggccct 195240
```

```
cccaaggctc ctgctccctg tcataagtct ccttgttgag gacattcaca gggttcagaa 195300
cccagggatc ctgcatggga tggtgctttg ctgattactt cacctctgat ttctttccac 195360
tttcagaata cataaaccag tccgttccca aaaggcccgc tggctctgtg cagaatcctg 195420
tctatcacaa tcagcctctg aaccccgcgc ccagcagaga cccacactac caggaccccc 195480
acagcactgc agtgggcaac cccgagtatc tcaacactgt ccagcccacc tgtgtcaaca 195540
gcacattcga cagccctgcc cactgggccc agaaaggcag ccaccaaatt agcctggaca 195600
accctgacta ccagcaggac ttctttccca aggaagccaa gccaaatggc atctttaagg 195660
gctccacagc tgaaaatgca gaatacctaa gggtcgcgcc acaaagcagt gaatttattg 195720
gagcatgacc acggaggata gtatgagccc taaaaatcca gactctttcg atacccagga 195780
ccaagccaca gcaggtcctc catcccaaca gccatgcccg cattagctct tagacccaca 195840
gactggtttt gcaacgttta caccgactag ccaggaagta cttccacctc gggcacattt 195900
tgggaagttg cattcctttg tcttcaaact gtgaagcatt tacagaaacg catccagcaa 195960
gaatattgtc cctttgagca gaaatttatc tttcaaagag gtatatttga aaaaaaaaaa 196020
aaaagtatat gtgaggattt ttattgattg gggatcttgg agtttttcat tgtcgctatt 196080
gatttttact tcaatgggct cttccaacaa ggaagaagct tgctggtagc acttgctacc 196140
ctgagttcat ccaggcccaa ctgtgagcaa ggagcacaag ccacaagtct tccagaggat 196200
gcttgattcc agtggttctg cttcaaggct tccactgcaa aacactaaag atccaagaag 196260
gccttcatgg ccccagcagg ccggatcggt actgtatcaa gtcatggcag gtacagtagg 196320
ataagccact ctgtcccttc ctgggcaaag aagaaacgga ggggatgaat tcttccttag 196380
acttactttt gtaaaaatgt ccccacggta cttactcccc actgatggac cagtggtttc 196440
cagtcatgag cgttagactg acttgtttgt cttccattcc attgttttga aactcagtat 196500
gccgcccctg tcttgctgtc atgaaatcag caagagagga tgacacatca aataataact 196560
cggattccag cccacattgg attcatcagc atttggacca atagcccaca gctgagaatg 196620
tggaatacct aaggataaca ccgcttttgt tctcgcaaaa acgtatctcc taatttgagg 196680
ctcagatgaa atgcatcagg tcctttgggg catagatcag aagactacaa aaatgaagct 196740
gctctgaaat ctcctttagc catcacccca accccccaaa attagtttgt gttacttatg 196800
gaagatagtt ttctcctttt acttcacttc aaaagctttt tactcaaaga gtatatgttc 196860
cctccaggtc agctgccccc aaaccccctc cttacgcttt gtcacacaaa aagtgtctct 196920
gccttgagtc atctattcaa gcacttacag ctctggccac aacagggcat tttacaggtg 196980
cgaatgacag tagcattatg agtagtgtga attcaggtag taaatatgaa actagggttt 197040
gaaattgata atgctttcac aacatttgca gatgttttag aaggaaaaaa gttccttcct 197100
aaaataattt ctctacaatt ggaagattgg aagattcagc tagttaggag cccatttttt 197160
cctaatctgt gtgtgccctg taacctgact ggttaacagc agtcctttgt aaacagtgtt 197220
ttaaactctc ctagtcaata tccaccccat ccaatttatc aaggaagaaa tggttcagaa 197280
aatattttca gcctacagtt atgttcagtc acacacacat acaaaatgtt ccttttgctt 197340
ttaaagtaat ttttgactcc cagatcagtc agagccccta cagcattgtt aagaaagtat 197400
ttgatttttg tctcaatgaa aataaaacta tattcatttc cactctatta tgctctcaaa 197460
tacccctaag catctatact agcctggtat gggtat                           197496
```

<210> SEQ ID NO 11

-continued

<211> LENGTH: 4530
<212> TYPE: DNA
<213> ORGANISM: Homo sapiens

<400> SEQUENCE: 11

```
aattctcgag ctcgtcgacc ggtcgacgag ctcgagggtc gacgagctcg agggcgcgcg     60
cccggccccc acccctcgca gcaccccgcg ccccgcgccc tcccagccgg gtccagccgg    120
agccatgggg ccggagccgc agtgagcacc atggagctgg cggccttgtg ccgctggggg    180
ctcctcctcg ccctcttgcc ccccggagcc gcgagcaccc aagtgtgcac cggcacagac    240
atgaagctgc ggctccctgc cagtcccgag acccacctgg acatgctccg ccacctctac    300
cagggctgcc aggtggtgca gggaaacctg gaactcacct acctgcccac caatgccagc    360
ctgtccttcc tgcaggatat ccaggaggtg cagggctacg tgctcatcgc tcacaaccaa    420
gtgaggcagg tcccactgca gaggctgcgg attgtgcgag gcacccagct ctttgaggac    480
aactatgccc tggccgtgct agacaatgga gacccgctga acaataccac ccctgtcaca    540
ggggcctccc caggaggcct gcgggagctg cagcttcgaa gcctcacaga gatcttgaaa    600
ggaggggtct tgatccagcg gaacccccag ctctgctacc aggacacgat tttgtggaag    660
gacatcttcc acaagaacaa ccagctggct ctcacactga tagacaccaa ccgctctcgg    720
gcctgccacc cctgttctcc gatgtgtaag ggctcccgct gctggggaga gagttctgag    780
gattgtcaga gcctgacgcg cactgtctgt gccggtggct gtgcccgctg caaggggcca    840
ctgcccactg actgctgcca tgagcagtgt gctgccggct gcacgggccc caagcactct    900
gactgcctgg cctgcctcca cttcaaccac agtggcatct gtgagctgca ctgcccagcc    960
ctggtcacct acaacacaga cacgtttgag tccatgccca atcccgaggg ccggtataca   1020
ttcggcgcca gctgtgtgac tgcctgtccc tacaactacc tttctacgga cgtgggatcc   1080
tgcaccctcg tctgccccct gcacaaccaa gaggtgacag cagaggatgg aacacagcgg   1140
tgtgagaagt gcagcaagcc ctgtgcccga gtgtgctatg gtctgggcat ggagcacttg   1200
cgagaggtga gggcagttac cagtgccaat atccaggagt ttgctggctg caagaagatc   1260
tttgggagcc tggcatttct gccggagagc tttgatgggg acccagcctc caacactgcc   1320
ccgctccagc cagagcagct ccaagtgttt gagactctgg aagagatcac aggttaccta   1380
tacatctcag catggccgga cagcctgcct gacctcagcg tcttccagaa cctgcaagta   1440
atccggggac gaattctgca caatggcgcc tactcgctga ccctgcaagg gctgggcatc   1500
agctggctgg ggctgcgctc actgagggaa ctgggcagtg gactggccct catccaccat   1560
aacacccacc tctgcttcgt gcacacggtg ccctgggacc agctctttcg gaacccgcac   1620
caagctctgc tccacactgc caaccggcca gaggacgagt gtgtgggcga gggcctggcc   1680
tgccaccagc tgtgcgcccg agggcactgc tggggtccag ggcccaccca gtgtgtcaac   1740
tgcagccagt tccttcgggg ccaggagtgc gtggaggaat gccgagtact gcaggggctc   1800
cccagggagt atgtgaatgc caggcactgt ttgccgtgcc accctgagtg tcagccccag   1860
aatggctcag tgacctgttt tggaccggag gctgaccagt gtgtggcctg tgcccactat   1920
aaggaccctc ccttctgcgt ggcccgctgc cccagcggtg tgaaacctga cctctcctac   1980
atgcccatct ggaagtttcc agatgaggag ggcgcatgcc agccttgccc catcaactgc   2040
acccactcct gtgtggacct ggatgacaag ggctgccccg ccgagcagag agccagccct   2100
ctgacgtcca tcgtctctgc ggtggttggc attctgctgg tcgtggtctt gggggtggtc   2160
tttgggatcc tcatcaagcg acggcagcag aagatccgga agtacacgat gcggagactg   2220
```

-continued

```
ctgcaggaaa cggagctggt ggagccgctg acacctagcg gagcgatgcc caaccaggcg   2280
cagatgcgga tcctgaaaga gacggagctg aggaaggtga aggtgcttgg atctggcgct   2340
tttggcacag tctacaaggg catctggatc cctgatgggg agaatgtgaa aattccagtg   2400
gccatcaaag tgttgaggga aaacacatcc cccaaagcca acaaagaaat cttagacgaa   2460
gcatacgtga tggctggtgt gggctcccca tatgtctccc gccttctggg catctgcctg   2520
acatccacgg tgcagctggt gacacagctt atgccctatg gctgcctctt agaccatgtc   2580
cgggaaaacc gcggacgcct gggctcccag gacctgctga actggtgtat gcagattgcc   2640
aaggggatga gctacctgga ggatgtgcgg ctcgtacaca gggacttggc cgctcggaac   2700
gtgctggtca agagtcccaa ccatgtcaaa attacagact tcgggctggc tcggctgctg   2760
gacattgacg agacagagta ccatgcagat gggggcaagg tgcccatcaa gtggatggcg   2820
ctggagtcca ttctccgccg gcggttcacc caccagagtg atgtgtggag ttatggtgtg   2880
actgtgtggg agctgatgac ttttggggcc aaaccttacg atgggatccc agcccgggag   2940
atccctgacc tgctggaaaa gggggagcgg ctgccccagc cccccatctg caccattgat   3000
gtctacatga tcatggtcaa atgttggatg attgactctg aatgtcggcc aagattccgg   3060
gagttggtgt ctgaattctc ccgcatggcc agggaccccc agcgctttgt ggtcatccag   3120
aatgaggact tgggcccagc cagtcccttg gacagcacct tctaccgctc actgctggag   3180
gacgatgaca tgggggacct ggtggatgct gaggagtatc tggtacccca gcagggcttc   3240
ttctgtccag accctgcccc gggcgctggg ggcatggtcc accacaggca ccgcagctca   3300
tctaccagga gtggcggtgg ggacctgaca ctagggctgg agccctctga agaggaggcc   3360
cccaggtctc cactggcacc ctccgaaggg gctggctccg atgtatttga tggtgacctg   3420
ggaatggggg cagccaaggg gctgcaaagc ctccccacac atgaccccag ccctctacag   3480
cggtacagtg aggaccccac agtacccctg ccctctgaga ctgatggcta cgttgccccc   3540
ctgacctgca gcccccagcc tgaatatgtg aaccagccag atgttcggcc ccagccccct   3600
tcgccccgag agggccctct gcctgctgcc cgacctgctg gtgccactct ggaaagggcc   3660
aagactctct ccccagggaa gaatggggtc gtcaaagacg tttttgcctt tgggggtgcc   3720
gtggagaacc ccgagtactt gacaccccag ggaggagctg cccctcagcc ccaccctcct   3780
cctgccttca gcccagcctt cgacaacctc tattactggg accaggaccc accagagcgg   3840
ggggctccac ccagcacctt caaagggaca cctacggcag agaacccaga gtacctgggt   3900
ctggacgtgc cagtgtgaac cagaaggcca agtccgcaga agccctgatg tgtcctcagg   3960
gagcagggaa ggcctgactt ctgctggcat caagaggtgg gagggccctc cgaccacttc   4020
caggggaacc tgccatgcca ggaacctgtc ctaaggaacc ttccttcctg cttgagttcc   4080
cagatggctg gaaggggtcc agcctcgttg gaagaggaac agcactgggg agtctttgtg   4140
gattctgagg ccctgcccaa tgagactcta gggtccagtg gatgccacag cccagcttgg   4200
ccctttcctt ccagatcctg ggtactgaaa gccttaggga agctggcctg agaggggaag   4260
cggccctaag ggagtgtcta agaacaaaag cgacccattc agagactgtc cctgaaacct   4320
agtactgccc cccatgagga aggaacagca atggtgtcag tatccaggct ttgtacagag   4380
tgcttttctg tttagttttt actttttttg ttttgttttt ttaaagacga aataaagacc   4440
caggggagaa tgggtgttgt atggggaggc aagtgtgggg ggtccttctc cacacccact   4500
ttgtccattt gcaaatatat tttggaaaac                                    4530
```